US011273166B2

(12) United States Patent
Dodd et al.

(10) Patent No.: US 11,273,166 B2
(45) Date of Patent: Mar. 15, 2022

(54) METHODS AND COMPOSITIONS FOR THE TREATMENT OF OBESITY

(71) Applicant: Monash University, Clayton (AU)

(72) Inventors: Garron Dodd, Clayton (AU); Tony Tiganis, Clayton (AU)

(73) Assignee: Monash University, Clayton (AU)

( * ) Notice: Subject to any disclaimer, the term of this patent is extended or adjusted under 35 U.S.C. 154(b) by 116 days.

(21) Appl. No.: 16/622,348

(22) PCT Filed: Jun. 13, 2018

(86) PCT No.: PCT/AU2018/050588
§ 371 (c)(1),
(2) Date: Dec. 13, 2019

(87) PCT Pub. No.: WO2018/227248
PCT Pub. Date: Dec. 20, 2018

(65) Prior Publication Data
US 2020/0197415 A1    Jun. 25, 2020

(30) Foreign Application Priority Data

Jun. 13, 2017   (AU) ............................... 2017902239

(51) Int. Cl.
*A61K 31/575* (2006.01)
*A61P 3/04* (2006.01)
*A61K 9/00* (2006.01)
*A61K 31/15* (2006.01)
*A61K 31/662* (2006.01)
(Continued)

(52) U.S. Cl.
CPC .......... *A61K 31/575* (2013.01); *A61K 9/0043* (2013.01); *A61K 31/15* (2013.01); *A61K 31/662* (2013.01); *A61P 3/04* (2018.01); *C12N 15/1137* (2013.01); *A61P 5/04* (2018.01)

(58) Field of Classification Search
CPC ...... A61K 31/136; A61K 31/15; A61K 31/56; A61K 31/575; A61K 31/662; A61K 38/06; A61K 9/0043; A61P 3/04; A61P 5/04; C12N 15/1137
See application file for complete search history.

(56) References Cited

U.S. PATENT DOCUMENTS

2003/0027802 A1   2/2003 Belanoff et al.
2008/0058300 A1   3/2008 McLane et al.

FOREIGN PATENT DOCUMENTS

WO   2011/057331 A1   5/2011

OTHER PUBLICATIONS

Dodd, G.T., et al., "A Hypothalamic Phosphatase Switch Coordinates Energy Expenditure with Feeding", Cell Metabolism, 2017, vol. 26, pp. 375-393 (Pub. Aug. 1, 2017). Abstract; Figs. 1-2, 7; p. 383, RH col.

(Continued)

*Primary Examiner* — Savitha M Rao
(74) *Attorney, Agent, or Firm* — Banner & Witcoff, Ltd.

(57) ABSTRACT

The present invention generally relates to methods and compositions for the treatment of overweight or obese individuals. In particular, the invention relates to reducing adiposity of an overweight or obese individual. The present invention provides a method for reducing adiposity or treating obesity in an individual, the method comprising inhibiting TCPTP and/or PTP1B in the hypothalamus of the individual, thereby reducing adiposity or treating obesity in the individual.

13 Claims, 89 Drawing Sheets

Specification includes a Sequence Listing.

(51) Int. Cl.
  *C12N 15/113*  (2010.01)
  *A61P 5/04*  (2006.01)

(56) References Cited

OTHER PUBLICATIONS

Dodd, G.T., et al., "Leptin and Insulin Act on POMC Neurons to Promote the Browning of White Fat", Cell, 2015, vol. 160, pp. 88-104 Abstract; Figs. 1, 3-4, 6; Discussion at pp. 98-100.

Liu, J., et al., "Treatment of Obesity with Celastrol", Cell, 2015, vol. 161, pp. 999-1011 Abstract; Figures 1-2 Discussion pp. 1009-1010.

Qin, Z., et al., "Functional properties ofClaramine: A novel PTP1B inhibitor and insulin-mimetic compound", Biochemical and Biophysical Research Communications, 2015, vol. 458, pp. 21-27 Abstract; Discussion at p. 26; Figs. 1, 4.

Van Den Heuvel, J.K., et al., "Identification of a selective glucocorticoid receptor modulator that prevents both diet-induced obesity and inflammation", British Journal of Pharmacology, 2016, vol. 173, pp. 1793-1804 Abstract; Methods at p. 1794; Figs. 1-4; Discussion at pp. 1801-1802.

Zhang, S., et al., "Acquisition of a Potent and Selective TC-PTP Inhibitor via a Stepwise Fluorophore-Tagged Combinatorial Synthesis and Screening Strategy", Journal of the American Chemical Society, 2009, vol. 131, pp. 13072-13079 Abstract; Compound 8; Scheme 2; Table 1.

The Wellcome Trust Case Control Consortium, "Genome-wide association study of 14,000 cases of seven common diseases and 3,000 shared controls" Nature, vol. 447, p. 661 678, Jun. 2007.

Wiede et al. "T cell protein tyrosine phosphatase attenuates T cell signaling to maintain tolerance in mice" The Journal of Clinical Investigation, 121(12), pp. 4758-4774, Dec. 2011.

Wiede et al. "PTPN2-deficiency exacerbates T follicular helper cell and B cell responses and promotes the development of autoimmunity" Journal of Autoimmunity, 76, pp. 85-100, 2017.

Wiede et al. "T-Cell-Specific PTPN2 Deficiency in NOD Mice Accelerates the Development of Type 1 Diabetes and Autoimmune Comorbidities" Diabetes, vol. 68, pp. 1251-1266, Jun. 2019.

Zikherman et al. "Unraveling the functional implications of GWAS: how T cell protein tyrosine Phosphatase drives autoimmune disease" The Journal of Clinical Investigation, vol. 121, No. 12, Dec. 2011.

Dodd et al. "Intranasal Targeting of Hypothalamic PTP1B and TCPTP Reinstates Leptin and Insulin Sensitivity and Promotes Weight Loss in Obesity" Cell Reports, 28, pp. 2905-2922, Sep. 10, 2019.

Loh et al. "Elevated Hypothalamic TCPTP in Obesity Contributes to Cellular Leptin Resistance" Cell Metabolism, 14, pp. 1-16, Nov. 2, 2011.

Todd et al. "Robust associations of four new chomosome regions from genome-wide analyses of type 1 diabetes" Mature Genetics, vol. 39, No. 7, pp. 857-864, Jul. 2007.

Dodd et al. "Insulin signaling in AgRP neurons regulates meal size to limit glucose excursions and insulin resistance" Science Advances, vol. 7, Feb. 26, 2021.

ingWAT homogenates from individual fed mice

I

J

K

L

F

D

E

SEQUENCE LISTING

<160> NUMBER OF SEQ ID NOS: 62

<210> SEQ ID NO 1
<211> LENGTH: 23
<212> TYPE: RNA
<213> ORGANISM: Artificial Sequence
<220> FEATURE:
<223> OTHER INFORMATION: Example siRNA sequence

<400> SEQUENCE: 1
aagauugaca gacaccuaau auu                                             23

<210> SEQ ID NO 2
<211> LENGTH: 57
<212> TYPE: DNA
<213> ORGANISM: Artificial Sequence
<220> FEATURE:
<223> OTHER INFORMATION: Example shRNA sequence

<400> SEQUENCE: 2
ccgggatgac caagagatgc tgtttctcga gaaacagcat ctcttggtca tctttttt      57

<210> SEQ ID NO 3
<211> LENGTH: 57
<212> TYPE: DNA
<213> ORGANISM: Artificial Sequence
<220> FEATURE:
<223> OTHER INFORMATION: Example shRNA sequence

<400> SEQUENCE: 3
ccggtgcaag atacaatgga ggagactcga gtctcctcca ttgtatcttg cattttt       57

<210> SEQ ID NO 4
<211> LENGTH: 57
<212> TYPE: DNA
<213> ORGANISM: Artificial Sequence
<220> FEATURE:
<223> OTHER INFORMATION: Example shRNA sequence

<400> SEQUENCE: 4
ccgggaagat gtgaagtcgt attatctcga gataatacga cttcacatct tctttttt     57

<210> SEQ ID NO 5
<211> LENGTH: 57
<212> TYPE: DNA
<213> ORGANISM: Artificial Sequence
<220> FEATURE:
<223> OTHER INFORMATION: Example shRNA sequence

<400> SEQUENCE: 5
ccgggtgcag tagaatagac atcaactcga gttgatgtct attctactgc acttttt      57

<210> SEQ ID NO 6
<211> LENGTH: 57
<212> TYPE: DNA
<213> ORGANISM: Artificial Sequence
<220> FEATURE:
<223> OTHER INFORMATION: Example shRNA sequence

<400> SEQUENCE: 6
ccggctcact ttcattatac tacctctcga gaggtagtat aatgaaagtg agttttt      57

<210> SEQ ID NO 7
<211> LENGTH: 58
<212> TYPE: DNA
<213> ORGANISM: Artificial Sequence

```
<220> FEATURE:
<223> OTHER INFORMATION: Example shRNA sequence

<400> SEQUENCE: 7
ccggattctc atacatggct ataatctcga gattatagcc atgtatgaga attttttg      58

<210> SEQ ID NO 8
<211> LENGTH: 58
<212> TYPE: DNA
<213> ORGANISM: Artificial Sequence
<220> FEATURE:
<223> OTHER INFORMATION: Example shRNA sequence

<400> SEQUENCE: 8
ccggagaaga tgtgaagtcg tattactcga gtaatacgac ttcacatctt cttttttg      58

<210> SEQ ID NO 9
<211> LENGTH: 58
<212> TYPE: DNA
<213> ORGANISM: Artificial Sequence
<220> FEATURE:
<223> OTHER INFORMATION: Example shRNA sequence

<400> SEQUENCE: 9
ccggatatga tcacagtcgt gttaactcga gttaacacga ctgtgatcat attttttg      58

<210> SEQ ID NO 10
<211> LENGTH: 58
<212> TYPE: DNA
<213> ORGANISM: Artificial Sequence
<220> FEATURE:
<223> OTHER INFORMATION: Example shRNA sequence

<400> SEQUENCE: 10
ccgggtggag aaagaatcgg ttaaactcga gtttaaccga ttctttctcc acttttg       58

<210> SEQ ID NO 11
<211> LENGTH: 58
<212> TYPE: DNA
<213> ORGANISM: Artificial Sequence
<220> FEATURE:
<223> OTHER INFORMATION: Example shRNA sequence

<400> SEQUENCE: 11
ccggtatgat cacagtcgtg ttaaactcga gtttaacacg actgtgatca tattttttg     58

<210> SEQ ID NO 12
<211> LENGTH: 57
<212> TYPE: DNA
<213> ORGANISM: Artificial Sequence
<220> FEATURE:
<223> OTHER INFORMATION: Example shRNA sequence

<400> SEQUENCE: 12
ccgggccaag attgacagac acctactcga gtaggtgtct gtcaatcttg gctttt        57

<210> SEQ ID NO 13
<211> LENGTH: 58
<212> TYPE: DNA
<213> ORGANISM: Artificial Sequence
<220> FEATURE:
<223> OTHER INFORMATION: Example shRNA sequence

<400> SEQUENCE: 13
ccgggtgcag tagaatagac atcaactcga gttgatgtct attctactgc acttttg       58
```

```
<210> SEQ ID NO 14
<211> LENGTH: 21
<212> TYPE: RNA
<213> ORGANISM: Artificial Sequence
<220> FEATURE:
<223> OTHER INFORMATION: Example siRNA sequence

<400> SEQUENCE: 14
aagcccauau gaucacaguc g                                              21

<210> SEQ ID NO 15
<211> LENGTH: 21
<212> TYPE: DNA
<213> ORGANISM: Artificial Sequence
<220> FEATURE:
<223> OTHER INFORMATION: TCPTP target sequence

<400> SEQUENCE: 15
gatgaccaag agatgctgtt t                                              21

<210> SEQ ID NO 16
<211> LENGTH: 21
<212> TYPE: DNA
<213> ORGANISM: Artificial Sequence
<220> FEATURE:
<223> OTHER INFORMATION: TCPTP target sequence

<400> SEQUENCE: 16
tgcaagatac aatggaggag a                                              21

<210> SEQ ID NO 17
<211> LENGTH: 21
<212> TYPE: DNA
<213> ORGANISM: Artificial Sequence
<220> FEATURE:
<223> OTHER INFORMATION: TCPTP target sequence

<400> SEQUENCE: 17
gaagatgtga agtcgtatta t                                              21

<210> SEQ ID NO 18
<211> LENGTH: 21
<212> TYPE: DNA
<213> ORGANISM: Artificial Sequence
<220> FEATURE:
<223> OTHER INFORMATION: TCPTP target sequence

<400> SEQUENCE: 18
gtgcagtaga atagacatca a                                              21

<210> SEQ ID NO 19
<211> LENGTH: 21
<212> TYPE: DNA
<213> ORGANISM: Artificial Sequence
<220> FEATURE:
<223> OTHER INFORMATION: TCPTP target sequence

<400> SEQUENCE: 19
ctcactttca ttatactacc t                                              21

<210> SEQ ID NO 20
<211> LENGTH: 21
<212> TYPE: DNA
<213> ORGANISM: Artificial Sequence
<220> FEATURE:
<223> OTHER INFORMATION: TCPTP target sequence
```

<400> SEQUENCE: 20
attctcatac atggctataa t                                           21

<210> SEQ ID NO 21
<211> LENGTH: 21
<212> TYPE: DNA
<213> ORGANISM: Artificial Sequence
<220> FEATURE:
<223> OTHER INFORMATION: TCPTP target sequence

<400> SEQUENCE: 21
agaagatgtg aagtcgtatt a                                           21

<210> SEQ ID NO 22
<211> LENGTH: 21
<212> TYPE: DNA
<213> ORGANISM: Artificial Sequence
<220> FEATURE:
<223> OTHER INFORMATION: TCPTP target sequence

<400> SEQUENCE: 22
atatgatcac agtcgtgtta a                                           21

<210> SEQ ID NO 23
<211> LENGTH: 21
<212> TYPE: DNA
<213> ORGANISM: Artificial Sequence
<220> FEATURE:
<223> OTHER INFORMATION: TCPTP target sequence

<400> SEQUENCE: 23
gtggagaaag aatcggttaa a                                           21

<210> SEQ ID NO 24
<211> LENGTH: 21
<212> TYPE: DNA
<213> ORGANISM: Artificial Sequence
<220> FEATURE:
<223> OTHER INFORMATION: TCPTP target sequence

<400> SEQUENCE: 24
tatgatcaca gtcgtgttaa a                                           21

<210> SEQ ID NO 25
<211> LENGTH: 21
<212> TYPE: DNA
<213> ORGANISM: Artificial Sequence
<220> FEATURE:
<223> OTHER INFORMATION: TCPTP target sequence

<400> SEQUENCE: 25
gccaagattg acagacacct a                                           21

<210> SEQ ID NO 26
<211> LENGTH: 21
<212> TYPE: DNA
<213> ORGANISM: Artificial Sequence
<220> FEATURE:
<223> OTHER INFORMATION: TCPTP target sequence

<400> SEQUENCE: 26
gtgcagtaga atagacatca a                                           21

<210> SEQ ID NO 27

```
<210> SEQ ID NO 27
<211> LENGTH: 22
<212> TYPE: DNA
<213> ORGANISM: Artificial Sequence
<220> FEATURE:
<223> OTHER INFORMATION: Oligonucleotide

<400> SEQUENCE: 27
gtaattatgc tttaagaaca gc                                    22

<210> SEQ ID NO 28
<211> LENGTH: 21
<212> TYPE: DNA
<213> ORGANISM: Artificial Sequence
<220> FEATURE:
<223> OTHER INFORMATION: Oligonucleotide

<400> SEQUENCE: 28
cagagtggtt aagagcactg g                                     21

<210> SEQ ID NO 29
<211> LENGTH: 19
<212> TYPE: DNA
<213> ORGANISM: Artificial Sequence
<220> FEATURE:
<223> OTHER INFORMATION: Oligonucleotide

<400> SEQUENCE: 29
gatgtgcacc ccatgtctg                                        19

<210> SEQ ID NO 30
<211> LENGTH: 20
<212> TYPE: DNA
<213> ORGANISM: Artificial Sequence
<220> FEATURE:
<223> OTHER INFORMATION: Oligonucleotide

<400> SEQUENCE: 30
ctgaatagct gagaccacag                                       20

<210> SEQ ID NO 31
<211> LENGTH: 18
<212> TYPE: DNA
<213> ORGANISM: Artificial Sequence
<220> FEATURE:
<223> OTHER INFORMATION: Oligonucleotide

<400> SEQUENCE: 31
gggtaggaaa caggatgg                                         18

<210> SEQ ID NO 32
<211> LENGTH: 21
<212> TYPE: DNA
<213> ORGANISM: Artificial Sequence
<220> FEATURE:
<223> OTHER INFORMATION: Oligonucleotide

<400> SEQUENCE: 32
actgccacac ctccagtcat t                                     21

<210> SEQ ID NO 33
<211> LENGTH: 21
<212> TYPE: DNA
<213> ORGANISM: Artificial Sequence
<220> FEATURE:
<223> OTHER INFORMATION: Oligonucleotide

<400> SEQUENCE: 33
```

```
ctttgcctca ctcaggattg g                                              21

<210> SEQ ID NO 34
<211> LENGTH: 22
<212> TYPE: DNA
<213> ORGANISM: Artificial Sequence
<220> FEATURE:
<223> OTHER INFORMATION: Oligonucleotide

<400> SEQUENCE: 34
agccgtgacc actgacaacg ag                                             22

<210> SEQ ID NO 35
<211> LENGTH: 23
<212> TYPE: DNA
<213> ORGANISM: Artificial Sequence
<220> FEATURE:
<223> OTHER INFORMATION: Oligonucleotide

<400> SEQUENCE: 35
gctgcatggt tctgagtgct aag                                            23

<210> SEQ ID NO 36
<211> LENGTH: 22
<212> TYPE: DNA
<213> ORGANISM: Artificial Sequence
<220> FEATURE:
<223> OTHER INFORMATION: Oligonucleotide

<400> SEQUENCE: 36
cgtgcagaac tcctgtgata ac                                             22

<210> SEQ ID NO 37
<211> LENGTH: 21
<212> TYPE: DNA
<213> ORGANISM: Artificial Sequence
<220> FEATURE:
<223> OTHER INFORMATION: Oligonucleotide

<400> SEQUENCE: 37
gtccacctat gctggagaag g                                              21

<210> SEQ ID NO 38
<211> LENGTH: 21
<212> TYPE: DNA
<213> ORGANISM: Artificial Sequence
<220> FEATURE:
<223> OTHER INFORMATION: Oligonucleotide

<400> SEQUENCE: 38
tgctcttctg tatcgcccag t                                              21

<210> SEQ ID NO 39
<211> LENGTH: 21
<212> TYPE: DNA
<213> ORGANISM: Artificial Sequence
<220> FEATURE:
<223> OTHER INFORMATION: Oligonucleotide

<400> SEQUENCE: 39
gccgtgttaa ggaatctgct g                                              21

<210> SEQ ID NO 40
<211> LENGTH: 21
<212> TYPE: DNA
```

```
<213> ORGANISM: Artificial Sequence
<220> FEATURE:
<223> OTHER INFORMATION: Oligonucleotide

<400> SEQUENCE: 40
gaagctgcgg tacaattcca g                                          21

<210> SEQ ID NO 41
<211> LENGTH: 21
<212> TYPE: DNA
<213> ORGANISM: Artificial Sequence
<220> FEATURE:
<223> OTHER INFORMATION: Oligonucleotide

<400> SEQUENCE: 41 cccccttgtac ccttcaccaa t                                         21

<210> SEQ ID NO 42
<211> LENGTH: 19
<212> TYPE: DNA
<213> ORGANISM: Artificial Sequence
<220> FEATURE:
<223> OTHER INFORMATION: Oligonucleotide

<400> SEQUENCE: 42
accctgtcat cccacagag                                             19

<210> SEQ ID NO 43
<211> LENGTH: 22
<212> TYPE: DNA
<213> ORGANISM: Artificial Sequence
<220> FEATURE:
<223> OTHER INFORMATION: Oligonucleotide

<400> SEQUENCE: 43
tgtttggtgg agtcctaagg tc                                         22

<210> SEQ ID NO 44
<211> LENGTH: 19
<212> TYPE: DNA
<213> ORGANISM: Artificial Sequence
<220> FEATURE:
<223> OTHER INFORMATION: Oligonucleotide

<400> SEQUENCE: 44
cagcacggtg aagccattc                                             19

<210> SEQ ID NO 45
<211> LENGTH: 17
<212> TYPE: DNA
<213> ORGANISM: Artificial Sequence
<220> FEATURE:
<223> OTHER INFORMATION: Oligonucleotide

<400> SEQUENCE: 45
gcgtgcatcc gcttgtg                                               17

<210> SEQ ID NO 46
<211> LENGTH: 20
<212> TYPE: DNA
<213> ORGANISM: Artificial Sequence
<220> FEATURE:
<223> OTHER INFORMATION: Oligonucleotide

<400> SEQUENCE: 46
accacagtcc atgccatcac                                            20
```

<210> SEQ ID NO 47
<211> LENGTH: 21
<212> TYPE: DNA
<213> ORGANISM: Artificial Sequence
<220> FEATURE:
<223> OTHER INFORMATION: Oligonucleotide

<400> SEQUENCE: 47
caccaccctg ttgctgtagc c                                           21

<210> SEQ ID NO 48
<211> LENGTH: 29
<212> TYPE: DNA
<213> ORGANISM: Artificial Sequence
<220> FEATURE:
<223> OTHER INFORMATION: Interfering RNA

<400> SEQUENCE: 48
aattgcacca ggaagataat gactatatc                                   29

<210> SEQ ID NO 49
<211> LENGTH: 19
<212> TYPE: RNA
<213> ORGANISM: Artificial Sequence
<220> FEATURE:
<223> OTHER INFORMATION: Interfering RNA

<400> SEQUENCE: 49
uagguacaga gacgucagu                                              19

<210> SEQ ID NO 50
<211> LENGTH: 19
<212> TYPE: RNA
<213> ORGANISM: Artificial Sequence
<220> FEATURE:
<223> OTHER INFORMATION: Interfering RNA

<400> SEQUENCE: 50
acugacgucu cuguaccua                                              19

<210> SEQ ID NO 51
<211> LENGTH: 19
<212> TYPE: RNA
<213> ORGANISM: Artificial Sequence
<220> FEATURE:
<223> OTHER INFORMATION: Interfering RNA

<400> SEQUENCE: 51
uagguacaga gacgucagu                                              19

<210> SEQ ID NO 52
<211> LENGTH: 19
<212> TYPE: RNA
<213> ORGANISM: Artificial Sequence
<220> FEATURE:
<223> OTHER INFORMATION: Interfering RNA

<400> SEQUENCE: 52
acugacgucu cuguaccua                                              19

<210> SEQ ID NO 53
<211> LENGTH: 21
<212> TYPE: DNA
<213> ORGANISM: Artificial Sequence
<220> FEATURE:

```
<223> OTHER INFORMATION: Interfering RNA

<400> SEQUENCE: 53
aaatcaacgg aagaagggtc t                                                  21

<210> SEQ ID NO 54
<211> LENGTH: 21
<212> TYPE: RNA
<213> ORGANISM: Artificial Sequence
<220> FEATURE:
<223> OTHER INFORMATION: Interfering RNA
<220> FEATURE:
<221> NAME/KEY: misc_feature
<222> LOCATION: (1)..(2)
<223> OTHER INFORMATION: n is a, c, g, or u

<400> SEQUENCE: 54
nnugaccaua gucggauuaa a                                                  21

<210> SEQ ID NO 55
<211> LENGTH: 25
<212> TYPE: RNA
<213> ORGANISM: Artificial Sequence
<220> FEATURE:
<223> OTHER INFORMATION: Interfering RNA

<400> SEQUENCE: 55
uugauguagu uuaauccgac uaugg                                              25

<210> SEQ ID NO 56
<211> LENGTH: 25
<212> TYPE: RNA
<213> ORGANISM: Artificial Sequence
<220> FEATURE:
<223> OTHER INFORMATION: Interfering RNA

<400> SEQUENCE: 56
ccauagucgg auuaaacuac aucaa                                              25

<210> SEQ ID NO 57
<211> LENGTH: 20
<212> TYPE: DNA
<213> ORGANISM: Artificial Sequence
<220> FEATURE:
<223> OTHER INFORMATION: Interfering RNA

<400> SEQUENCE: 57
ttcgagcaga tcgacaagtc                                                    20

<210> SEQ ID NO 58
<211> LENGTH: 20
<212> TYPE: DNA
<213> ORGANISM: Artificial Sequence
<220> FEATURE:
<223> OTHER INFORMATION: Interfering RNA

<400> SEQUENCE: 58
gatgtagttt aatccgacta                                                    20

<210> SEQ ID NO 59
<211> LENGTH: 20
<212> TYPE: DNA
<213> ORGANISM: Artificial Sequence
<220> FEATURE:
<223> OTHER INFORMATION: Interfering RNA

<400> SEQUENCE: 59
```

```
gagctgggcg gccatttacc                                              20

<210> SEQ ID NO 60
<211> LENGTH: 20
<212> TYPE: DNA
<213> ORGANISM: Artificial Sequence
<220> FEATURE:
<223> OTHER INFORMATION: Interfering RNA

<400> SEQUENCE: 60
tgacgtctct gtacctattt                                              20

<210> SEQ ID NO 61
<211> LENGTH: 20
<212> TYPE: DNA
<213> ORGANISM: Artificial Sequence
<220> FEATURE:
<223> OTHER INFORMATION: Interfering RNA

<400> SEQUENCE: 61
caaaagtgac cgcatgtgtt                                              20

<210> SEQ ID NO 62
<211> LENGTH: 20
<212> TYPE: DNA
<213> ORGANISM: Artificial Sequence
<220> FEATURE:
<223> OTHER INFORMATION: Interfering RNA

<400> SEQUENCE: 62
gtctttcagt tgaccatagt                                              20
```

METHODS AND COMPOSITIONS FOR THE TREATMENT OF OBESITY

RELATED APPLICATIONS

This application is a National Stage application under 35 U.S.C. 371 of PCT application PCT/AU2018/050588 designating the United States and filed Jun. 13, 2018; which claims the benefit of AU application number 2017902239 filed on Jun. 13, 2017 each of which are hereby incorporated by reference in their entireties.

FIELD OF THE INVENTION

The present invention generally relates to methods and compositions for the treatment of overweight or obese individuals. In particular, the invention relates to reducing adiposity of an overweight or obese individual.

BACKGROUND OF THE INVENTION

The recent identification of both classical brown adipose tissue (BAT) and brown-like or beige adipocytes in white fat depots in adult humans, has heralded a new era in adipose tissue biology with a focus on energy homeostasis. In particular, the capacity of brown/beige adipocytes to utilise lipids and glucose as a fuel source, and to expend the energy as heat, accompanied by their decreased abundance in older and overweight individuals, has garnered interest in promoting brown and beige fat thermogenesis to combat the obesity epidemic.

Brown and beige adipocytes arise from distinct precursors, with brown adipocytes arising prenatally from Myf5$^+$ Pax7$^+$ precursors in the embryonic mesoderm and beige adipocytes arising from distinct Myf5$^-$ precursors present in white fat depots. Brown and activated beige adipocytes contain a high density of mitochondria with high amounts of uncoupling protein-1 (UCP-1), allowing for the uncoupling of fatty acid oxidation and glucose oxidation from ATP production to generate heat and prevent hypothermia. Although Ucp-1 and other thermogenic genes are present in brown adipocytes under basal/unstimulated conditions, beige adipocytes only express Ucp-1 in response to β-adrenergic agonists and stimuli such as cold. Since fully activated brown and beige adipocytes exhibit comparable levels of UCP-1 and thermogenic activity, the process of beige adipocyte activation among white adipocytes can be referred to as white adipose tissue (WAT) browning. Unless subjected to persistent cold exposure WAT browning in rodents occurs predominantly in inguinal fat, a major subcutaneous depot. In adult humans, beige adipocytes have been detected in the supraclavicular depot, as well as in the supraspinal, pericardial and neck regions. Strikingly, beige adipocytes lose UCP-1 when stimuli such as cold are removed, and function as white adipocytes. Moreover, such cells can subsequently re-instate Ucp-1 expression and their thermogenic program when re-exposed to cold.

Although the heat produced by brown and beige adipocytes is essential for the survival of small mammals in cold environments, clothing and adequate shelter in modern humans have largely diminished the need for cold-induced brown and beige thermogenesis. Beyond cold-induced thermogenesis, activated brown and beige adipocytes can contribute to energy homeostasis, with their genetic ablation promoting, and their activation protecting from the development of obesity. However, the extent to which brown and beige adipocytes normally influence energy balance remains unclear.

One school of thought suggests that for body weight to remain stable over time, changes in food intake must be matched by commensurate changes in energy expenditure. This concept of 'diet-induced thermogenesis' originated from observations that rats fed a cafeteria diet put on less weight than expected (based on calories consumed) and that this was accompanied by BAT hypertrophy and thermogenesis. Although diet-induced thermogenesis typically refers to the diet-recruited increase in metabolic capacity over time, several studies have shown that a single bout of feeding can acutely increase BAT activation and thermogenesis. Conversely, food restriction in rats was associated with a reduced metabolic rate and BAT inactivation. These findings aligned with observations that overfeeding or food restriction, resulting in increased or decreased weight gain in humans respectively, were matched by commensurate changes in energy expenditure opposing the change in body weight. Precisely how feeding/overfeeding versus fasting influence thermogenesis and energy expenditure remains unclear. Moreover, it remains unknown to what extent, if any, WAT browning contributes to the alterations in energy expenditure associated with feeding.

There is a need for new and/or improved treatments for treating overweight and obese individuals, particularly treatments for reducing adiposity of those individuals.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

The present invention provides a method for reducing adiposity in an individual in need thereof, the method comprising inhibiting TCPTP and/or PTP1B in the hypothalamus of the individual, thereby reducing adiposity in the individual.

The present invention provides a method for treating obesity in an individual in need thereof, the method comprising inhibiting TCPTP and/or PTP1B, in the hypothalamus of the individual, thereby treating obesity in the individual.

The present invention provides a method of reducing the body weight of an individual in need thereof, the method comprising inhibiting TCPTP and/or PTP1B, in the hypothalamus of the individual, thereby reducing body weight of the individual. Typically, the body weight of the individual is reduced without any substantially change in lean muscle mass and/or bone density. Typically, the reduction in body weight is a result of a reduction in the total adipose weight of the individual, The present invention provides a method for treating obesity in an individual in need thereof, the method comprising administering an inhibitor of TCPTP and/or PTP1B to the central nervous system in the individual, thereby treating obesity in the individual.

The present invention provides a method for increasing white adipose tissue browning in an individual in need thereof, the method comprising inhibiting TCPTP and/or PTP1B in the hypothalamus of the individual, thereby increasing white adipose tissue browning in the individual.

The present invention provides a method of preventing or minimising the weight gain of an individual consuming a high energy/caloric diet, the method comprising inhibiting TCPTP and/or PTP1B in the hypothalamus of the individual, thereby preventing or minimising the weight gain of the individual consuming a high energy/caloric diet.

The present invention also provides a method of preventing or minimising adiposity in individual consuming a high energy/caloric diet, the method comprising inhibiting TCPTP and/or PTP1B in the hypothalamus of the individual, thereby preventing or minimising adiposity in the individual consuming a high energy/caloric diet.

The present invention also provides a method for improving exercise capacity or mobility in an individual in need thereof, the method comprising inhibiting TCPTP and/or PTP1B in the hypothalamus of the individual, thereby improving exercise capacity or mobility in the subject.

The present invention also provides a method for enhancing energy expenditure in an individual in need thereof, the method comprising inhibiting TCPTP and/or PTP1B in the hypothalamus of the individual, thereby enhancing energy expenditure in the individual.

In any aspect of the invention, the inhibitor is administered in any route that allows a reduction in TCPTP and/or PTP1B activity or level in cells of the hypothalamus. Typically, the inhibitor is administered via any route that allows it to enter the ventricular system of the brain (i.e., administration to the central nervous system). Preferably, the route of administration is intranasal or intracerebroventrical (ICV) administration. Preferably, the intranasal administration of the TCPTP and/or PTP1B inhibitor is by contacting the olfactory epithelium and/or the trigeminal neurons in the nasal cavity, thereby enabling uptake of the inhibitors into the brain.

The cell(s) of the hypothalamus in which TCPTP and/or PTP1B is inhibited are located in the arcuate nucleus (ARC). Most preferably, the cells are agouti-related peptide (AgRP) neurons and/or proopiomelanocortin (POMC) neurons.

The present invention also provides a method for reducing adiposity in an individual in need thereof, the method comprising administering an inhibitor of TCPTP and/or PTP1B intranasally to the individual, thereby reducing adiposity in the individual.

The present invention provides a method for treating obesity in an individual in need thereof, the method comprising administering an inhibitor of TCPTP and/or PTP1B intranasally to the individual, in the hypothalamus of the individual, thereby treating obesity in the individual.

The present invention provides a method for increasing white adipose tissue browning in an individual in need thereof, the method comprising administering an inhibitor of TCPTP and/or PTP1B intranasally to the individual, thereby increasing white adipose tissue browning in the individual.

The present invention provides a method of preventing or minimising the weight gain of an individual, the method comprising administering an inhibitor of TCPTP and/or PTP1B intranasally to the individual, thereby preventing or minimising the weight gain of the individual. Typically, the individual has, or is, consuming a high caloric diet.

In any aspect of the present invention, the individuals in need thereof are typically those that are overweight, obese, morbidly obese or extremely obese. Preferably, the individual has a BMI greater than 20, 21, 22, 23, 24, 25, 26, 27, 28 or 29 kg/m$^2$. The individual may have a BMI of between 25 kg/m$^2$ to 29.9 kg/m$^2$. The individual may have a BMI of 30 kg/m$^2$ or greater, or a BMI of 40 kg/m$^2$ or greater.

An overweight adult may have a BMI of 25 kg/m$^2$ to 29.9 kg/m$^2$, and an obese adult a BMI of 30 kg/m$^2$ or greater. A BMI of 40 kg/m$^2$ or greater may be indicative of morbid obesity or extreme obesity. The individual may be unable to conduct any exercise or be limited in their capacity to do so. In any aspect of the invention, any degree of obesity is diet-induced.

In any method of the invention, the obesity is treated, adiposity is reduced, or weight gain may be minimised without a change in diet or an increase in exercise. However, in any method of the invention, the method may further comprise the step of reducing the caloric intake in the individual and/or increasing the level of exercise undertaken by the individual.

In any method of the invention, a reduction in adiposity may be a reduction in visceral obesity and/or subcutaneous obesity. In particular, the reduction in adiposity may be a reduction in subcutaneous adiposity. Alternatively, the reduction in adiposity may be a reduction in visceral adiposity.

The present invention provides a method of promoting weight loss in an individual in need thereof, the method comprising inhibiting TCPTP and/or PTP1B in the hypothalamus of the individual, thereby promoting weight loss in the individual. Typically, the individual is consuming a low caloric diet or has had their caloric intake reduced. Typically, promoting weight loss is increasing the rate of weight loss compared to an individual without having TCPTP and/or PTP1B inhibited.

The present invention also provides the use of an inhibitor of TCPTP and/or PTP1B in the manufacture of a medicament for:
  preventing or reducing adiposity in an individual;
  treating obesity in an individual;
  reducing body weight of an individual;
  increasing energy expenditure in an individual;
  improving exercise capacity;
  increasing white adipose browning in an individual; or
  preventing or minimising the weight gain of an individual consuming a high energy/caloric diet.

The present invention also provides an inhibitor of TCPTP and/or PTP1B for use in:
  preventing or reducing adiposity in an individual;
  treating obesity in an individual;
  reducing body weight of an individual;
  increasing energy expenditure in an individual;
  improving exercise capacity;
  increasing white adipose browning in an individual; or
  preventing or minimising the weight gain of an individual consuming a high energy/caloric diet.

In any method of the invention, the method further comprises identifying an individual in need thereof. Typically, the individual is in need of a reduction in adiposity or a reduction in body weight. The individual may be one who has not displayed a significant reduction in body weight after consuming a reduced caloric diet.

The present invention also provides a composition for use in treating obesity, reducing adiposity, or minimising weight gain in an individual in need thereof, the composition comprising an inhibitor of TCPTP and/or PTP1B, and optionally a physiologically acceptable carrier, diluent or excipient.

The present invention also provides a pharmaceutical composition for use in treating obesity, reducing adiposity, preventing or minimising weight gain in an individual in need thereof, the composition comprising an inhibitor of TCPTP and/or PTP1B, and a pharmaceutically acceptable carrier, diluent or excipient.

The invention provides a pharmaceutical composition for use in treating obesity, reducing adiposity, preventing or minimising weight gain comprising as an active ingredient an inhibitor of TCPTP and/or PTP1B and a pharmaceutically acceptable diluent, excipient or carrier. In one embodiment, the only active ingredient present in the composition is an inhibitor of TCPTP and/or PTP1B.

The invention provides a pharmaceutical composition for use in treating obesity, reducing adiposity, preventing or minimising weight gain comprising as a main ingredient an inhibitor of TCPTP and/or PTP1B and a pharmaceutically acceptable diluent, excipient or carrier. In one embodiment, the only main ingredient present in the composition is an inhibitor of TCPTP and/or PTP1B.

The present invention provides a synergistic composition for use in treating obesity, reducing adiposity, preventing or minimising weight gain in an individual, the composition comprising an inhibitor of TCPTP, an inhibitor of PTP1B and a pharmaceutically acceptable diluent, excipient or carrier.

In any method or use of the invention, inhibiting TCPTP and/or PTP1B may be by administering a composition or pharmaceutical composition as described herein.

In any aspect of the invention, the inhibitor of TCPTP or PTP1B is any inhibitor as described herein. Typically, the inhibitor of TCPTP or PTP1B directly inhibits the enzymatic activity of TCPTP or PTP1B. Preferably, the inhibitor binds to the active site of TCPTP or PTP1B. More preferably, the inhibitor of TCPTP competes with, or prevents the binding of a substrate of TCPTP for binding to TCPTP. More preferably, the inhibitor of PTP1B competes with, or prevents the binding of a substrate of PTP1B for binding to PTP1B.

The inhibitor of TCPTP or PTP1B may exhibit a Ki value of less than 1 mM, preferably less than 100 µM, more preferably less than 10 µM, as determined by an assay as described herein.

An inhibitor of TCPTP or PTP1B may be selected from the group consisting of a small molecule, an antibody, a peptide, an interfering RNA (including an antisense RNA, siRNA, microRNA or shRNA or a gRNA) or may be a gRNA for gene editing (for example using CRISPR-Cas9 genome editing methods).

In any aspect of the present invention, the TCPTP inhibitor or PTP1B inhibitor is a small molecule.

In any aspect of the present invention, the TCPTP inhibitor is a glucocorticoid receptor (GR) antagonist that reduces expression of the PTPN2 gene. Typically, the GR antagonist is any one as described herein, including mifepristone (i.e. RU486).

In any aspect of the present invention, the PTP1B inhibitor is selected from claramine and trodusquemine. Preferably the PTP1B inhibitor is claramine.

The present invention provides a kit for use in:
preventing or reducing adiposity in an individual;
treating obesity in an individual;
reducing body weight of an individual;
increasing energy expenditure in an individual;
improving exercise capacity;
increasing white adipose browning in an individual;
preventing or minimising the weight gain of an individual consuming a high energy/caloric diet;
the kit comprising a PTP1B inhibitor, a TCPTP inhibitor or both.

Preferably, the kit also comprises written instructions for use of the kit in a method of the invention as described herein.

The present invention also provides for the use of agents in the manufacture of a kit as described herein.

As used herein, except where the context requires otherwise, the term "comprise" and variations of the term, such as "comprising", "comprises" and "comprised", are not intended to exclude further additives, components, integers or steps.

Further aspects of the present invention and further embodiments of the aspects described in the preceding paragraphs will become apparent from the following description, given by way of example and with reference to the accompanying drawings.

DETAILED DESCRIPTION OF THE EMBODIMENTS

Figure 1:
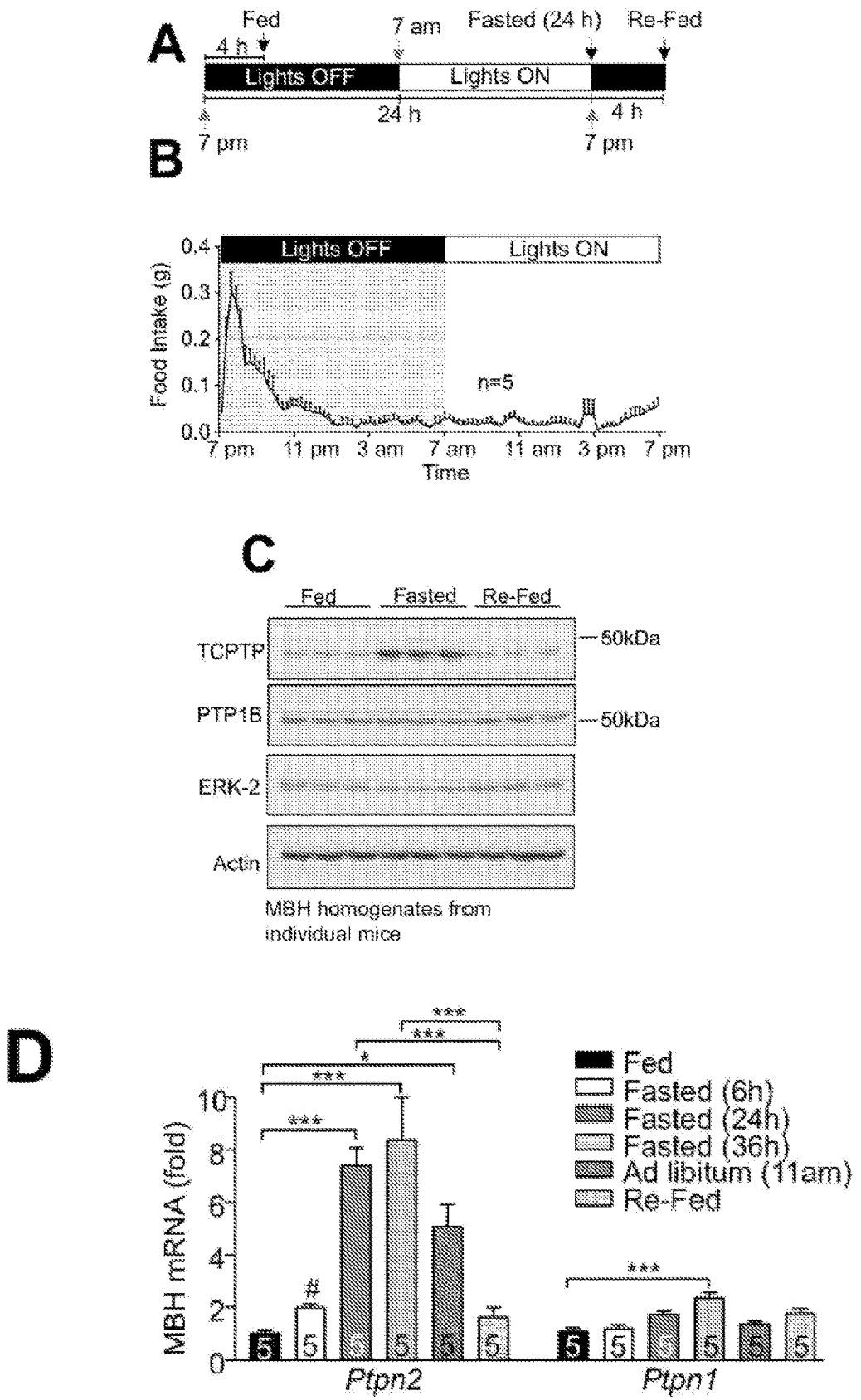
FIG. 1. Feed-fast alterations in hypothalamic TCPTP. a) Experimental feeding paradigm. b) C57BL/6 mouse diurnal feeding profile. Brains from C57BL/6, Npy-hrGFP (C57BL/6) or Pomc-eGFP (C57BL/6) reporter mice fed, fasted (24 h) or re-fed as indicated were microdissected and mediobasal hypothalami (MBH) processed for c, e) immunoblotting and d) quantitative PCR or f-g) immunohistochemistry. h) Fasted C57BL/6 were re-fed or re-fed after the ICV administration of MG132 (2 µl 50 µM) with a repeat administration 2 h before hypothalamic extraction and processed for immunoblotting. 8-week-old male C57BL/6 fed mice were ICV administered vehicle or dexamethasone (2 µl 319 µM) and hypothalami extracted for i) quantitative PCR or k) immunohistochemistry. j) Plasma corticosterone levels in fed, fasted and re-fed C57BL/6 male mice determined by ELISA. l) Fed C57BL/6 mice administered ICV vehicle, or dexamethasone or dexamethasone plus glucocorticoid receptor antagonist RU486 (1 µg) as indicated and hypothalami extracted for quantitative PCR. m) C57BL/6 mice were fed, fasted or fasted and ICV administered 0.2 µg or 1 µg RU486 as indicated and hypothalami extracted for quantitative PCR. Primary cortical neuronal cells were treated with 200 µM dexamethasone for 48 h and processed for n) quantitative PCR or o) immunoblotting. Brightness and contrast in colour merge image have been adjusted to assess co-incidence. Results shown are means±SEM for the indicated number of mice or experiments. In (d) significance between fed versus 6 h fasted assessed using a two-tailed t-test; #p<0.05.
Figure 1:
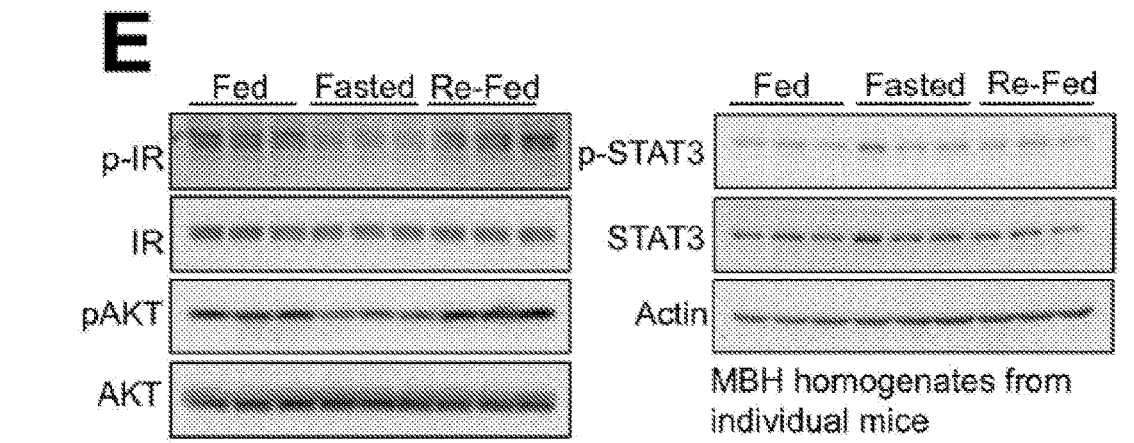
Figure 1:
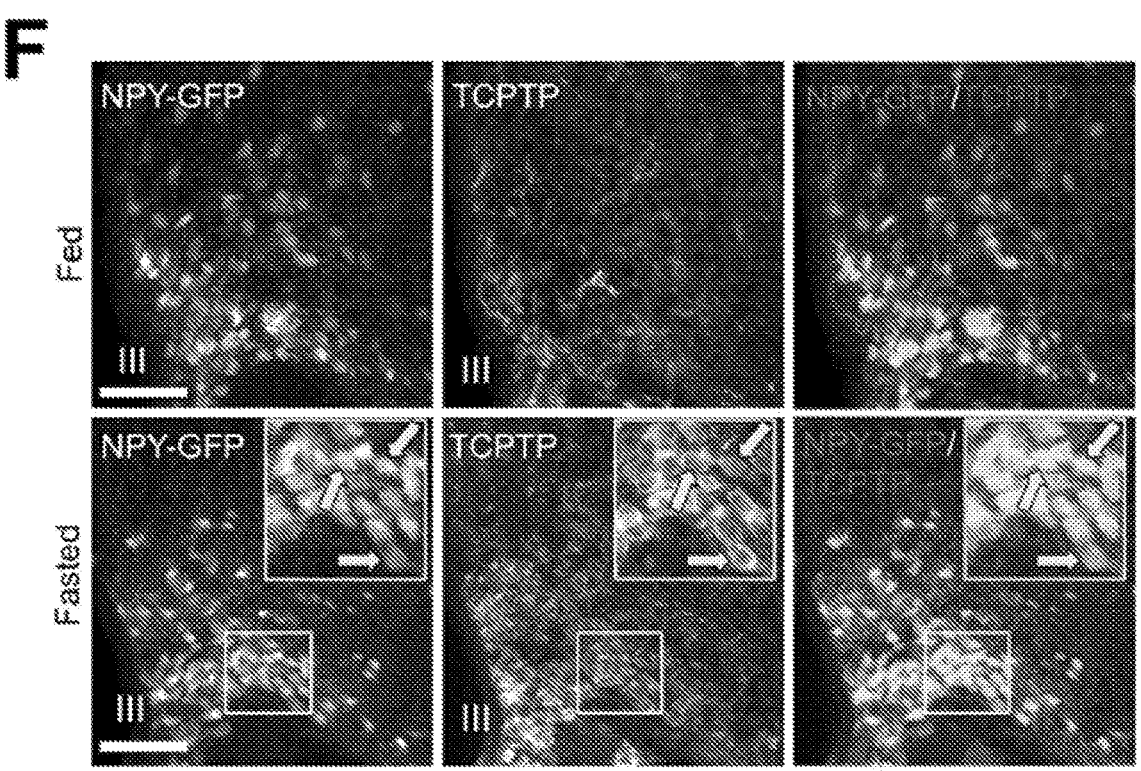
Figure 1:
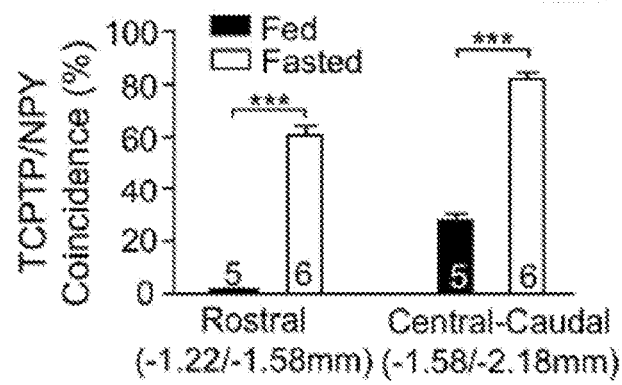
Figure 1:
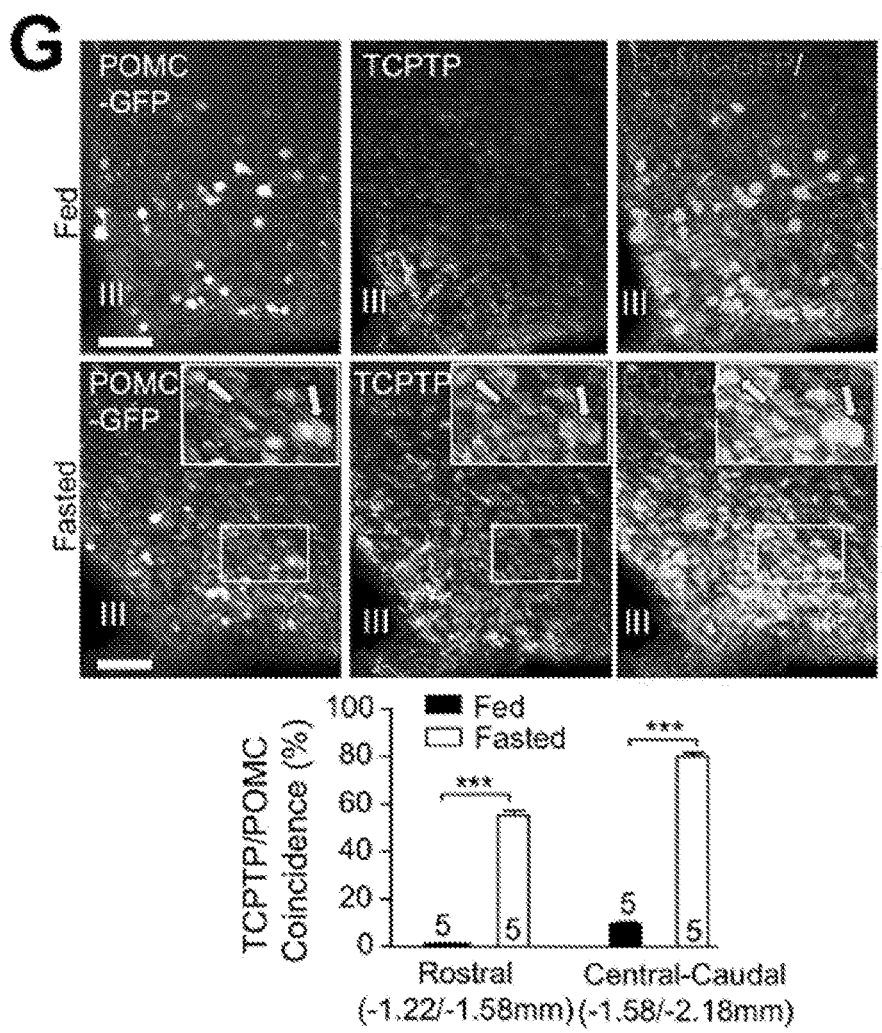
Figure 1:
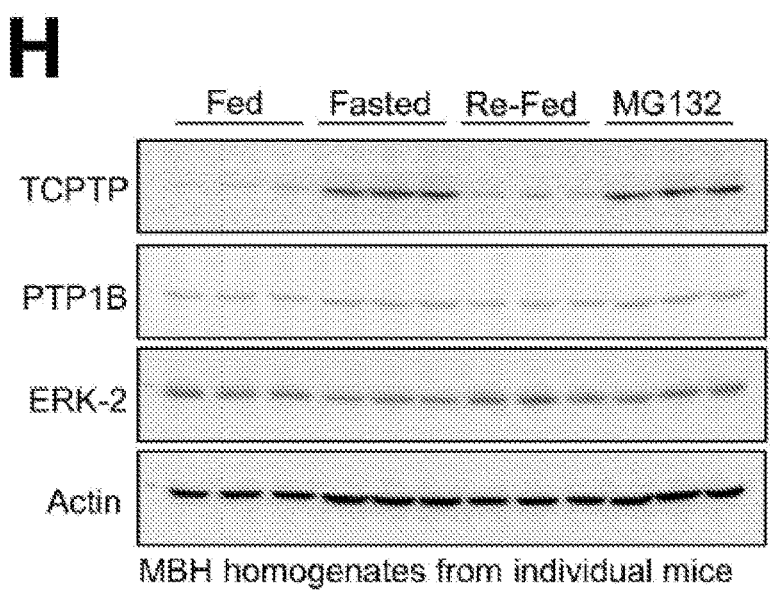
Figure 1:
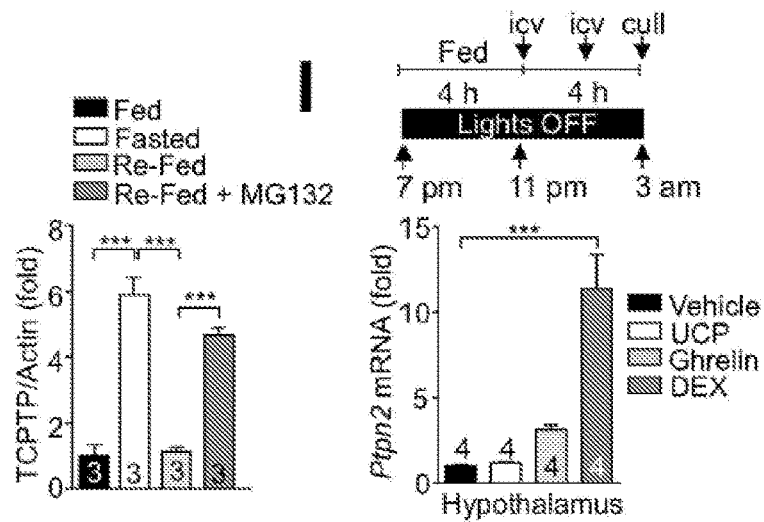
Figure 1:
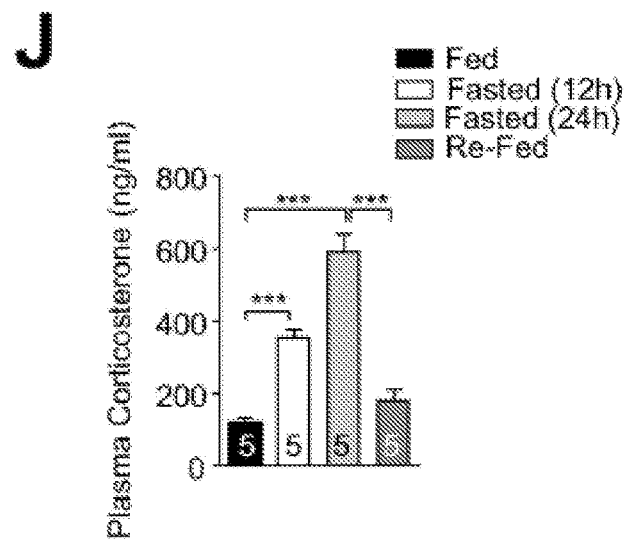
Figure 1:
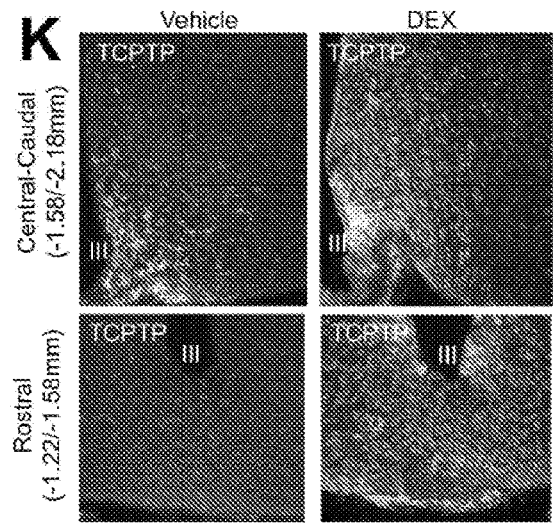
Figure 1:
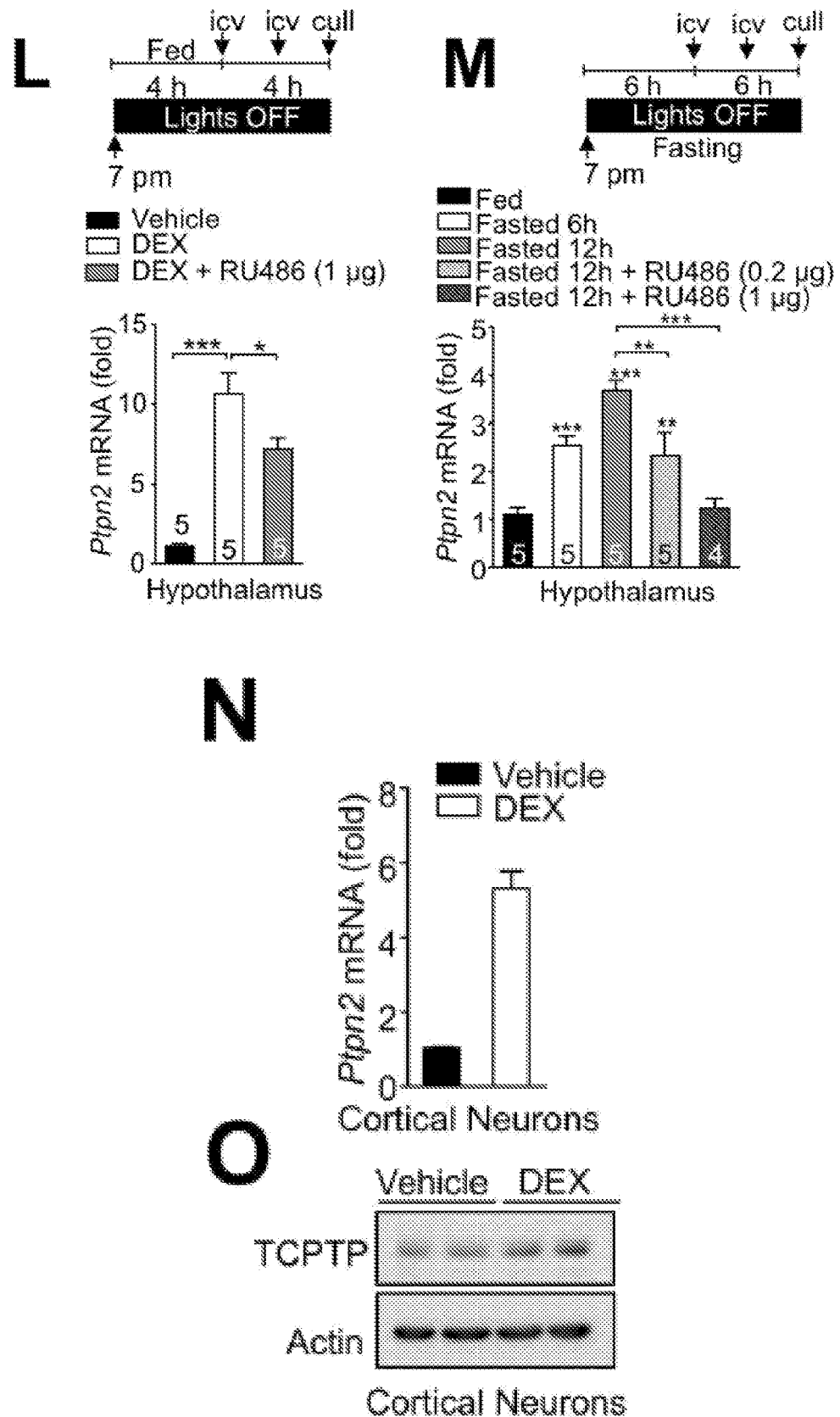

It will be understood that the invention disclosed and defined in this specification extends to all alternative combinations of two or more of the individual features mentioned or evident from the text or drawings. All of these different combinations constitute various alternative aspects of the invention.

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described. It will be understood that the invention disclosed and defined in this specification extends to all alternative combinations of two or more of the individual features mentioned or evident from the text or drawings. All of these different combinations constitute various alternative aspects of the invention.

All of the patents and publications referred to herein are incorporated by reference in their entirety.

For purposes of interpreting this specification, terms used in the singular will also include the plural and vice versa.

The inventors have determined that diurnal fluctuations of the insulin receptor phosphatase TCPTP coordinates insulin signaling in AgRP/NPY neurons, so that WAT browning is increased in response to feeding and repressed during fasting. The inventors have demonstrated that the CNS-mediated promotion of browning is essential for feeding-induced energy expenditure and the maintenance of energy balance. Surprisingly, the inventors have identified that defective feeding-induced and CNS-mediated WAT browning, due to sustained hypothalamic TCPTP levels, contributes to the development and maintenance of obesity. Further, the inventors have shown that inhibiting the activity or cellular level of TCPTP alone, PTP1B alone or of both, reduces body weight and adiposity. Without being bound by any theory or mode of action, it is believed that the reduction in adiposity results from enhanced energy expenditure and promotion of white adipose tissue (WAT) browning.

Advantageously, the methods of the present invention result in reduction in body weight and adiposity without a corresponding decrease in lean muscle mass nor a reduction in bone density.

Further, an advantage of an aspect of the invention is that the reduction in body weight and adiposity does not require a change in activity level or caloric intake. Therefore, the methods of the present invention result, amongst other things, in weight loss or a reduction in adiposity via a mechanism that contrasts with existing therapies for weight loss (including e.g., calorie or energy restricted diets) that target central control of food intake and that may have adverse side effects (e.g. adverse neurological side effects). The methods of the present invention advantageously provide for diet-induced weight loss by inhibiting the activity or cellular level of TCPTP alone, PTP1B alone or both.

Still further, the inventors have found that TCPTP and PTP1B inhibitors act synergistically to reduce adiposity and reduce body weight in diet-induced obesity. For example, the combined inhibition of TCPTP and PTP1B in the ARC of diet-induced obese mice has a more dramatic effect on weight-loss than inhibition of TCPTP or PTP1B alone. In particular, the inventors have observed that targeting of both TCPTP and PTP1B results in synergistic attenuation of body weights and adiposity mediated by effects on both food intake and energy expenditure. This suggests that the combined targeting of hypothalamic TCPTP and PTP1B via, for example, intranasal delivery of TCPTP and PTP1B inhibitors in humans is a therapeutically significant approach to the treatment of obesity.

TCPTP (also known as PTPN2, T cell PTP, PTN2, PTPT, TC-PTP or TCELLPTP) is a ubiquitous phosphatase that is expressed abundantly in hematopoietic cells, including T cells. Two splice variants of TCPTP are expressed that have identical N termini and catalytic domains but varied C termini: a 48-kDa form (TC48) that is targeted to the endoplasmic reticulum (ER) by a hydrophobic C terminus and a 45-kDa variant (TC45) that is targeted to the nucleus by a nuclear localization sequence. Despite an apparently exclusive nuclear localization in resting cells, TC45 can shuttle between the nucleus and cytoplasm to access substrates in both compartments. Genome-wide association studies have linked PTPN2 single nucleotide polymorphisms (SNPs) with the development of several human autoimmune diseases including type 1 diabetes, rheumatoid arthritis, Crohn's disease and celiac disease. In particular, an intronic PTPN2 variant, rs1893217(C), has been linked with the development of type 1 diabetes. This SNP is associated with an approximate 40% decrease in PTPN2 mRNA in CD4+ T cells. TCPTP is a key regulator of TCR signalling in naive CD4+ and CD8+ T cells and functions to dephosphorylate and inactivate Lck and Fyn. TCPTP dephosphorylates the insulin receptor (IR) beta subunit to attenuate insulin-induced PI3K/AKT signalling. TCPTP also dephosphorylates Src family kinases including c-Src, Fyn and Lck, Janus-activated kinases (JAK)-1/3 and signal transducers and activator of transcription (STAT)-1/3/5/6 to attenuate cytokine signalling.

In order to determine if the presence of a TCPTP inhibitor has inhibited TCPTP, experiments such as the following could be performed: measure TCPTP activity in TCPTP immunoprecipitates using p-NPP (para-nitrophenylphosphate) and p-tyr-RCML (p-tyr-reduced, carboxyamidomethylated and maleylated lysozyme) as substrates as described previously (Bukczynska P et al. Biochem J. 2004 Jun. 15; 380(Pt 3): 939-49; Tiganis T et al. J Biol Chem. 1997 Aug. 22; 272(34):21548-57). Alternatively, analysis of known substrates of TCPTP such as Src-family kinase members c-Src and Fyn and transcription factors STAT3 and STAT5 in the hypothalamus for tyrosine-phosphorylation by immunohistochemistry and immuno-blotting can be performed. An analysis of insulin signalling by monitoring for the activation of AKT by immunoblotting or immunohistochemistry could also be used as a surrogate measure for effects of TCPTP inhibition As used herein, a TCPTP inhibitor may be any molecule that inhibits the phosphatase activity of TCPTP or reduced the level of TCPTP in a cell. The inhibitor may be a direct inhibitor of the phosphatase active site, may act allosterically to inhibit phosphatase activity, inhibit interaction of TCPTP with its substrate, or may reduce the level of TCPTP by reducing the transcriptional activity of the TCPTP gene, or reducing the amount of TCPTP mRNA or protein present in the cell.

An example of a direct inhibitor of the phosphatase active site, an inhibitor that acts allosterically to inhibit phosphatase activity, or inhibits interaction of TCPTP with its substrate is a small molecule, for example ethyl-3,4-dephospatin or compound 8 as described herein, peptide, or peptidomimetic.

An example of an inhibitor that may reduce the amount of TCPTP mRNA or protein present in the cell is an inhibitory or interfering RNA, such as antisense RNA, siRNA, microRNA or shRNA. Preferably, the siRNA has the sequence as shown in SEQ ID NO: 1. Preferably, the shRNA has the sequence shown in any one of SEQ ID NO: 2 to 13, or a sequence with at least 50%, 60%, 70%, 80%, 90%, 91%, 92%, 93%, 94%, 95%, 96%, 97%, 98% or 99% identity to any one of SEQ ID NO: 2 to 13 provided the shRNA still retains the ability to reduce TCPTP levels in a cell.

An example of an inhibitor that reduces the transcriptional activity of the TCPTP gene and thereby reduces the amount of TCPTP mRNA, is a glucocorticoid receptor (GR) antagonist. Exemplary GR antagonists are mifepristone (i.e. RU486), C108297, C113176 and RU43044.

A TCPTP inhibitor useful in the present invention is one that completely or partially reduces one or more functions of TCPTP as described herein. Preferably, a TCPTP inhibitor reduces phosphatase activity of TCPTP (such as a small molecule, peptide or peptidomimetic), reduces the transcriptional activity of the TCPTP gene, or reduces the amount of TCPTP mRNA or protein present in the cell. Exemplary small molecules that inhibit TCPTP and that are useful in the present invention are ethyl-3,4-dephospatin, compound 8 (Zhang et al. (2009), JACS, 131, 13072 to 13079) or celastrol (CAS No: 34157-83-0). Other inhibitors that may be useful in the invention include molecules with TCPTP inhibitory activity as described in WO03/073987 A2; WO 03/097621 A1; US 2012/0088720 A1; U.S. Pat. No. 7,393,869; and US 2006/0235061 A1.

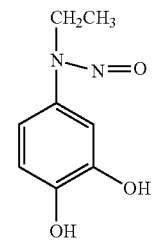 [SMILES: CCN(N=O)c1ccc(O)c(O)c1]

Chemical structure of ethyl-3,4-dephospatin.

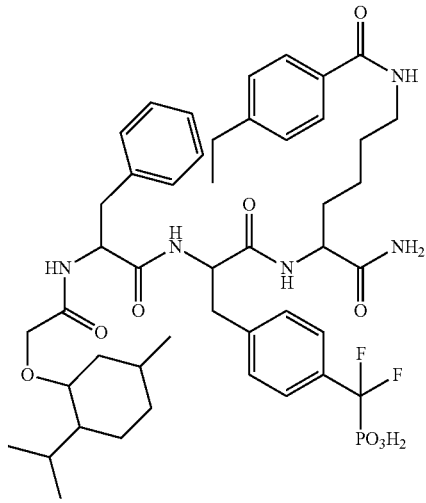

Chemical structure of compound 8.

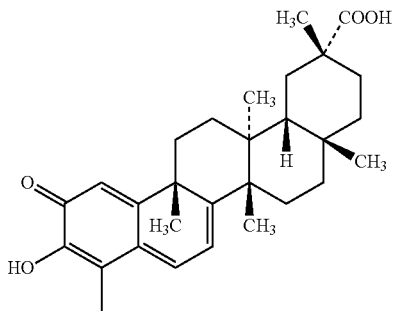

Chemical structure of celastrol.

The expression of TCPTP can be reduced by any means that reduces the level of TCPTP transcription. For example, miRNA, shRNA or siRNA approaches can be used. Exemplary siRNA and shRNA include any one or more of the following sequences or sequences having sufficient homology to reduce expression of TCPTP by targeting the coding sequence of TCPTP or the 3'UTR.

Exemplary siRNA includes:

```
                                SEQ ID NO: 1
('5-AAGAUUGACAGACACCUAAUAUU'3');
and

SEQ ID NO: 14
('5-AAGCCCAUAUGAUCACAGUCG-3');
``` and exemplary shRNA include:

TRCN0000002781, with a target sequence of GATGACCAAGAGATGCTGTTT (SEQ ID NO: 15) beginning at position 582 of TCPTP sequence from NM_001207013.1 and a hairpin sequence of:

```
                                SEQ ID NO: 2
5'-CCGG-GATGACCAAGAGATGCTGTTT-CTCGAG-

AAACAGCATCTCTTGGTCATC-TTTTT-3';;
```

TRCN0000002782, with a target Sequence of TGCAAGATACAATGGAGGAGA (SEQ ID NO: 16) beginning at position 1273 of TCPTP sequence from NM_001207013.1 and a hairpin sequence of:

```
                                SEQ ID NO: 3
5'-CCGG-TGCAAGATACAATGGAGGAGA-CTCGAG-

TCTCCTCCATTGTATCTTGCA-TTTTT-3';;
```

TRCN0000002783, with a target sequence of GAAGATGTGAAGTCGTATTAT (SEQ ID NO: 17) beginning at position 636 of TCPTP sequence from NM_001207013.1 and a hairpin sequence of:

```
                                SEQ ID NO: 4
5'-CCGG-GAAGATGTGAAGTCGTATTAT-CTCGAG-

ATAATACGACTTCACATCTTC-TTTTT-3';;
```

TRCN0000002784, with a target sequence of GTGCAGTAGAATAGACATCAA (SEQ ID NO: 18) beginning at position 1542 of TCPTP sequence from NM_002828.3 and a hairpin sequence of:

```
                                SEQ ID NO: 5
5'-CCGG-GTGCAGTAGAATAGACATCAA-CTCGAG-

TTGATGTCTATTCTACTGCAC-TTTTT-3';;
```

TRCN0000002785, with a target sequence of CTCACTTTCATTATACTACCT (SEQ ID NO: 19) beginning at position 781 of TCPTP sequence from NM_001207013.1 and a hairpin sequence of:

```
                                SEQ ID NO: 6
5'-CCGG-CTCACTTTCATTATACTACCT-CTCGAG-

AGGTAGTATAATGAAAGTGAG-TTTTT-3';;
```

TRCN0000314692, with a target sequence of ATTCTCATACATGGCTATAAT (SEQ ID NO: 20) beginning at position 1061 of TCPTP sequence from NM_001207013.1 and a hairpin sequence of:

```
                                SEQ ID NO: 7
5'-CCGG-ATTCTCATACATGGCTATAAT-CTCGAG-

ATTATAGCCATGTATGAGAAT-TTTTTG-3';;
```

TRCN0000314609, with a target sequence of AGAAGATGTGAAGTCGTATTA (SEQ ID NO: 21) beginning at position 635 of TCPTP sequence from NM_001207013.1 and a hairpin sequence of:

```
                                SEQ ID NO: 8
5'-CCGG-AGAAGATGTGAAGTCGTATTA-CTCGAG-

TAATACGACTTCACATCTTCT-TTTTTG-3';;
```

TRCN0000279329, with a target sequence of ATATGATCACAGTCGTGTTAA (SEQ ID NO: 22) beginning at position 270 of TCPTP sequence from NM_001127177.1 and a hairpin sequence of:

```
                                SEQ ID NO: 9
5'-CCGG-ATATGATCACAGTCGTGTTAA-CTCGAG-

TTAACACGACTGTGATCATAT-TTTTTG-3';;
```

TRCN0000314612, with a target sequence of GTGGAGAAAGAATCGGTTAAA (SEQ ID NO: 23) beginning at position 540 of TCPTP sequence from NM_001207013.1 and a hairpin sequence of:

```
                                SEQ ID NO: 10
5'-CCGG-GTGGAGAAAGAATCGGTTAAA-CTCGAG-

TTTAACCGATTCTTTCTCCAC-TTTTTG-3';
```

TRCN0000314693, with a target sequence of TATGATCACAGTCGTGTTAAA (SEQ ID NO: 24) beginning at position 354 of TCPTP sequence from NM_001207013.1 and a hairpin sequence of:

```
                                SEQ ID NO: 11
5'-CCGG-TATGATCACAGTCGTGTTAAA-CTCGAG-

TTTAACACGACTGTGATCATA-TTTTTG-3';
```

TRCN0000029891, with a target sequence of GCCAAGATTGACAGACACCTA (SEQ ID NO: 25) beginning at position 8031 of TCPTP sequence from NM_001127177.1 and a hairpin sequence of:

```
                                         SEQ ID NO: 12
5'-CCGG-GCCAAGATTGACAGACACCTA-CTCGAG-

TAGGTGTCTGTCAATCTTGGC-TTTTT-3';
```

TRCN0000314551, with a target sequence of GTGCAGTAGAATAGACATCAA (SEQ ID NO: 26) beginning at position 1542 of TCPTP sequence from NM_002828.3 and a hairpin sequence of:

```
                                         SEQ ID NO: 13
5'-CCGG-GTGCAGTAGAATAGACATCAA-CTCGAG-

TTGATGTCTATTCTACTGCAC-TTTTTG-3':.
```

Further, the inhibition of TCPTP may also include genome editing to remove or modify all or part of a sequence encoding TCPTP. An exemplary genome editing technique is the CRISPR/Cas9 system (Jinek, M., et al. (2012) Science, 337, 816-821; Cong L., et al. (2013) Science, 339, 819-823; and Qi, L. S., et al. (2013) Cell, 152, 1173-1183).

The term "glucocorticoid receptor" ("GR") refers to a family of intracellular receptors also referred to as the cortisol receptor, which specifically bind to cortisol and/or cortisol analogs. The term includes isoforms of GR, recombinant GR and mutated GR.

The term "glucocorticoid receptor antagonist" refers to any composition or compound which partially or completely inhibits (antagonizes) the binding of a glucocorticoid receptor (GR) agonist, such as cortisol, or cortisol analogs, synthetic or natural, to a GR. A "specific glucocorticoid receptor antagonist" also refers to any composition or compound which inhibits any biological response associated with the binding of a GR to an agonist. By "specific", we intend the drug to preferentially bind to the GR rather than the mineralocorticoid receptor (MR) with an affinity at least 100-fold, and frequently 1000-fold.

The term "mifepristone" refers to a family of compositions also referred to as RU486, or RU38.486, or 17-beta-hydroxy-11-beta-(4-dimethyl-aminophenyl)-17-alpha(1-propynyl)-estra-4,9-dien-3-one), or 11-beta-(4-dimethylaminophenyl)-17-beta-hydroxy-17-alpha-(1-propynyl)-estra-4,9-dien-3-one), or analogs thereof, which bind to the GR, typically with high affinity, and inhibit the biological effects initiated/mediated by the binding of any cortisol or cortisol analogue to a GR receptor. Chemical names for RU-486 vary; for example, RU486 has also been termed: 11B-[p-(Dimethylamino)phenyl]-17B-hydroxy-17-(1-propynyl)-estra-4,9-dien-3-one; 11B-(4-dimethyl-aminophenyl)-17B-hydroxy-17A-(prop-1-ynyl)-estra-4,9-dien-3-one; 17B-hydroxy-11B-(4-dimethylaminophenyl-1)-17A-(propynyl-1)-estra-4,9-diene-3-one; 17B-hydroxy-11B-(4-dimethylaminophenyl-1)-17A-(propynyl-1)-E; (11B,17B)-11-[4-dimethylamino)-phenyl]-17-hydroxy-17-(1-propynyl)estra-4,9-dien-3-one; and 11B-[4-(N,N-dimethylamino) phenyl]-17A-(prop-1-ynyl)-D-4,9-estradiene-17B-ol-3-one.

PTP1B (also known as PTPN1, PTP1B, protein tyrosine phosphatase, non-receptor type 1, Tyrosine-protein phosphatase non-receptor type 1 or protein-tyrosine phosphatase 1B) is a ubiquitous phosphatase anchored in the endoplasmic reticulum by its C-terminal end and has its catalytic regions exposed to the cytosol. PTP1B is known to dephosphorylate a wide variety of phosphoproteins, such as receptors for the growth factors insulin and epidermal growth factor (EGF), c-Src and beta-catenin. PTP1B also dephosphorylates Janus-activated protein kinase 9JAK) family members including Tyk-2 and JAK-2. PTP1B is reported to be a major negative regulator of the insulin receptor and also of leptin signalling. The PTPN1 gene, which encodes PTP1B, is located in 20q13, a genomic region that is linked to insulin resistance and diabetes in human populations from different geographical origins.

As used herein, a PTP1B inhibitor may be any molecule that inhibits the phosphatase activity of PTP1B or reduced the level of PTP1B in a cell. The inhibitor may be a direct inhibitor of the phosphatase active site, may act allosterically to inhibit phosphatase activity, inhibit interaction of PTP1B with its substrate, or may reduce the level of PTP1B by reducing the transcriptional activity of the PTP1B gene, or reducing the amount of PTP1B mRNA or protein present in the cell.

An example of a direct inhibitor of the phosphatase active site, an inhibitor that acts allosterically to inhibit phosphatase activity, or inhibits interaction of PTP1B with its substrate is a small molecule, peptide, or peptidomimetic.

Examples of small molecule inhibitors of PTP1B include:

Claramine (Sigma, 1545; also referred to as (3β3,6β3)-6-[[3-[[4-[(3-Aminopropyl)amino]butyl]amino]propyl]amino]-cholestan-3-ol), Trodusquemine (MSI-1436, produlestan, Trodulamine, troduscemine, CAS No: 186139-09-3), 3-(3,5-dibromo-4-hydroxy-benzoyl)-2-ethyl-benzofuran-6-sulfonicacid-(4-(thiazol-2-ylsulfamyl)-phenyl)-amide (also referred to as PTP Inhibitor XXII, CAS no: 765317-72-4, Thermofisher Scientific or Calbiochem), 3-Hexadecanoyl-5-hydroxymethyl-tetronic acid calcium salt (RK-682, CAS no: 332131-32-5, Santa Cruz Biotechnology), 2-[(Carboxycarbonyl)amino]-4,5,6,7-tetrahydrothieno[2,3-c]pyridine-3-carboxylic acid hydrochloride (TCS-401, CAS no: 243966-09-8, Santa Cruz Biotechnology), 6-Methyl-2-(oxalylamino)-4,5,6,7-tetrahydrothieno[2,3-c]pyridine-3-carboxylic acid trifluoroacetic acid salt (BML-267, Santa Cruz Biotechnology).

An example of an inhibitor that may reduce the amount of PTP1B mRNA or protein present in the cell is an inhibitory or interfering RNA, such as antisense RNA, siRNA, microRNA or shRNA. Preferably, the siRNA and shRNA target (GenBank NCBI Reference Sequences referred to):

exon 2, preferably starting at position 291 of NM_001278618.1;

exon 3, preferably starting at position 382 of NM_002827.3;

exons 3 and 4, preferably starting at position 466 of NM_001278618.1;

exons 4 and 5, preferably starting at position 557 of NM_002827.3; or exons 2 and 3, preferably starting at position 360 of NM_002827.3.

An example of an shRNA sequence which may reduce the amount of PTP1B mRNA includes:

```
AATTGCACC-AGGAAGATAATGACTATATC  (SEQ ID NO: 48)
```

Exemplary siRNA sequences include:

```
                                            (SEQ ID NO: 49)
Sense:          5'-UAGGUACAGAGACGUCAGUdTdT-3';

(SEQ ID NO: 50)
Antisense:      5'-ACUGACGUCUCUGUACCUAdTdT-3
```

```
Sense,       5'-UAGGUACAGAGACGUCAGUdTdT-3';     (SEQ ID NO: 51)

Antisense,   5'-ACUGACGUCUCUGUACCUAdTdT-3'      (SEQ ID NO: 52)

Sense,       5'-AAATCAACGGAAGAAGGGTCT-3'        (SEQ ID NO: 53)

Sense:       5'-NNUGACCAUAGUCGGAUUAAA-3'        (SEQ ID NO: 54)

Sense:       5'-UUGAUGUAGUUUAAUCCGACUAUGG-3'    (SEQ ID NO: 55)

Anti-sense:  5'-CCAUAGUCGGAUUAAACUACAUCAA-3'    (SEQ ID NO: 56)
```

The skilled person will also appreciate that it is possible to obtain shRNAs or siRNAs, which can be used to reduce PTP1B mRNA, from a number of commercial sources, including from Dharmacon (Madrid, Spain) and Thermofisher (USA). Commercially available shRNA targeted to ptp1b can be purchased, for example, from Open Biosystems (Dharmacon) under catalog no. RHS3979-9571385.

Preferably, the shRNA has a sequence of at least 50%, 60%, 70%, 80%, 90%, 91%, 92%, 93%, 94%, 95%, 96%, 97%, 98% or 99% identity to any sequence described herein provided the shRNA still retains the ability to reduce PTP1B levels in a cell.

Further, the inhibition of PTP1B may also include genome editing to remove or modify all or part of a sequence encoding PTP1B. An exemplary genome editing technique is the CRISPR/Cas9 system (Jinek, M., et al. (2012) Science, 337, 816-821; Cong L., et al. (2013) Science, 339, 819-823; and Qi, L. S., et al. (2013) Cell, 152, 1173-1183). As such, in accordance with the present invention, the PTP1B inhibitor may include a gRNA for use in CRISPR-Cas9 genome editing to inhibit or delete PTP1B activity.

The skilled person will be able to purchase or design gRNAs or crRNAs which target a variety of PTP1B sequences. Examples of such gRNA target sequences include:

```
TTCGAGCAGATCGACAAGTC    (SEQ ID NO: 57)

GATGTAGTTTAATCCGACTA    (SEQ ID NO: 58)

GAGCTGGGCGGCCATTTACC    (SEQ ID NO: 59)

TGACGTCTCTGTACCTATTT    (SEQ ID NO: 60)

CAAAAGTGACCGCATGTGTT    (SEQ ID NO: 61)

GTCTTTCAGTTGACCATAGT.   (SEQ ID NO: 62)
```

The skilled person will be able to determine whether PTP1B mRNA levels have been reduced using standard quantitative PCR methods. For example, the Taqman gene expression assay to determine Ptpn1 expression can be used (Mm00448427_m1, Thermofisher Scientific). The skilled person will understand that such assays can be used to confirm PTP1B mRNA reduction resulting from siRNA or shRNA targeting or alternatively as the result of gRNA-derived CRISPR-Cas9 genome editing to reduce PTP1B activity.

The terms obesity and "being overweight" refers to an excess of fat in proportion to lean body mass. Excess fat accumulation is associated with an increase in size (hypertrophy) as well as number (hyperplasia) of adipose tissue cells. Obesity is variously measured in terms of absolute weight, weight:height ratio, degree of excess body fat, distribution of subcutaneous fat, and societal and aesthetic norms. A common measure of body fat is Body Mass Index (BMI). The BMI refers to the ratio of body weight (expressed in kilograms) to the square of height (expressed in meters). Body mass index may be accurately calculated using the formulas: SI units: BMI=weight (kg)/(height$^2$(m$^2$), or US units: BMI=(weight (lb)*703)/(height$^2$(in$^2$).

In accordance with the U.S. Centers for Disease Control and Prevention (CDC), an overweight adult has a BMI of 25 kg/m$^2$ to 29.9 kg/m$^2$, and an obese adult has a BMI of 30 kg/m$^2$ or greater. A BMI of 40 kg/m$^2$ or greater is indicative of morbid obesity or extreme obesity. For children, the definitions of overweight and obese take into account age and gender effects on body fat.

BMI does not account for the fact that excess adipose can occur selectively in different parts of the body, and development of adipose tissue can be more dangerous to health in some parts of the body rather than in other parts of the body. For example, "central obesity", typically associated with an "apple-shaped" body, results from excess adiposity especially in the abdominal region, including belly fat and visceral fat, and carries higher risk of co-morbidity than "peripheral obesity", which is typically associated with a "pear-shaped" body resulting from excess adiposity especially on the hips. Measurement of waist/hip circumference ratio (WHR) can be used as an indicator of central obesity. A minimum WHR indicative of central obesity has been variously set, and a centrally obese adult typically has a WHR of about 0.85 or greater if female and about 0.9 or greater if male.

In any method of the invention, a reduction in adiposity may be a reduction in central obesity and/or peripheral obesity. In particular, the reduction in adiposity may be a reduction in subcutaneous adiposity. The subcutaneous adiposity may be abdominally located. Alternatively, the reduction in adiposity may be a reduction in visceral adiposity.

Methods of determining whether a subject is overweight or obese that account for the ratio of excess adipose tissue to lean body mass may involve obtaining a body composition of the subject. Body composition can be obtained by measuring the thickness of subcutaneous fat in multiple places on the body, such as the abdominal area, the subscapular region, arms, buttocks and thighs. These measurements are then used to estimate total body fat with a margin of error of approximately four percentage points. Another method is bioelectrical impedance analysis (BIA), which uses the resistance of electrical flow through the body to estimate body fat. Another method is using a large tank of water to measure body buoyancy. Increased body fat will result in greater buoyancy, while greater muscle mass will result in a tendency to sink. Another method is fan-beam dual energy X-ray absorptiometry (DEXA). DEXA allows body composition, particularly total body fat and/or regional fat mass, to be determined non-invasively.

As used herein, 'preventing' or 'prevention' is intended to refer to at least the reduction of likelihood of the risk of (or susceptibility to) acquiring a disease or disorder (i.e., causing at least one of the clinical symptoms of the disease not to develop in a patient that may be exposed to or predisposed to the disease but does not yet experience or display symptoms of the disease). Biological and physiological parameters for identifying such patients are provided herein and are also well known by physicians.

The terms 'treatment' or 'treating' of a subject includes the application or administration of an inhibitor or composition comprising the inhibitor, as described herein, to a subject (or application or administration of inhibitor or composition comprising the inhibitor to a cell or tissue from a subject) with the purpose of delaying, slowing, stabilizing, curing, healing, alleviating, relieving, altering, remedying, less worsening, ameliorating, improving, or affecting the disease or condition, the symptom of the disease or condition, or the risk of (or susceptibility to) the disease or condition. The term "treating" refers to any indication of success in the treatment or amelioration of an injury, pathology or condition, including any objective or subjective parameter such as abatement; remission; lessening of the rate of worsening; lessening severity of the disease; stabilization, diminishing of symptoms or making the injury, pathology or condition more tolerable to the subject; slowing in the rate of degeneration or decline; making the final point of degeneration less debilitating; or improving a subject's physical or mental well-being.

The existence of, improvement in, treatment of or prevention of obesity may be by any clinically or biochemically relevant method (e.g. as described herein) of the subject or a biopsy therefrom. For example, treatment may result in a reduction in excess fat, either a reduction in size (hypertrophy) or number (hyperplasia) of adipose tissue cells. In addition, or alternatively, there may be an improvement in various measurements of absolute weight, weight:height ratio, degree of excess body fat, distribution of subcutaneous fat, and societal and aesthetic norms. Further, there may be a reduction in Body Mass Index (BMI). Treatment may result in a reduction in adiposity throughout the entire individual or at certain sites. There may be a reduction in central obesity and/or peripheral obesity. In particular, the reduction in adiposity may be a reduction in subcutaneous adiposity. The subcutaneous adiposity may be abdominally located. Alternatively, the reduction in adiposity may be a reduction in visceral adiposity In addition, an improvement in exercise capacity or mobility may be observed.

An advantage of an aspect of the present invention is that the reduction in body weight and adiposity does not result in a substantial decrease in lean muscle mass nor a substantial reduction in bone density. In one embodiment, the individual retains substantially more muscle mass as compared to body fat reduction in a subject using an energy restricted diet alone. Typically for an effective therapy for treating a subject having an overweight or obese condition, the treatment should reduce adipose tissue without resulting in substantial deleterious side effects, for example, significant wasting. Wasting is characterized by degradation and loss of a substantial amount of lean body mass (muscle tissue, bones, and/or organs) in addition to adipose tissue. In particular, lean body mass refers to structural and functional elements in cells, body water, muscle, bones, and other body organs such as the heart, liver, and kidneys. Although weight loss may involve loss of fat along with slight loss of muscle or fluid, weight loss for the purposes of maintaining health should aim to lose fat while conserving lean body mass. Wasting involves uncontrollable weight loss.

It will be clearly understood that, although this specification refers specifically to applications in humans, the invention is also useful for veterinary purposes. Thus in all aspects the invention is useful for domestic animals such as cattle, sheep, horses and poultry; for companion animals such as cats and dogs; and for zoo animals. Therefore, the general term "individual" or "individual to be/being treated" is understood to include all animals (such as humans, apes, dogs, cats, horses, and cows).

The term 'administered' means administration of a therapeutically effective dose of the aforementioned inhibitor(s) or composition(s) to an individual. By 'therapeutically effective amount' is meant a dose that produces the effects for which it is administered. The exact dose will depend on the purpose of the treatment, and will be ascertainable by one skilled in the art using known techniques. As is known in the art and described above, adjustments for systemic versus localized delivery, age, body weight, general health, sex, diet, time of administration, drug interaction and the severity of the condition may be necessary, and will be ascertainable with routine experimentation by those skilled in the art.

As used herein, "intranasal administration" or "administered intranasally" refers to delivery to the nose, nasal passageways or nasal cavity by spray, drops, powder, gel, film, inhalant or other means. Intranasal administration may also refer to delivery to the mucosal surfaces of the nose, nasal passageways, nasal cavity. Preferably, the intranasal administration is using a formulation and delivery method that provides for delivery of the inhibitors described herein to the central nervous system of the individual receiving treatment.

Intranasal administration may also include delivery to the pulmonary system (i.e., the lungs and trachea) and interaction with the pulmonary parenchyma and/or entry to the systemic circulation via the lung mucosa.

Absorption of the TCPTP and/or PTP1B inhibitors, once introduced into the nasal cavity, may occur via absorption across the olfactory epithelium, which is found in the upper third of the nasal cavity. The olfactory region is a small area that is typically about 2-10 $cm^2$ in humans, located on the roof of the nasal cavity, and is known to be a site for absorption of drugs into the central nervous system, bypassing the blood-brain barrier. Alternatively, absorption may occur across the nasal respiratory epithelium, which is innervated with trigeminal nerves, in the lower two-thirds of the nasal cavity. Both the olfactory and trigeminal nerves innervate the nasal cavity, providing a direct connection with the CNS.

One exemplary formulation for intranasal delivery of the TCPTP/PTP1B inhibitors is a liquid preparation, preferably an aqueous based preparation, suitable for application as drops into the nasal cavity. For example, nasal drops can be instilled in the nasal cavity by tilting the head back sufficiently and apply the drops into the nares. The drops may also be snorted up the nose.

Alternatively, a liquid preparation may be placed into an appropriate device so that it may be aerosolized for inhalation through the nasal cavity. For example, the therapeutic agent may be placed into a plastic bottle atomizer. In one embodiment, the atomizer is advantageously configured to allow a substantial amount of the spray to be directed to the upper one-third region or portion of the nasal cavity. Alternatively, the spray is administered from the atomizer in such a way as to allow a substantial amount of the spray to be directed to the upper one-third region or portion of the nasal cavity. By "substantial amount of the spray" it is meant herein that at least about 50%, further at least about 70%, but preferably at least about 80% or more of the spray is directed to the upper one-third portion of the nasal cavity.

Additionally, the liquid preparation may be aerosolized and applied via an inhaler, such as a metered-dose inhaler. One example of a preferred device is that disclosed in U.S. Pat. No. 6,715,485 to Djupesland, and which involves a bi-directional delivery concept. In using the device, the end of the device having a sealing nozzle is inserted into one nostril and the patient or subject blows into the mouthpiece. During exhalation, the soft palate closes due to positive pressure thereby separating the nasal and oral cavities. The combination of closed soft palate and sealed nozzle creates an airflow in which drug particles are released entering one nostril, turning 180 degrees through the communication pathway and exiting through the other nostril, thus achieving bi-directional flow.

The inhibitors can also be delivered in the form of a dry powder, as in known in the art. An example of a suitable device is the dry powder nasal delivery device marketed under the name DirectHaler™ nasal, and which is disclosed in PCT publication No. 96/222802. This device also enables closing of the passage between the nasal and oral cavity during dose delivery. Another device for delivery of a dry preparation is the device sold under the trade designation OptiNose™. The phrase 'therapeutically effective amount' generally refers to an amount of one or more inhibitors, or, if a small molecule inhibitor, a pharmaceutically acceptable salt, polymorph or prodrug thereof of the present invention that (i) treats the particular disease, condition, or disorder, (ii) attenuates, ameliorates, or eliminates one or more symptoms of the particular disease, condition, or disorder, or (iii) delays the onset of one or more symptoms of the particular disease, condition, or disorder described herein.

In other embodiments there is provided a kit for use in a therapeutic or prophylactic application mentioned above, the kit including:
  a container holding a therapeutic composition in the form of one or more inhibitors of TCPTP and/or PTP1B as described herein, or a pharmaceutically acceptable salt, polymorph or prodrug thereof or pharmaceutical composition;
  a label or package insert with instructions for use.

In certain embodiments the kit may contain one or more further active principles or ingredients for treatment of obesity.

The kit or "article of manufacture" may comprise a container and a label or package insert on or associated with the container. Suitable containers include, for example, bottles, vials, syringes, blister pack, etc. The containers may be formed from a variety of materials such as glass or plastic. The container holds a therapeutic composition which is effective for treating the condition and may have a sterile access port (for example the container may be an intravenous solution bag or a vial having a stopper pierceable by a hypodermic injection needle). The label or package insert indicates that the therapeutic composition is used for treating the condition of choice. In one embodiment, the label or package insert includes instructions for use and indicates that the therapeutic or prophylactic composition can be used to treat obesity, or any other condition, as described herein.

The kit may comprise (a) a therapeutic or prophylactic composition; and (b) a second container with a second active principle or ingredient contained therein. The kit in this embodiment of the invention may further comprise a package insert indicating the composition and other active principle can be used to treat or prevent a disorder described herein. Alternatively, or additionally, the kit may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain embodiments the therapeutic composition may be provided in the form of a device, disposable or reusable, including a receptacle for holding the therapeutic, prophylactic or pharmaceutical composition. In one embodiment, the device is a syringe. The device may hold 1-2 mL of the therapeutic composition. The therapeutic or prophylactic composition may be provided in the device in a state that is ready for use or in a state requiring mixing or addition of further components.

A pharmaceutical composition may be formulated as inhaled or intranasal formulations, including drops, gels, sprays, mists, or aerosols. The inhaled formulation may be for application to the upper (including the nasal cavity, pharynx and larynx) and/or lower respiratory tract (including trachea, bronchi and lungs). For inhalation formulations, the composition or combination provided herein may be delivered via any inhalation methods known to a person skilled in the art. Such inhalation or intranasal methods and devices include, but are not limited to, metered dose inhalers with propellants such as HFA or propellants that are physiologically and environmentally acceptable. Other suitable devices are breath operated inhalers, multidose dry powder inhalers and aerosol nebulizers. Aerosol formulations for use in the subject method typically include propellants, surfactants and co-solvents and may be filled into conventional aerosol containers that are closed by a suitable metering valve. Different devices and excipients can be used depending on whether the application is to the upper (including the nasal cavity, pharynx and larynx) or lower respiratory tract (including trachea, bronchi and lungs) and can be determined by those skilled in the art. Further, processes for micronisation and nanoparticle formation for the preparation of compounds described herein for use in an inhaler, such as a dry powder inhaler, are also known by those skilled in the art.

Inhalant compositions may comprise liquid or powdered compositions containing the active ingredient that are suitable for nebulization and intrabronchial use, or aerosol compositions administered via an aerosol unit dispensing metered doses. Suitable liquid compositions comprise the active ingredient in an aqueous, pharmaceutically acceptable inhalant solvent such as isotonic saline or bacteriostatic water. The solutions are administered by means of a pump or squeeze-actuated nebulized spray dispenser, or by any other conventional means for causing or enabling the requisite dosage amount of the liquid composition to be inhaled into the patient's nose or lungs. Suitable formulations, wherein the carrier is a liquid, for administration, as for example, a nasal spray or as nasal drops, include aqueous or oily solutions of the active ingredient. Examples of inhalation drug delivery devices are described in Ibrahim et al. Medical Devices: Evidence and Research 2015:8 131-139, are contemplated for use in the present invention.

The means to deliver TCPTP and/or PTP1B inhibitors to the nasal cavity as a powder can be in a form such as microspheres delivered by a nasal insufflator device (a device to blow a gas, powder, or vapor into a cavity of the body) or pressurized aerosol canister. The insufflator produces a finely divided cloud of the dry powder or microspheres. The insufflator may be provided with means to ensure administration of a substantially metered amount of the pharmaceutical composition. The powder or microspheres should be administered in a dry, air-dispensable form. The powder or microspheres may be used directly with an insufflator which is provided with a bottle or container for the powder or microspheres. Alternatively the powder or microspheres may be filled into a capsule such as a gelatin capsule, or other single dose device adapted for nasal administration. The insufflator can have means such as a needle to break open the capsule or other device to provide holes through which jets of the powdery composition can be delivered to the nasal cavity.

Nasal delivery devices can be constructed or modified to dispense a composition comprising the TCPTP and/or PTP1B inhibitors as herein described, wherein the composition is delivered predominantly to the superior one third of the nasal cavity. For example, the angle of dispersion from a delivery device such as a nebulizer or an insufflator can be set so that the pharmaceutical composition is mechanically directed to the superior (upper) third of the nasal cavity (for olfactory absorption), and preferably away from the inferior two-thirds region of the nasal cavity. Alternatively, a pharmaceutical composition as herein described can be delivered to the superior third of the nasal cavity by direct placement of the composition in the nasal cavity, for example, with a gel, an ointment, a nasal tampon, a dropper, or a bioadhesive strip.

Thus in some embodiments of the disclosure, the methods comprise administering to an individual a TCPTP inhibitor and/or a PTP1B inhibitor, or pharmaceutical composition comprising same, wherein administration to the nasal cavity is by a nasal delivery device. The nasal delivery device can include, but is not limited to, unit dose containers, pump sprays, droppers, squeeze bottles, airless and preservative-free sprays, nebulizers, dose inhalers, pressurized dose inhalers, insufflators, and bi-directional devices. The nasal delivery device can be metered to administer an accurate effective dosage amount to the nasal cavity. The nasal delivery device can be for single unit delivery or multiple unit delivery. In some embodiments of the disclosure, the pharmaceutical composition is a gel, film, cream, ointment, impregnated in a nasal tampon or bioadhesive strip whereby the composition is placed in the upper third of the nasal cavity.

It will be understood, that the specific dose level for any particular patient will depend upon a variety of factors including the activity of the specific compound employed, the age, body weight, general health, sex, diet, time of administration, route of administration, and rate of excretion, drug combination (i.e. other drugs being used to treat the patient), and the severity of the particular disorder undergoing therapy.

An exemplary dose range may be 300-1500 mg provided orally. Timing of administration may be 30 minutes to 1 h before a meal. Preferably, a dose is administered prior to the morning and evening meal.

By intranasally administering the compositions by the methods described herein, it is realized that a smaller amount of the composition may be administered compared to systemic administration, including intravenous, oral, intramuscular, intraperitoneal, transdermal, etc. The amount of active agent and/or compositions required to achieve a desired clinical endpoint or therapeutic effect when intranasally administered as described herein may be less compared to systemic administration. Additionally, upon administering the compositions intranasally in the delivery and treatment methods described herein, about 5-fold to about 500-fold, and further about 10-fold to about 100-fold, less systemic exposure may be obtained compared to administration of the same amount systemically.

Furthermore, at least about 5-fold, further at least about 10-fold, preferably at least about 20-fold and further at least about 50-fold less systemic exposure may be obtained compared to administration of the same amount systemically.

It will be understood that the invention disclosed and defined in this specification extends to all alternative combinations of two or more of the individual features mentioned or evident from the text or drawings. All of these different combinations constitute various alternative aspects of the invention.

It will be understood that these examples are intended to demonstrate these and other aspects of the invention and although the examples describe certain embodiments of the invention, it will be understood that the examples do not limit these embodiments to these things. Various changes can be made and equivalents can be substituted and modifications made without departing from the aspects and/or principles of the invention mentioned above. All such changes, equivalents and modifications are intended to be within the scope of the claims set forth herein.

EXAMPLES

Example 1

Mice

Mice were maintained on a 12 h light-dark cycle in a temperature-controlled high barrier facility with free access to food and water. Mice were fed a standard chow (6% fat) or a high-fat diet (23% fat; 45% energy from fat) as indicated. Experiments were approved by the Monash University School of Biomedical Sciences Animal Ethics Committee.

Immunohistochemistry

Immunohistochemistry for p-STAT3, p-AKT in hypothalami was performed as described (Dodd et al., 2015 Cell 160, 88-104; Loh et al., 2011 Cell Metab 14, 684-699) and staining for TCPTP, eGFP, mCherry, and c-Fos performed as described in the Extended Experimental Procedures. For inguinal WAT tissue was formalin-fixed and processed for UCP-1 or TH immune reactivity as described in the Extended Experimental Procedures.

Metabolic Measurements

Insulin and glucose tolerance tests and blood glucose and plasma insulin were measured as described previously (Dodd et al., 2015 as above; Loh et al., 2009 Cell Metab 10, 260-272). Plasma corticosterone was measured by ELISA (Arbor Assays). Ambulatory activity, 24 h food intake and energy expenditure were assessed using a Promethion Metabolic Screening System (Sable Systems International) or a Comprehensive Lab Animal Monitoring System (Columbus Instruments) and body composition assessed by dual-energy X-ray absorptiometry (DEXA) or EchoMRI.

Quantitative PCR

RNA was extracted using TRIzol (Sigma), reverse transcribed and processed for quantitative ($\Delta\Delta$CT) real-time PCR using TaqMan Gene Expression Assays (Applied Biosystems) or SsoAdvanced Universal SYBR Green Supermix (BioRad) as described in Extended Experimental Procedures.

Sympathetic Denervation

Mice received 20 microinjections of vehicle or 6-hydroxydopamine [6-OHDA (Sigma); 1 µl per injection, 9 mg/ml in 0.15 M NaCl containing 1% (w/v) ascorbic acid as described previously (Chao et al., 2011. Cell Metab 13, 573-583) throughout one or both inguinal fat pads.

18F-FDG PET-CT Imaging

18F-FDG (18F-fluoro-2-deoxy-D-glucose) BAT and ing-WAT uptake in overnight fasted Ptpn2$^{fl/fl}$ and AgRP-TC mice was assessed after intravenous administration of 15 MBq of 18F-FDG (Cyclotek, Victoria, Australia) on a docked Inveon PET-CT (positron emission tomography-computed tomography) multimodal system (Siemens, Munich, Germany). 18F-FDG uptake in fed versus food-restricted C57BL/6 mice was assessed 4-6 h post lights off. PET-CT imaging and analysis was conducted as described in Extended Experimental Procedures.

DREADDs

Agrp-Ires-Cre; Npy-hrGFP mice were stereotaxically injected with rAAV-hM4Di-mCherry (Krashes et al., 2011. J Clin Invest 121, 1424-1428) bilaterally into the ARC (coordinates, bregma: anterior-posterior, −1.40 mm; dorsal-ventral, −5.80 mm; lateral, +/−0.20 mm, 200 nl/side). Two weeks after rAAV delivery, mice were unilaterally denervated with 6-OHDA. Mice received daily injections of vehicle or CNO (1.5 mg/kg, IP, Sigma) for 14 days. Body weights and food intake were recorded and ARC targeting determined by post-mortem immunohistochemistry.

Intra-ARC rAAV Injections

Ptpn2$^{fl/fl}$ mice high fat fed for 12 weeks were sterotaxically injected with rAVV expressing Cre recombinase and GFP (rAAV-CMV-Cre-GFP) or GFP alone (rAAV-CMV-GFP; UNC Vector Core) bilaterally into the ARC (coordinates, bregma: anterior-posterior, −1.40 mm; dorsal-ventral, −5.80 mm; lateral, +/−0.20 mm, 100 nl/side). Mice were allowed to recover for 4 weeks post-surgery before experimentation and ARC targeting confirmed by post-mortem GFP immunohistochemistry.

Statistical Analyses

Statistical significance was determined by a one-way or two-way ANOVA with multiple comparisons or repeated measures, or a two-tailed paired Student's t-test as appropriate. $p<0.05$ was considered significant: * $p<0.05$,  $p<0.01$ and * $p<0.001$.

Mice

Aged-matched male mice were used for experiments. To generate Agrp-Ires-Cre; Ptpn2$^{fl/fl}$ (AgRP-TC), Ptpn2$^{fl/fl}$ (C57BL/6) mice (Loh et al., 2011 as above; Wiede et al., 2011. J Clin Invest 121, 4758-477) were bred with Agrp-Ires-Cre (C57BL/6) mice (Tong et al., 2008). To generate AgRP-TC; Npy-GFP mice AgRP-TC mice were mated with Npy-hrGFP (C57BL/6) reporter mice (van den Pol et al., 2009). AgRP-TC mice were mated with Insr1$^{fl/fl}$ mice (Bruning et al., 1998. Mol Cell 2, 559-569) to generate Agrp-Ires-Cre; Ptpn2$^{fl/fl}$; Insr$^{fl/fl+}$ (AgRP-TC-IR) mice. Pomc-eGFP (Cowley et al., 2001. Nature 411, 480-484), Ptpn2$^{−1}$ (Wiede et al., 2012. PlosOne 7, e36703) and Nestin-Cre; Ptpn2$^{fl/fl}$ (Loh et al., 2011. as above) mice have been described previously.

Genotyping

Genotyping was performed by PCR on DNA extracted from tail biopsies using primers previously described for the Agrp-Ires-Cre (Tong et al., 2008. Nature Neurosci 11, 998-1000), Pomc-eGFP (Cowley et al., 2001. as above), Npy-hrGFP (van den Pol et al., 2009. J Neurosci 29, 4622-4639) and Ptpn2$^{fl/fl}$ (Loh et al., 2011. as above; Wiede et al., 2011. as above) alleles. The following primers were used to monitor the recombined Ptpn2$^{fl/fl}$ allele (ΔPtpn2): forward primer 5'GTA ATT ATG CTT TAA GAA CAG C'3, (SEQ ID NO: 27) reverse primer 5'CAG AGT GGT TAA GAG CAC TGG'3 (SEQ ID NO: 28) (Wiede et al., 2011. as above). The following primers were used to monitor the Insr$^{fl/fl}$ allele: 5'GAT GTG CAC CCC ATG TCT G'3, (SEQ ID NO: 29) 5'CTG AAT AGC TGA GAC CAC AG'3 (SEQ ID NO: 30) and 5'GGG TAG GAA ACA GGA TGG'3 (SEQ ID NO: 31)

Feeding

Mice were maintained on a 12 h light-dark cycle from 7 μm (lights off) to 7 am (lights on). Mice were fed a standard chow (6% fat; Barastoc 10-30, Ridley AgriProducts, Australia) or a high-fat diet (23% fat; 45% energy from fat; SF024-027; Specialty Feeds) as indicated. For ad libitum fed mice, measurements were performed at 11 am. For 'fed' mice, food was restricted 4 h prior to lights off to ensure uniform satiety between groups. Mice then received access to food from the start of the dark cycle (7 μm) for 4 h until satiated. For 'food-restricted' mice food was withheld from 6.30 μm onwards. For 'fasted' mice food was removed at lights off for 6 h, 12 h or 24 h. Unless otherwise indicated 'fasted' mice were fasted for 24 h. For 're-fed' mice, food was removed at lights off for 24 h and mice then allowed access to food for 4 h.

Where necessary, experiments were undertaken under reverse light cycle conditions (lights off, 7 am) with mice acclimated for 10-12 days prior to any intervention.

Diurnal feeding in 8-week-old male C57BL/6 mice was assessed using BioDAQ E2 cages (Research Diets, NJ). Mice were singly housed and food intake measured every second over a 24 h time period and grouped into 15 min time bins.

Immunohistochemistry

For brain immunohistochemistry, mice were anaesthetized with 5% isoflurane (Concord Pharmaceuticals Ltd., Essex, UK) in oxygen (1 l/min) and perfused transcardially with heparinized saline [10,000 units/l heparin in 0.9% (w/v) NaCl] followed by 4% (w/v) paraformaldehyde in phosphate buffer (0.1 M, pH 7.4). Brains were post-fixed overnight and then kept for two days in 30% (w/v) sucrose in 0.1 M phosphate buffer to cryoprotect the tissue, before freezing on dry ice. 30 mm sections (120 mm apart) were cut in the coronal plane throughout the entire rostral-caudal extent of the hypothalamus.

For detection of eGFP, mCherry, or TCPTP, sections were subjected to antigen retrieval in citrate acid buffer [10 mM Sodium Citrate, 0.05% (v/v) Tween 20, pH 6.0] at 85° C. for 20 min. Sections were incubated at room temperature for 1 h in blocking buffer [0.1 M phosphate buffer, 0.2% (v/v) Triton X-100, 10% (v/v) normal goat serum (Sigma, St. Louis, Mo.); TCPTP staining blocking buffer contained unlabeled Mouse IgG (1:500, Vector, Burlingame, Calif.)] and then overnight at 4° C. in either chicken anti-eGFP (1/1000; ab13970, Abcam, Cambridge, UK), rabbit anti-dsRed (1:2500, Clontech), or mouse anti-TCPTP (1/500; 6F3 from Medimabs, Quebec, Canada) in blocking buffer. After washing with PBS, sections were incubated with goat anti-chicken Alexa-Fluor 488-, goat anti-mouse Alexa-Fluor 568-, donkey anti-goat Alexa-Fluor 594 conjugated secondary antibodies (1/1000, Life Technologies, VIC, Australia) in blocking buffer for 2 h at room temperature. Sections were mounted with Mowiol 4-88 mounting media and visualized using an Olympus Provis AX70 microscope. Images were captured with an Olympus DP70 digital camera and processed using AnalySIS software (Olympus, Notting Hill, VIC, Australia).

For inguinal WAT immunohistochemistry animals were culled and inguinal fat immediately dissected and fixed in buffered formalin solution for 48 h. Tissues were embedded in paraffin and 4 mm sections of the entire block prepared. Every tenth to fourteenth section of the tissue was used to detect UCP-1 or tyrosine hydroxylase (TH) immunohistochemistry as described previously (Dodd et al., 2015. as above).

Hypothalamic Leptin and Insulin Signaling

Mice were injected intraperitoneally with either vehicle, leptin (0.5-1.0 µg/g; Peprotech, Rehovot, Israel) for p-STAT-3 (Y705) or human insulin (0.85 mU/g, SIGMA, St Louis, Mo.) for p-AKT (Ser-473). Mice were transcardially perfused either 15 min (for p-AKT staining) or 45 min (for p-STAT3 staining) post-injection with a solution of 4% w/v (for p-AKT staining) paraformaldehyde. The brains were post-fixed overnight and then kept for two days in 30% (w/v) sucrose in 0.1 M phosphate buffer to cryoprotect the tissue, before freezing on dry ice. 30 µm sections (120 µm apart) were cut in the coronal plane throughout the entire rostro-caudal extent of the hypothalamus. Sections were pre-treated for 20 min in 0.5% (w/v) NaOH and 0.5% (v/v) $H_2O_2$ in PBS, followed by immersion in 0.3% (w/v) glycine for 10 min. Sections were then placed in 0.03% (w/v) SDS for 10 min and placed in 4% (v/v) normal goat serum plus, 0.4% (v/v) Triton X-100 plus 1% (w/v) BSA (fraction V) for 20 min before incubation for 48 h with a rabbit anti-p-STAT3 (Y705) antibody (1:1000; #9131, Cell Signaling Technology, Beverly, Mass.) or rabbit anti-p-AKT (Ser-473) (1:300; #4060, Cell Signaling Technology, Beverly, Mass.). p-STAT3 and p-AKT-positive cells were visualized using rabbit IgG VECTORSTAIN ABC Elite and DAB (3,30-diaminobenzidine) Peroxidase Substrate Kits (Vector Laboratories, UK). p-STAT3 and p-AKT immunopositive cells were counted throughout the rostral-caudal extent of the hypothalamus using a bright field. In some experiments p-Akt and p-STAT3 was visualized by immunofluorescence following 2 h incubation with goat anti-rabbit Alexa-Fluor 568 at room temperature and visualized using an Olympus Provis AX70 microscope.

Functional c-Fos Immunohistochemistry

For the determination of fed and fasted AgRP c-fos expression 8-10 week old AgRP-TC; Npy-GFP or Ptpn2$^{fl/fl}$; Npy-GFP control mice were transcardially perfused in the 'fed' or 'fasted' state. For the determination of ghrelin-induced c-Fos expression 8-week old AgRP-TC; Npy-GFP or Ptpn2$^{fl/fl}$; Npy-GFP were intraperitoneally administered vehicle or ghrelin (0.3 mg/kg, NeoMPS, Strasbourg, France) in the 'fed' state (11 µm). Upon administration all food was removed from the cage and the mice were transcardially perfused 90 minutes post injection. 30 µm sections (120 µm apart) were cut in the coronal plane throughout the entire rostral-caudal extent of the hypothalamus. Sections were blocked in 10% (v/v) normal goat serum and then incubated overnight (4° C.) with rabbit anti-c-Fos antibody (1:4000, sc-52, Santa Cruz, Calif., USA) in 1% (v/v) blocking buffer. After washing with PBS sections were incubated for 2 h room temperature with goat anti-rabbit Alexa-Fluor 568-conjugated secondary antibody (Life Technologies, VIC, Australia) in 5% (v/v) blocking buffer. Sections were mounted with Mowiol 4-88 mounting media and visualized using an Olympus Provis AX70 microscope. Images were captured with an Olympus DP70 digital camera and processed using AnalySIS software (Olympus, Notting Hill, VIC, Australia).

Cell Culture

Cortex from E14.5 C57BL/6 embryos were harvested in ice cold complete HBSS (Hepes pH 7.4, 2.5 mM, D-Glucose 30 mM, $CaCl_2$) 1 mM, $MgSO_4$ 1 mM, $NaHCO_3$ 4 mM in Hanks Buffered Salt Solution) to remove the meninges. Cortical tissue was dissociated (250 µg/mL trypsin, 10 µg/mL DNase I, 10 mM HEPES, 200 µg/mL EDTA in $Ca^{2+}/Mg^{2+}$-free Hanks Buffered Salt Solution) for 5 min at 37° C. and then quenched with 140 µg/mL soybean trypsin inhibitor in HEPES-buffered MEM. The dissociated tissue was centrifuged (1,000 rpm, 5 min, 4° C.), the supernatant discarded and the tissue mechanically dissociated in 0.2% w/v BSA PBS at 4° C. The cell suspension was filtered with a 40 µm cell strainer and cells pelleted (1,000 rpm, 5 min, 4° C.) and resuspended in serum-free Neurobasal medium (1% v/v B27, 25 mM KCl, 1× GlutaMAX, 3 g/L glucose, penicillin/streptomycin). Cells were cultured on plates coated with 50 µg/ml poly-L-lysine and 20 µg/ml laminin at 37° C. for 12 h and then treated with 200 µM dexamethasone for 48 h and processed for real-time PCR.

Biochemical Analyses

Mouse tissues were dissected and immediately frozen in liquid $N_2$. For mediobasal hypothalamic micro-dissections, brains were snap frozen in liquid $N_2$ then 160 µm sections were cut in the coronal plane throughout the entire rostral-caudal extent of the hypothalamus. After each section was cut, the mediobasal hypothalamus (MBH) was microdissected using microdissection scissors. To obtain sufficient protein for detection, all mediobasal hypothalamic sections from one brain were pooled into one sample, snap frozen in liquid $N_2$ and stored at −80° C. for subsequent processing.

Tissues were mechanically homogenized in 5-20 volumes of ice cold RIPA lysis buffer (50 mM HEPES [pH 7.4], 1% (v/v) Triton X-100, 1% (v/v) sodium deoxycholate, 0.1% (v/v) SDS, 150 mM NaCl, 10% (v/v) glycerol, 1.5 mM $MgCl_2$, 1 mM EGTA, 50 mM NaF, leupeptin (5 mg/ml), pepstatin A (1 mg/ml), 1 mM benzamidine, 2 mM phenylmethylsulfonyl fluoride, 1 mM sodium vanadate) and clarified by centrifugation (100,000×g for 20 min at 4° C.). Tissue lysates were resolved by SDS-PAGE and immunoblotted as described previously (Tiganis et al., 1998). Antibodies used are rabbit α-phospho-IRβ-Y1162/Y1163 (p-IRβ) from Invitrogen, mouse α-Ptpn2 (6F3) from Medimabs, rabbit α-IR-β, mouse α-β-actin from Santa Cruz Biotechnology and α-phospho-HSL-S660 (Watt et al., 2006) and α-phospho-ATGL-S406 (Pagnon et al., 2012) were gifts from Matthew Watt, Monash University. All other antibodies were from Cell Signaling Technology.

Metabolic Measurements

Insulin tolerance tests, glucose tolerance tests and pyruvate tolerance tests were performed on 4 h, 6 h and 6 h fasted conscious mice respectively by injecting human insulin (0.5-0.65 mU insulin/g body weight), D-glucose (2 mg/g body weight), or sodium pyruvate (1-2 mg/g body weight) into the peritoneal cavity and measuring glucose in tail blood immediately before and at 15, 30, 45, 60, 90 and 120 min after injection using a Accu-Check glucometer (Roche, Germany). Plasma insulin and corticosterone levels were determined using a Rat insulin RIA kit (Linco Research, St. Charles, Mo.) and Mouse Corticosterone ELISA (Arbor Assays, MI) according to the manufacturer's instructions. For the determination of fed and fasted blood glucose and corresponding plasma insulin levels, blood was collected by retro-orbital bleeding after a 6 h fast.

Body composition [lean, fat, and bone mineral density (BMD)] was measured by dual energy X-ray absorptiometry (DEXA; Lunar PIXImus2; GE Healthcare) and analyzed using PIXImus2 software; the head region was excluded from analyses. Alternatively, body composition was assessed using EchoMRI (Echo Medical Systems, Houston, Tex.).

Mice were acclimated for 24 h and then monitored for 48 h in an environmentally controlled Comprehensive Lab Animal Monitoring System (CLAMS; Columbus Instruments, Columbus Ohio) or using a Promethion Metabolic Screening System (Sable Systems International, NV) fitted with indirect open circuit calorimetry and food consumption and activity monitors to measure activity, food intake and energy expenditure. When stated, food was restricted at 6:30 μm. Energy expenditure and the respiratory exchange ratio (RER=$VCO_2/VO_2$) were calculated from the gas exchange data. Data was smoothed to plus/minus one data point.

To assess the influence of melanocortin receptor antagonist HS014 on WAT browning, 8-week-old AgRP-TC male mice were ICV administered HS014 (2.4 nmol/animal at 9 am and 7 μm) for 2 consecutive days and inguinal WAT extracted for quantitative real time PCR and immunohistochemistry.

Real-Time PCR

RNA was extracted using TRIzol reagent (Invitrogen, Carlsbad, Calif.) and total RNA quality and quantity determined using a NanoDrop 3300 (Thermo Scientific, Wilmington, Del., USA). mRNA was reverse transcribed using a High-Capacity cDNA Reverse Transcription Kit (Applied Biosystems, Foster City, Calif.) and processed for quantitative real-time PCR either using the TaqMan Universal PCR Master Mix and TaqMan Gene Expression Assays (Applied Biosystems, Foster City, Calif.) or SsoAdvanced Universal SYBR Green Supermix (Bio-Rad, Hercules, Calif.). The following TaqMan gene expression assays were used: Ptpn2 (Mm00501226_m1), Ptpn1 (Mm00448427_m1), Pomc (Mm00475829_g1), Npy (Mm03048253_m1), Agrp (Mm00475829_g1), Gapdh (Mm99999915_g1), Srebf1 (Mm00550338_m1), Fasn (Mm00662319_m1), Pnpla2 (Mm00503040_m1). The following primers were used for SYBR green expression assays: Ucp-1 (f-ACTGCCACACCTCCAGTCATT, (SEQ ID NO: 32) r-CTTTGCCTCACTCAGG ATTGG (SEQ ID NO: 33)), Pgc1-α (f-AGCCGTGACCACTGACAACGAG, (SEQ ID NO: 34) r-GCTGCATGGTTCTGAGTGCTAAG (SEQ ID NO: 35)), Cd137 (f-CGTGCAGAACTCCTGTGATAAC, (SEQ ID NO: 36) r-GTCCACCTATGCTGGAGA AGG (SEQ ID NO: 37)), Cidea (f-TGCTCTTCTGTATCGCCCAGT, (SEQ ID NO: 38) r-GCCGTGTTAAGGAATCTG CTG (SEQ ID NO: 39)), Tbp (f-GAAGCTGCGGTACAATTCCAG, (SEQ ID NO: 40) r-CCCCTTGTACCCTTC ACCAAT (SEQ ID NO: 41)), Tmem26 (f-ACCCTGTCATCCCACAGAG, (SEQ ID NO: 42) r-TGTTTGGTGGAGTCCT AAGGTC (SEQ ID NO: 43)), Prdm16 (f-CAGCACGGTGAAGCCATTC, (SEQ ID NO: 44) r-GCGTGCATCCGCTT GTG (SEQ ID NO: 45)), Gapdh (f-ACCACAGTCCATGCCATCAC, (SEQ ID NO: 46) r-CACCACCCTGTTGCTGTA GCC (SEQ ID NO: 47)). Inguinal white adipose gene comparisons were made using TATA boxbinding protein (Tbp) as the housekeeping gene; all other gene expression was normalized to Gapdh. Relative quantification was achieved using the ΔΔCT method. Reactions were performed using a BioRad CFX 384 touch (Bio-Rad, Hercules, Calif.).

For hypothalamic neuropeptide gene expression (Pomc, Agrp, Npy) 8-10 week old AgRP-TC or $Ptpn2^{fl/fl}$ control mice were fasted for 18 h and injected intraperitoneally with either PBS, 1 μg/g leptin or 0.85 mU/g human insulin. Hypothalami were extracted 2 h post-injection, snap frozen in liquid $N_2$ and processed for quantitative (ΔΔCT) real time PCR.

DREADDs 10-12-week-old AgRP-Ires-Cre: Npy-hrGFP mice were sterotaxically injected with rAAV-hSyn-DIO-hM4D(Gi)-mCherry [rAAV-hM4Di-Cherry (Krashes et al., 2011. as above)] bilaterally into the ARC (coordinates, bregma: anterior-posterior, −1.40 mm; dorsal-ventral, −5.80 mm; lateral, +/−0.20 mm, 200 nl/side) as described previously (Dodd et al., 2015). Two weeks after rAAV delivery, mice were unilaterally denervated with 6-OHDA. One-week post-denervation, mice received daily injections of vehicle or CNO (1.5 mg/kg intraperitoneal, Sigma) for 14 days. Body weights and food intake were recorded. Mice were anaesthetized, ingWAT extracted, and mice perfused with paraformaldehyde for hypothalamic immunohistochemical assessment.

Sympathetic Denervation

Mice received 20 microinjections of 6-hydroxydopamine [6-OHDA (Sigma); 1 ul per injection, 9 mg/ml in 0.15 M NaCl containing 1% (w/v) ascorbic acid] as described previously (Chao et al., 2011; Dodd et al., 2015) throughout the right (unilateral) or both (bilateral) inguinal fat pads. Sham operated fat pads received an equal volume of vehicle. Body weights were monitored and mice were culled and ingWAT and BAT extracted and either formalin-fixed for histological/immunohistochemical assessment or processed for quantitative (ΔΔCt) real time PCR.

Lateral Ventricle Cannulations

Under 2% (v/v) isoflurane in 1 l/min oxygen 8-week-old AgRP-TC, $Ptpn2^{fl/fl}$ or C57BL/6 mice were implanted stereotaxically with guide cannulas into the right lateral ventricle (0.2 mm posterior, 1.0 mm lateral from bregma). The tip of the guide cannula was positioned 1 mm above the injection site (1 mm ventral to the surface of the skull). All mice were allowed 4-5 days recovery before experimental manipulation. Where indicated mice received ad libitum access to food at the start of the dark cycle (7 μm) for 4 h so that mice were satiated. Food was then removed and mice administered ICV vehicle (PBS), uridine 5'-diphosphate (UDP; 2 μl 30 μM, Sigma), ghrelin (0.2 □g, NeoMPS, Strasbourg, France), dexamethasone (2 μl 319 μM, Sigma) or dexamethasone (2 μl 319 μM) plus RU486 (1 μg/animal, Tocris Bioscience, Bristol, UK). Mice received a second injection 2 h later and after a further 2 h mice were perfused with paraformaldehyde for immunohistochemical analysis, or hypothalami extracted for quantitative real time PCR.

To assess the influence of the glucocorticoid antagonist RU486 on the hypothalamic expression of TCPTP, mice were fasted at the start of the dark cycle (7 μm) and 6 h (1 am) later ICV administered vehicle (PBS) or RU486 (0.2 μg or 1 μg in 2 μl). Mice received a second injection 3 h later (4 am) and culled after a further 3 h and hypothalami extracted for quantitative real time PCR.

To assess the influence of the melanocortin system on the AgRP-mediated promotion of WAT browning, 8-week-old AgRP-TC male mice were intracerebroventricularly administered melanocortin receptor antagonist (HS014, 2.4 nmol/animal, twice daily for 2 consecutive days), culled and inguinal WAT extracted for quantitative real time PCR and immunohistochemistry.

ICV Insulin Infusions 15-week-old male AgRP-TC or $Ptpn2^{fl/fl}$ male mice were anesthetized and stereotaxically implanted with sterile osmotic pump connector cannulas (Alzet Brain Infusion Kit 3; Cupertino, Calif.) into the left lateral brain ventricle. The cannulas were connected to Alzet mini-osmotic pump (model 1007D; Alzet, Cupertino, Calif.) to infuse vehicle or insulin (3 mU/day, 0.5 μl/h over a 7 days). By filling 4 cm of the cannula tubing (preceding the osmotic minipump) with sterile water, all mice received a 2-day recovery infusion period.

$^{18}$F-FDG PET-CT Imaging

To assess the $^{18}$F-FDG ($^{18}$F-fluoro-2-deoxy-D-glucose) uptake in the ingWAT and BAT of AgRP-TC and Ptpn2$^{fl/fl}$ mice 8-10 week-old male mice were fasted overnight, intravenously injected with 15 MBq of $^{18}$F-FDG (Cyclotek, Victoria, Australia) in a total volume of 0.1 ml and then immediately anaesthetized with isoflurane. Imaging was performed using a docked Inveon PET-CT (positron emission tomography-computed tomography) multimodal system (Siemens, Munich, Germany).

To assess the $^{18}$F-FDG uptake in the ingWAT and BAT in fed versus food restricted mice, 7-9 week-old C57BL/6 male mice were intravenously injected with 15 MBq of $^{18}$F-FDG 4-6 h post lights off and imaging as described above.

For both experiments, mice were rested for 30 min under anaesthesia and placed onto a heated mouse imaging bed with the hind legs extended and secured to aid exposure of the inguinal fat pad. The CT and PET field of view was 10 cm×10 cm and data was acquired for 10 min/mouse. Both CT and PET data sets were co-registered, attenuation corrected and analysed using the Inveon Research Workplace (IRW) software (Siemens, Munich, Germany). Interscapular BAT was identified and quantified by viewing attenuation corrected PET images and drawing a Region of Interest (ROI) window and then manually contouring the $^{18}$F-FDG-positive volume of interest (VOI) using the IRW contouring tool. The area containing the ingWAT was manually segmented from the CT-image and transferred to the PET image. $^{18}$F-FDG update in ingWAT and BAT was quantified by determining the standard uptake value (SUV)=FDG uptake (kBq/ml) in the VOI/[injected dose (kBq)×animal weight (g)]. For ingWAT the normalised $^{18}$F-FDG uptake was derived from the area (mm3) within the inguinal bed that showed an SUV value greater than 13; this cut off was derived by visually defining the increased area of activity using a contour tool and then normalising that minimum value across all the scans to the injected dose (SUV) and applying that cut off to all mice. The injected dose was decay-corrected to the actual start time of the PET scan.

Telemetric Transponder Implantation and ingWAT Temperature Measurements

Remote biotelemetry was performed using pre-calibrated sensitive transmitters (PDT-4000 G2 E-Mitter sensors, Mini Mitter Company, Starr Life Science, Holliston, Mass.). IngWAT temperature was measured as described previously (Enriori et al., 2011. J Neurosci 31, 12189-12197). E-Mitters were implanted under isoflurane anaesthesia beneath the ingWAT pad and secured in place by suture. Mice were allowed one-week recovery before studies were commenced. Signals emitted by the E-Mitter telemetric transponders were detected by a receiver positioned underneath the animal's home cage and analyzed using VitalView software (Mini Mitter Company, Starr Life Science, Holliston, Mass.). 10-week-old C57BL/6 male mice were allowed access to food (fed) for at least 72 h and the same mice subsequently food-restricted (from 7 μm to 7 am). IngWAT temperature measurements were taken every min and averaged over the indicated times.

Patch Clamp Electrophysiology

AgRP-TC; Npy-GFP (n=14) or Ptpn2$^{fl/fl}$; Npy-GFP (n=20) male mice were anaesthetized using isoflurane and brains removed and cut in cold aCSF (127 mM NaCl, 1.2 mM KH$_2$PO$_4$, 1.9 mM KCL, 26 mM NaHCO$_3$, 3 mM D-glucose, 7 mM mannitol, 2.4 mM CaCl$_2$, 1.3 mM MgCl$_2$) saturated with 95% O$_2$, 5% CO$_2$ (pH 7.4). Coronal hypothalamic 250 μm slices were cut using a vibratome (Leica VT1000S). Slices were then heated for 20 min at 34° C. and incubated at RT prior to recording.

Slices were transferred to the recording chamber and continuously perfused with room temperature aCSF. Npy-GFP neurons in the ARC were identified and visualised using fluorescence and differential interference contrast optics with infrared video microscopy (Axioskop FS2, Zeiss). Patch pipettes were pulled using a horizontal puller (Sutter Instruments Co., Novato, Calif., USA) from thin-walled borosilicate glass (Harvard Apparatus LTD, GC150TF-10). The intracellular pipette solution contained 140 mM K-gluconate, 10 mM HEPES, 1 mM EGTA, 4 mM ATP and 0.3 mM GTP with osmolality and pH adjusted with sucrose and KOH respectively. Recombinant human insulin (#3435, Tocris Bioscience, UK) was diluted to 10 pM-30 nM in aCSF immediately before electrophysiological recordings. Whole-cell recordings were made using an Axopatch 1D amplifier and Clampex 9.2 (Axon Instruments) and all current clamp data was filtered at 2 kHz. All signals were captured on a personal computer running pClamp 9.2 (MDS Analytical Technologies). Membrane responses to insulin were averaged for each concentration. If a cell had already responded to insulin at a lower concentration, the response at higher concentrations represents cumulative data.

Example 2

The experimental data described in this Example and the associated Figures show, amongst other things, the following:

Hypothalamic TCPTP expression is regulated by physiological fluctuations in feeding and fasting. Hypothalamic TCPTP levels are low in a fed state and significantly elevated in a fasted state. We demonstrate that glucocorticoids (GR; corticosterone in mice) which promote hypothalamic TCPTP expression in the fasted state whereas hypothalamic TCPTP is rapidly degraded upon feeding. We don't see such changes in TCPTP in other tissues.

Changes in TCPTP expression functionally regulates insulin signalling within ARC (more specifically in AgRP neurons). In the fasted state when hypothalamic TCPTP levels are high, ARC insulin signalling is attenuated. Conversely in the fed state when TCPTP level are low insulin signalling is increased Feeding and fasting regulates energy expenditure via the promotion of white adipose tissue (WAT) browning. Feeding promote and fasting represses WAR browning. WAT browning refers to the process by which the body promotes the recruitment and activation of beige adipocytes within WAT depots. Unlike white adipocytes, which store energy, beige adipocytes function to expend energy. Promoting WAT browning has been shown to protect against diet-induced obesity and T2D.

Feeding and fasting alterations in AgRP TCPTP expression coordinates WAT browning. In the fed state when AgRP TCPTP levels are low, insulin signalling is elevated and WAT browning is promoted. Conversely, in the fasted state when AgRP TCPTP levels are high, insulin signalling is repressed and WAT browning is attenuated.

In summary, the feed/fast alterations in TCPTP expression coordinates WAT browning and energy expenditure with feeding for the maintenance of energy balance.

Feed-Fast Alterations in Hypothalamic TCPTP

Figure 8:
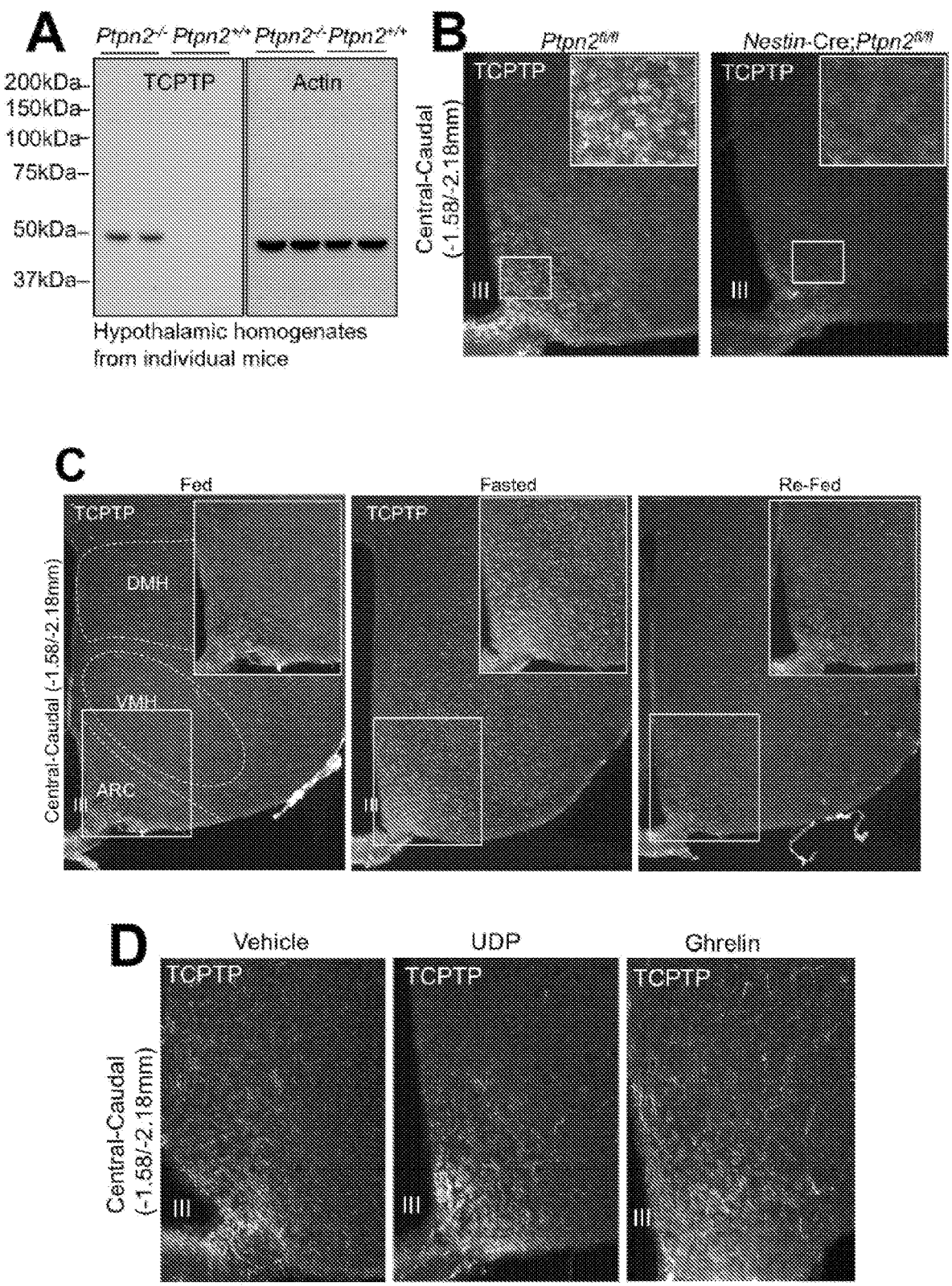
FIG. 8. TCPTP regulates insulin sensitivity in AgRP neurons. a) Hypothalami were extracted from 3-week old Ptpn2$^{-/-}$ male mice (Wiede et al., 2012) and processed for immunoblotting. b) 8-week old Nestin-Cre: Ptpn2$^{fl/fl}$ (Loh et al., 2011) and Ptpn2$^{fl/fl}$ male mice were perfused with paraformaldehyde and brains extracted for central-caudal arcuate nucleus (ARC) TCPTP immunohistochemistry. c) 10-week-old male C57BL/6 mice were fed, fasted (24 h), or re-fed (4 h), and perfused with paraformaldehyde and brains extracted for immunohistochemistry monitoring for TCPTP in the central-caudal ARC, ventromedial hypothalamus (VMH) and dorsomedial hypothalamus (DMH). d) 8-week-old male C57BL/6 fed mice were ICV administered uridine 5'-diphosphate (UDP; 2 µl 30 µM) or ghrelin (0.2 µg) as indicated. Paraformaldehyde-fixed brains were extracted and processed for TCPTP immunohistochemistry. e) 8-week-old fed or 24 h fasted C57BL/6 male mice were administered (intraperitoneal) saline, or leptin (0.5 µg/g body weight, 45 min) and paraformaldehyde-fixed brains extracted for immunohistochemistry monitoring for STAT3 Y705 phosphorylation (p-STAT3) in the central-caudal ARC. f) Tissues from 8-week-old AgRP-TC mice were screened for the presence of the recombined Ptpn2 allele (ΔPtpn2) by PCR (Wiede et al., 2011). g) 8-week-old Ptpn2$^{fl/fl}$; Npy-hrGFP or AgRP-TC; Npy-hrGFP mice were perfused with paraformaldehyde and brains extracted and processed for immunohistochemistry monitoring for TCPTP in GFP-positive AgRP/NPY neurons in the central-caudal ARC. Yellow arrows depict TCPTP positive NPY cells, blue arrows depict TCPTP negative NPY cells. h) Brains from 8-week-old fed or 24 h fasted Ptpn2$^{fl/fl}$; Npy-hrGFP or AgRP-TC; Npy-hrGFP male mice were paraformaldehyde-fixed and processed for ARC p-AKT immunohistochemistry. i-j) 8-week-old Ptpn2$^{fl/fl}$ or AgRP-TC male mice were fasted and injected (intraperitoneal) with saline, insulin (0.85 mU/g) or leptin (1 µg/g body weight) and hypothalami extracted 2 h later for quantitative PCR. k) 8-week-old Ptpn2$^{fl/fl}$; Npy-hrGFP or AgRP-TC; Npy-hrGFP male mice were fasted overnight and administered vehicle PBS or leptin (0.5 µg/g body weight, intraperitoneal) for 45 min and paraformaldehyde-fixed brains extracted and processed for immunofluorescence microscopy monitoring for p-STAT3 and GFP. l) Plasma insulin levels in 8-10-week-old fed or food restricted (just prior to lights out, 6:30 µm) C57BL/6 male mice. Representative and quantified results are shown (means±SEM) for the indicated number of mice.
Figure 8:
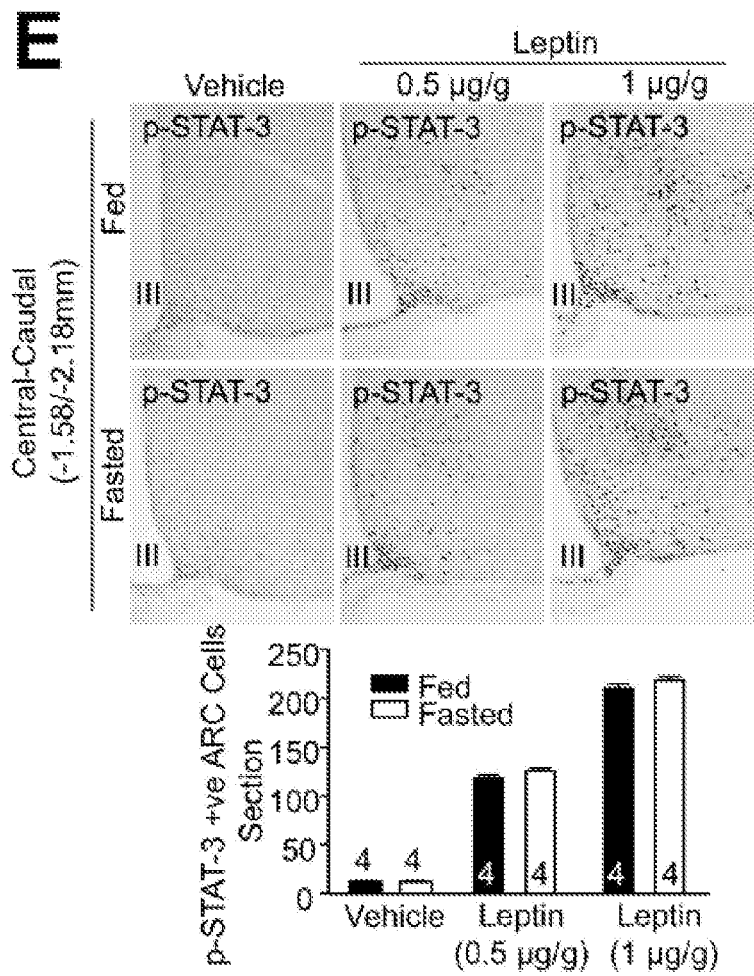
Figure 8:
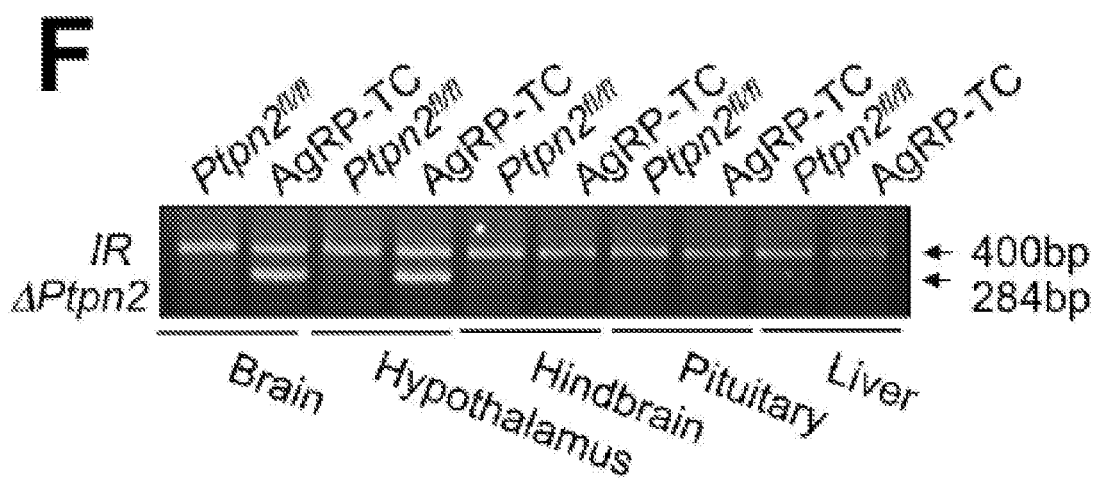
Figure 8:
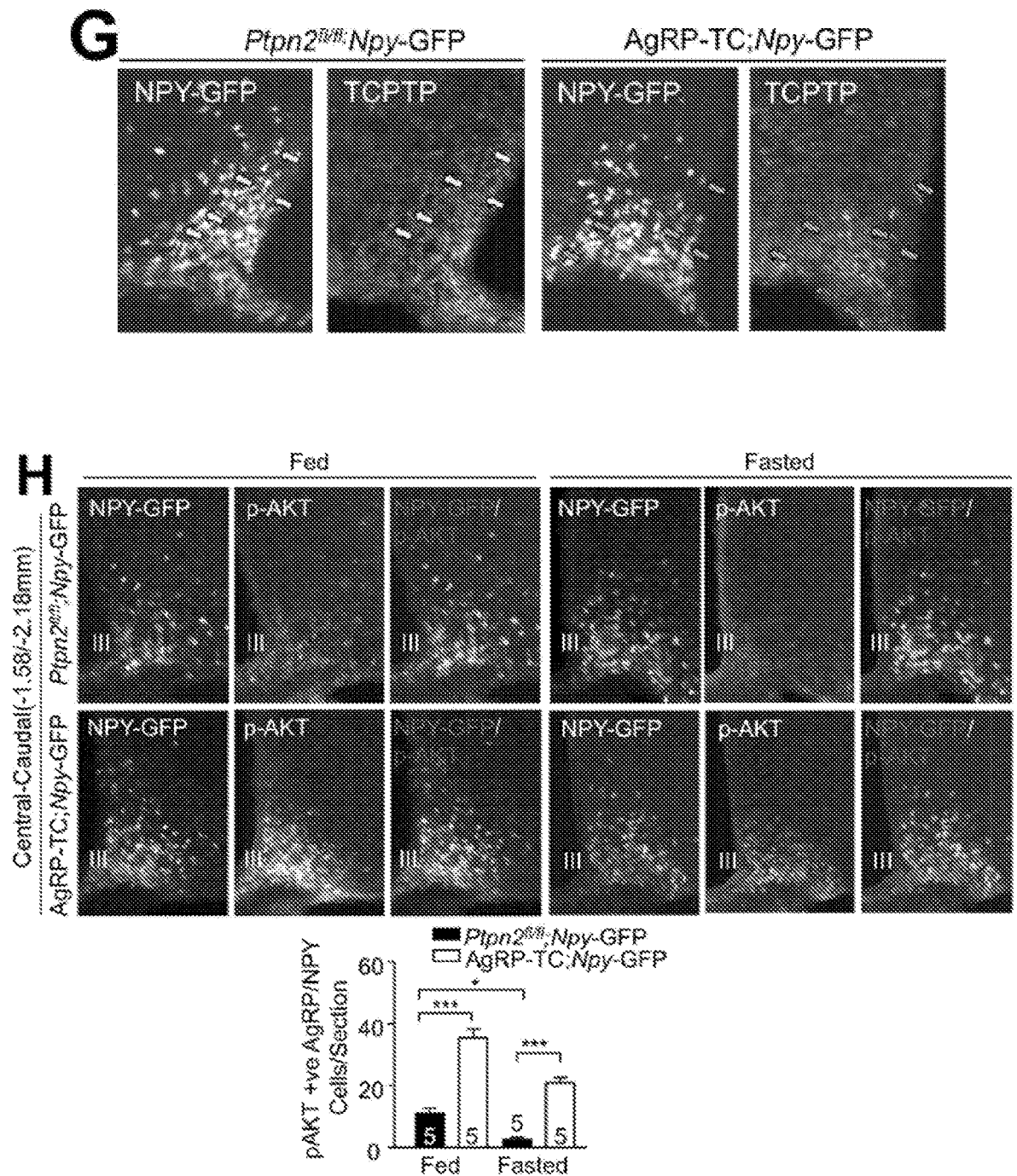
Figure 8:
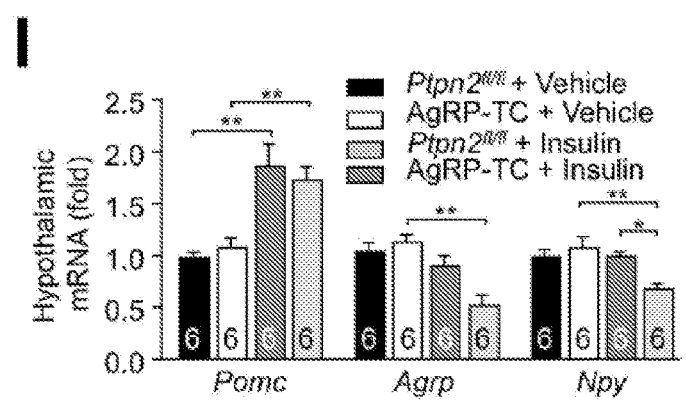
Figure 8:
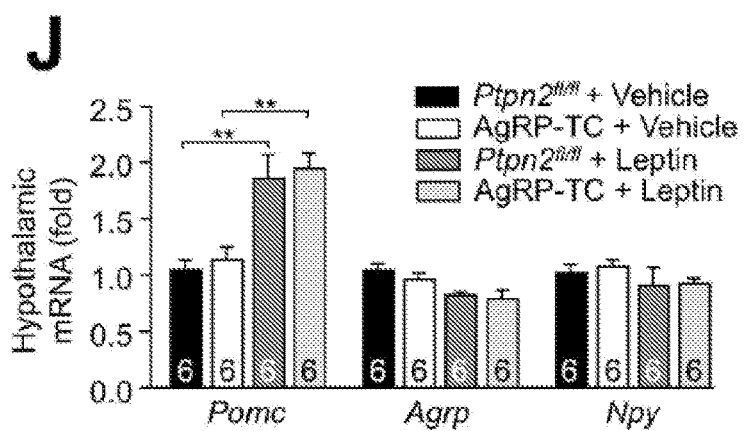
Figure 8:
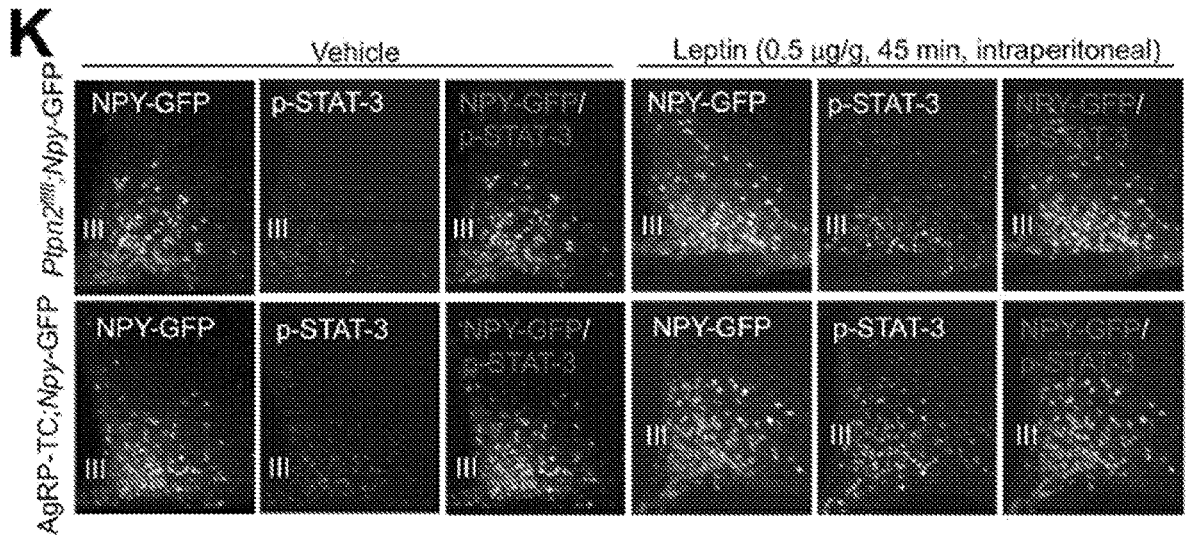
Figure 8:
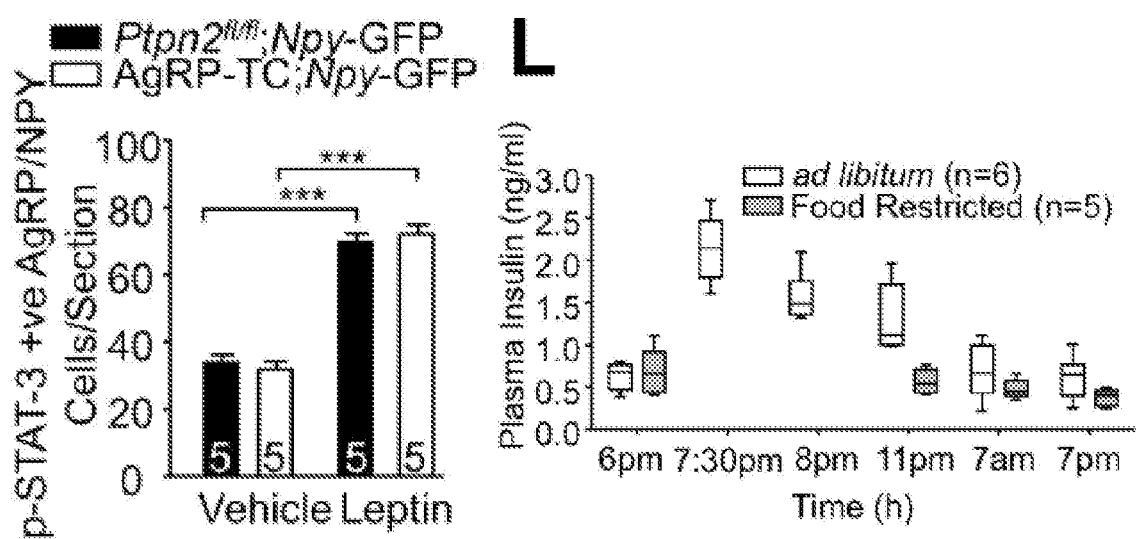

The protein tyrosine phosphatases TCPTP and PTP1B dephosphorylate the insulin receptor (IR) and JAK2 tyrosine kinases to antagonise insulin and leptin signaling respectively in POMC neurons. To determine whether PTP1B and TCPTP may serve to coordinate hypothalamic signaling to varying nutritional cues, hypothalamic PTP1B and TCPTP levels were assessed in mice that were allowed to feed for 4 h after the start of the dark cycle (7 pm) at which point mice were satiated (FIG. 1a-b); these mice are hereon referred to as 'fed' mice. Hypothalamic PTP and TCPTP levels in 'fed' mice were compared to those in mice that were fasted for 24 h from the start of the dark cycle (FIG. 1a-b). TCPTP protein levels, as assessed by immunoblotting mediobasal hypothalamic (MBH) extracts using validated antibodies (FIG. 8a-b), was increased 5.36±0.36 fold in 24 h fasted versus 'fed' mice (FIG. 1c). The increase in TCPTP protein coincided with a 7.4±1.5 fold increase in Ptpn2 (encodes TCPTP) mRNA (FIG. 1d); Ptpn2 mRNA increased after 6 h of fasting and plateaued by 24 h (FIG. 1d). Notably Ptpn2 levels were also elevated in ad libitum fed mice at 11 am as compared to 'fed' mice, so that Ptpn2 levels in ad libitum fed mice at 11 am were not significantly different from those in 24 h fasted mice. By contrast PTP1B protein (FIG. 1c) and Ptpn1 (encodes PTP1B) mRNA (FIG. 1d) were not significantly altered in 24 h fasted versus 'fed' mice but increased by approximately 2.2 fold after prolonged fasting (36 h). Fasting increased TCPTP in different hypothalamic nuclei (as assessed by immunohistochemistry using validated antibodies; FIG. 8a-b) including the arcuate nucleus (ARC), ventromedial hypothalamus (VMH), and albeit variable, also in the dorsomedial hypothalamus (DMH) (FIG. 8c). The increase in TCPTP after 24 h of fasting was accompanied by decreased insulin receptor (IR) β-subunit Y1162/Y1162 (p-IR) and AKT Ser-473 (p-AKT) phosphorylation, but unaltered STAT-3 Y705 (p-STAT-3) phosphorylation, as assessed by immunoblotting MBH extracts (FIG. 1e), consistent with the increase in TCPTP potentially repressing insulin, but not leptin signaling.

To determine whether TCPTP protein may be increased in AgRP/NPY and/or POMC neurons that mediate many of the hypothalamic responses to insulin and leptin, changes in TCPTP in fed and fasted (24 h) Npy-rGFP and Pomc-GFP transgenic mice (reporter mice for AgRP/NPY and POMC neurons respectively) were monitored. TCPTP expression was increased in both AgRP/NPY (FIG. 1f) and POMC (FIG. 1g) neurons in fasted versus fed mice, so that TCPTP coincided with 56±13.2% of rostral and 82±6.2% of caudal AgRP/NPY neurons (FIG. 1f) and 57±2.9% of rostral and 83±8.0% of caudal POMC neurons (FIG. 1g).

The alterations in hypothalamic TCPTP in fed and fasted mice might be a specific response to nutritional signals. To explore this, experiments were performed to determined when the hypothalamic TCPTP levels returned to the pre-fasted state, when 24 h fasted mice were re-fed for 4 h (FIG. 1a). Hypothalamic TCPTP protein, as assessed by immunoblotting MBH homogenates (FIG. 1c), or Ptpn2 expression, as assessed by real time PCR (FIG. 1d), declined to pre-fasted levels in re-fed mice. The decline in TCPTP occurred throughout the ARC (FIG. 8c). The decline in TCPTP was accompanied by increased IR and AKT phosphorylation (FIG. 1e), consistent with the potential enhancement of insulin sensitivity. Since the half-life for TCPTP protein is roughly 16 h (Bukczynska et al., 2004), we reasoned that the decline in TCPTP might reflect increased degradation. The proteasome can influence hypothalamic protein abundance in response to feeding (Sasaki et al., 2010). To test its contribution to TCPTP degradation in re-fed mice, we administered fasted (24 h) mice the proteasome inhibitor MG132 intracerebroventricularly (ICV) and assessed the influence on TCPTP protein in the MBH after 4 h of re-feeding. We found that MG132 completely prevented the feeding-induced degradation of TCPTP without affecting PTP1B levels (FIG. 1h). These results point towards TCPTP being actively regulated by energy intake, with fasting increasing TCPTP expression, and feeding both repressing TCPTP expression and promoting its degradation.

Glucocorticoids Promote Hypothalamic TCPTP Expression

In exploring the molecular mechanism by which fasting promotes hypothalamic Ptpn2 expression, experiments were performed to determine whether ghrelin or uridine-diphosphate (UDP), which are elevated in the fasted and/or obese state and induce feeding by activating ARC AgRP neurons, promote TCPTP expression in the fed state. Fasted mice were re-fed for 4 h to repress Ptpn2 expression, and the mice administered ICV vehicle, ghrelin or UDP twice over the subsequent 4 h and the hypothalami extracted for immunohistochemistry or real time PCR. Neither ghrelin nor UDP overtly altered TCPTP protein levels, as assessed by immunohistochemistry (FIG. 8d), although ghrelin increased Ptpn2 message by ~3 fold (FIG. 1i). It is well established that stress and fasting can lead to elevations in plasma glucocorticoids, which amongst other things can increase Agrp and Npy expression and lead to an increase in body weight and food intake. Corticosterone, which is the principal glucocorticoid in rodents, was elevated in the plasma of fasted mice and reduced within 4 h of re-feeding (FIG. 1j). To determine whether glucocorticoids increase TCPTP expression in the fasted state the synthetic glucocorticoid dexamethasone was administered by ICV to fasted and re-fed (4 h) mice and assessed TCPTP levels by immunohistochemistry and real time PCR after 4 h. Dexamethasone treatment induced TCPTP expression in the ARC (FIG. 1k) and increased Ptpn2 mRNA to a similar extent to that seen after fasting (FIG. 1i, l). Importantly the effects of dexamethasone on Ptpn2 expression could be suppressed by the co-administration of glucocorticoid receptor antagonist RU486 (FIG. 1l). To determine the extent to which the fasting-associated increase in Ptpn2 may be mediated by glucocorticoid signalling mice were fasted for 12 h after the start of the dark cycle and administered RU486 over the last 6 h. The glucocorticoid antagonist RU486 effectively repressed the increased Ptpn2 associated with fasting (FIG. 1m). In keeping with glucocorticoids driving Ptpn2 expression, treatment of human SH-SY5Y neuroblastoma cells (data not shown) or murine cortical neurons with dexamethasone was found to induce Ptpn2 gene expression and increase TCPTP protein (FIG. 1n-o). Taken together these results indicate that the fasting-induced increase in TCPTP is mediated by glucocorticoids.

TCPTP Represses Hypothalamic Insulin Signaling in Fasted Mice

Figure 2:
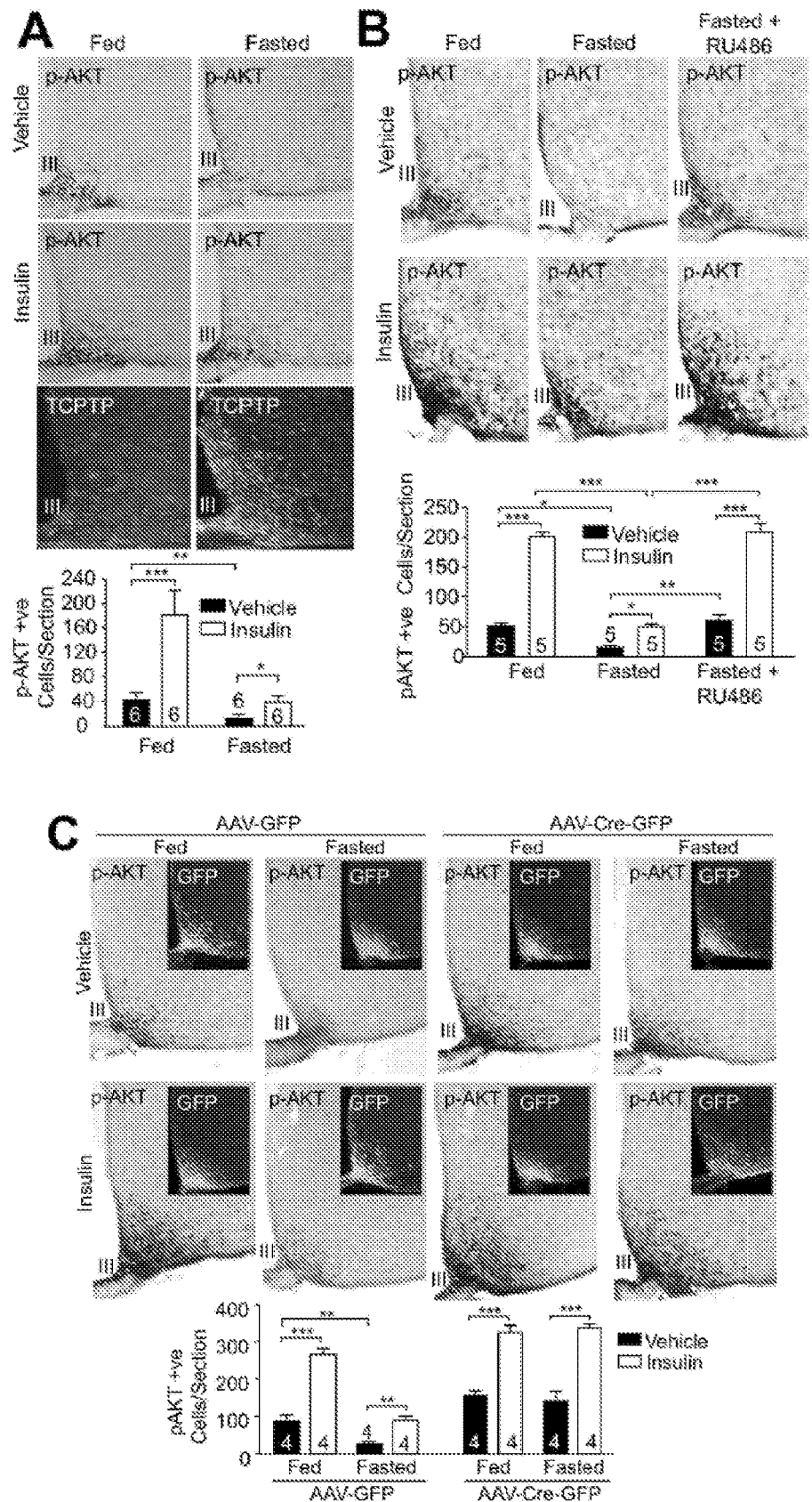
FIG. 2. TCPTP attenuates hypothalamic insulin signaling in fasted mice. a-b) C57BL/6 mice were fed, fasted, or fasted and administered (intracerebroventricularly) vehicle or RU486 (1 µg) for the last 4 h as indicated, injected (intraperitoneal) saline or insulin (0.85 mU/g, 15 min) and brains extracted for ARC immunohistochemistry monitoring for AKT S473 phosphorylation (p-AKT). c) 12-week-old Ptpn2$^{fl/fl}$ male mice were injected bilaterally with rAAV-eGFP or rAAV-Cre-eGFP into the ARC. 4 weeks post rAAV injection mice were administered (intraperitoneal) saline or insulin (0.85 mU/g, 15 min) and paraformaldehyde-fixed brains extracted for ARC p-AKT or GFP (insert) immunohistochemistry. d) Fed or fasted Ptpn2$^{fl/fl}$ or AgRP-TC male mice were administered (intraperitoneal) saline or insulin (0.85 mU/g, 15 min) and paraformaldehyde-fixed brains extracted for ARC p-AKT immunohistochemistry. e) Fed or fasted Ptpn2$^{fl/fl}$ versus AgRP-TC male mice on the Npy-hrGFP reporter background processed for c-Fos ARC immunohistochemistry. f) Whole-cell patch clamp recordings of hypothalamic NPY neurons from Ptpn2$^{fl/fl}$; Npy-hrGFP versus AgRP-TC; Npy-hrGFP male mice in response to insulin. Representative traces and membrane potential changes in response to varied insulin doses are shown (n=2/8, 2/8, 3/9 and 4/8 for AgRP-TC and n=0/6, 0/5, 3/14 and 3/14 for Ptpn2$^{fl/fl}$ at 10 μM, 30 μM, 10 nM and 30 nM insulin respectively). g) 8-10-week-old Ptpn2$^{fl/fl}$ versus AgRP-TC overnight fasted male mice were administered (intraperitoneal) saline or 0.85 mU/g insulin and 90 min later brains fixed and processed for paraventricular hypothalamus (PVN) c-Fos immunoreactivity. h) Fed Ptpn2$^{fl/fl}$; Npy-hrGFP or AgRP-TC; Npy-hrGFP male mice were administered 0.33 mg/kg ghrelin as indicated and brains processed for c-Fos immunohistochemistry. Representative and quantified results (means±SEM) are shown for the indicated number of mice.
Figure 2:
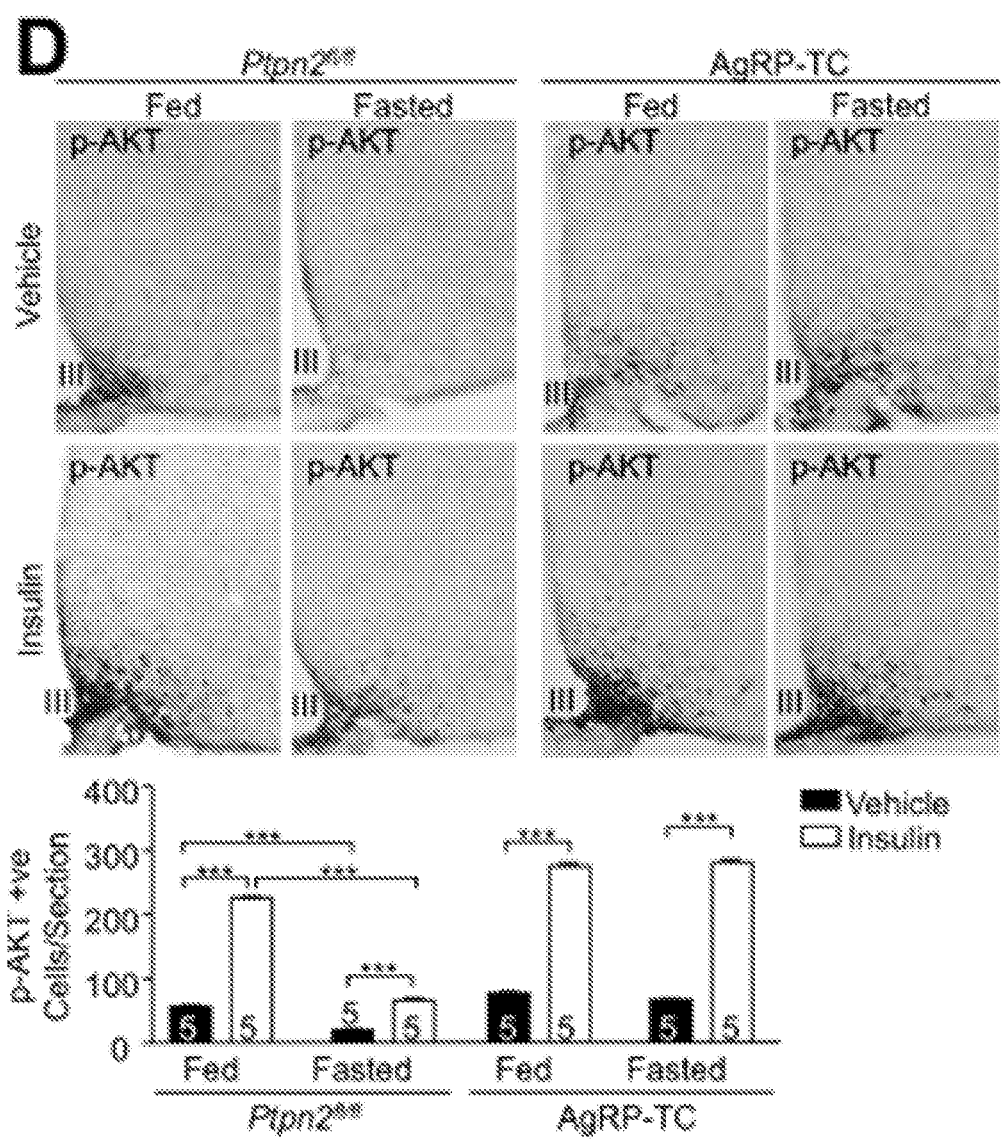
Figure 2:
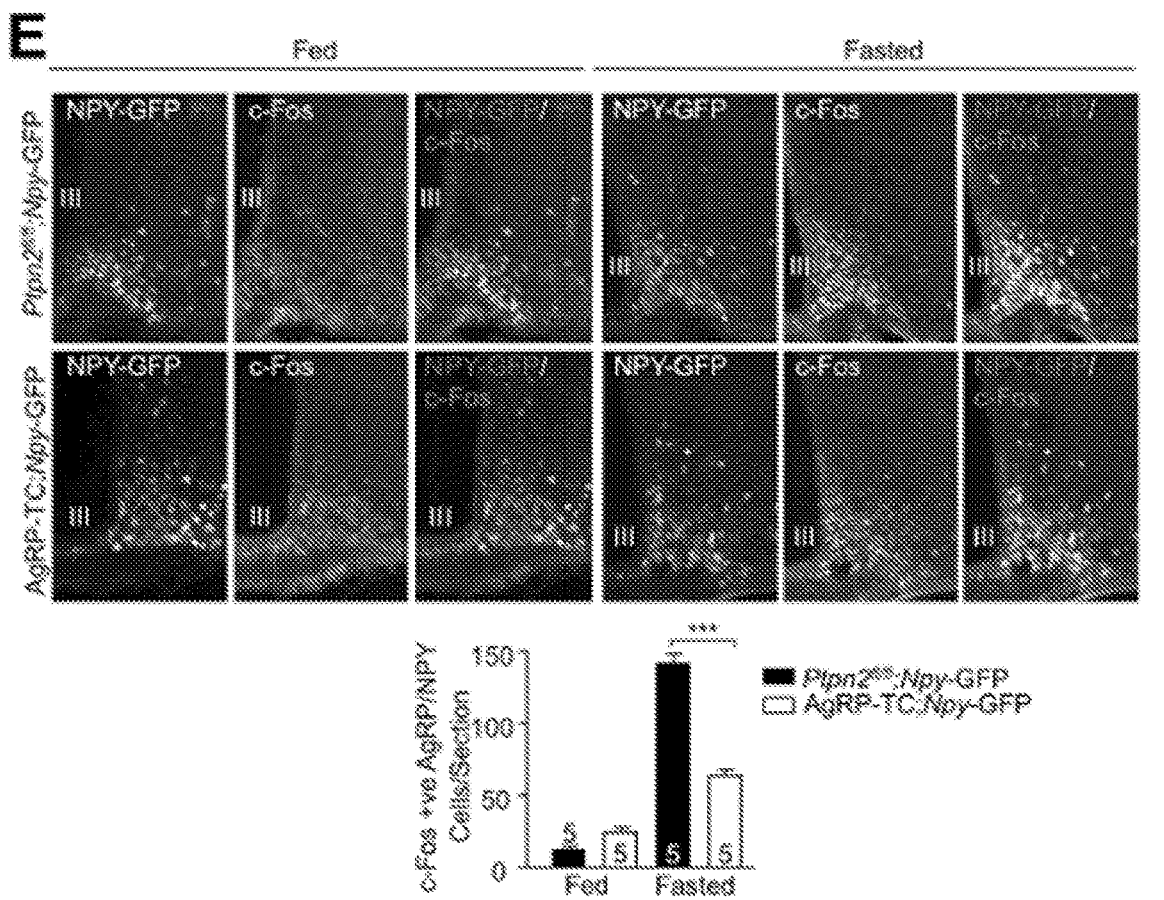
Figure 2:
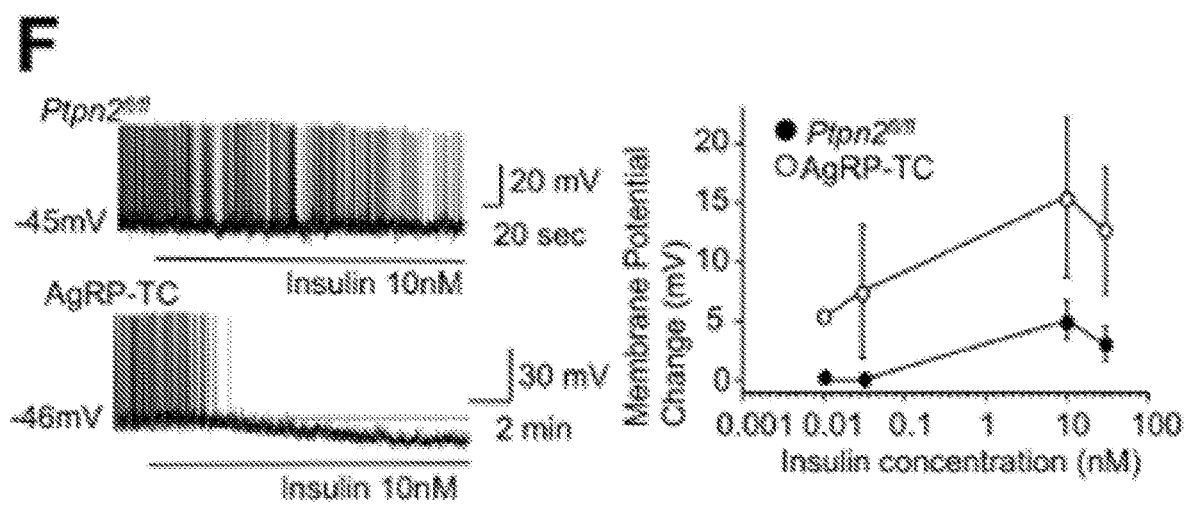
Figure 2:
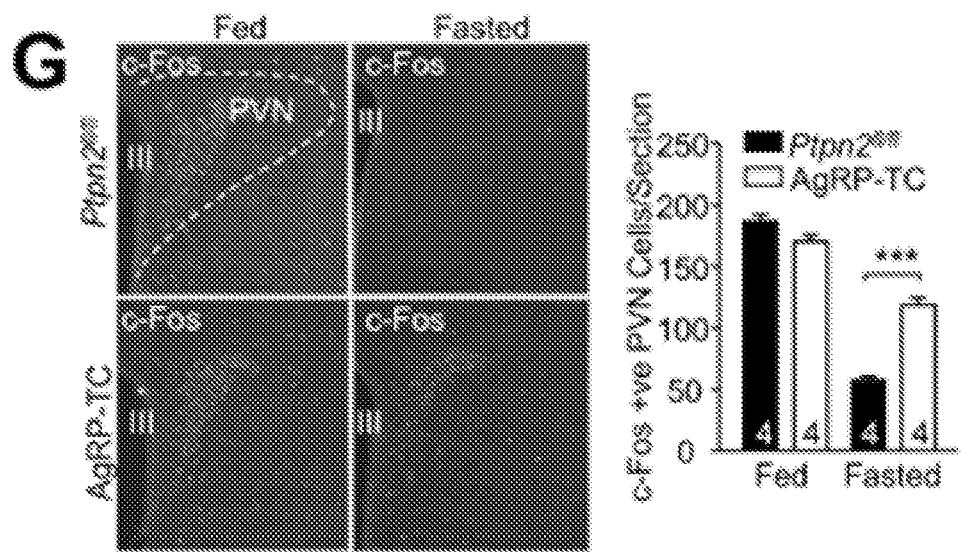
Figure 2:
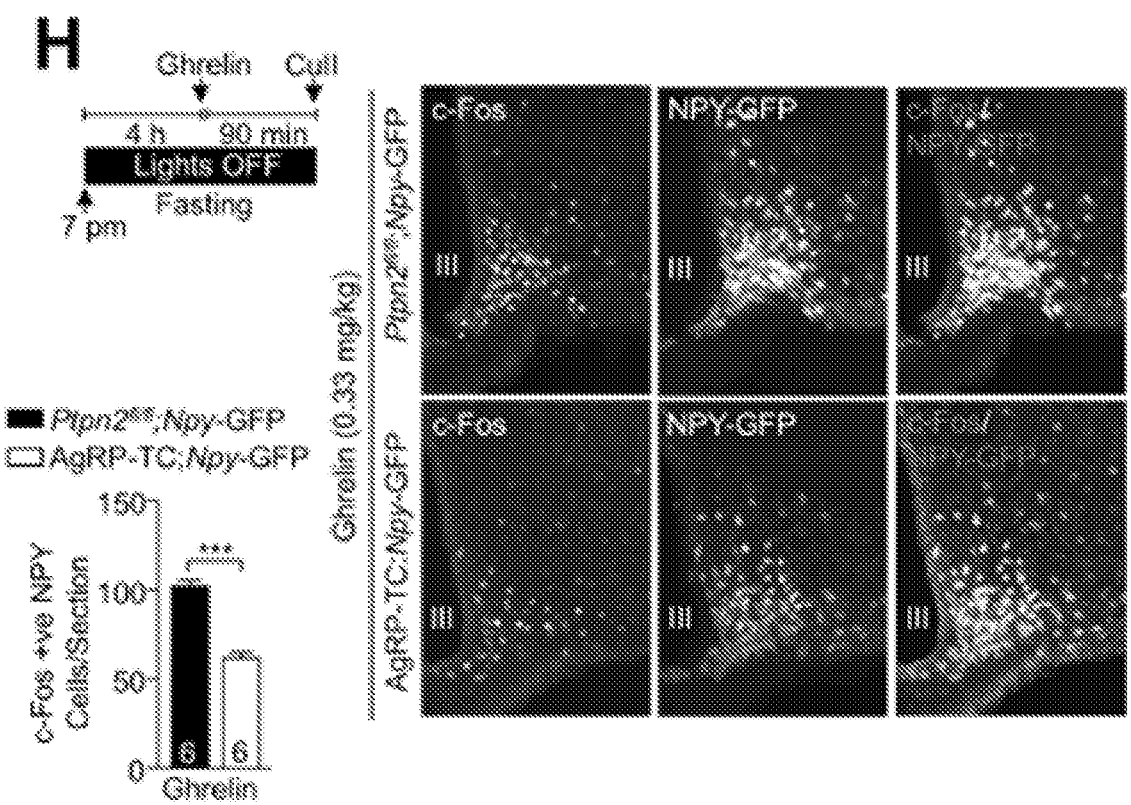

The elevated hypothalamic TCPTP in fasted mice coincided with decreased MBH IR phosphorylation and PI3K/AKT signaling (FIG. 1e). Although this may be due to the decline in insulin levels in fasted mice, it is important to note that TCPTP inhibits insulin signaling by dephosphorylating and inactivating the IR and TCPTP-deficiency or inhibition promotes insulin-induced PI3K/AKT signaling in POMC neurons. Thus, it was reasoned that alterations in TCPTP in response to feeding and fasting may alter the sensitivity of ARC neurons to insulin, so that insulin responses are repressed in the fasted state and enhanced in the fed state. This would provide a molecular switch for coordinating hypothalamic insulin signaling with the nutritional/energy status of the organism. To explore this, basal and insulin-induced ARC PI3K/AKT signaling by immunohistochemistry, staining for p-AKT in fed versus 24 h fasted C57BL6 mice (FIG. 2a) was assessed. In the fed state, basal p-AKT was evident in the ARC (FIG. 2a; data not shown), whereas little or no basal p-AKT staining was evident in fasted mice (FIG. 2a). Importantly, in response to insulin, p-AKT was induced by approximately 3-4-fold in fed mice, but only modestly increased in fasted mice (FIG. 2a). By contrast basal and leptin-induced Y705 phosphorylated STAT3 (p-STAT3) were unaltered by feeding or fasting (FIG. 8e). Therefore, ARC neurons are inherently more sensitive to insulin in the fed state, when TCPTP levels are reduced.

To examine whether increases in TCPTP may be responsible for the fasting-induced repression of ARC insulin signaling, the glucocorticoid receptor (GR) antagonist RU486 was administered by ICV (to suppress the fasting-induced increase in hypothalamic TCPTP). RU486 ameliorated the repression of insulin-induced p-AKT signaling in the ARC in fasted C57BL/6 mice (FIG. 2b). Similarly, the bilateral injection of a recombinant adeno-associated virus (rAAV) expressing GFP and Cre recombinase (rAAV-CMV-Cre-GFP), but not rAAV-CMV-GFP control, into the ARC of Ptpn2$^{fl/fl}$ mice to delete TCPTP, prevented the fasting-induced repression of basal and insulin-induced p-AKT (FIG. 2c); post-mortem analyses for GFP fluorescence confirmed efficient targeting of the ARC (FIG. 2c inserts). Taken together these results indicate that the glucocorticoid-mediated induction of TCPTP in fasted mice represses ARC insulin signaling.

TCPTP Regulates AgRP Neuronal Insulin Sensitivity and Activation

The specific ARC neurons in which fasting-associated increases in TCPTP might suppress insulin signalling were sought to be defined. Although it has previously been reported that TCPTP can inhibit insulin signaling in POMC neurons, we noted that the ARC p-AKT staining in fed mice, which was lost in fasted mice, was proximal to the median eminence (FIG. 2a), where AgRP/NPY neurons predominate (Lemus et al., 2015; Olofsson et al., 2013). Therefore we crossed Ptpn2$^{fl/fl}$ mice with Agrp-Ires-Cre transgenic mice to excise Ptpn2 in AgRP-expressing neurons (Agrp-Ires-Cre; Ptpn2$^{fl/fl}$: AgRP-TC; FIG. 8f-g) and assessed ARC p-AKT in fed and fasted mice with and without insulin stimulation by immunohistochemistry. p-AKT staining was increased by TCPTP-deficiency across the rostral-caudal extent of the ARC (FIG. 2d; data not shown). In particular, TCPTP-deficiency resulted in sustained/elevated basal and insulin-induced p-AKT staining in fasted mice, where little to no staining was otherwise evident in controls (FIG. 2d). The increased basal (in fed and fasted mice) and insulin-induced p-AKT staining (in fasted mice) occurred predominantly in AgRP neurons (marked by the Npy-rGFP reporter) as assessed by immunofluorescence microscopy (FIG. 8h; data not shown). The increased p-AKT staining in fasted AgRP-TC mice was accompanied by reduced c-Fos (a marker of neuronal activation) staining in ARC AgRP/NPY neurons (FIG. 2e). This is consistent with the established role for insulin signaling to inhibit AgRP/NPY neuronal activation (Konner et al., 2007). Indeed, TCPTP-deficiency enhanced the insulin-mediated repression of Agrp and Npy gene expression in fasted mice (FIG. 8i) and enhanced the insulin-induced inhibition of AgRP/NPY neurons, as assessed ex vivo by measuring neuronal firing and membrane potential changes using the whole-cell patch clamp technique (FIG. 2f). Moreover the inhibition of AgRP neurons was accompanied by increased c-Fos staining in the paraventricular nucleus (PVN) of the hypothalamus (FIG. 2g), where AgRP neurons otherwise inhibit the α-melanocyte stimulating hormone (α-MSH)-induced activation of second order neurons. By contrast TCPTP deletion in AgRP neurons did not affect the leptin-induced repression of Agrp expression (FIG. 8j), or leptin-induced p-STAT3 in AgRP/NPY neurons (FIG. 8k). Therefore, alterations in TCPTP in fed versus fasted mice regulate insulin but not leptin signaling to influence the activation of AgRP neurons.

These results indicate that elevated ARC TCPTP in the fasted state attenuates insulin signaling to facilitate AgRP/NPY neuronal activation. Inhibition of insulin signaling may be necessary, as plasma insulin fluctuates diurnally, but is always present, even in 24 h fasted mice (FIG. 8l). To determine whether the increased TCPTP may be necessary for the repression of insulin signaling and the activation of AgRP neurons following a fast, the influence of TCPTP deletion on the activation of AgRP neurons by the hormone ghrelin, whose circulating levels are elevated when the stomach is empty (Muller et al., 2015), was determined. Ptpn2$^{fl/fl}$ and AgRP-TC mice were fed for 4 h after the start of the dark cycle (so that AgRP neuronal activation would be repressed) and then administered ghrelin (ICV 0.3 µg/g) to activate AgRP neurons and brains subsequently extracted for c-fos immunohistochemistry. Although TCPTP levels are reduced in fed mice, we found that the complete ablation of TCPTP reduced the ghrelin-mediated activation of AgRP neurons by 40% (FIG. 2h). These results indicate the fasting-induced increases in TCPTP and the inhibition of insulin signaling might allow for the concomitant activation of AgRP neurons by ghrelin during a fast. Conversely the repression of Ptpn2 expression and coordinated degradation of TCPTP after feeding may facilitate inhibitory insulin signaling in AgRP neurons to influence melanocortin-dependent and -independent responses. Thus, the feed-fast alterations in ARC TCPTP may be critical in coordinating hypothalamic and AgRP neuronal responses to disparate energy states.

Increased WAT Browning in AgRP-TC Mice

Figure 3:
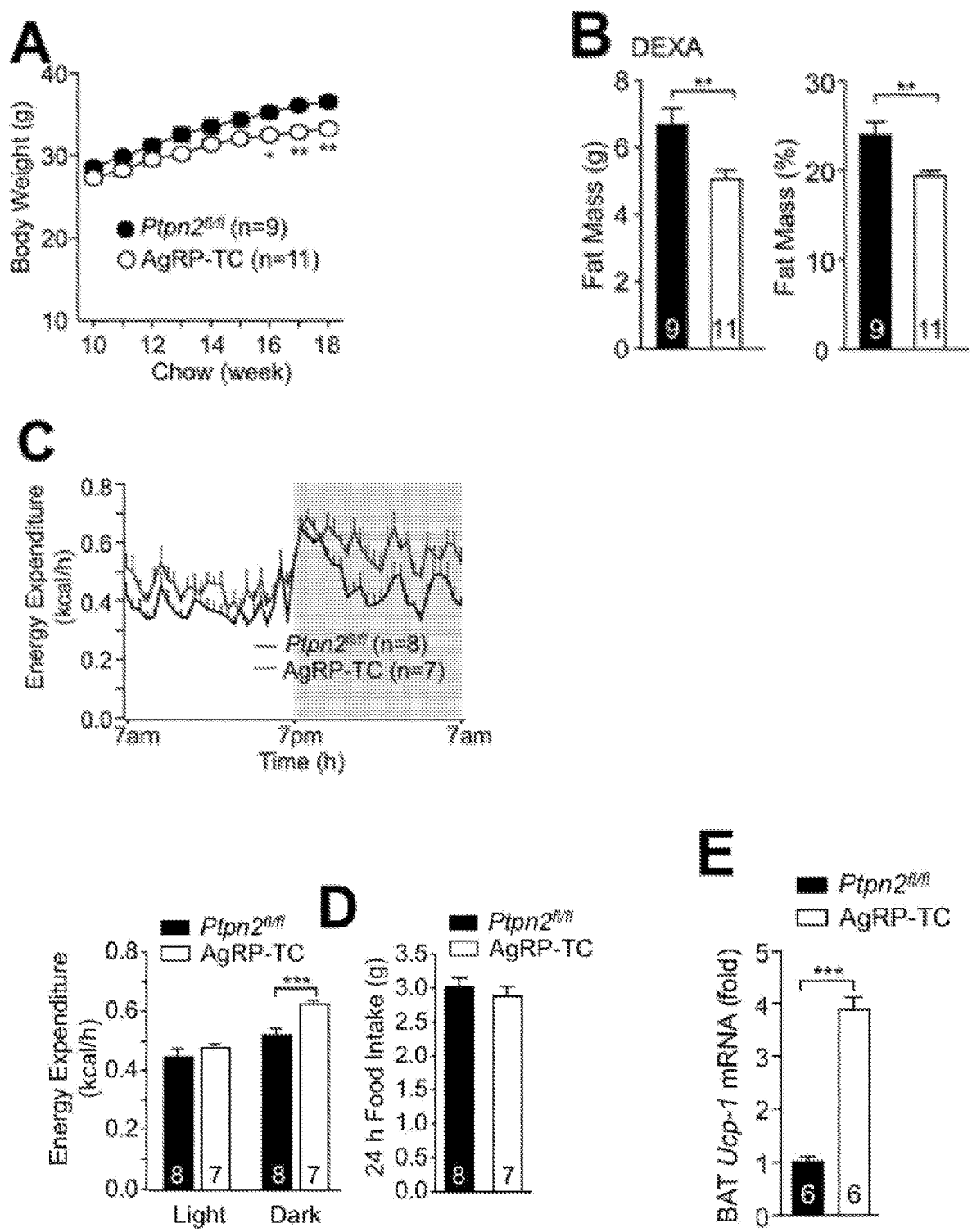
FIG. 3. TCPTP deletion in AgRP neurons or AgRP neuronal inhibition promotes WAT browning and energy expenditure. a) Body weights, b) body composition, c) energy expenditure, d) daily food intake and e) BAT Ucp-1 gene expression in 18-week-old AgRP-TC and Ptpn2$^{fl/fl}$ male mice. Inguinal WAT (ingWAT) was extracted from Ptpn2$^{fl/fl}$ and AgRP-TC male mice and processed for f) histology (hematoxylin and eosin: H&E) and immunohistochemistry, g) quantitative PCR and h) immunoblotting. i) Ptpn2$^{fl/fl}$ and AgRP-TC and Ptpn2$^{fl/fl}$ male mice were subjected to $^{18}$F-fluoro-2-deoxy-D-glucose ($^{18}$F-FDG) positron emission tomography (PET)-computed tomography (CT). Representative images and ingWAT $^{18}$F-FDG standard uptake values (SUV) and normalised uptake per tissue volume are shown. Ptpn2$^{fl/fl}$ and AgRP-TC male mice ingWAT depots were bilaterally sham-operated or denervated with 6-ODHA and j) weekly body weights recorded and k) energy expenditure measured. l) Ptpn2$^{fl/fl}$, AgRP-TC or AgRP-TC-IR male mice were fasted overnight and administered (intraperitoneal) insulin (0.85 mU/g, 15 min) and brains extracted for ARC p-AKT immunohistochemistry. m) Energy expenditure, n) body weights and o) ingWAT weights in 14-week-old Ptpn2$^{fl/fl}$, AgRP-TC or AgRP-TC-IR male mice. p-r) IngWAT and BAT were extracted from Ptpn2$^{fl/fl}$, AgRP-TC or AgRP-TC-IR male mice for gene expression analyses or histology/immunohistochemistry. s-t) 10-week-old Npy-hrGFP; Agrp-Ires-Cre mice were bilaterally injected with rAAV-hM4Di-mCherry into the ARC. Contralateral ingWAT depots were sham operated or denervated with 6-ODHA and two weeks later mice were administered vehicle or clozapine-N-oxide (CNO; 1.5 mg/kg/day, intraperitoneal) for 14 consecutive days prior to s) measuring ingWAT mRNA expression and t) ingWAT histology/immunohistochemistry. Representative and quantified results (means±SEM) are shown for the indicated number of mice. * for significance between Ptpn2$^{fl/fl}$ and AgRP-TC mice; # for significance between treated AgRP-TC or AgRP verses AgRP-TC-IR mice.
Figure 3:
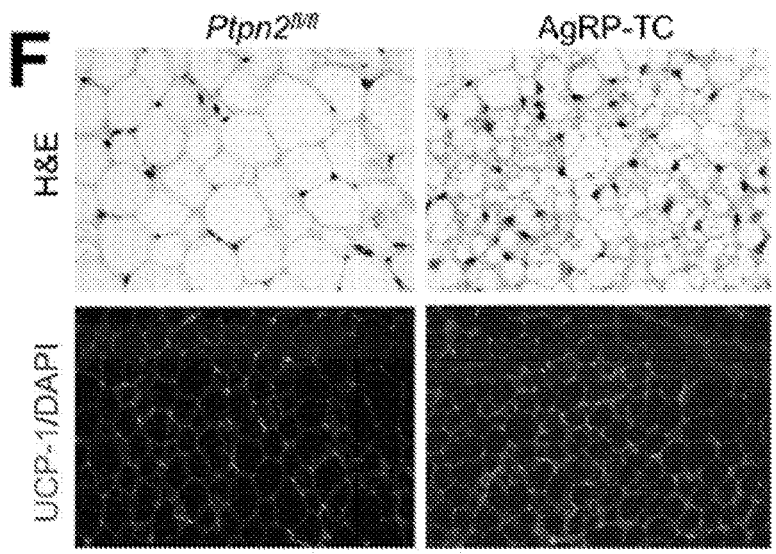
Figure 3:
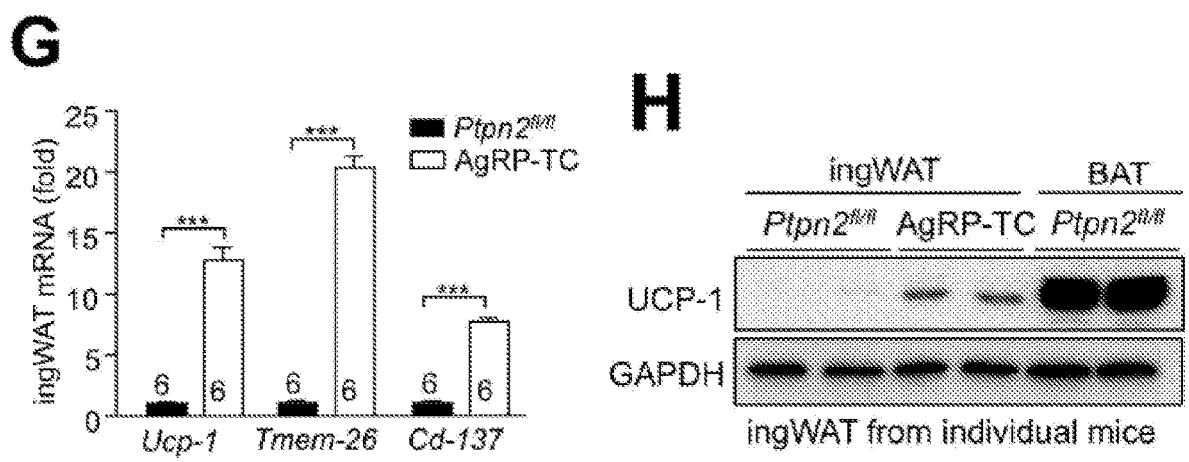
Figure 3:
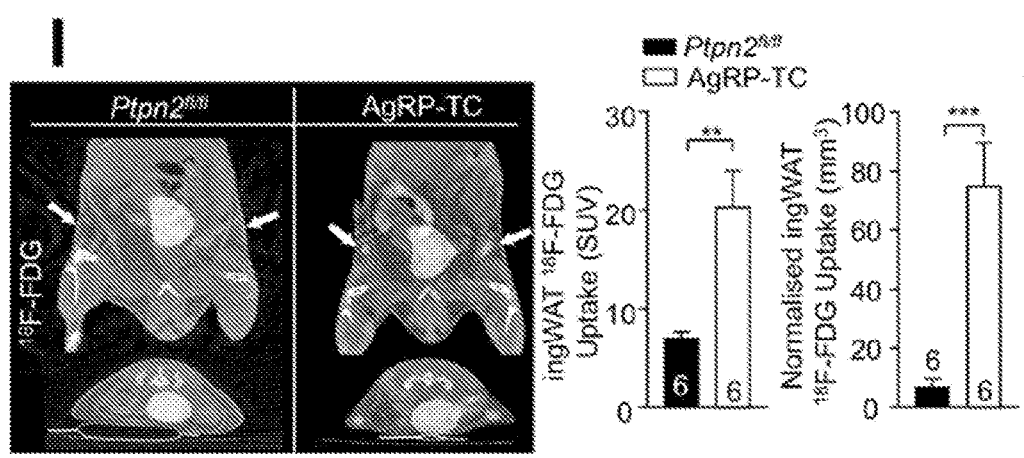
Figure 3:
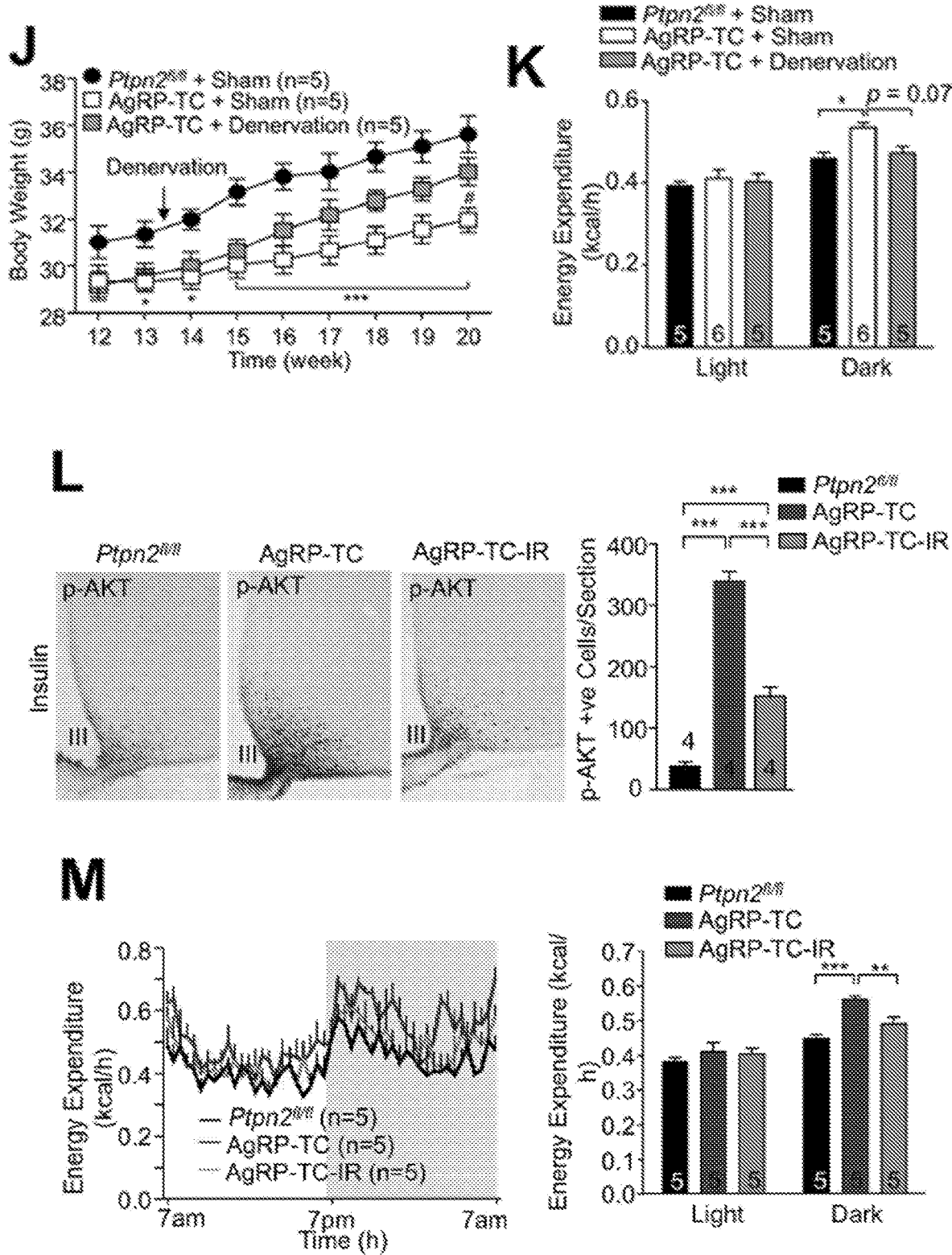
Figure 3:
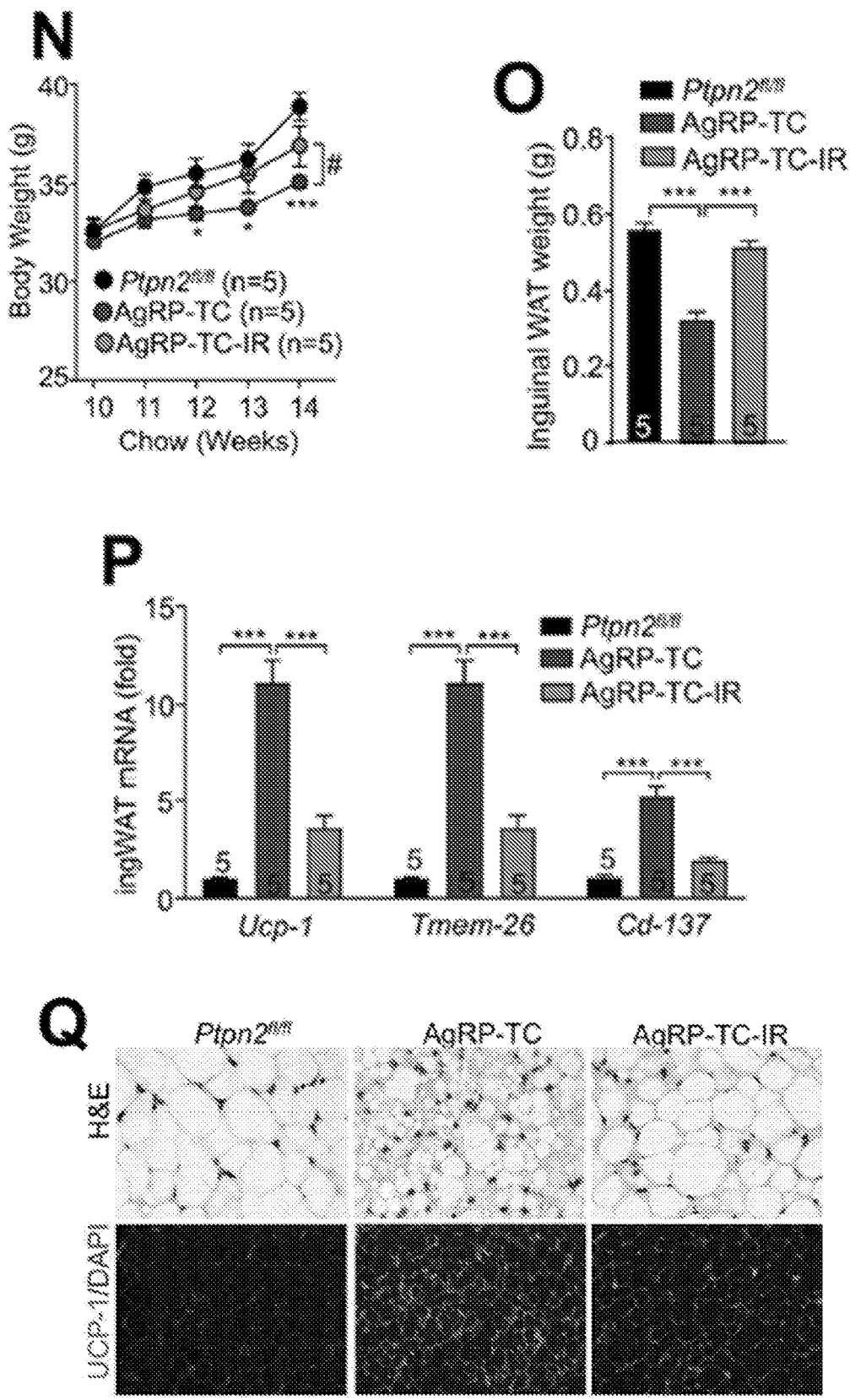
Figure 3:
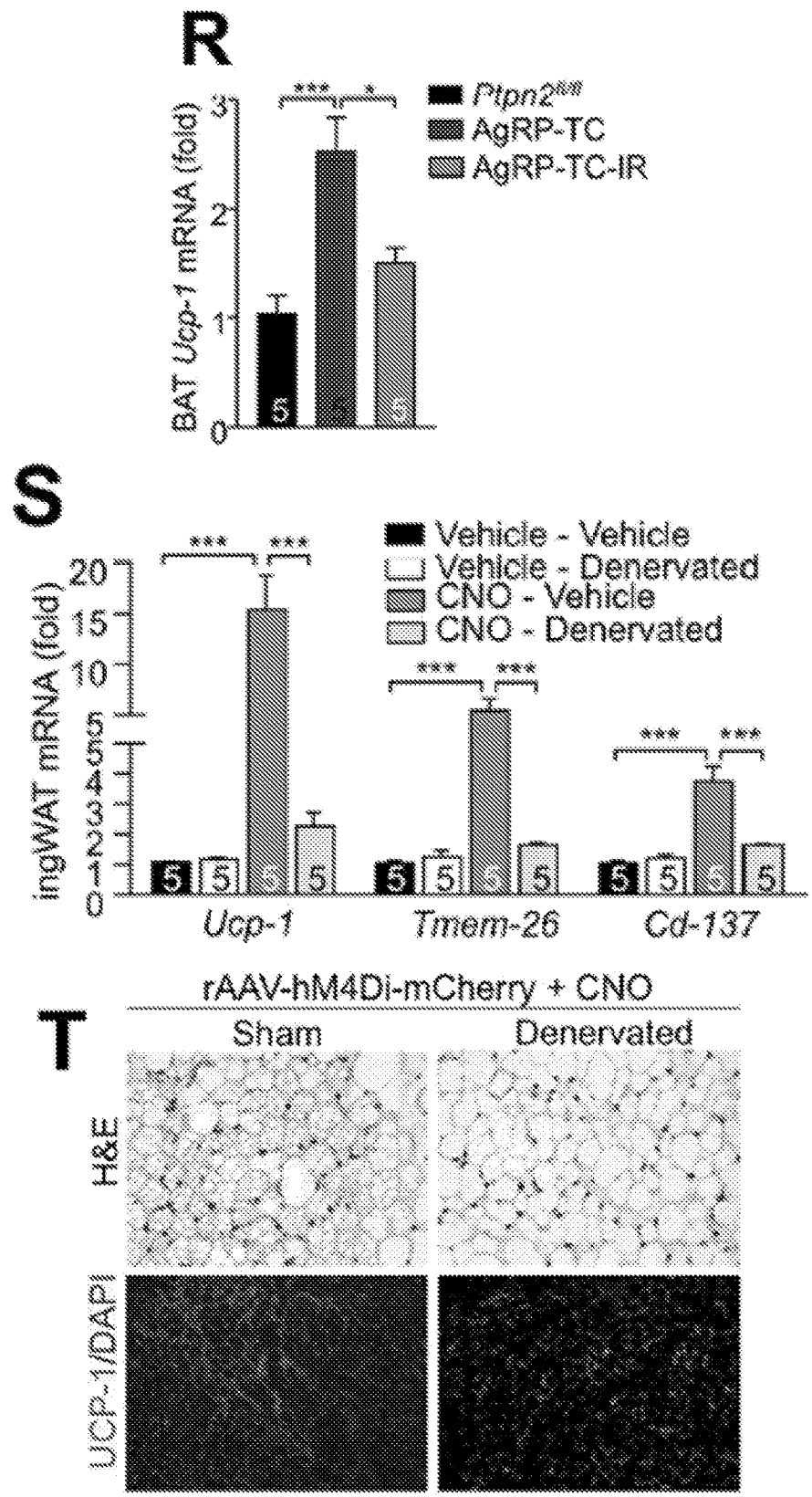
Figure 9:
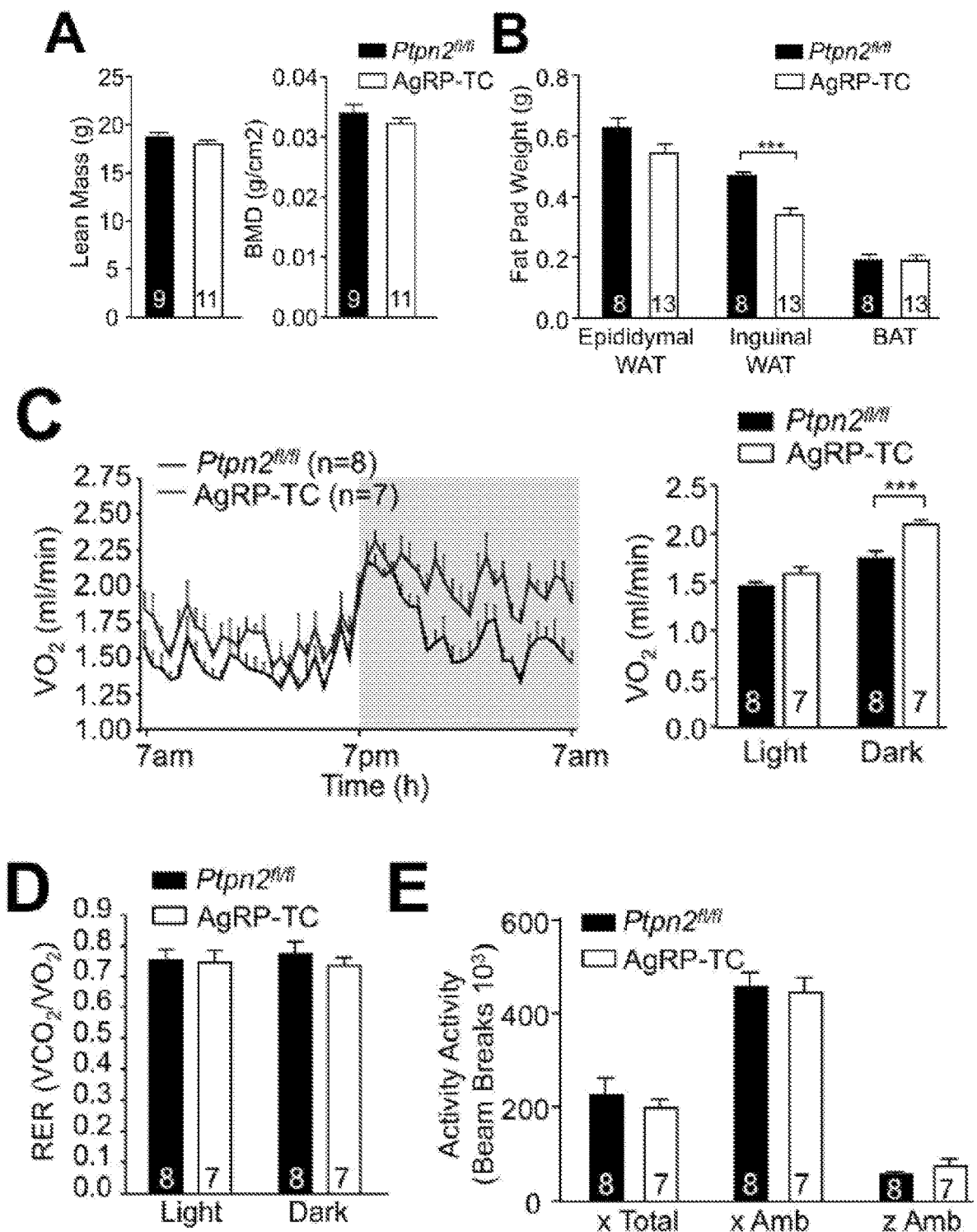
FIG. 9. Insulin increases WAT browning and energy expenditure in AgRP-TC mice. a) Body composition (DEXA), b) fat pad weight, c) oxygen consumption, d) respiratory exchange ratios (RER) and e) ambulatory activity (x and z axes) for Ptpn2$^{fl/fl}$ and AgRP-TC male mice. f) AgRP-TC and Ptpn2$^{fl/fl}$ male mice were subjected to $^{18}$F-fluoro-2-deoxy-D-glucose ($^{18}$F-FDG) positron emission tomography (PET)-computed tomography (CT). Representative images and quantified BAT $^{18}$F-FDG uptake measurements are shown. White arrows highlight BAT depot. g) Inguinal WAT (ingWAT) was extracted from Ptpn2$^{fl/fl}$ and AgRP-TC male mice and processed for analysis of gross morphology. 8-week-old Ptpn2$^{fl/fl}$ or AgRP-TC male mice were fed or fasted (24 h) and ingWAT was extracted for h) immunoblotting and i) gene expression. j) 8-week-old AgRP-TC male mice were ICV administered HS014 (2.4 nmol/animal, twice daily at 9 am and 7 µm for 2 consecutive days) and ingWAT extracted for gene expression. k) Tyrosine hydroxylase (TH) immunohistochemistry in ingWAT from Ptpn2$^{fl/fl}$ or AgRP-TC male mice. l)) 8-week-old AgRP-TC male mice were ICV administered HS014 and ingWAT extracted for immunohistochemistry. Representative and quantified results (means±SEM) are shown for the indicated number of mice.
Figure 9:
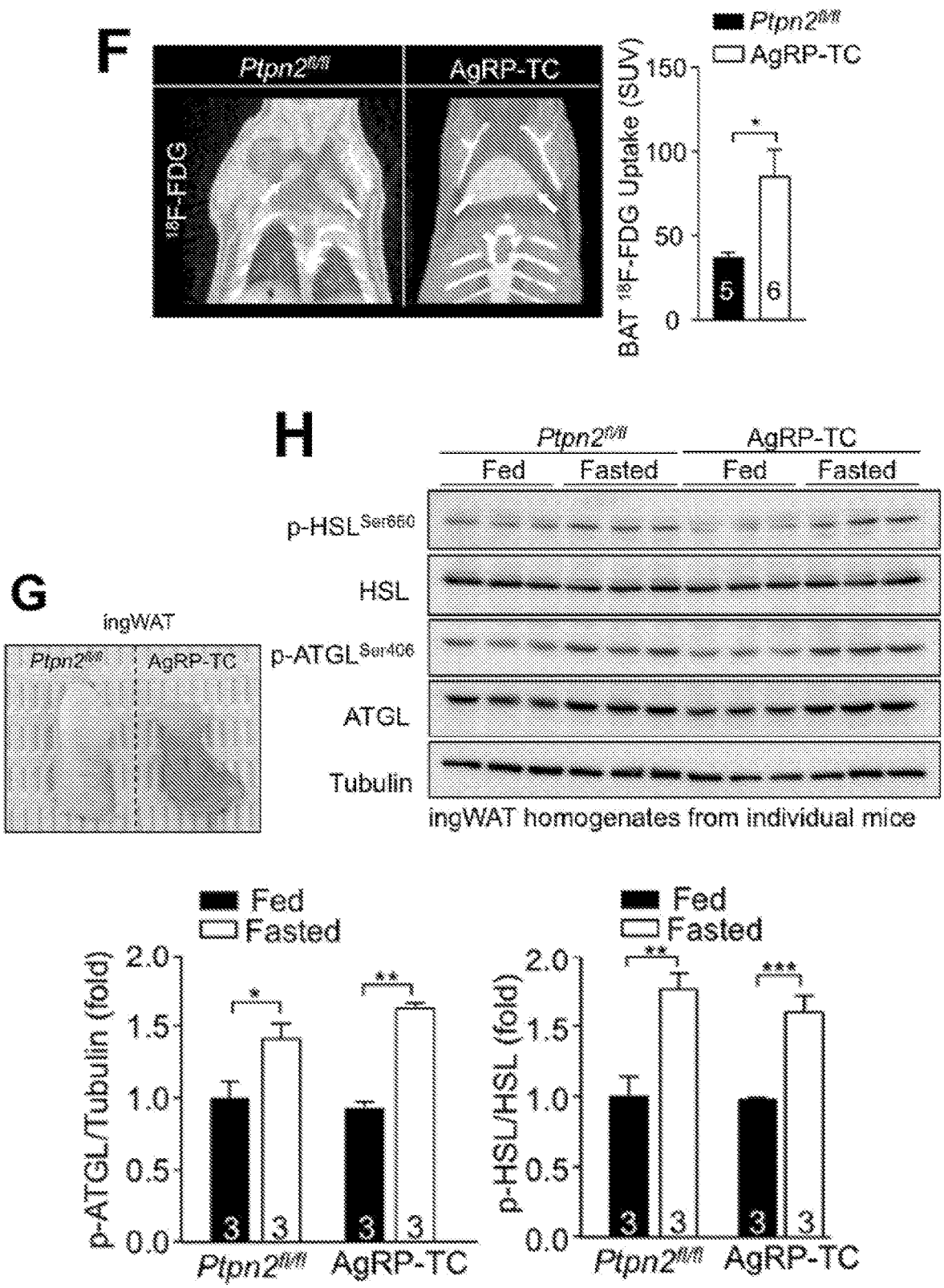
Figure 9:
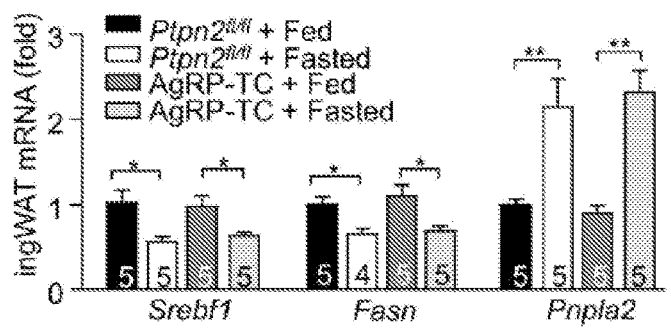
Figure 9:
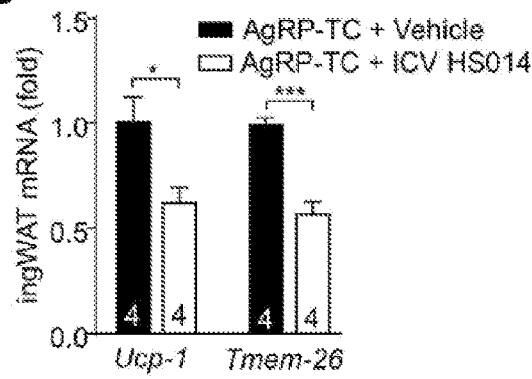
Figure 9:
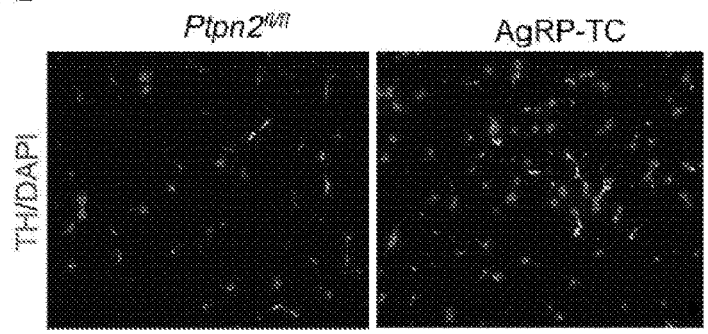
Figure 9:
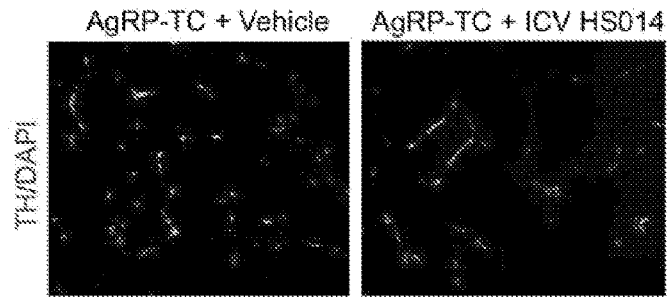

Given the enhanced basal and insulin-induced PI3K/AKT signalling and the inhibition of AgRP/NPY neurons in AgRP-TC mice, it was reasoned that TCPTP-deficiency would promote melanocortin signaling and the sympathetic nerve activity (SNA)-dependent browning of white fat and the expenditure of energy to decrease adiposity. In keeping with this it was found that AgRP-TC mice fed a standard chow diet had a reduced body weight at 16 weeks of age (FIG. 3a) accompanied by decreased whole-body adiposity as reflected by dual-energy X-ray absorptiometry (DEXA) without changes in lean mass or bone density (FIG. 3b; FIG. 9a). The decreased adiposity was fat depot-specific, with decreased inguinal (subcutaneous) WAT mass, where browning predominates in mice, but unaltered epididymal WAT or interscapular BAT weights (FIG. 9b). The reduction in inguinal WAT was accompanied by increased energy expenditure and oxygen consumption during the dark cycle (FIG. 3c; FIG. 9c), in the absence of any change in fuel utilisation (as determined by the respiratory exchange ratio; FIG. 9d). Although optogenetic or pharmacogenetic activation of AgRP neurons promotes feeding and Agrp deletion increases locomotor activity, neither daily food intake (FIG. 3d), nor ambulatory activity (FIG. 9e) were overtly altered in AgRP-TC mice. Instead TCPTP deficiency was associated with increased interscapular BAT Ucp-1 expression (FIG. 3e) and BAT $^{18}$F-FDG uptake (monitored by PET/CT), consistent with increased BAT thermogenesis (FIG. 9f). TCPTP-deficiency was also associated with a striking increase in inguinal WAT browning, as assessed by i) gross morphology (FIG. 9g) and histology (small adipocyte clusters with multilocular lipid droplets; FIG. 3f), ii) the increased expression of Ucp-1, Prdm16 and Cidea, found in brown and beige adipocytes, and Tmem26 and Cd137 that are specific to beige adipocytes (Wu et al., 2012) (FIG. 3g), iii) increased UCP-1 protein, as assessed by immunoblotting (FIG. 3h) and immunohistochemistry (FIG. 3f), and iv) increased $^{18}$F-FDG uptake (PET/CT) (FIG. 3i), consistent with increased beige adipocyte thermogenic activity. No differences were evident in Ptpn2$^{fl/fl}$ versus AgRP-TC inguinal WAT lipolytic or lipogenic responses, as assessed by the phosphorylation of the lipolytic enzymes ATGL (S406) and HSL (S660) (FIG. 9h), Pnpla2 gene (encodes ATGL) expression, or the expression of the genes for the lipogenic enzymes SREBP-1c (Srebf1) and FAS (Fasn) (FIG. 9i) in response to feeding or fasting. Therefore, the increased WAT browning in AgRP-TC mice is not accompanied by changes in WAT lipolysis or lipogenesis.

To determine if the increased WAT browning and weight loss in AgRP-TC mice might be attributed to increased melanocortin signalling and the sympathetic innervation of white fat, the melanocortin antagonist HS014 was administered by ICV into AgRP-TC mice. HS014 attenuated WAT browning in AgRP-TC mice (FIG. 9j). Inguinal WAT from AgRP-TC mice exhibited increased staining for tyrosine hydroxylase (TH) (FIG. 9k), the rate-limiting step in catecholamine synthesis and a marker of sympathetic innervation, and HS014 attenuated this (FIG. 9l). To determine if the enhanced WAT browning in AgRP-TC might contribute to weight loss, the inguinal fat pads of AgRP-TC mice were bilaterally denervated by injecting the neurotoxin 6-hydroxydopamine (6-OHDA) (Chao et al., 2011) and then assessed the impact on body weight (FIG. 3j). Bilaterally denervating the inguinal fat pads in AgRP-TC mice prevented WAT browning (data not shown), but did not alter lipolytic (Pnpla2) and lipogenic (Srebf1, Fasn) gene expression (data not shown), and decreased energy expenditure while increasing body weight so that AgRP-TC mice more closely approximated Ptpn2$^{fl/fl}$ controls (FIG. 3j-k). Therefore TCPTP deletion in AgRP neurons and increased melanocortin signalling drives BAT Ucp-1 expression and glucose uptake, and robust SNA-dependent WAT browning and energy expenditure to promote weight loss.

IR-Dependent WAT Browning in AgRP-TC Mice

Figure 10:
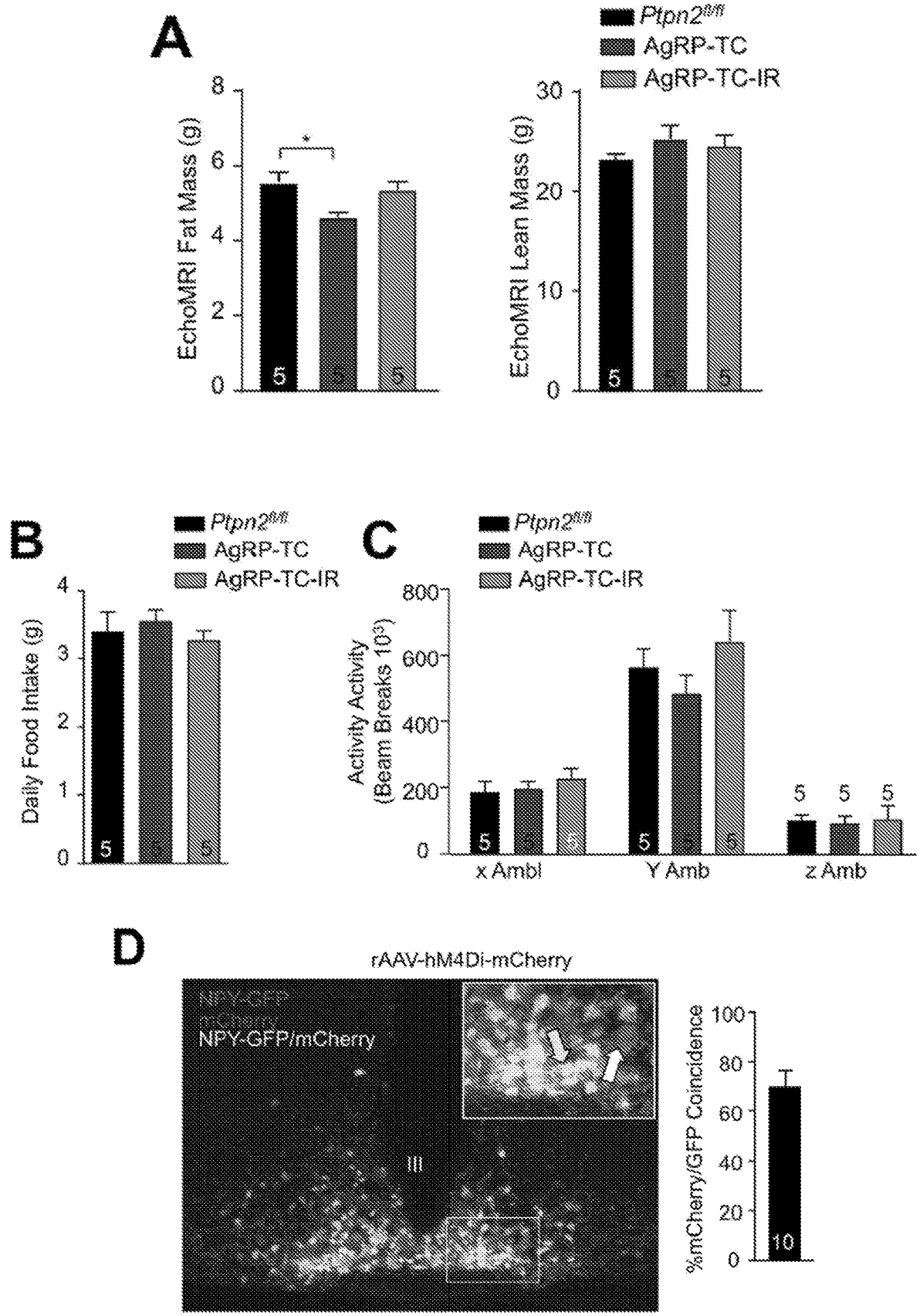
FIG. 10. Insulin receptor signaling in AgRP neurons regulates adiposity and body weight. a) Body composition (EchoMRI), b) daily food intake and c) ambulatory activity of 14-week-old Ptpn2$^{fl/fl}$, AgRP-TC or AgRP-TC-IR male mice. 10-week-old Npy-hrGFP; Agrp-Tres-Cre mice were bilaterally injected with rAAV-hM4Di-Cherry into the ARC. Contralateral ingWAT depots were sham operated or denervated with 6-ODHA (20×1 µl 9 mg/ml injections) and two weeks later mice were administered vehicle or clozapine-N-oxide (CNO; 1.5 mg/kg/day, intraperitoneal) for 14 consecutive days. d) Mice were perfused with paraformaldehyde and processed for hypothalamic mCherry/GFP immunohistochemistry; yellow arrows highlight GFP/mCherry co-incidence and white arrows GFP alone. e) Body weights and f) daily food intake were measured and g) ingWAT gross morphology assessed. Representative and quantified results (means±SEM) are shown for the indicated number of mice.
Figure 10:
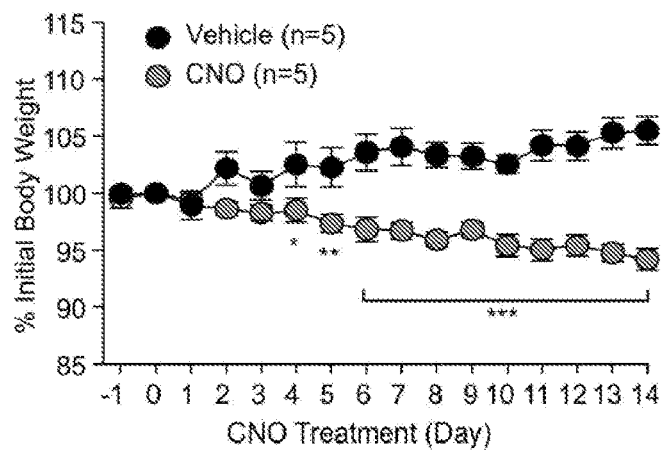
Figure 10:
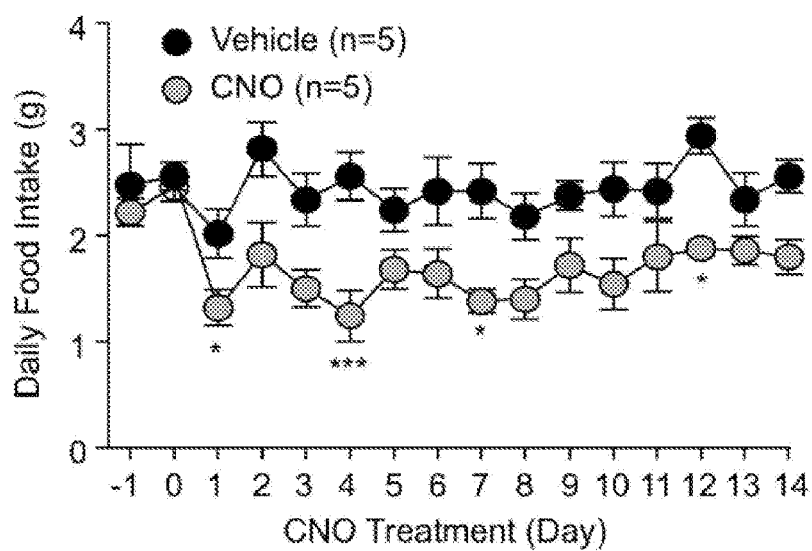
Figure 10:
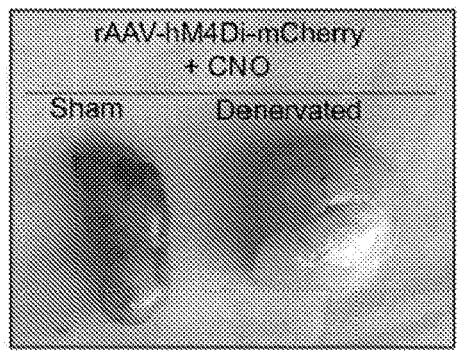

To explore the extent to which the enhanced insulin signaling in AgRP neurons in AgRP-TC mice might contribute to promotion of WAT browning, energy expenditure and weight loss, AgRP-TC mice were crossed onto the Insr$^{fl/+}$ heterozygous background. In this way Insr expression would be reduced by 50% specifically in AgRP neurons so that insulin signalling might more closely approximate that in Ptpn2$^{fl/fl}$ control mice. The enhanced insulin-induced ARC p-AKT signalling in AgRP-TC was reduced by approximately 55% in AgRP-TC; Insr$^{fl/+}$ (AgRP-TC-IR) mice (FIG. 3l). IR heterozygosity in AgRP neurons largely corrected the enhanced dark-phase energy expenditure (FIG. 3m) and increased body weight and adiposity without affecting food intake or ambulatory activity (FIG. 3n-o; FIG. 10a-c). The increased body weight was accompanied by the repression of WAT browning, as assessed histologically and by the expression of Ucp-1, Tmem26 and Cd-137 (FIG. 3p-q). IR heterozygosity also largely corrected the increased BAT Ucp-1 expression otherwise seen in AgRP-TC mice (FIG. 3r). These results show that TCPTP deletion in AgRP neurons promotes weight loss and WAT browning and BAT thermogenesis by enhancing IR signalling and inhibiting AgRP neurons.

AgRP Neuronal Inhibition Promotes WAT Browning

To independently assess the impact of AgRP neuronal inhibition on WAT browning, ARC AgRP neurons were non-selectively inhibited with the $G_i$-coupled hM4Di DREADD (designer receptors exclusively activated by designer drugs) that is activated by clozapine-N-oxide (CNO) and induces neuronal silencing. rAAV-hM4Di-mCherry, capable of expressing hM4Di fused to mCherry in a Cre-dependent manner (Krashes et al., 2011), was administered into the ARC of 12-week-old Agrp-Ires-Cre; Npy-rGFP mice. Post-mortem analyses confirmed mCherry expression in approximately 70% of GFP-positive NPY/AgRP neurons (FIG. 10d). We subsequently unilaterally denervated the inguinal fat pads of these mice by injecting 6-OHDA and then after a period of recovery administered mice vehicle or CNO (1.5 mg/kg/day) daily for 14 days to hyperpolarise and inhibit AgRP neurons. Body weights, food intake and WAT browning were assessed after 14 days. CNO decreased body weights (FIG. 10e) and food intake (FIG. 10f) and resulted in marked WAT browning in the sham-operated, but not in the contralateral 6-OHDA denervated inguinal fat pads (denervation efficiency assessed by TH immunohistochemistry) that was evident by gross morphology (FIG. 10g), quantitative real-time PCR (monitoring for Ucp-1, Prdm-16, Cidea, Tmem-26 and Cd137 gene expression; FIG. 3s), histology and immunohistochemistry (monitoring for UCP-1) (FIG. 3t). Therefore AgRP neuronal inhibition can promote robust WAT browning. Taken together, our results indicate that TCPTP-deficiency in AgRP neurons inhibits AgRP neurons to increase SNA-dependent browning of WAT.

TCPTP is Essential for the Fasting-Induced Repression of WAT Browning

Figure 4:
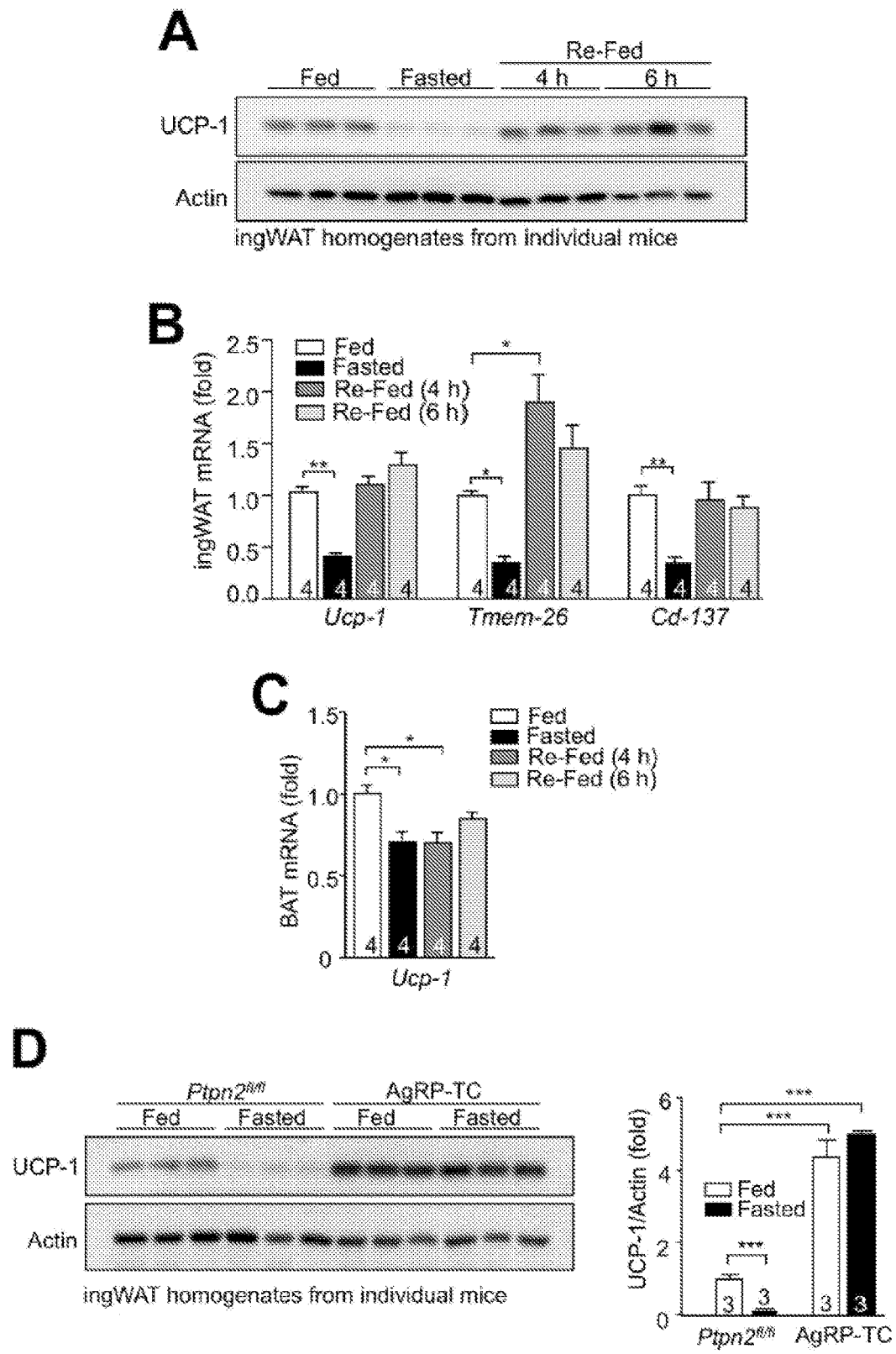
FIG. 4. TCPTP in AgRP neurons coordinates feed-fast alterations in WAT browning and energy expenditure. IngWAT and BAT was extracted from 8-week-old C57BL/6 male fed, fasted, or fasted and re-fed mice and processed for a) immunoblotting or b-c) quantitative PCR. IngWAT was extracted from 10-12-week-old Ptpn2$^{fl/fl}$ or AgRP-TC male mice fed or 24 h fasted mice and processed for d) immunoblotting or e) quantitative PCR. f) Energy expenditure in 8-week-old Ptpn2$^{fl/fl}$ or AgRP-TC fed and food restricted (FR; just prior to lights out, 6:30 pm) male mice. g) Energy expenditure in 11-week-old Ptpn2$^{fl/fl}$, AgRP-TC or AgRP-TC-IR male mice. h) 10-week-old Ptpn2$^{fl/fl}$ or AgRP-TC male mice ingWAT depots were bilaterally sham operated or denervated with 6-ODHA and energy expenditure. Grey shading represents dark cycle. Representative and quantified results (means±SEM) are shown for the indicated number of mice.
Figure 4:
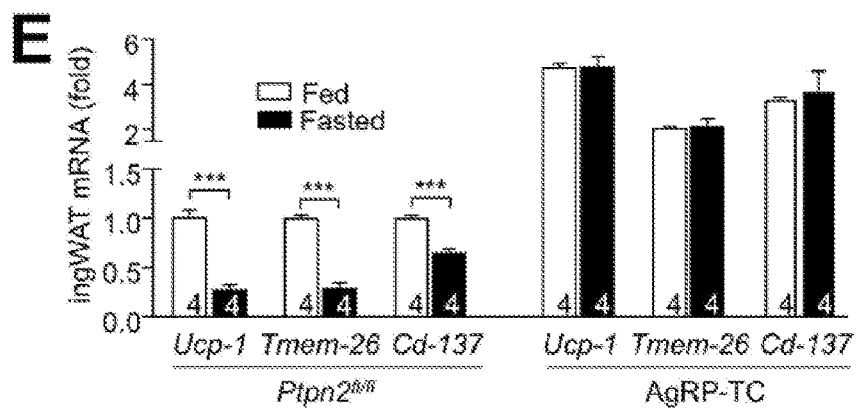
Figure 4:
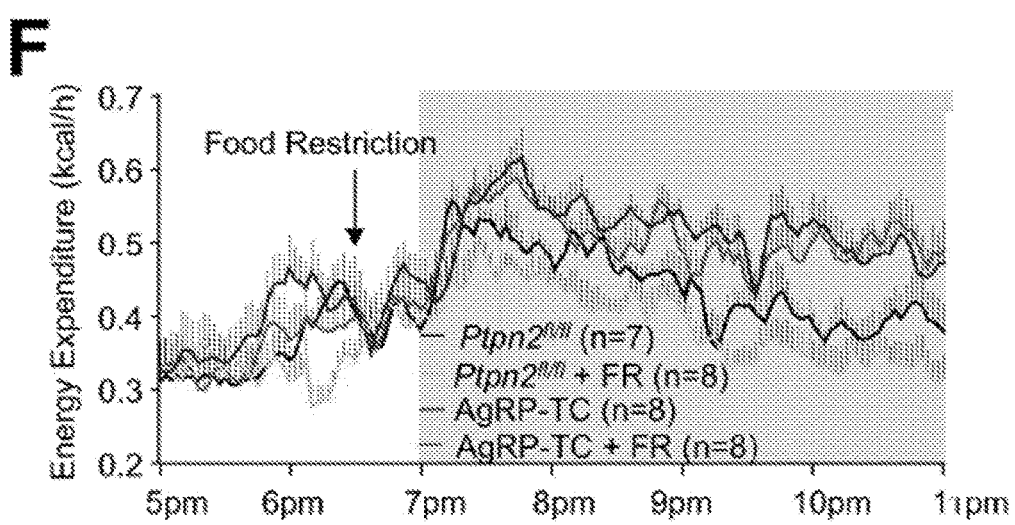
Figure 4:
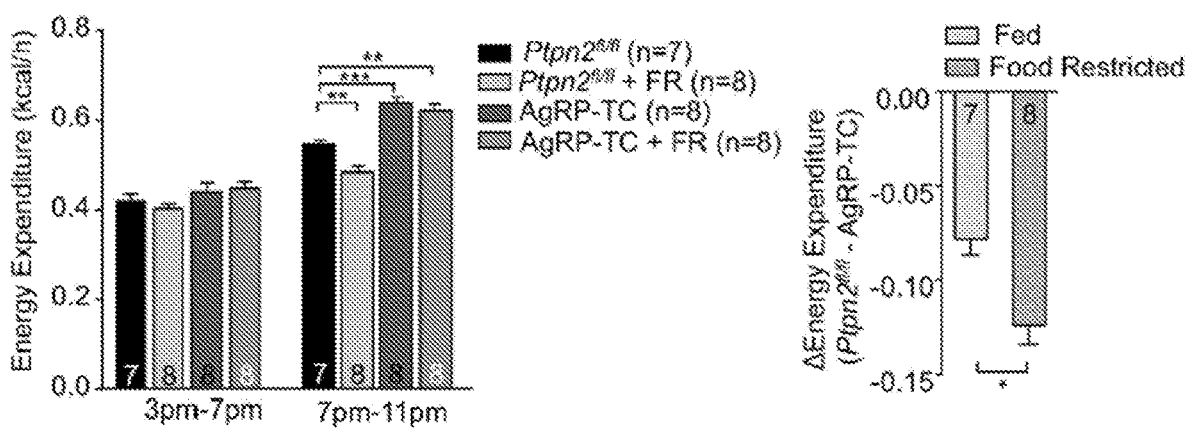
Figure 4:
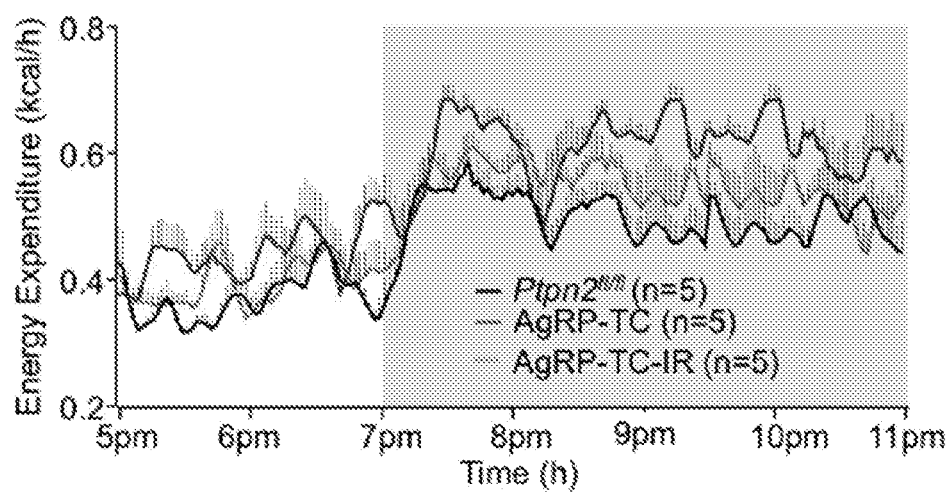
Figure 4:
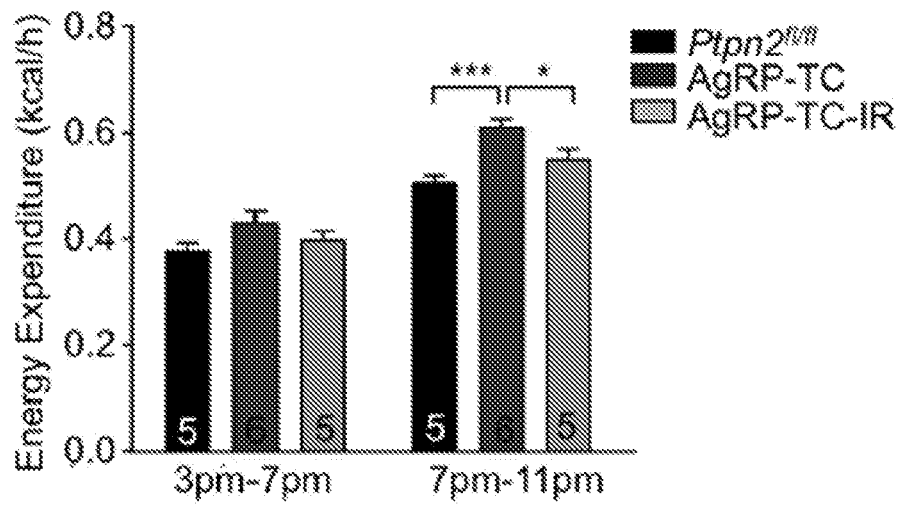
Figure 4:
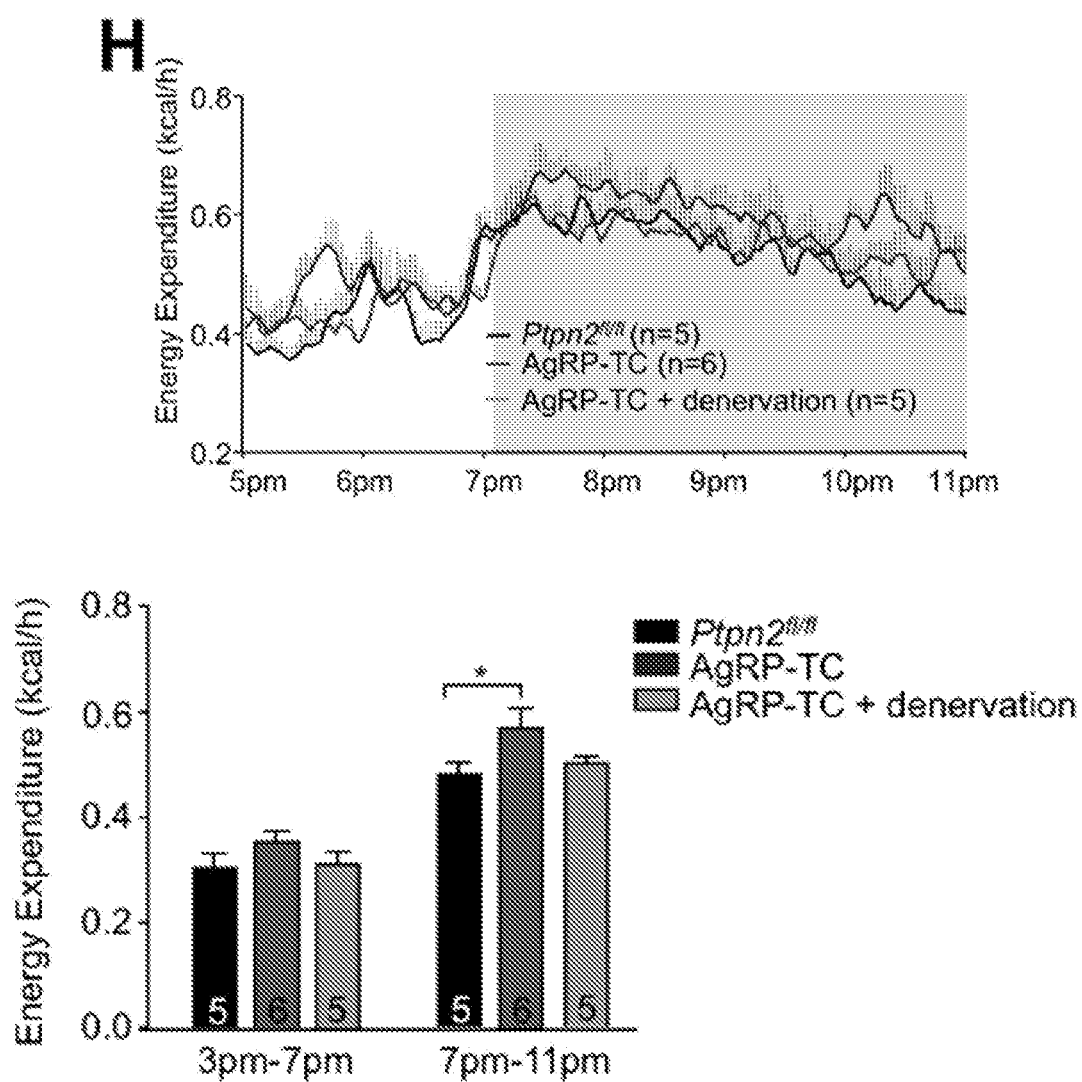

These studies are consistent with TCPTP acting as a molecular switch in AgRP neurons with alterations in TCPTP levels coordinating insulin signaling and AgRP neuronal activation with the browning of WAT and the expenditure of energy to maintain energy balance in response to feeding versus fasting. To test this, it was first determined whether the impact of feeding and fasting on WAT browning in C57BL/6 mice. It was found that fasting was associated with the overt repression of browning, as assessed by UCP-1 protein levels (FIG. 4a) and the repressed expression of Ucp-1, Tmem26 and Cd137 in inguinal WAT (FIG. 4b). Fasting also repressed BAT Ucp-1 expression (FIG. 4c). Notably we found that the repressed WAT browning was reversed after re-feeding (FIG. 4a-b). By contrast, the reversal of BAT Ucp-1 expression was not evident after 4 h of re-feeding (FIG. 4c). These findings highlight the plasticity of the inguinal fat pad and its capacity to readily interconvert between beige and white adipocytes in response to feeding and fasting respectively.

Next the extent to which alterations in hypothalamic TCPTP might influence WAT plasticity were assessed by comparing browning in fed (mice sacrificed 4 h after lights out) versus fasted Ptpn2$^{fl/fl}$ and AgRP-TC mice. It was reasoned that deleting TCPTP in AgRP neurons and promoting insulin signaling would abrogate the fasting-induced repression of WAT browning, otherwise associated with the activation of AgRP neurons by ghrelin (Ruan et al., 2014). Inguinal WAT UCP-1 protein levels were repressed in Ptpn2$^{fl/fl}$ mice in response to a fast and this was accompanied by the repression of WAT browning genes (FIG. 4e). It was found inguinal WAT UCP-1 protein levels and the expression of browning genes were not only elevated in AgRP-TC mice, but importantly were unaltered by fasting (FIG. 4d-e).

These results indicate that TCPTP in AgRP neurons is essential for the fasting-induced repression of WAT browning.

WAT Browning Contributes to Feeding-Induced Thermogenesis

Figure 5:
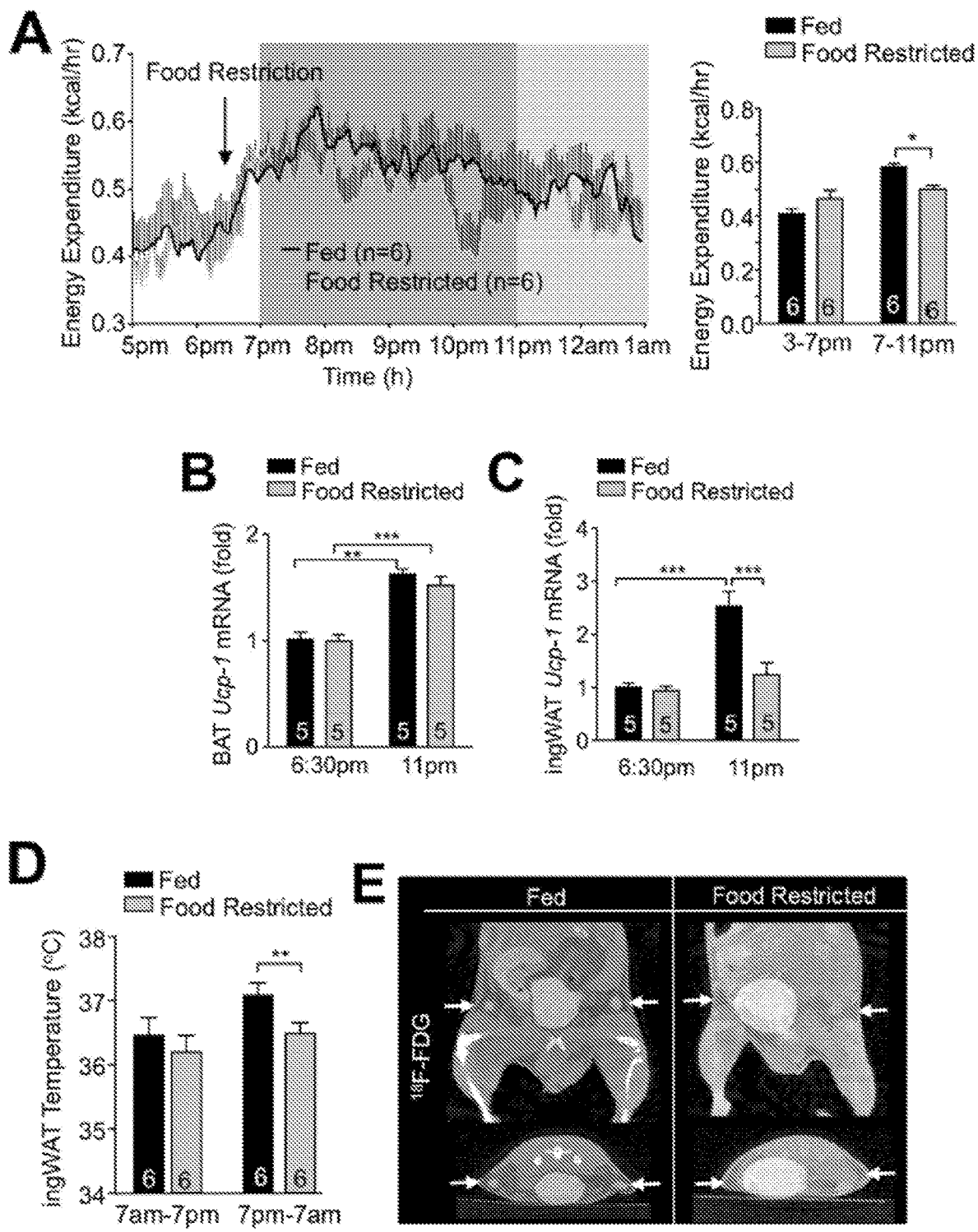
FIG. 5. Diurnal feeding-associated changes in hypothalamic TCPTP, WAT browning and energy expenditure. a) Energy expenditure, b) BAT and c) IngWAT gene expression in 8-week-old C57BL/6 fed and food-restricted (just prior to lights out, 6:30 pm) mice. d) IngWAT temperature measured with implanted telemetry probes in 8-week-old C57BL/6 fed and food-restricted mice. e) 8-week-old C57BL/6 fed or food-restricted mice were subjected to $^{18}$F-FDG PET-CT. Representative images and ingWAT $^{18}$F-FDG standard uptake values (SUV) and normalised uptake per tissue volume are shown. f-h) 8-week-old C57BL/6 male mice ingWAT depots were bilaterally sham-operated or denervated with 6-ODHA and energy expenditure and ingWAT and BAT Ucp-1 gene expression were determined two weeks later. i) Hypothalami, BAT and ingWAT were extracted from 8-10-week-old C57BL/6 fed and food-restricted male mice as indicated and processed for quantitative PCR. j) IngWAT was extracted from 8-10-week-old C57BL/6 fed male mice at the indicated times and processed for immunoblotting. Representative and quantified results (means±SEM) are shown for the indicated number of mice.
Figure 5:
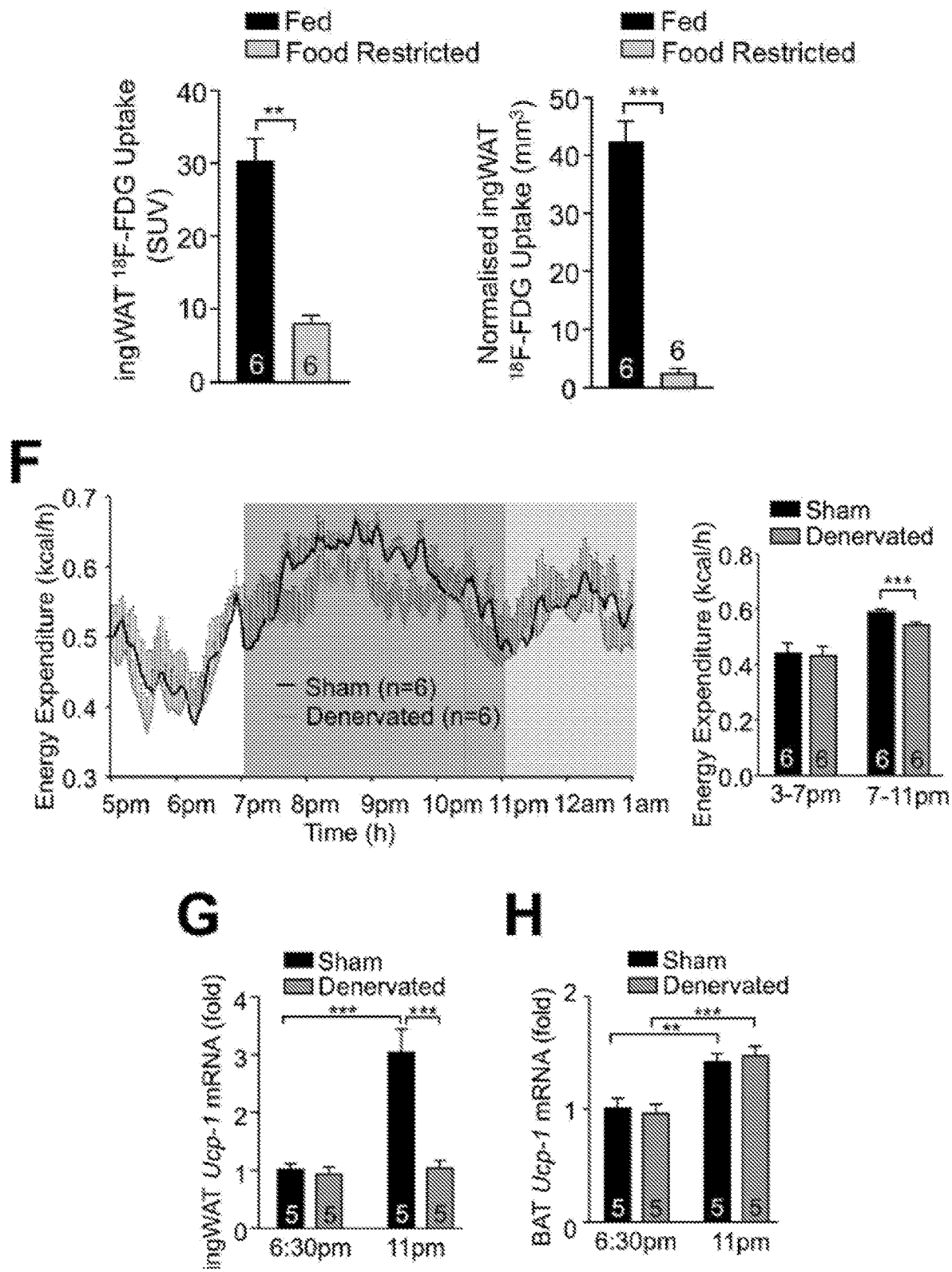
Figure 5:
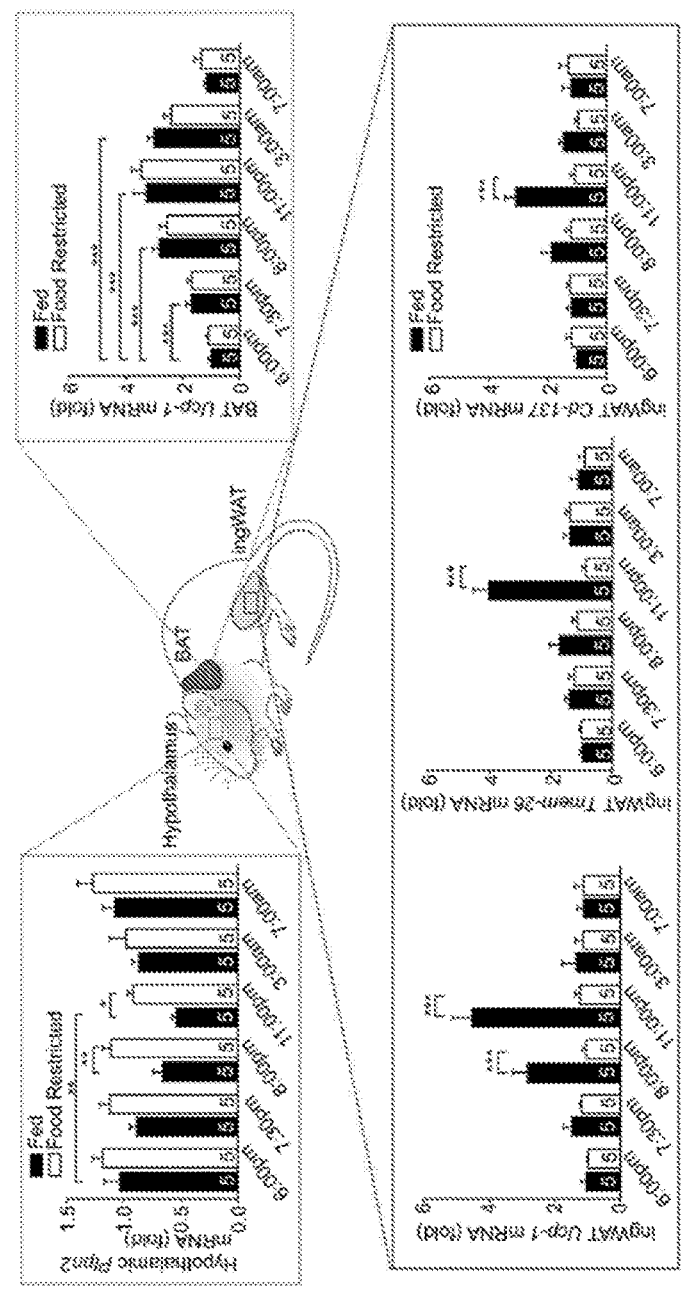
Figure 5:
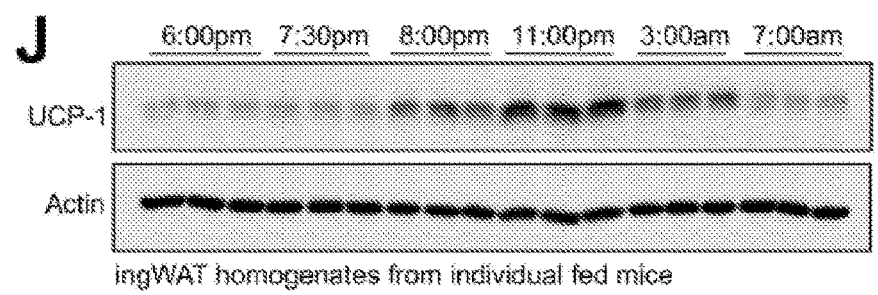
Figure 12:
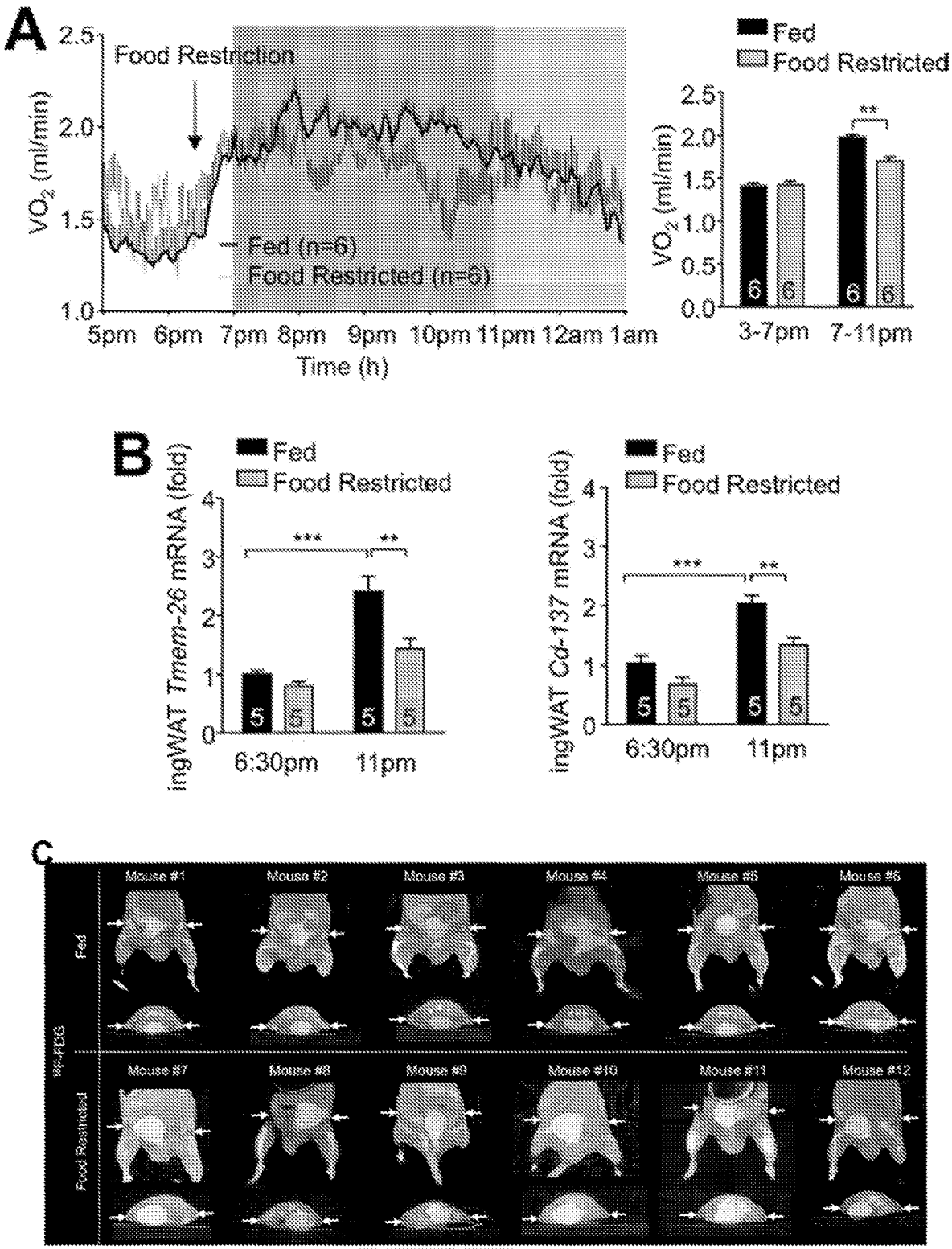
FIG. 12. Feeding promotes WAT browning and energy expenditure. a) Oxygen consumption, b) ingWAT gene expression in 8-10 week-old C57BL/6 fed or food restricted (just prior to lights out, 6:30 µm) mice. c-d) fed or food restricted C57BL/6 male mice were subjected to $^{18}$F-FDG PET-CT. c) Images from individual experimental mice depicting ingWAT $^{18}$F-FDG uptake and d) representative images and quantified BAT $^{18}$F-FDG uptake are shown; white arrows highlight ingWAT depots. 8-week-old C57BL/6 male mice ingWAT depots were bilaterally sham-operated or denervated with 6-ODHA and e) oxygen consumption and f) ingWAT gene expression assessed. IngWAT was extracted from 8-10 week-old fed, food-restricted, sham-operated or denervated (6-OHDA) mice and processed for g) immunoblotting and h) gene expression. Representative and quantified results (means±SEM) are shown for the indicated number of mice.
Figure 12:
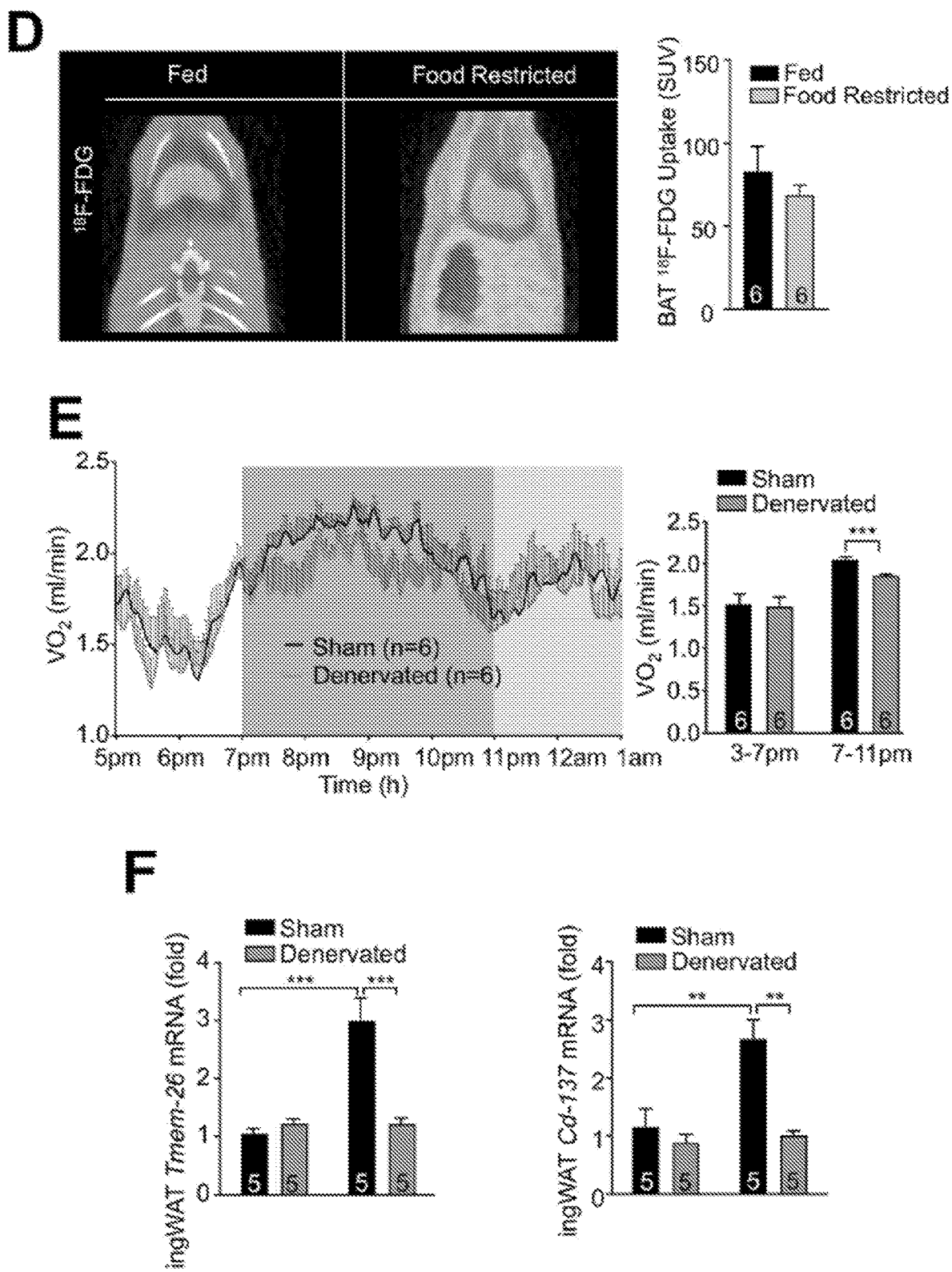
Figure 12:
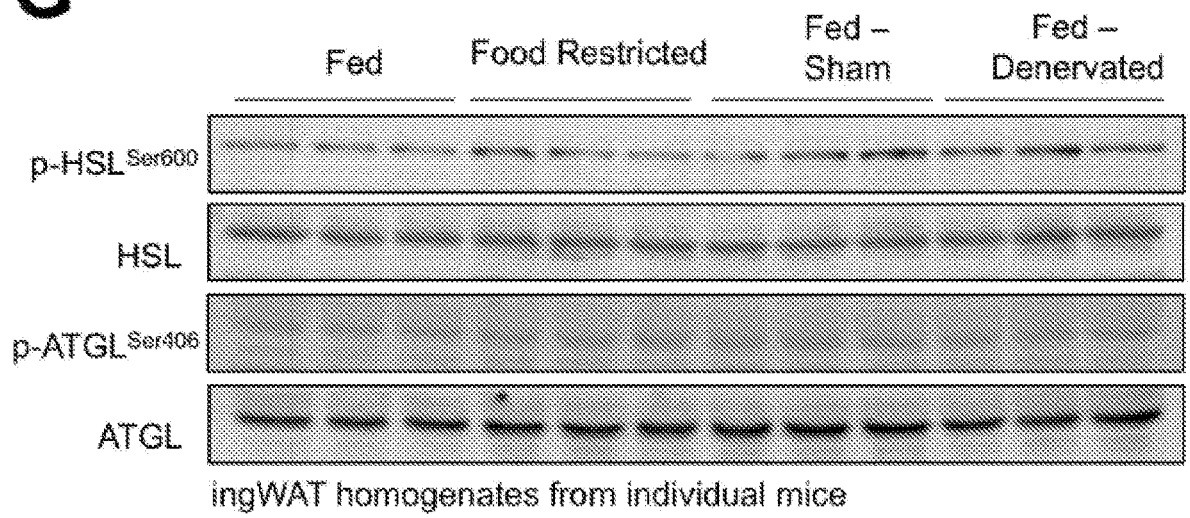
Figure 12:
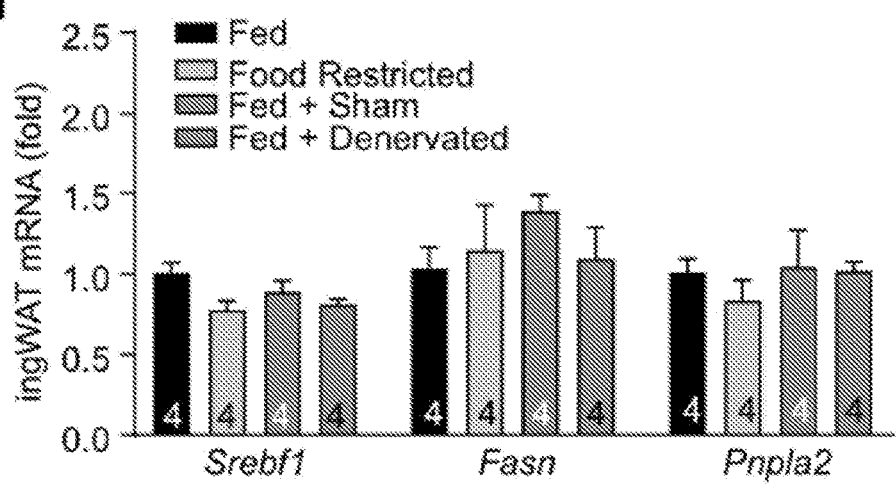

These studies indicate that the fasting-induced increase in hypothalamic TCPTP is essential for the inhibition of WAT browning. To determine whether this might reflect a stress response to prolonged fasting, or otherwise represent a diurnal feeding response important for the control of energy balance, whether BAT thermogenesis and WAT browning may influence feeding-associated changes in energy expenditure was first determined. It was found that oxygen consumption and energy expenditure, as assessed by indirect calorimetry, were increased at the start of the dark cycle when mice feed (FIG. 5a; FIG. 12a) and this was accompanied by increased BAT Ucp-1 expression (FIG. 5b) and WAT browning, as inferred by the increased expression of Ucp-1, Tmem26 and Cd137 in inguinal WAT (FIG. 5c; FIG. 12b). The increase in energy expenditure was diminished (FIG. 5a) and WAT browning (FIG. 5c; FIG. 12b) not evident if food was withheld (food restricted) immediately before the start of the dark cycle, consistent with this being a feeding response, rather than an entrained circadian response. By contrast, BAT Ucp-1 increased at the start of the dark cycle irrespective of whether food was withheld (FIG. 5b), consistent with this being controlled by the circadian rhythm. Importantly, the feeding-induced increase in WAT browning was accompanied by an increase in inguinal WAT temperature in the dark phase, as assessed using implanted telemetry probes, which was attenuated if food was withheld (FIG. 5d). Moreover, a striking increase in inguinal WAT BAT $^{18}$F-FDG uptake (PET/CT) was noted in mice that were fed (4 h after start of dark cycle) versus mice where food was withheld (FIG. 5e; FIG. 12c). By contrast BAT $^{18}$F-FDG uptake (PET/CT) was not overtly altered in fed versus food-restricted mice (FIG. 12d). Therefore, WAT browning and thermogenesis, but not BAT activity (as inferred by $^{18}$F-FDG uptake), are increased in response to feeding.

Next the extent to which the feeding-induced WAT browning and thermogenesis might contribute to the feeding-associated increases in energy expenditure was determined. It was found that the feeding-dependent increase in oxygen consumption and energy expenditure were ablated if the inguinal fat pads were denervated with 6-OHDA (FIG. 5f; FIG. 12e) to prevent browning (FIG. 5g; FIG. 12f); neither BAT Ucp-1 expression (FIG. 5h) nor inguinal WAT ATGL Ser-406 or HSL Ser-660 phosphorylation, or lipogenic (Srebf1, Fasn) or lipolytic (Pnpla2) gene expression were altered in fed versus food restricted mice after inguinal WAT denervation (FIG. 12g-h). Strikingly the decrease in oxygen consumption and energy expenditure in denervated mice occurred primarily within the first 4 h after the start of the dark cycle (FIG. 5f; FIG. 12e) coinciding with feeding (FIG. 1b). These results causally link feeding-associated increases in energy expenditure with WAT browning and the control of energy balance.

Diurnal TCPTP fluctuations coordinate feeding-induced WAT browning.

Having established that WAT browning is important in feeding-associated energy expenditure in mice, whether the repression of hypothalamic TCPTP upon feeding might contribute to this process was next explored. To this end, hypothalamic Ptpn2 levels before the start of the dark cycle (when mice do not feed; FIG. 5i) and at various times after lights were turned off in either fed mice, or mice where food was withheld at the start of the dark cycles were compared. It was found that Ptpn2 expression was significantly reduced 1 h after lights were turned off in fed, but not in food-restricted mice (FIG. 5i). The repression of Ptpn2 expression in fed mice was sustained for the first 4 h of the dark cycle when mice feed, but increased thereafter to levels evident in food-restricted mice (FIG. 5i). These results demonstrate that hypothalamic Ptpn2 expression exhibits a diurnal rhythm linked to feeding.

To determine if the diurnal fluctuations in TCPTP might influence WAT browning and BAT activity, diurnal Ptpn2 expression in fed and food-restricted mice was correlated with the expression of browning genes in inguinal WAT and the expression of Ucp-1 in BAT. It was found that the feeding-induced repression of Ptpn2 expression at the start of the dark cycle coincided with the promotion inguinal WAT Ucp-1, Tmem26 and Cd137 expression (FIG. 5i) and an increase in inguinal WAT UCP-1 protein (FIG. 5j). WAT browning was not evident in food-restricted mice, or at later times in fed mice when mice do not feed and Ptpn2 levels were increased (FIG. 5i). By contrast BAT Ucp-1 increased in the dark phase, remained elevated throughout the night and was unaffected by feeding (FIG. 5i). These results indicate that WAT browning mirrors the feeding-associated diurnal fluctuations in hypothalamic Ptpn2.

Figure 11:
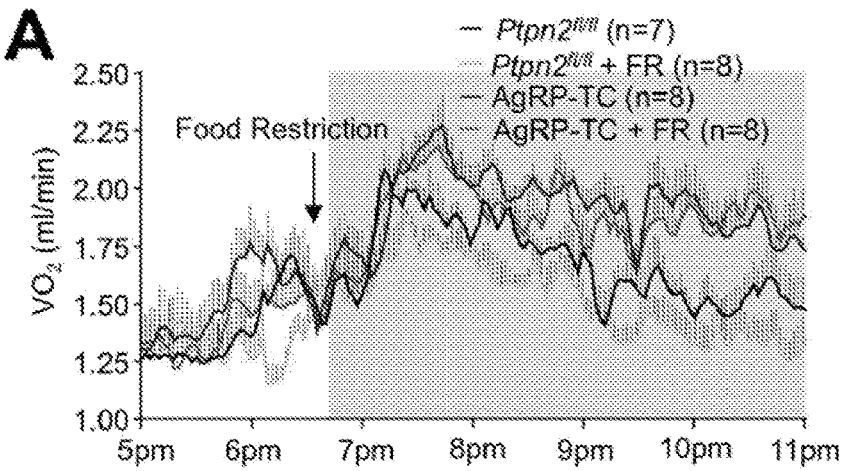
FIG. 11. TCPTP in AgRP neurons coordinates feed-fast alterations in oxygen consumption and energy expenditure through the control of insulin receptor signaling and WAT browning. a-b) Oxygen consumption and c) energy expenditure in fed or food-restricted (food withheld at 6.30 µm immediately before lights off at 7 µm) Ptpn2$^{fl/fl}$ and AgRP-TC male mice. d) Oxygen consumption in 11-week-old Ptpn2$^{fl/fl}$, AgRP-TC or AgRP-TC-IR male mice. e) 10-week-old Ptpn2$^{fl/fl}$ or AgRP-TC male mice ingWAT depots were bilaterally sham operated or denervated with 6-ODHA and oxygen consumption was determined two weeks later. Grey shading indicates dark cycle. Representative and quantified results (means±SEM) are shown for the indicated number of mice.
Figure 11:
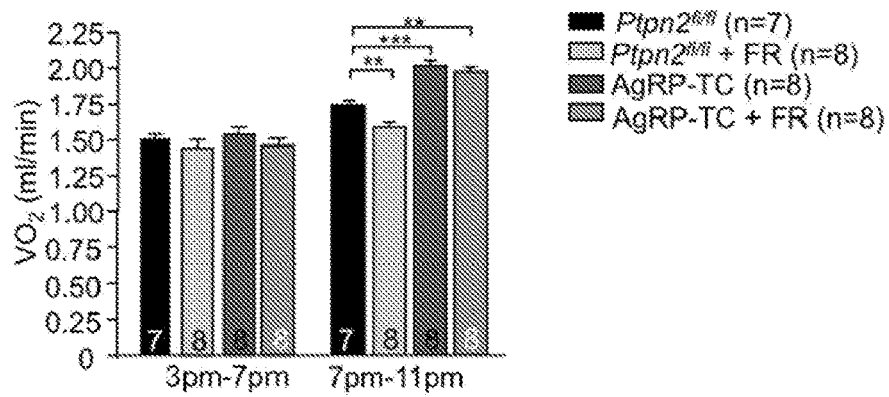
Figure 11:
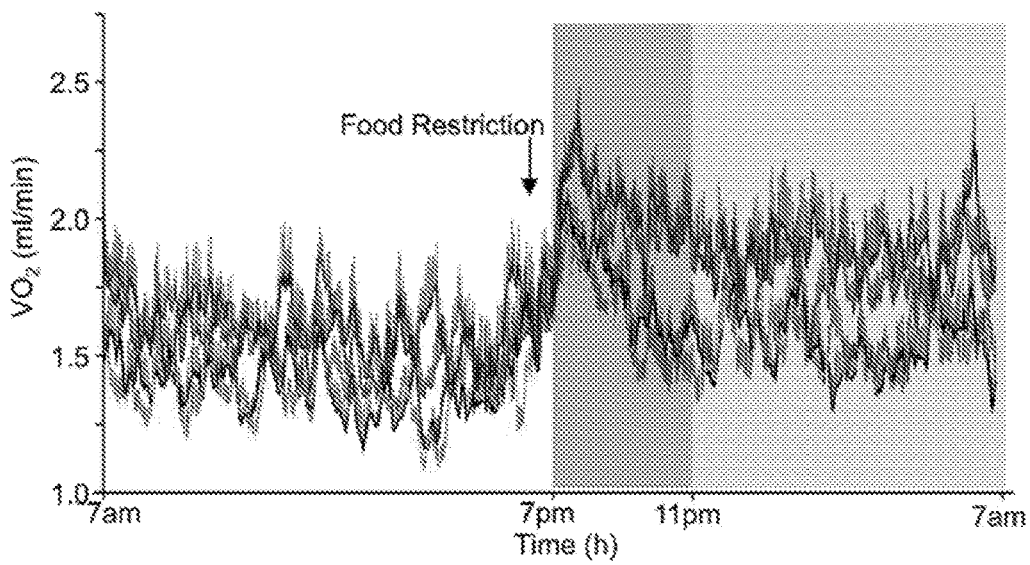
Figure 11:
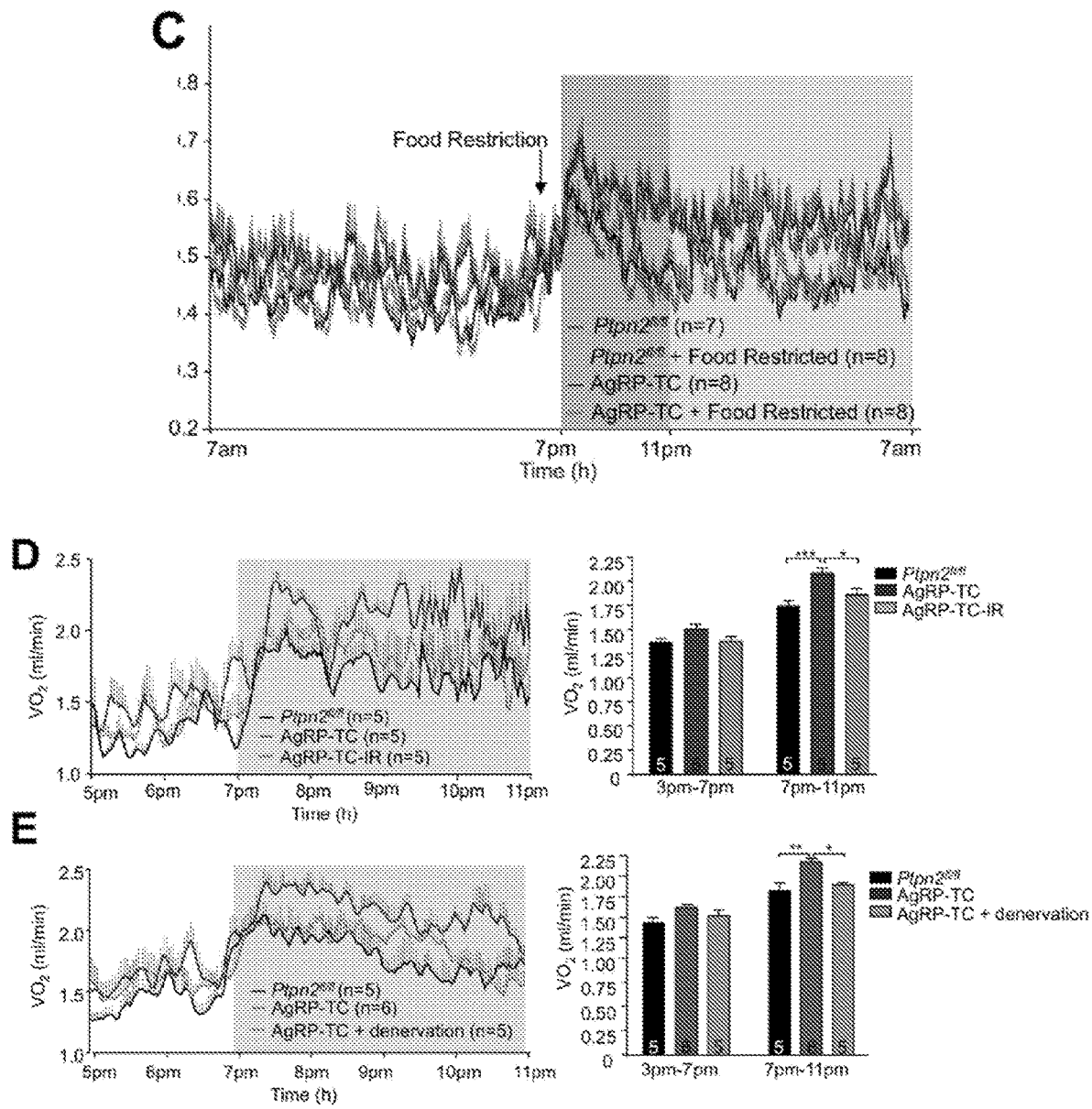

To determine if the feeding-induced repression of hypothalamic TCPTP might be required for the accompanying promotion of browning and energy expenditure advantage was taken of Ptpn2$^{fl/fl}$ and AgRP-TC mice. It was reasoned that if the repression of TCPTP was necessary to increase energy expenditure, then differences in energy expenditure between Ptpn2$^{fl/fl}$ and AgRP-TC mice would be greatest in food-restricted mice, since hypothalamic TCPTP levels in Ptpn2$^{fl/fl}$ mice would remain elevated and browning would be repressed. On the other hand in fed mice, differences in energy expenditure at the start of the dark cycle would be diminished, since hypothalamic TCPTP would be decreased in Ptpn2$^{fl/fl}$ mice and this would promote browning as seen in AgRP-TC mice. Energy expenditure was increased in AgRP-TC versus Ptpn2$^{fl/fl}$ mice during the first 4 h of the dark cycle irrespective of feeding, but the differences in energy expenditure were greatest in food-restricted mice (FIG. 4f; FIG. 11a-c). The increased energy expenditure during the first 4 h of the dark-phase in AgRP-TC mice was attenuated in AgRP-TC-IR mice, or in AgRP-TC mice where the inguinal fat pads had been denervated to prevent browning (FIG. 4g-h; FIG. 11d-e). Therefore, these results are consistent with the feeding-induced repression of TCPTP in AgRP neurons increasing IR signalling to promote SNA-dependent WAT browning and energy expenditure.

These studies have identified a molecular mechanism whereby feeding rhythms influence energy expenditure through the control of WAT browning. It was demonstrated that the nutritional state of the organism alters the abundance of TCPTP, a key negative regulator of insulin signaling in the hypothalamus, to control sympathetic outflow and the browning of white fat in response to feeding and fasting to maintain energy balance. The diurnal alterations in hypothalamic TCPTP levels associated with feeding and the resultant promotion or repression of browning and thermogenesis provide a flexible physiological mechanism by which to calibrate energy expenditure with energy intake, which is fundamentally important for the control of body weight.

These studies provide evidence for IR signaling in AgRP neurons being critical in the control of WAT browning and energy expenditure. It was demonstrated that TCPTP deficiency in AgRP/NPY neurons promotes insulin signalling and the insulin-mediated inhibition of AgRP neurons to drive SNA-dependent WAT browning, energy expenditure and weight loss. The effects of TCPTP deficiency in AgRP neurons on browning, energy expenditure and weight loss were largely corrected when Insr gene expression in AgRP neurons was halved, so that insulin signaling approximated that in control mice. Therefore, even subtle alterations in IR signaling might profoundly influence WAT browning and energy expenditure.

These studies point towards TCPTP fluctuations associated with diurnal feeding and fasting being instrumental in gating responses to insulin and thereby the activation of AgRP neurons to control the SNA-dependent WAT browning. We demonstrate that feeding represses TCPTP to promote insulin signaling in AgRP neurons, whereas fasting increases TCPTP to repress insulin signaling. Importantly we demonstrate that TCPTP-deficiency opposes the activation of AgRP neurons by ghrelin. Accordingly, we propose that the activation of AgRP neurons by ghrelin and potentially other orexigenic factors may be dictated by the level of TCPTP and the response to insulin, and that feeding-associated diametric fluctuations in insulin and TCPTP might afford a means by which to acutely tune AgRP neurons and thereby WAT browning and energy expenditure.

In this study it was demonstrated that TCPTP is increased in both AgRP and POMC neurons in response to fasting. Therefore, the TCPTP switch may concordantly regulate insulin signaling in POMC and AgRP neurons to coordinate the melanocortin response and WAT browning in response to feeding and fasting. Increased ARC TCPTP in response to fasting would inhibit POMC and activate AgRP neurons to repress browning, whereas decreased ARC TCPTP after feeding would activate POMC and inhibit AgRP neurons to promote browning. This would afford an exquisitely sensitive system for integrating peripheral signals and coordinating melanocortin signaling and energy expenditure in response to divergent nutritional states to maintain energy balance and a stable body weight over time.

These results indicate that glucocorticoids may be pivotal in the fasting-induced promotion of TCPTP expression and the repression of ARC insulin signaling to facilitate AgRP neuronal activation by factors such as ghrelin.

These studies demonstrate a physiologically relevant role for WAT browning that is distinct from its well-established role in cold-induced thermogenesis. It was demonstrated that feeding acutely promotes WAT browning, as assessed not only by the expression of browning genes, but also by the uptake of glucose and the generation of heat, and that this essential for the expenditure of energy. Although BAT Ucp-1 expression and glucose uptake were increased in AgRP-TC mice, as a consequence of the exacerbated insulin response in AgRP neurons, we did not observe any differences in BAT Ucp-1 gene expression or glucose uptake in response to feeding. Instead BAT Ucp-1 gene expression was unaffected by feeding and exhibited a circadian rhythm, which we propose may override any feeding-induced thermogenic response. Therefore we propose that beige adipocytes may have a distinct role in diet-induced thermogenesis and the maintenance of body weight.

Example 3

The experimental data described in this Example and the associated Figures show, amongst other things, the following:
Mice lacking TCPTP in AgRP neurons are resistant to diet-induced obesity, as a consequence of enhanced WAT browning.
The feeding induced repression of hypothalamic TCPTP expression is lost in diet-induce obese mice, resulting in chronically elevated hypothalamic TCPTP expression and suppressed insulin signalling.
As a consequence of elevated hypothalamic TCPTP expression, feeding-induced WAT browning is lost in diet-induce obese mice.
In summary, the defective repression of hypothalamic TCPTP expression after feeding in obese mice prevents WAT browning and contributes to the development and maintenance of obesity.

Figure 6:
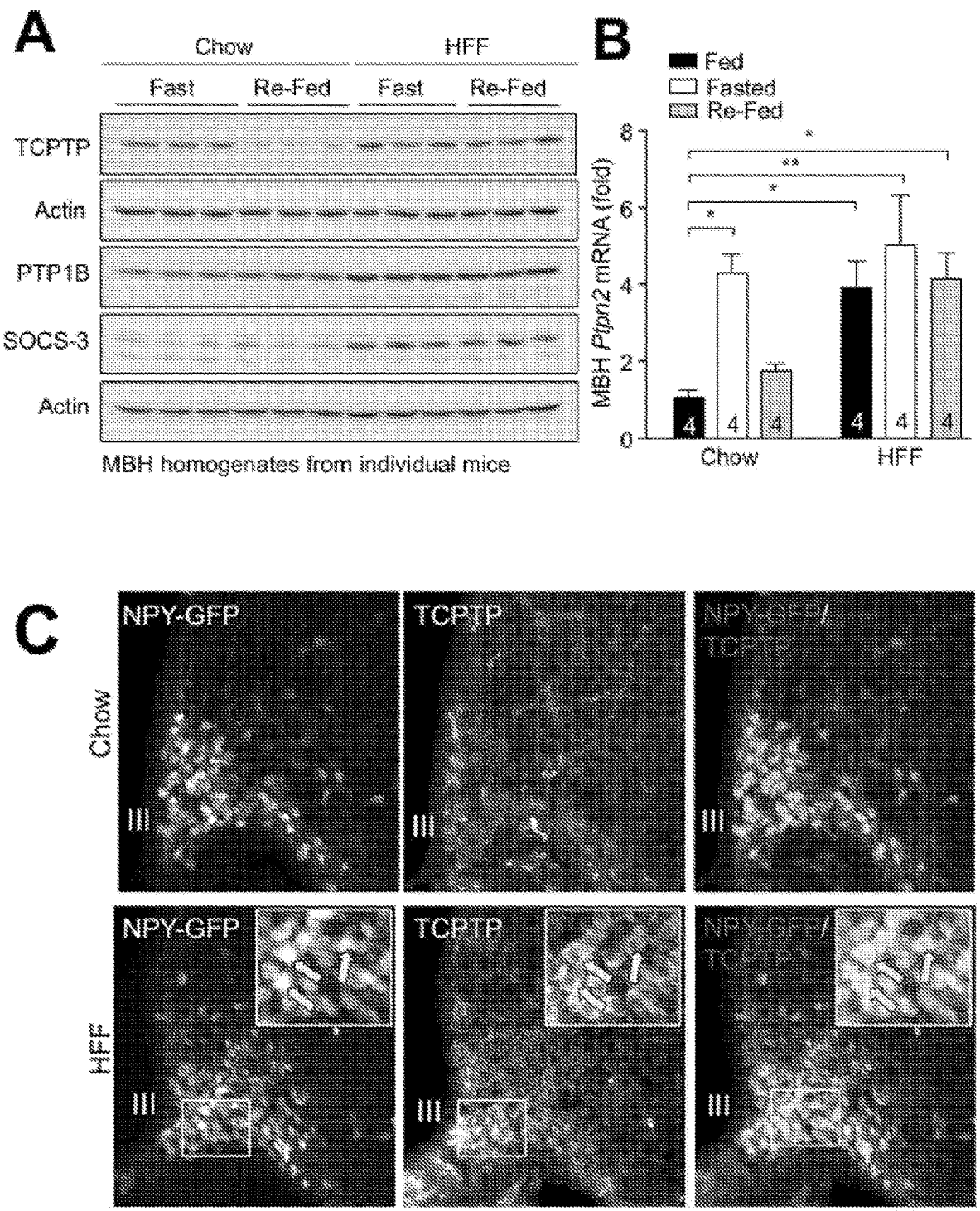
FIG. 6. The feed-fast TCPTP switch is abrogated in obesity. 8-10-week-old male C57BL/6 or Npy-hrGFP (C57BL/6) mice were chow-fed or high fat fed (HFF) for 8 weeks and mediobasal hypothalami (MBH) processed for a) immunoblotting, b) quantitative PCR or c) extracted after paraformaldehyde fixation and processed for hypothalamic immunohistochemistry. d) Body weights, e) tissue weights, f) 24 h food intake and g) energy expenditure in 12 week HFF Ptpn2$^{fl/fl}$ and AgRP-TC male mice. IngWAT or BAT were extracted from chow-fed or high fat fed (HFF) Ptpn2$^{fl/fl}$ and AgRP-TC male mice and processed for h) immunoblotting, i) histology (H&E) and immunohistochemistry, or j-k) quantitative PCR. HFF Ptpn2$^{fl/fl}$ and AgRP-TC male mice were bilaterally sham-operated or denervated with 6-ODHA after 3 weeks of high fat feeding and after a further 6 weeks of high fat feeding ingWAT and BAT extracted for l) histology (H&E) and immunohistochemistry and m-n) quantitative PCR. o) Body weights, p) tissue weights and q) energy expenditure were measured. Brightness and contrast in colour merge image have been adjusted to assess co-incidence. Representative and quantified results (means±SEM) are shown for the indicated number of mice.
Figure 6:
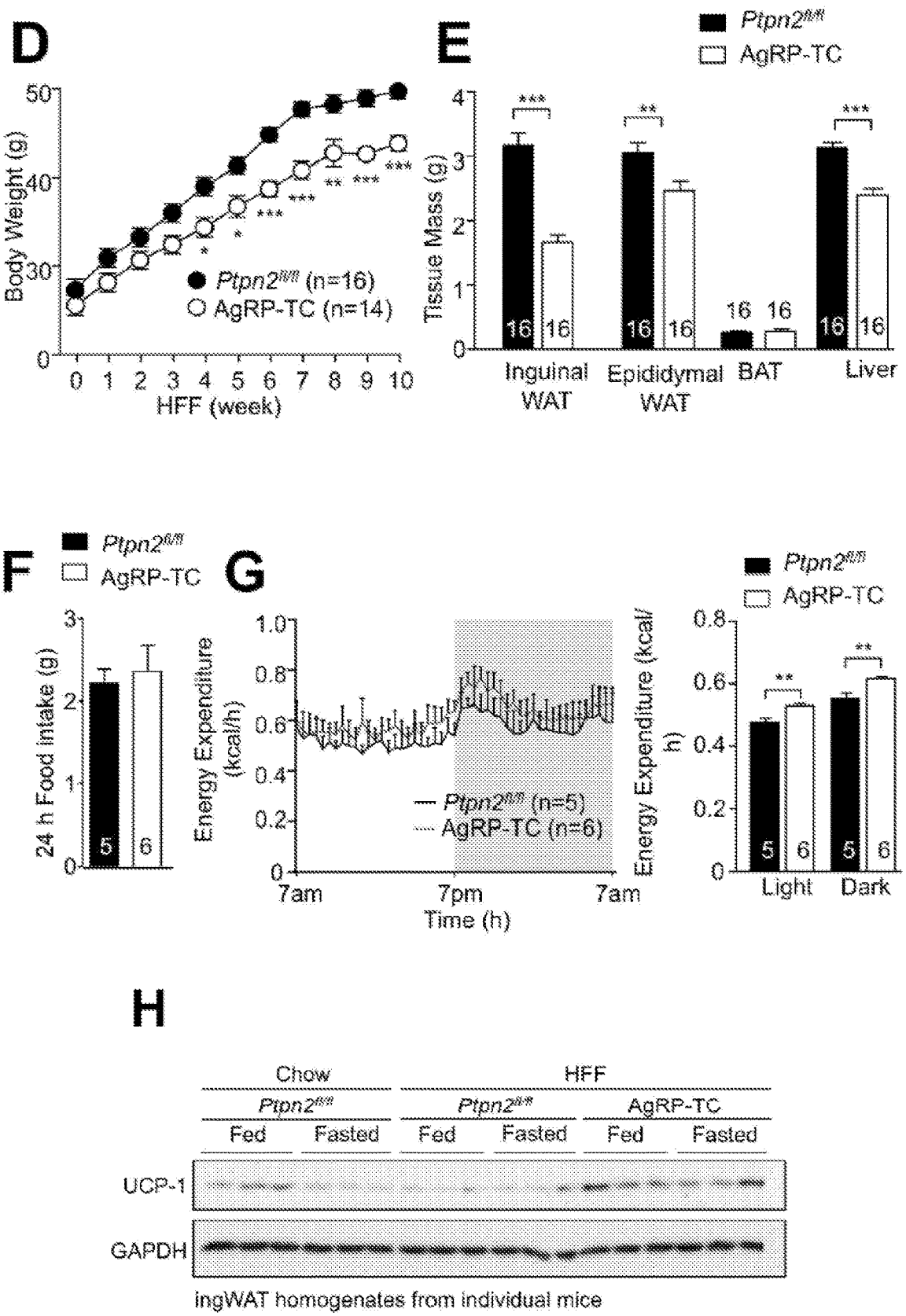
Figure 6:
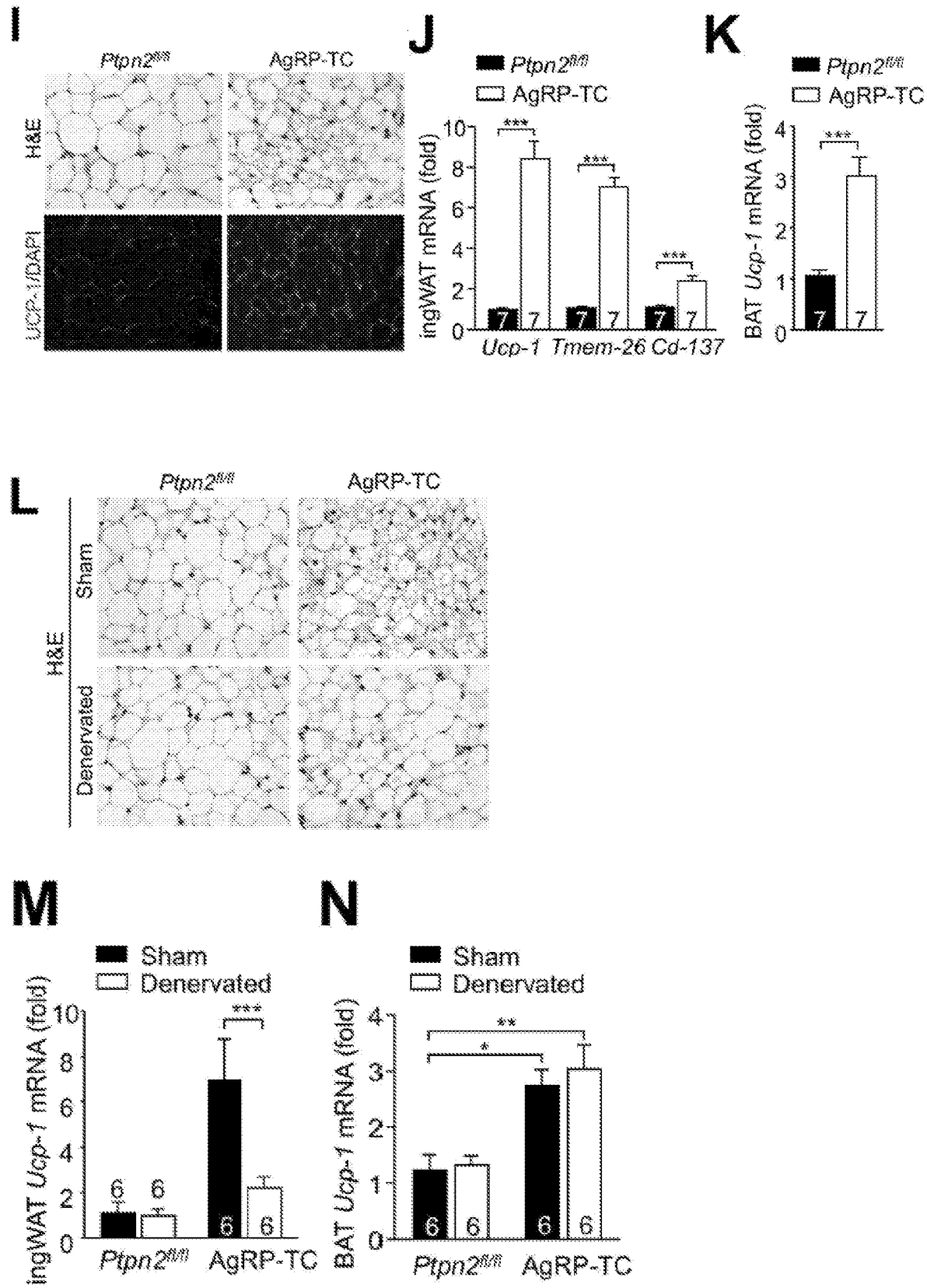
Figure 6:
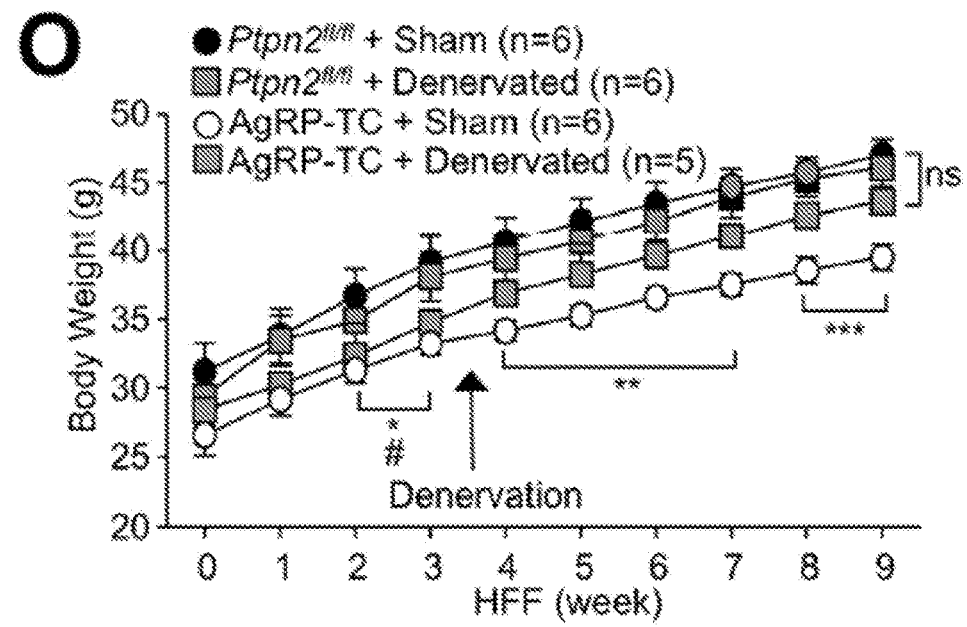
Figure 6:
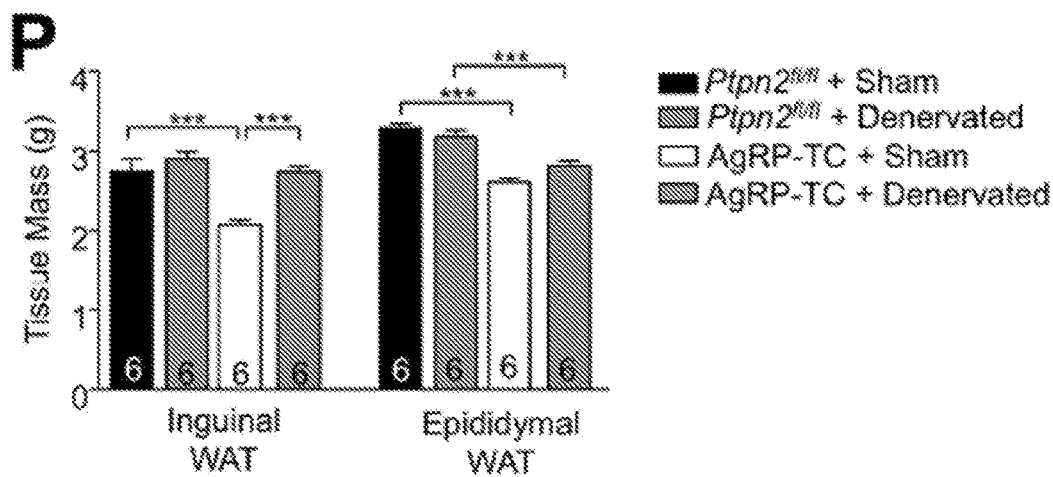
Figure 6:
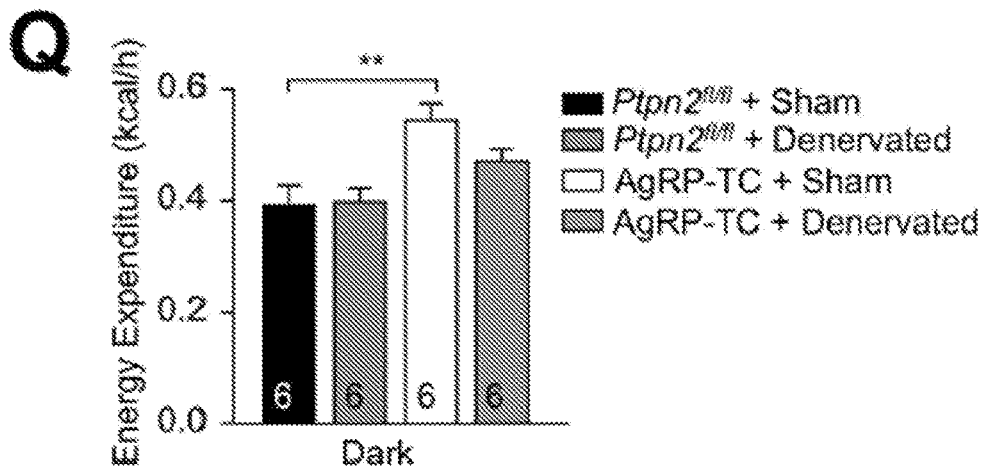
Figure 13:
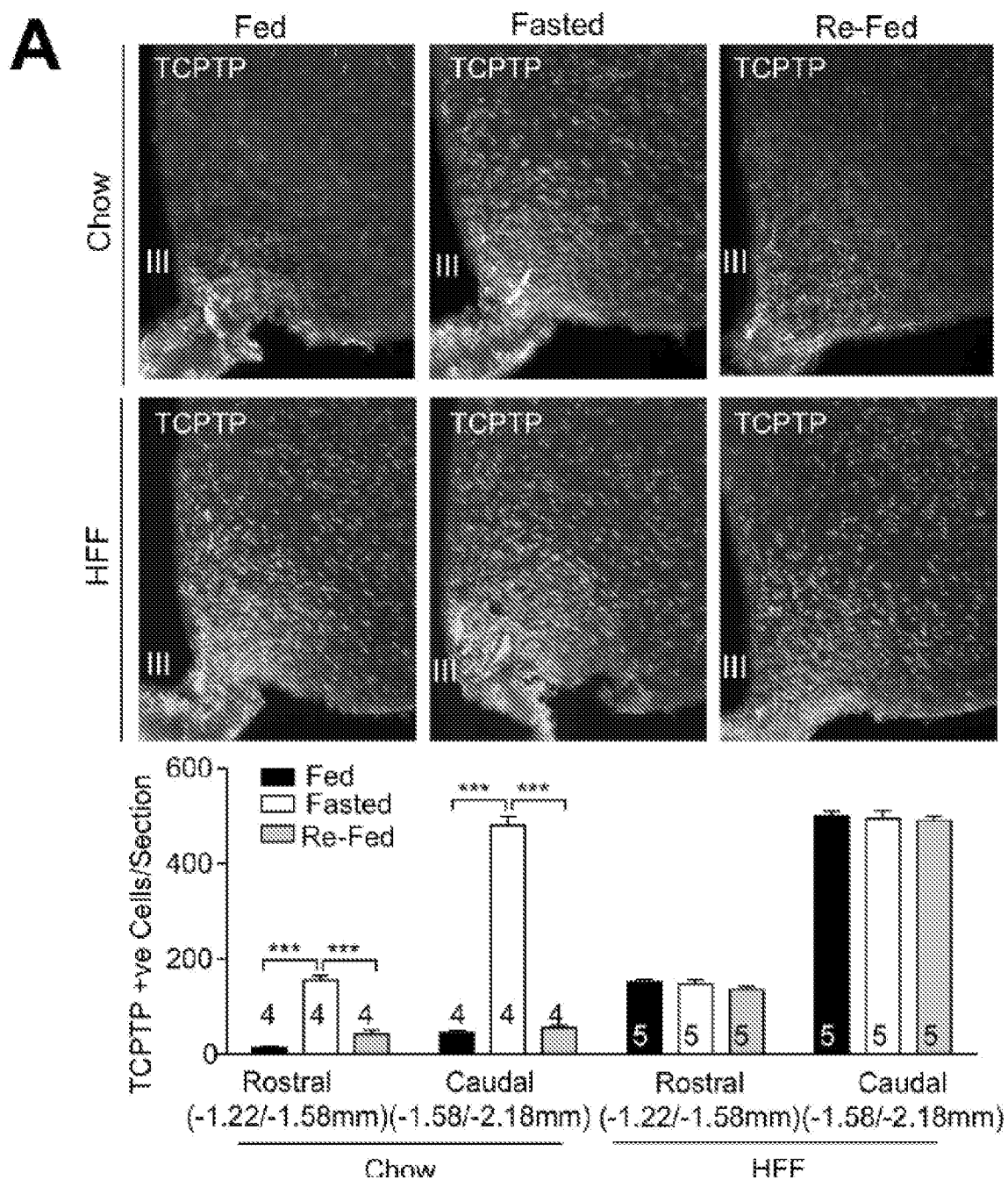
FIG. 13. The feed-fast TCPTP switch in diet-induced obesity and glucose metabolism and WAT browning in Ptpn2$^{fl/fl}$ and AgRP-TC mice. 8-10-week-old male a) C57BL/6 or b) Pomc-eGFP (C57BL/6) mice were chow-fed or high fat fed (HFF) for 8 weeks and brains extracted from fed, fasted (24 h) or re-fed (4 h) mice for hypothalamic immunohistochemistry monitoring for TCPTP and GFP as indicated. c) Body composition (DEXA), d) oxygen consumption, e) RERs and ambulatory activity, in 12 week HFF Ptpn2$^{fl/fl}$ and AgRP-TC male mice. IngWAT depots in Ptpn2$^{fl/fl}$ and AgRP-TC male mice were bilaterally sham-operated or denervated with 6-ODHA (20×1 µl 9 mg/ml injections) after 3 weeks of high fat feeding and after a further 6 weeks of high fat feeding. f) IngWAT extracted and processed for immunohistochemistry. g) Body composition (DEXA) were measured and h) RERs and ambulatory activity determined. Brightness and contrast in colour merge image have been adjusted to assess co-incidence. Representative and quantified results (means±SEM) are shown for the indicated number of mice.
Figure 13:
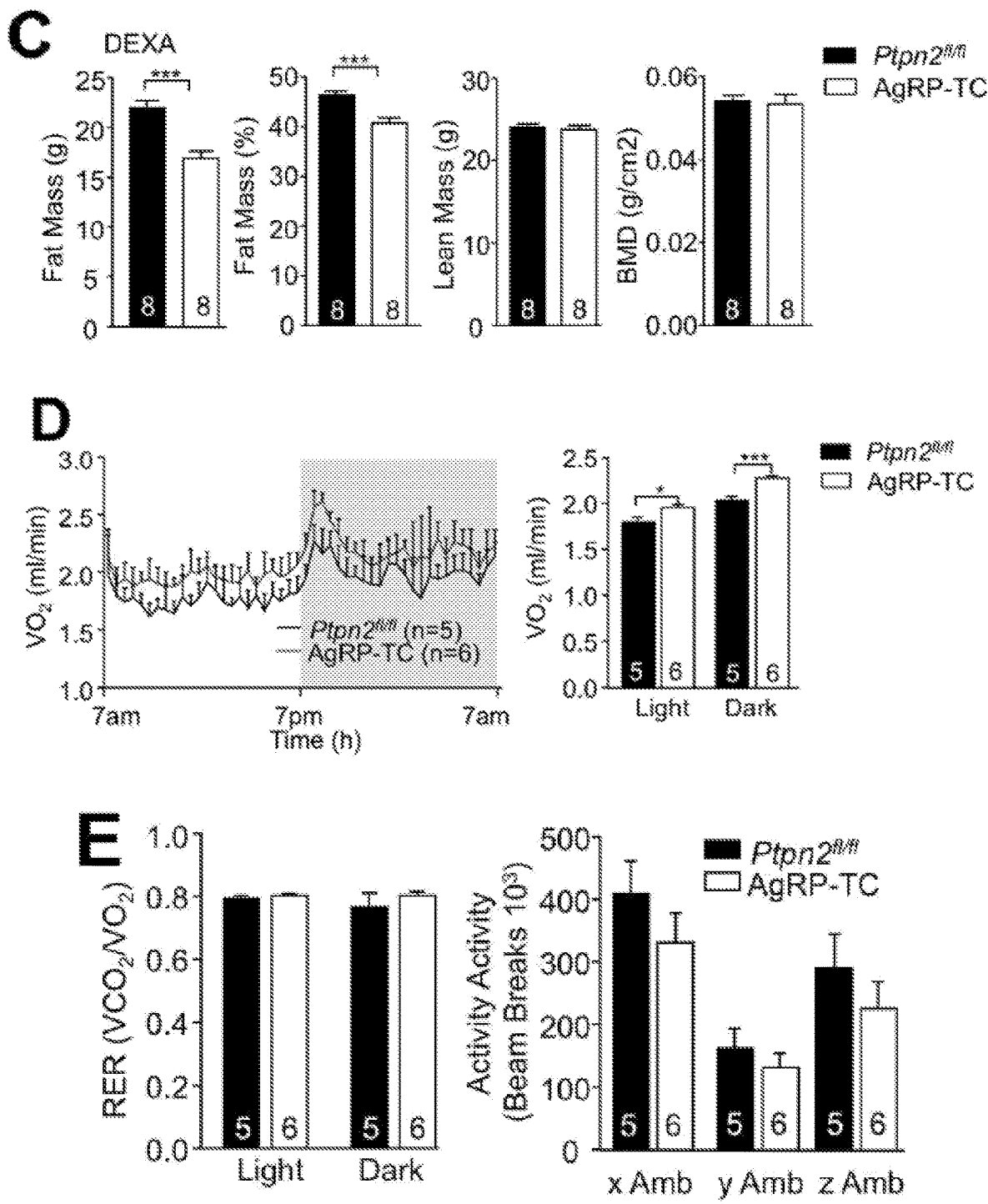
Figure 13:
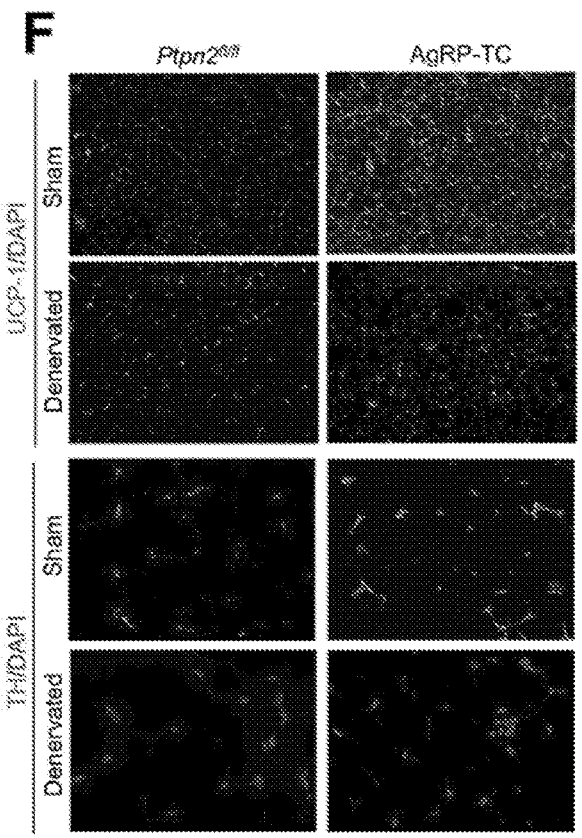
Figure 13:
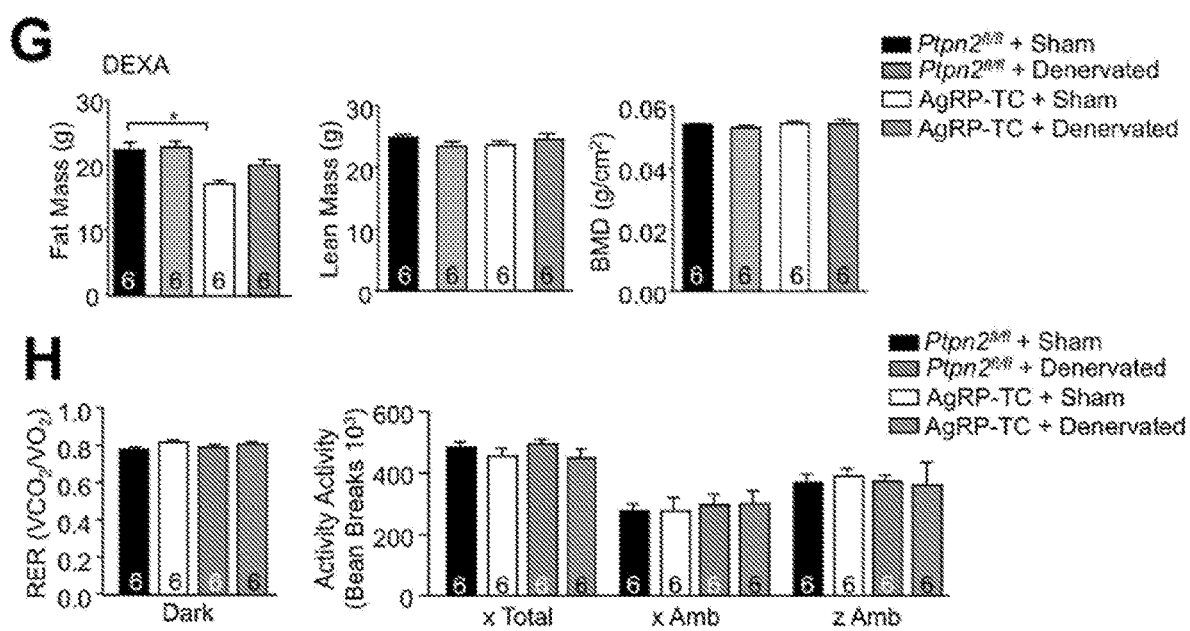

The Feed-Fast TCPTP Switch is Abrogated in Obesity
Hypothalamic TCPTP, along with PTP1B and SOCS3, are elevated in diet-induced obesity and this is thought to contribute to cellular leptin and insulin resistance and exacerbate the development of obesity. It was determined whether the feed-fast TCPTP switch in chow-fed lean mice might be defective in high fat fed obese mice and whether this may be due to sustained Ptpn2 expression. PTP1B, TCPTP and SOCS3 proteins were elevated in the hypothalami of 12-week high fat fed obese mice (FIG. 6a). Neither PTP1B nor SOCS3 protein levels were altered during fasting (24 h) or re-feeding (4 h) in either chow-fed lean, or high fat fed obese mice (FIG. 6a). In contrast, TCPTP levels as assessed by immunoblotting and real time PCR were decreased in chow-fed fasted mice that had been re-fed for 4 h, but not in the corresponding high fat fed mice (FIG. 6a-b). Notably TCPTP levels in re-fed high fat fed mice approximated those in fasted chow-fed mice (FIG. 6a-b; FIG. 13a). Increased TCPTP in re-fed high fat fed mice was evident in both AgRP/NPY (FIG. 6c) and POMC neurons (FIG. 13b). The sustained TCPTP in re-fed high fat fed mice was at least in part due to the defective repression of Ptpn2 expression (FIG. 6b). Therefore the feed-fast TCPTP switch is abrogated in obesity and accompanied by sustained Ptpn2 expression.

AgRP-TC Mice are Resistant to Diet-Induced Obesity
These studies indicate that the feed-fast TCPTP molecular switch is abrogated in obesity, so that ARC POMC and AgRP neuronal TCPTP levels remain elevated in the fed state. Accordingly it was surmised that the elevated TCPTP in AgRP/NPY neurons might inhibit insulin signaling and thereby repress the inactivation of AgRP neurons in the fed state, to suppress WAT browning and energy expenditure and contribute to the development of obesity. To test this, the impact of deleting TCPTP in AgRP neurons on the development of diet-induced obesity was assessed. It was found that TCPTP deletion in AgRP-expressing neurons alone afforded mice resistance to high fat diet-induced obesity (FIG. 6d), associated with a reduction in whole-body adiposity and decreased inguinal and epididymal fat, without changes in lean mass or bone density (FIG. 6e; FIG. 13c). The decreased adiposity was accompanied by unaltered daily food intake (FIG. 6f). In addition, high fat fed AgRP-TC mice exhibited increased light and dark cycle oxygen consumption and energy expenditure (FIG. 6g; FIG. 13d), without changes in ambulatory activity or RER (FIG. 13e).

Inguinal WAT browning as assessed by UCP-1 levels was diminished in 12-week high fat fed Ptpn2$^{fl/fl}$ mice, when compared to chow-fed controls (FIG. 6h). By contrast WAT browning in high fat fed AgRP-TC mice was elevated, approximating that seen in 'fed' chow-fed lean control mice (as assessed by UCP-1 protein levels) (FIG. 6h). The increased WAT browning in AgRP-TC mice was substantiated by the appearance of multi-locular adipocytes expressing UCP-1 (FIG. 6i) and the increased expression of browning genes (Ucp-1, Prdm-16, Cidea, Tmem-26, Cd137; FIG. 6j). AgRP-TC mice also had increased BAT Ucp-1 expression (FIG. 6k) consistent with increased BAT thermogenesis. To determine the extent to which the increased WAT browning may prevent obesity in AgRP-TC mice bilaterally denervation (6-OHDA) of the inguinal fat pads in Ptpn2$^{fl/fl}$ versus AgRP-TC mice was performed after 3 weeks of high fat feeding and measured effects on body weight, adiposity, WAT browning and energy expenditure after a further 6 weeks of high-fat feeding. Bilaterally denervating the inguinal fat pads in high fat fed AgRP-TC mice corrected the increased WAT browning (FIG. 6l-m; FIG. 13f) without affecting BAT Ucp-1 expression (FIG. 6n) and increased weight gain and adiposity so that denervated AgRP-TC mice approximated the corresponding Ptpn2$^{fl/fl}$ controls (FIG. 6o-p; FIG. 13g). The increased adiposity was accompanied by decreased oxygen consumption and dark cycle energy expenditure without overt alterations in RER or ambulatory activity (FIG. 6q; FIG. 13h). Therefore, TCPTP deficiency in AgRP neurons to emulate the 'fed' chow-fed state attenuates the development of diet-induced obesity by promoting SNA-dependent WAT browning.

TCPTP Deletion in Obese Mice Promotes WAT Browning and Weight Loss

Figure 7:
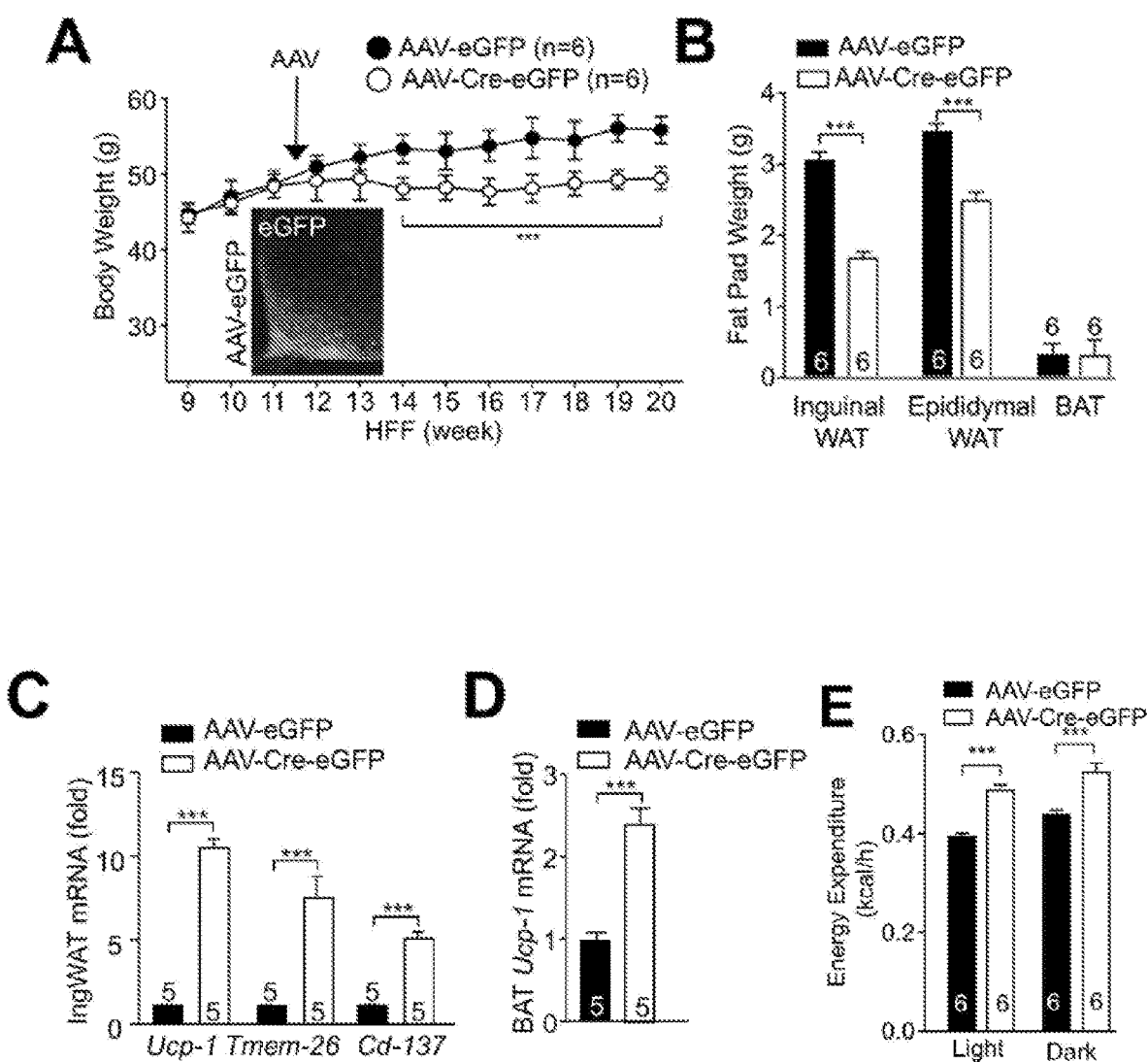
FIG. 7. TCPTP deletion in diet-induced obesity reinstates WAT browning and feeding-induced thermogenesis to promote weight loss. Ptpn2$^{fl/fl}$ male mice were HFF for 12 weeks and bilaterally injected with rAAV-eGFP or rAAV-Cre-eGFP into the ARC. a) Body weights, b) fat pad weights, c) ingWAT mRNA expression, d) BAT mRNA expression and e) energy expenditure were assessed 8 weeks post intra-ARC rAAV injection. ARC targeting was confirmed by the post-mortem analysis of hypothalamic GFP immunofluorescence. Ptpn2$^{fl/fl}$ male mice were HFF for 12 weeks and bilaterally injected with rAAV-eGFP or rAAV-Cre-eGFP into the ARC and ingWAT depots bilaterally sham-operated or denervated with 6-ODHA and f) energy expenditure, g) body weights, h) fat mass (EchoMRI), i) fat pad weights, j) ingWAT gene expression, k) ingWAT histology (H&E), l) in WAT UCP-1 immunohistochemistry and m) BAT gene expression were assessed. Results are shown are means±SEM for the indicated number of mice. * AAV-GFP+Sham versus AAV-Cre-GFP+sham; #AAV-Cre-GFP+sham versus AAV-Cre-GFP+denervation.
Figure 7:
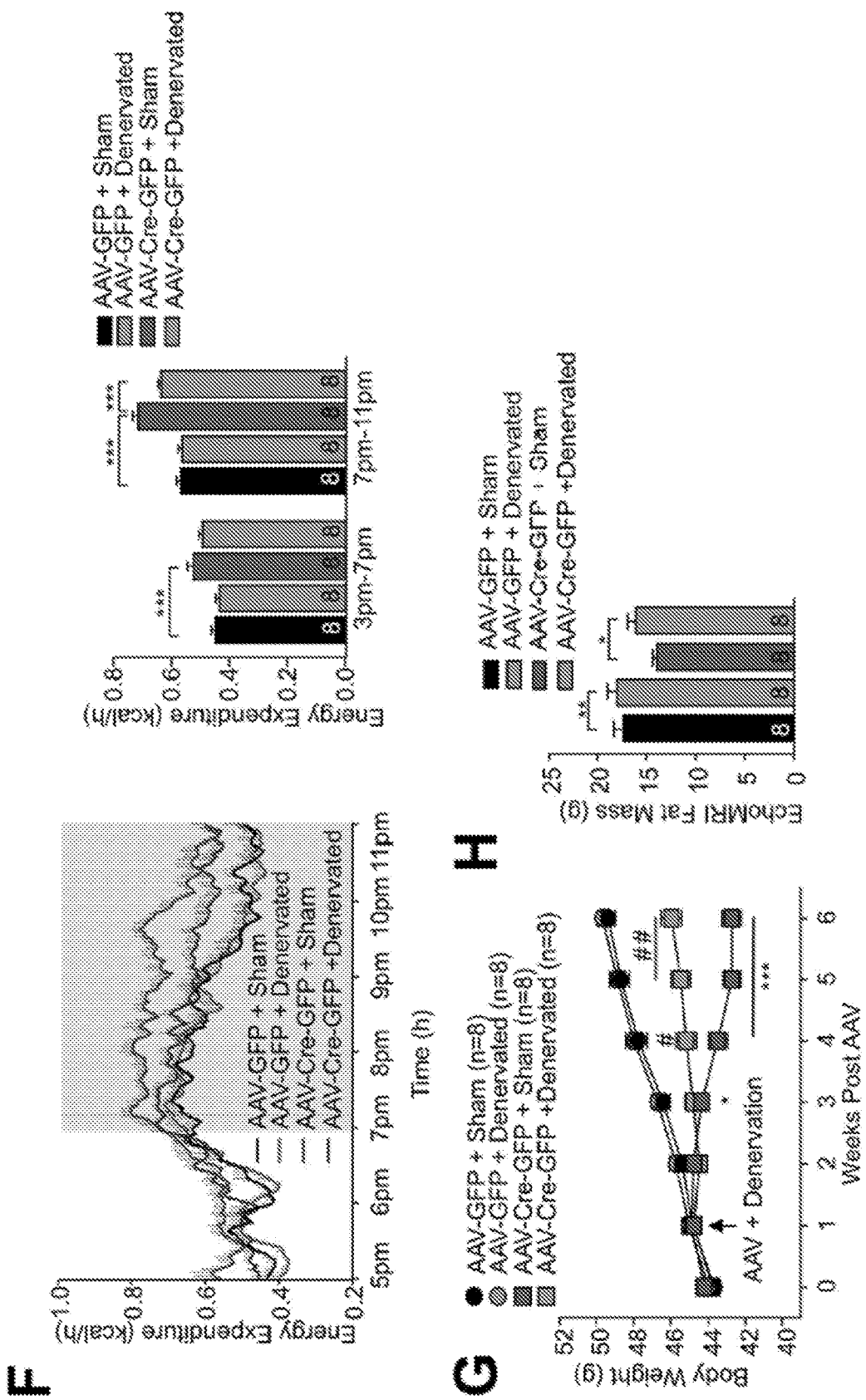
Figure 7:
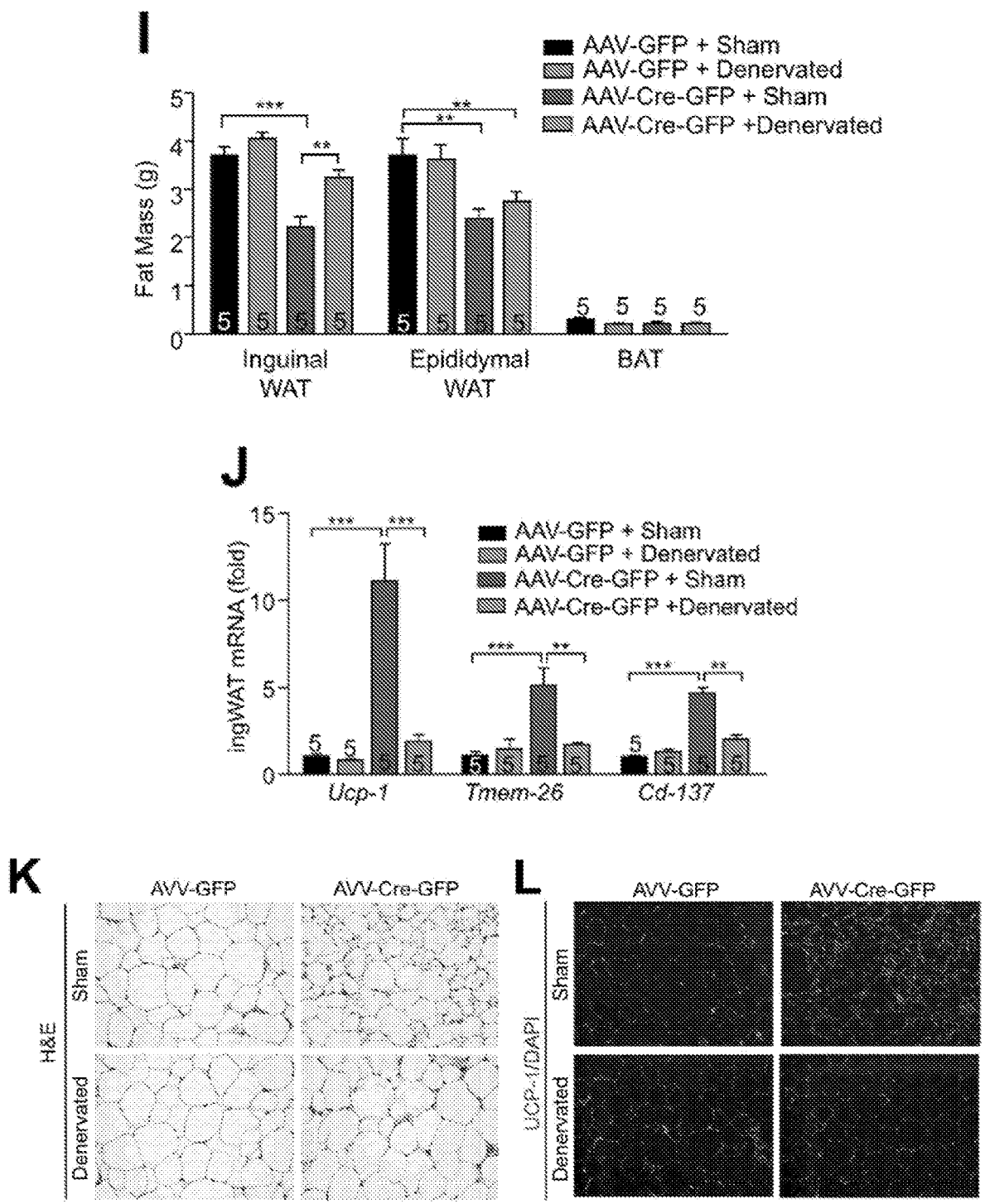
Figure 7:
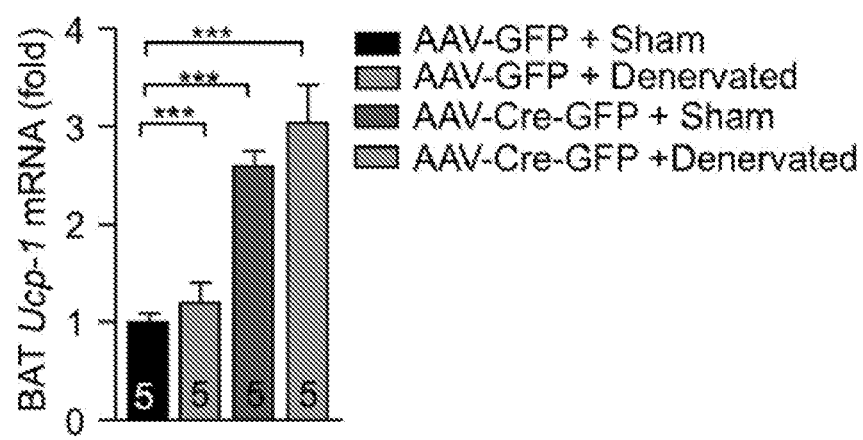
Figure 14:
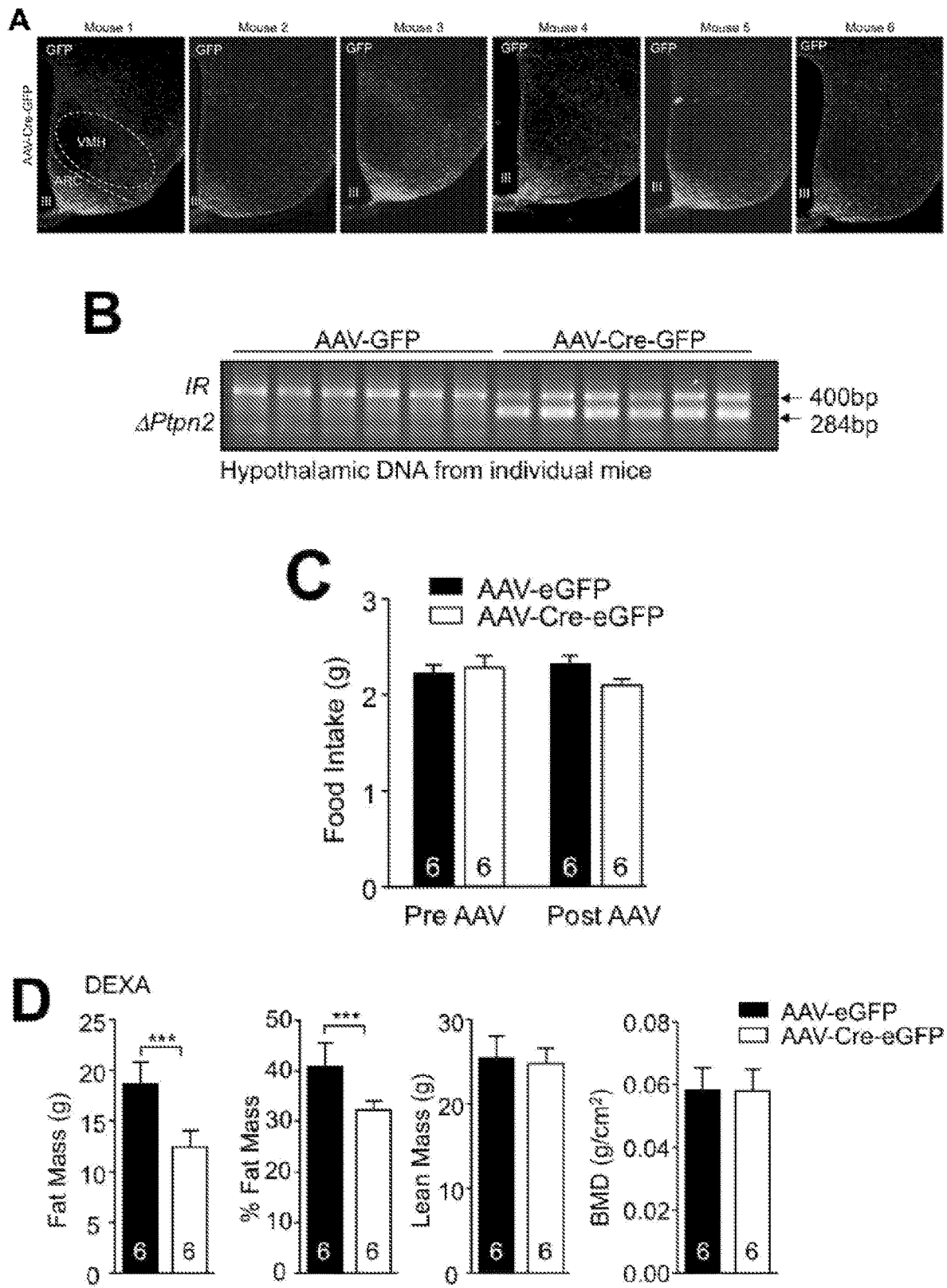
FIG. 14. ARC rAAV-Cre-GFP-mediated recombination in obese Ptpn2$^{fl/fl}$ mice. Ptpn2$^{fl/fl}$ male mice were high fat fed for 12 weeks and bilaterally injected with rAAV-GFP or rAAV-Cre-GFP into the ARC. After 8 weeks brains from individual rAAV-Cre-GFP-administered Ptpn2$^{fl/fl}$ mice (1-6) were extracted and either a) paraformaldehyde-fixed and processed for hypothalamic GFP immunofluorescence to assess ARC targeting, or b) hypothalamic DNA extracted screened for the presence of the recombined Ptpn2 allele (ΔPtpn2) by PCR. After 8 weeks c) 24 h food intake, d) body composition (DEXA), e) oxygen consumption, RER, ambulatory activity and f) daily food intake were determined. Ptpn2$^{fl/fl}$ male mice were high fat fed for 12 weeks and bilaterally injected with rAAV-GFP or rAAV-Cre-GFP into the ARC and ingWAT depots either bilaterally sham-operated or denervated with 6-ODHA (20×1 μl 9 mg/ml injections) and g-h) oxygen consumption and i) energy expenditure measured. Grey shading indicates dark cycle; darker grey shading indicates period where mice feed. Representative and quantified results (means±SEM) are shown for the indicated number of mice.
Figure 14:
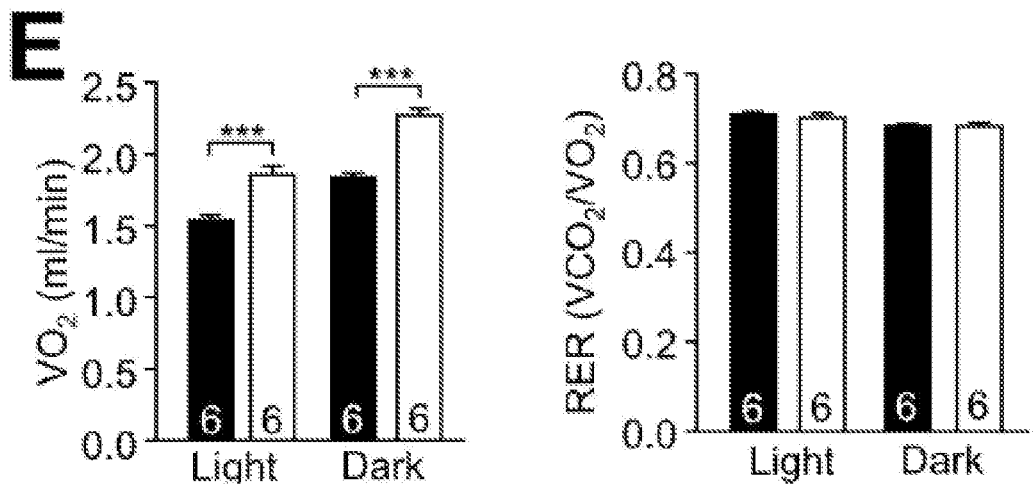
Figure 14:
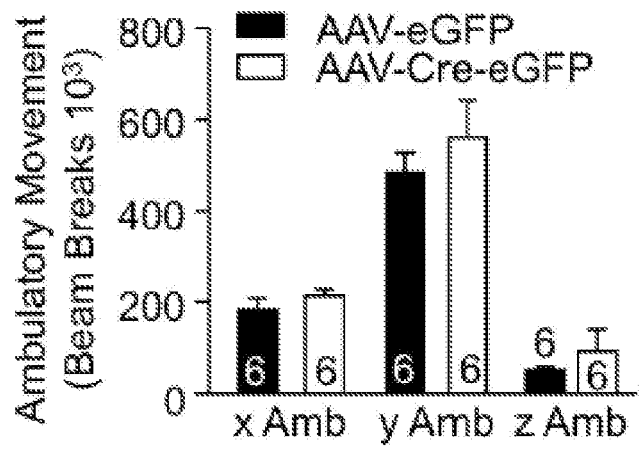
Figure 14:
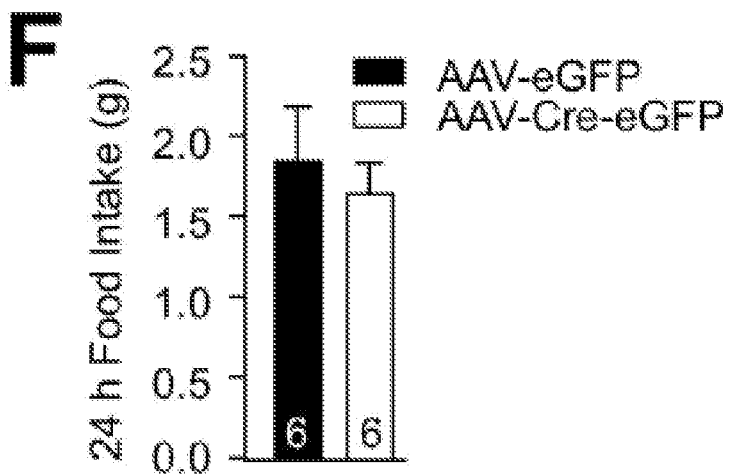
Figure 14:
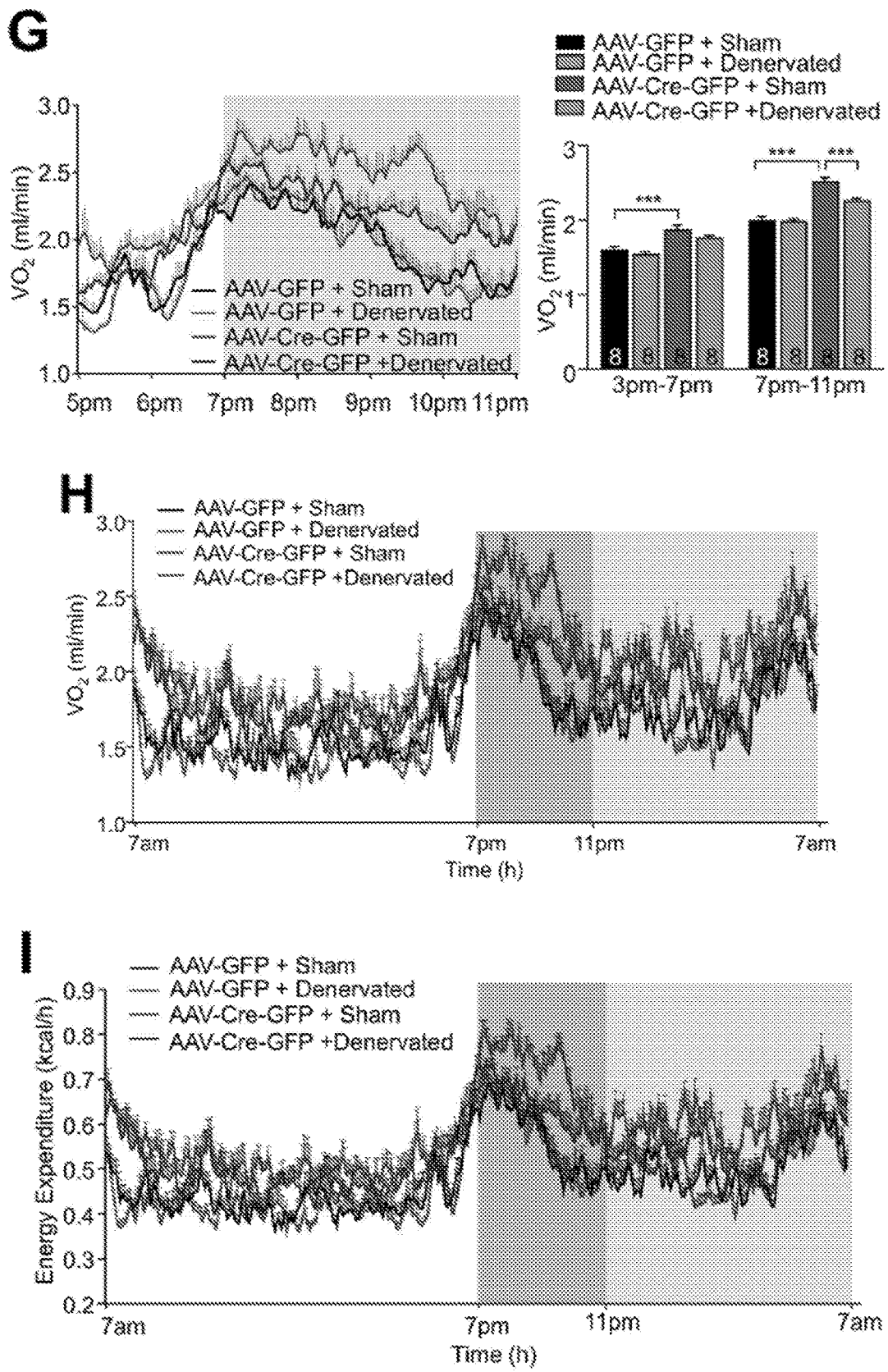

The perturbed hypothalamic TCPTP switch in obesity, was evident not only in AgRP/NPY neurons (FIG. 6c), but also in POMC neurons (FIG. 13b) where sustained TCPTP levels might also serve to repress insulin signaling and coordinately inhibit the melanocortin response. Therefore, to ascertain the extent to which the sustained hypothalamic TCPTP expression contributes to the maintenance of obesity TCPTP was deleted in the ARC of 12-week high fat fed obese mice and monitored for effects on weight loss and WAT browning (FIG. 7; FIG. 14a-b). rAAVs expressing Cre and GFP (rAAV-CMV-Cre-GFP) or GFP alone (rAAV-CMV-GFP) were injected bilaterally into the ARC of high fat fed Ptpn2$^{fl/fl}$ mice and high fat feeding continued for 8 weeks. Post-mortem analyses confirmed efficient targeting of the ARC (FIG. 14a) and TCPTP deletion (FIG. 14b). It was found that TCPTP deletion in the ARC resulted in a sustained apprbrief descoximately 13% weight loss (FIG. 7a), despite the mice continuing to eat a high fat diet (FIG. 14c). The decreased weight was associated with reduced whole body adiposity (FIG. 7b; FIG. 14d). Furthermore, the decreased adiposity was accompanied by increased WAT browning (FIG. 7c), BAT Ucp-1 expression (FIG. 7d) and increased oxygen consumption and energy expenditure without changes in ambulatory activity or daily food intake (FIG. 7e; FIG. 14e-f). The increased energy expenditure was particularly evident during the first 4 h after the start of the dark cycle (FIG. 7f; FIG. 14g-i) consistent with the promotion of feeding-associated energy expenditure. The decreased body weight and adiposity and increased energy expenditure and oxygen consumption could be attenuated by the bilateral denervation (6-OHDA) of the inguinal fat pads (FIG. 7f-i; FIG. 14g-i), which ablated WAT browning (FIG. 7j-l) without affecting BAT Ucp-1 expression (FIG. 7m). Taken together these results are consistent with the defective feeding-induced repression of TCPTP in the ARC, so that TCPTP levels remain elevated, preventing feeding-induced and SNA-dependent WAT browning and energy expenditure and thereby contributing to the development and maintenance of obesity.

Example 4

CNS administration of the glucocorticoid (GR) antagonist (RU486) attenuates obesity driven increases in hypothalamic TCPTP expression.

Figure 15:
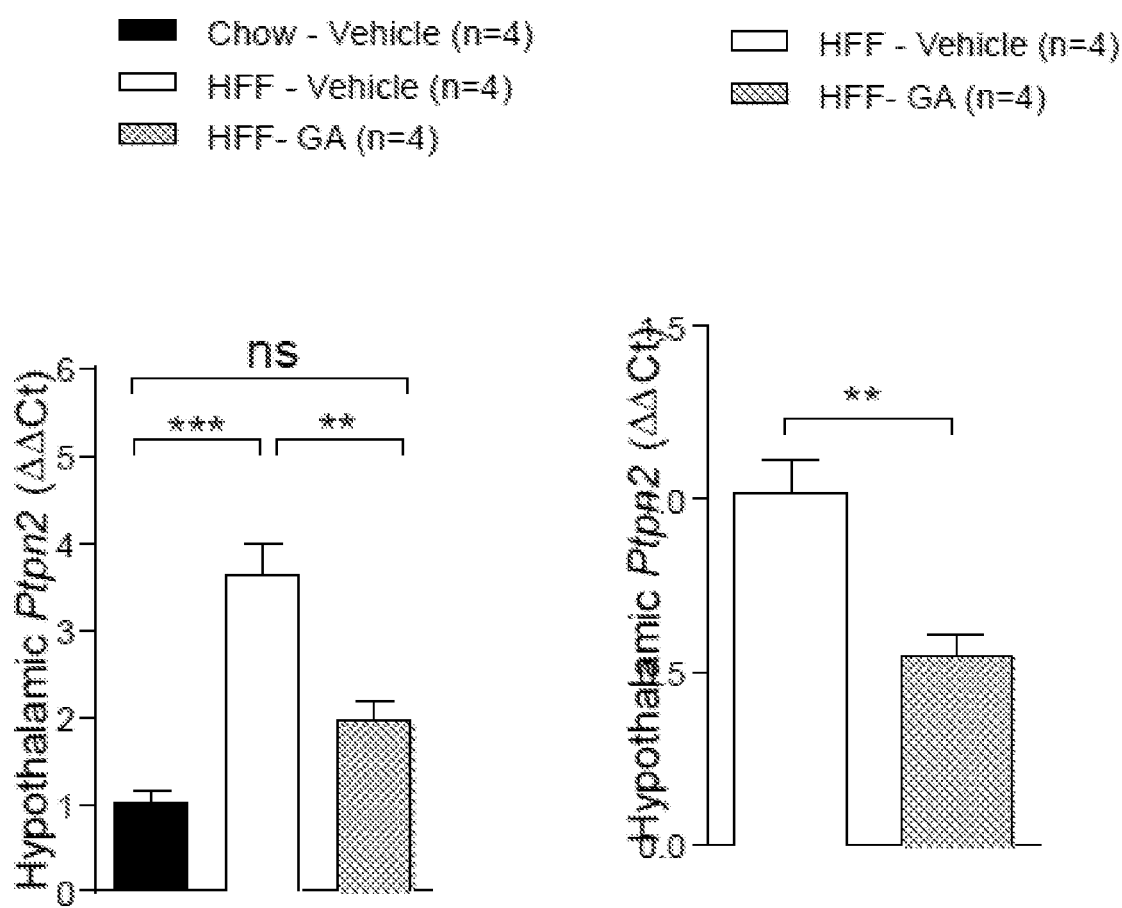
FIG. 15. A glucocorticoid antagonist attenuates obesity driven increases in hypothalamic TCPTP expression. 12 week high fat fed or aged matched chow fed C57BL/6 male mice were administered glucocorticoid antagonist RU486 intracerebroventricularly (ICV; 1 μg/animal), twice daily (10 am & 12 μm) and culled 2 h later (2 μm) for hypothalamic Ptpn2 (encodes TCPTP) gene expression analysis.
Figure 21:
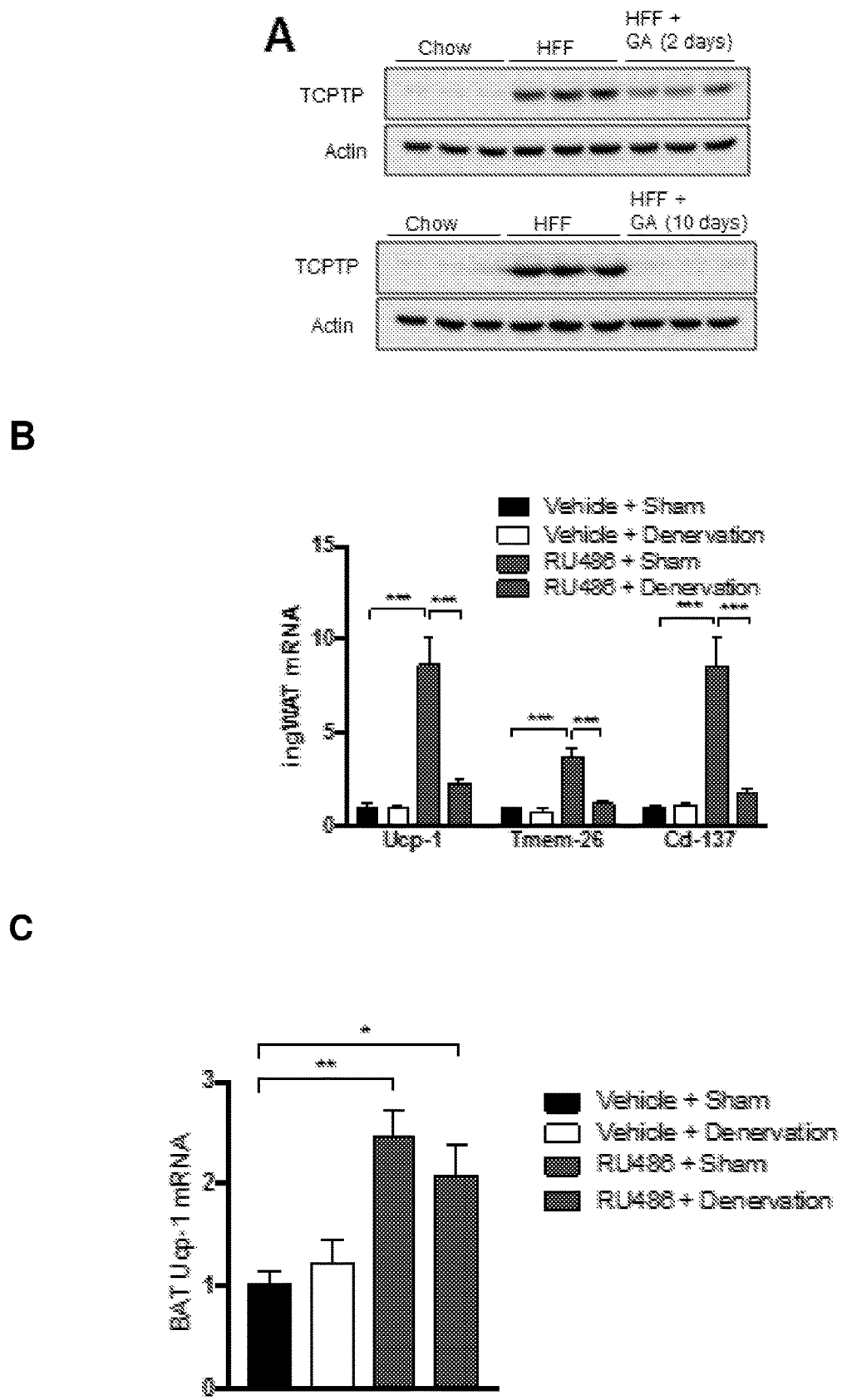
FIG. 21. CNS administration of the glucocorticoid antagonist (RU486) attenuates hypothalamic TCPTP expression to protect against diet-induced obesity via the promotion of WAT browning and energy expenditure. 12-week high fat fed or aged matched chow fed mice C57BL/6 male mice received glucocorticoid antagonist (RU486; 1 ug/animal/day; ICV) for 2 or 10 consecutive days and mediobasal hypothalami were extracted for TCPTP a) protein expression. b) Inguinal white adipose tissue and b) brown adipose tissue was extracted for quantitative PCR analysis.

12-week high fat fed or aged matched chow fed mice C57 male mice were mice received glucocorticoid (GR) antagonist RU486 administration intracerebroventricularly (1 μg/animal), and culled 2 h later (2 μm) for hypothalamic TCPTP protein and gene expression analysis (FIG. 15 and FIG. 21a). Abbreviation; HFF, high fat fed. GR antagonist (Mifepristone, RU486, FDA approval as a foetal abortive and for the treatment of Cushing's syndrome) delivered intracebroventrically (into the brains ventricular system, by-passing any peripheral effects of the drug) significant attenuates the elevated hypothalamic TCPTP (as encoded by the Ptpn2 gene) expression of diet-induced obese mice (fed a high fat diet for 8 weeks). This attenuation of TCPTP expression is similar to that of lean mice (fed a standard laboratory diet). This evidence suggests that GR antagonists delivered directly into the brain attenuates hypothalamic TCPTP expression.

The GR antagonist (RU486) delivered into the CNS promotes weight loss and attenuates adiposity.

Figure 16:
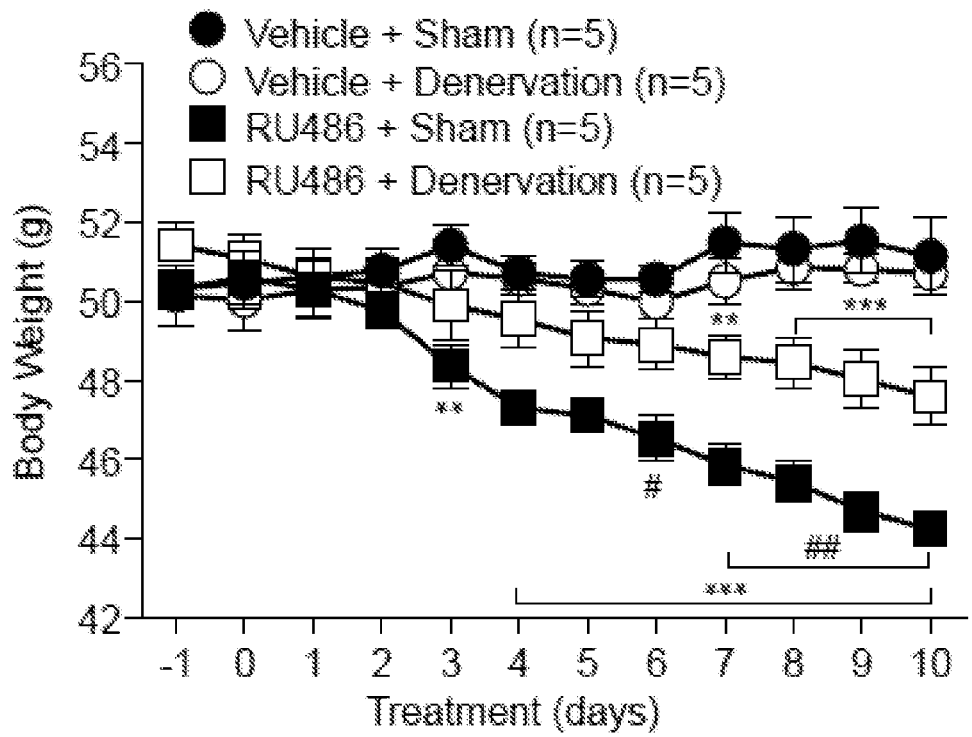
FIG. 16. A glucocorticoid antagonist reduces body weight/adiposity in obese mice by promoting white adipose tissue (WAT) browning. 12 week high fat fed C57BL/6 male mice were mice were sham or bi-laterally denervated (6-ODHA) to prevent WAT browning and then administered the glucocorticoid antagonist RU486 intracerebroventricularly (ICV; 1 μg/animal), twice daily (9 am & 7 μm) for 10 consecutive days. Effects on body weight and adiposity (EchoMRI and fad pad weight) were determined. WAT browning was assessed by gross morphology.
Figure 16:
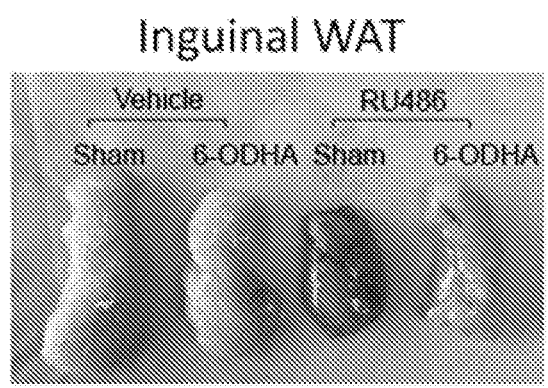
Figure 16:
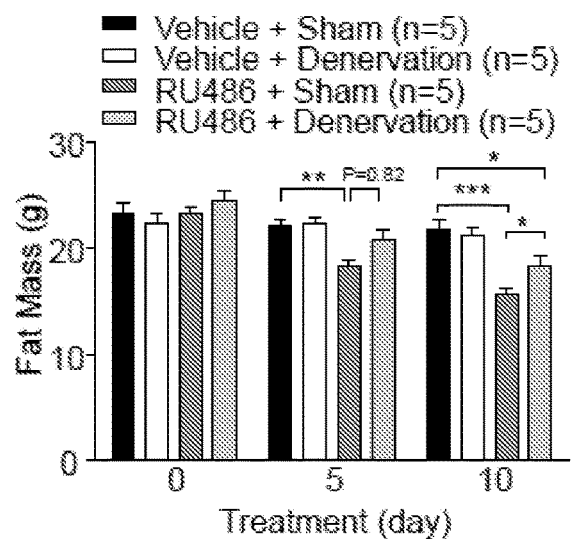
Figure 16:
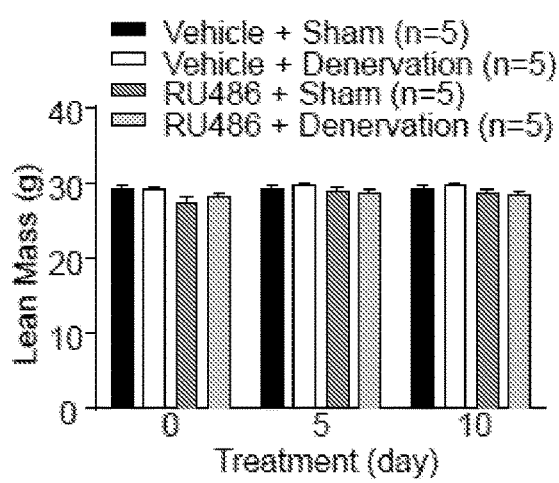
Figure 16:
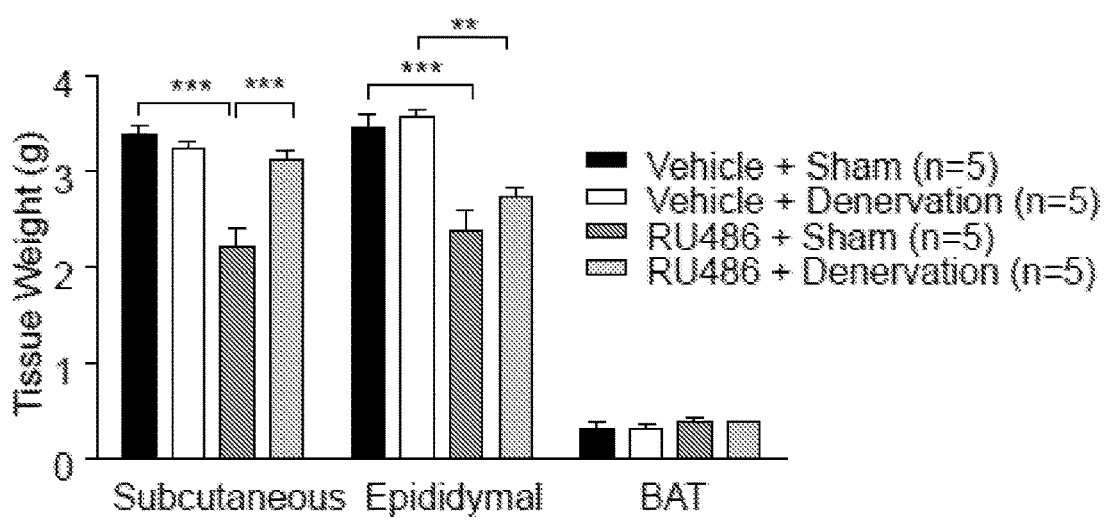

FIG. 16 shows results from 12-week high fat fed C57BL/6 male mice that were mice were sham or bi-laterally denervated (6-ODHA) and received GR antagonist RU486 administration intracerebroventricularly (1 μg/animal) for 10 consecutive days. Effects on body weight and adiposity (EchoMRI and fat pad weight) were determined. GR antagonist (Mifepristone, RU486) delivered intracebroventrically daily for 10 days dramatically attenuates body weight and adiposity by promoting energy expenditure via adaptive thermogenesis (FIG. 21m-n). Importantly these effects on body weight are not accompanied by adverse behaviours such as inactivity, hyperactivity or sedation. This is direct evidence that targeting CNS GR action in a diet-induced obese state leads to significant weight-loss in mice. Targeting CNS GR via intranasal delivery of GR antagonists in humans may therefore be a therapeutically significant viable way to treat metabolic disease.

CNS administration of the GR antagonist (RU486) promotes energy expenditure without any obvious adverse behavioural effects.

Figure 17:
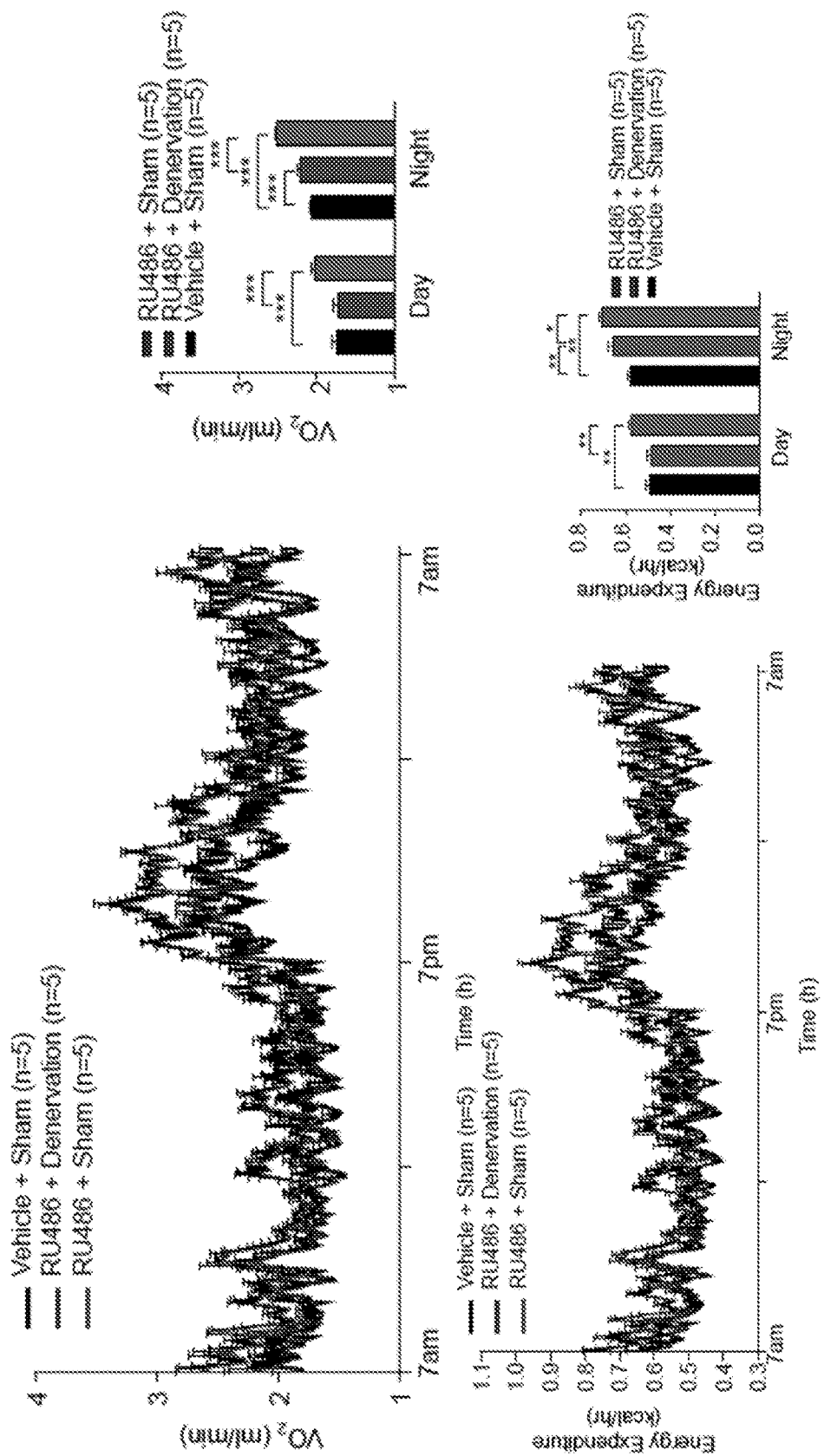
FIG. 17. A glucocorticoid antagonist promotes WAT browning and increases energy expenditure without any obvious adverse behavioral effects. 12 week high fat fed C57BL/6 male mice were mice were sham operated or bi-laterally denervated (6-ODHA) and administered glucocorticoid antagonist RU486 intracerebroventricularly (ICV; 1 μg/animal), twice daily (9 am & 7 μm) for 10 consecutive days. Effects on energy expenditure (indirect calorimetry) and stereotypical behaviors were determined using the Promethion metabolic cage system.
Figure 17:
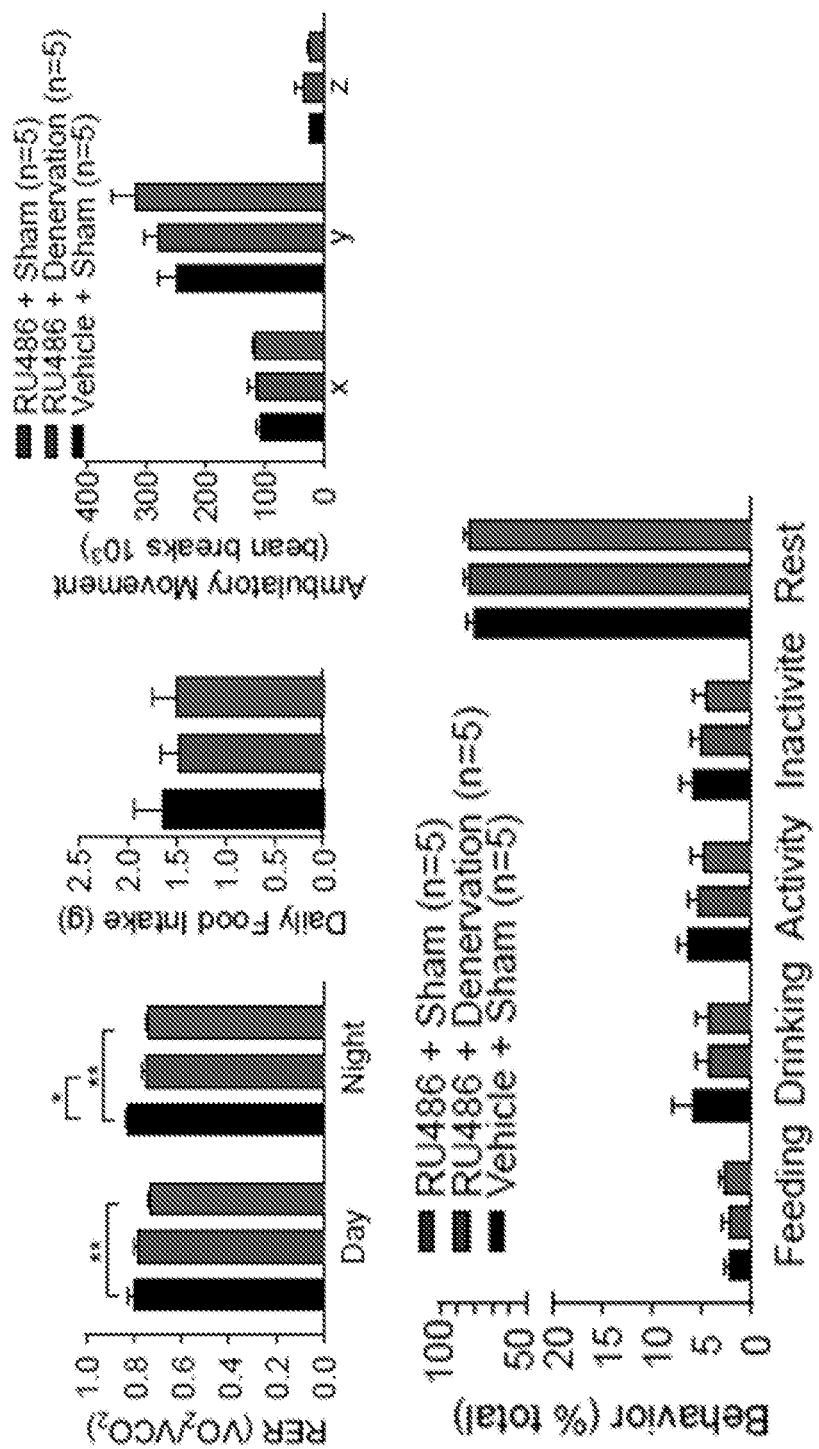

FIG. 17 shows 12-week high fat fed C57BL/6 male mice were sham or bi-laterally denervated (6-ODHA) and received GR antagonist RU486 administration intracerebroventricularly (1 μg/animal) for 10 consecutive days. Effects on energy expenditure and stereotypical behaviours were determined using the Promethion metabolic cages system.

ARC deletion of TCPTP or intra-ARC infusion of TCPTP inhibitor enhances diet-induced weight loss.

Figure 18:
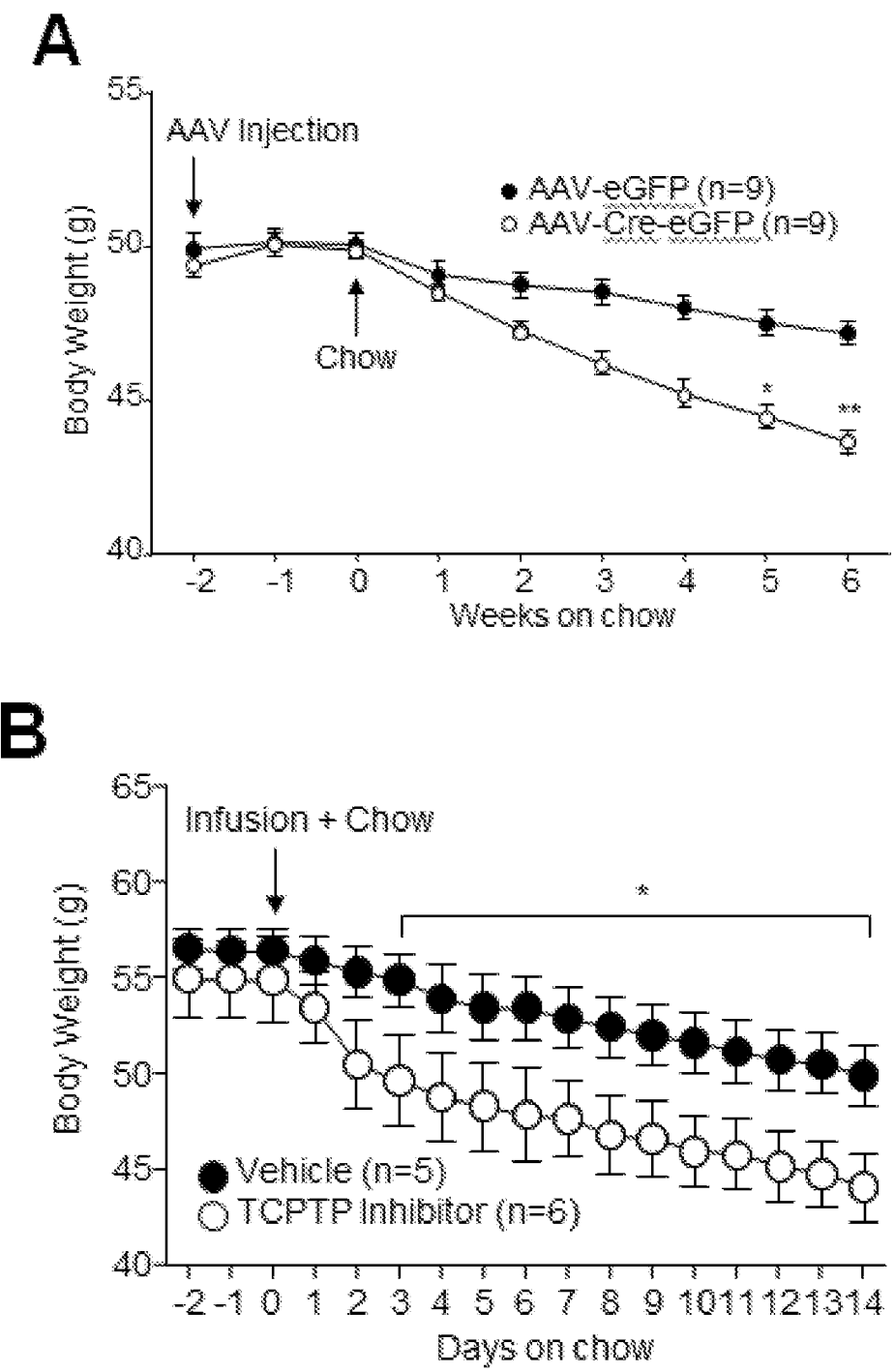
FIG. 18. ARC deletion of TCPTP or intra-ARC infusion of TCPTP inhibitor enhances diet-induced weight loss. a) 20-week high-fat fed (23% fat) Ptpn2$^{fl/fl}$ male mice were bilaterally injected with AAV-control or AAV-Cre into the ARC. 2-weeks post AAV injection mice were placed on chow diet (9% fat) and weekly body weight was monitored. b) 20-week high fat fed (23% fat) C57BL/6 male mice were implanted with bilateral intraARC cannula connected to Alzet osmotic minipumps (Alzet, 1002) and infused with vehicle or TCPTP inhibitor (compound 8 as described herein, 0.5 nmol/day at a rate of 0.25 ul/h). Mice were placed on chow diet (9% fat) and daily body weight was monitored.

FIG. 18 shows in a) 20-week high-fat fed (23% fat) Ptpn2$^{fl/fl}$ male mice were bilaterally injected with AAV-control or AAV-Cre into the ARC. 2-weeks post AAV injection mice were placed on chow diet (9% fat) and weekly body weight was monitored. b) 20-week high fat fed (23% fat) C57BL/6 male mice were implanted with bilateral intra-ARC cannula connected to Alzet osmotic minipumps (Alzet, 1002) and infused with vehicle or TCPTP inhibitor (compound 8, 0.5 nmol/day at a rate of 0.25 ul/h). Mice were placed on chow diet (9% fat) and daily body weight was monitored. These results clearly show that genetic ablation or pharmacological inhibition of TCPTP enhances diet-induced weight loss.

Genetic ARC deletion of TCPTP and PTP1B combined has a synergistic action on body weight loss.

Figure 19:
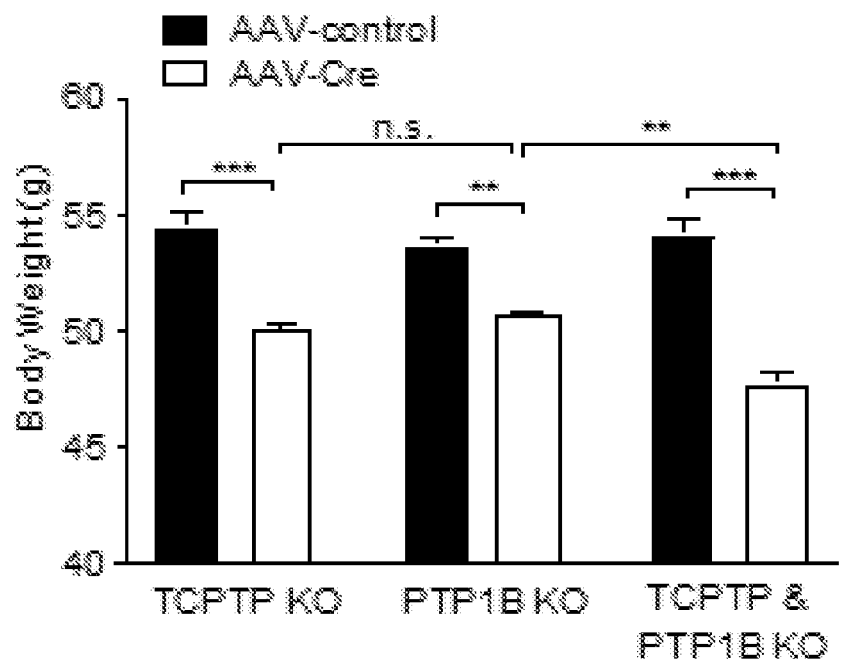
FIG. 19. Genetic deletion of TCPTP and PTP1B in the ARC combined has a synergistic action on body weight loss. Ptpn2$^{fl/fl}$, Ptp1b$^{fl/fl}$ or Ptpn2$^{fl/fl}$; Ptpn1b$^{fl/fl}$ male mice were HFF for 12-weeks and bilaterally injected with AAV-control or AAV-Cre into the ARC and body weight monitored 8 weeks post AAV injection. Abbreviation; AAV, adeno-associated virus.

FIG. 19 shows $Ptpn2^{fl/fl}$, $Ptp1b^{fl/fl}$ or $Ptpn2^{fl/fl}$; $Ptpn1b^{fl/fl}$ male mice that were HFF for 12-weeks and bilaterally injected with AAV-control or AAV-Cre into the ARC and body weight monitored 8 weeks post AAV injection. Abbreviation; AAV, adeno-associated virus. Combined genetic deletion of TCPTP and PTP1B in the ARC of diet-induced obese mice has a more dramatic effect on weight-loss than deletion of TCPTP or PTP1B alone. This suggests that the combined targeting of hypothalamic TCPTP and PTP1B via, for example, intranasal delivery of GR antagonists (or a direct TCPTP inhibitor) and PTP1B inhibitors in humans is a highly therapeutically significant viable way to treat obesity.

Deletion of TCPTP and PTP1B in the ARC enhances energy expenditure in diet-induced obese mice.

Figure 20:
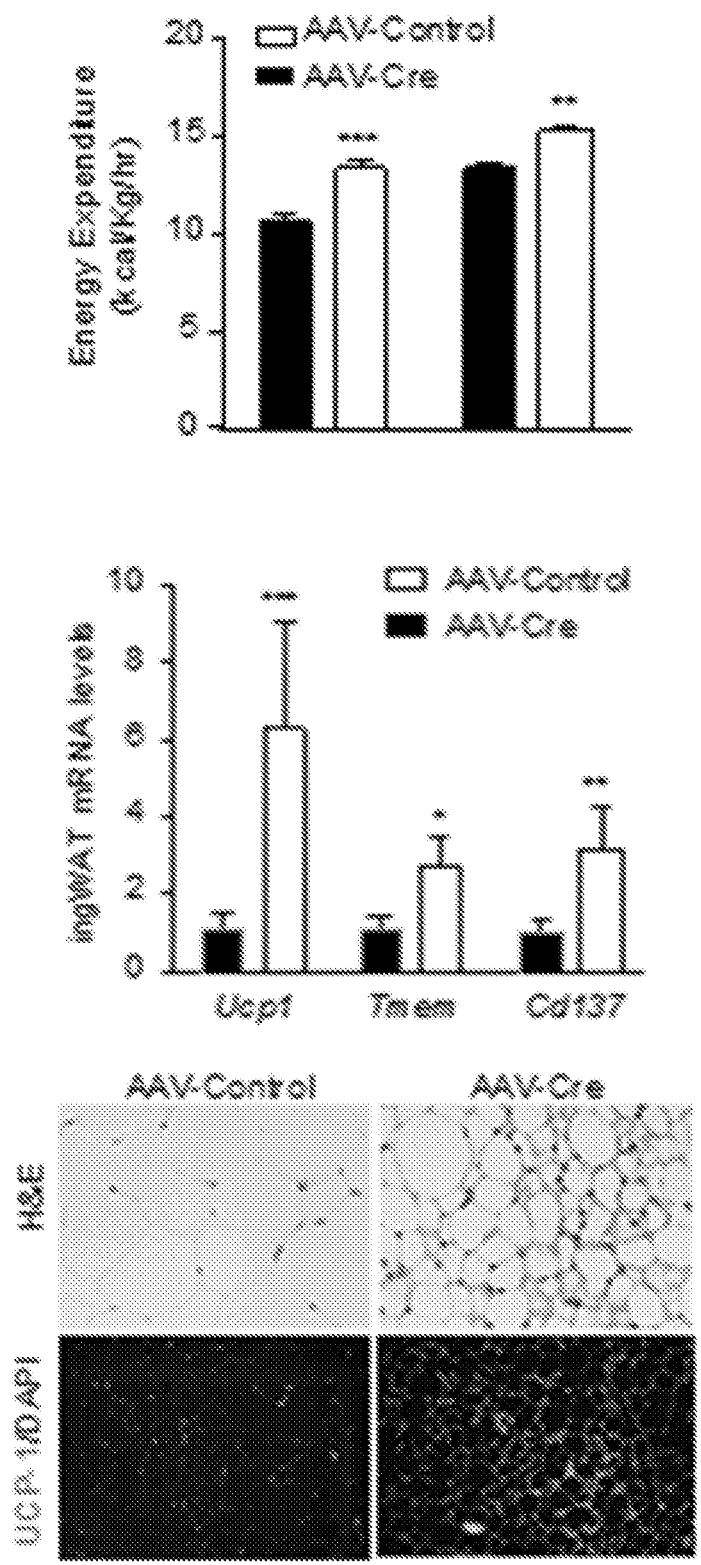
FIG. 20. Deletion of TCPTP and PTP1B in the ARC enhances energy expenditure in diet-induced obese mice. Ptpn2$^{fl/fl}$; Ptpn1b$^{fl/fl}$ male mice were HFF for 12-weeks and bilaterally injected with AAV-control or AAV-Cre into the ARC and energy expenditure, WAT browning was assessed 5-8 weeks post AAV injection. Abbreviations; AAV, adeno-associated virus; WAT; white adipose tissue.

FIG. 20 shows $Ptpn2^{fl/fl}$; $Ptpn1b^{fl/fl}$ male mice that were HFF for 12-weeks and bilaterally injected with AAV-control or AAV-Cre into the ARC and energy expenditure, WAT browning was assessed 5-8 weeks post AAV injection. Abbreviation; AAV, adeno-associated virus; WAT; white adipose tissue. Combined genetic deletion of TCPTP and PTP1B in the ARC of diet-induced obese mice enhanced energy expenditure via the promotion of WAT browning. This suggests that the combined targeting of hypothalamic TCPTP and PTP1B via, for example, intranasal delivery of GR antagonists (or a direct TCPTP inhibitor) and PTP1B inhibitors in humans may attenuate obesity by enhancing energy expenditure via the promotion of WAT browning.

These studies indicate that the energy expenditure specifically associated with feeding in chow-fed lean mice is reduced in diet-induced obesity. It is proposed that this might occur as a consequence of the sustained hypothalamic TCPTP and/or PTP1B levels and repressed WAT browning, since reinstating the feeding-induced TCPTP and/or PTP1B switch by deleting TCPTP and/or PTP1B in the ARC of obese mice, or pharmacologically inhibiting TCPTP and/or PTP1B promoted WAT browning, energy expenditure and weight loss even in the context of ongoing high fat feeding.

Obesity is recognised as the world's fastest growing chronic conditions, costing more than $2 trillion of global health expenditure and >6.5 million deaths globally each year. With the ever-increasing obesity epidemic and the unsustainable treatment costs of associated co-morbidities (cancer, cardiovascular disease and stroke), there has never been a more desperate need to devise effective treatment strategies. The inventors have shown that pharmacologically inhibiting TCPTP and/or PTP1B, for example by delivering glucocorticoid antagonists or direct TCPTP inhibitors to the brain, enhances energy expenditure and reduces adiposity via the promotion of white adipose tissue (WAT) browning. The inventors demonstrate that pharmacologically repressing the expression of the phosphatase TCPTP and/or PTP1B enhances the response of hypothalamic neurons to insulin and thereby promote WAT browning. Finally, the inventors have demonstrated that pharmacological small molecules such as direct TCPTP or PTP1B phosphatase inhibitors or glucocorticoid antagonists delivered to the brain can promote energy expenditure and weight loss in obesity.

Example 5

CNS administration of GR antagonist (RU486) dose dependently attenuates body weight, adiposity and energy expenditure but not food intake in diet-induced obese mice.

Figure 22:
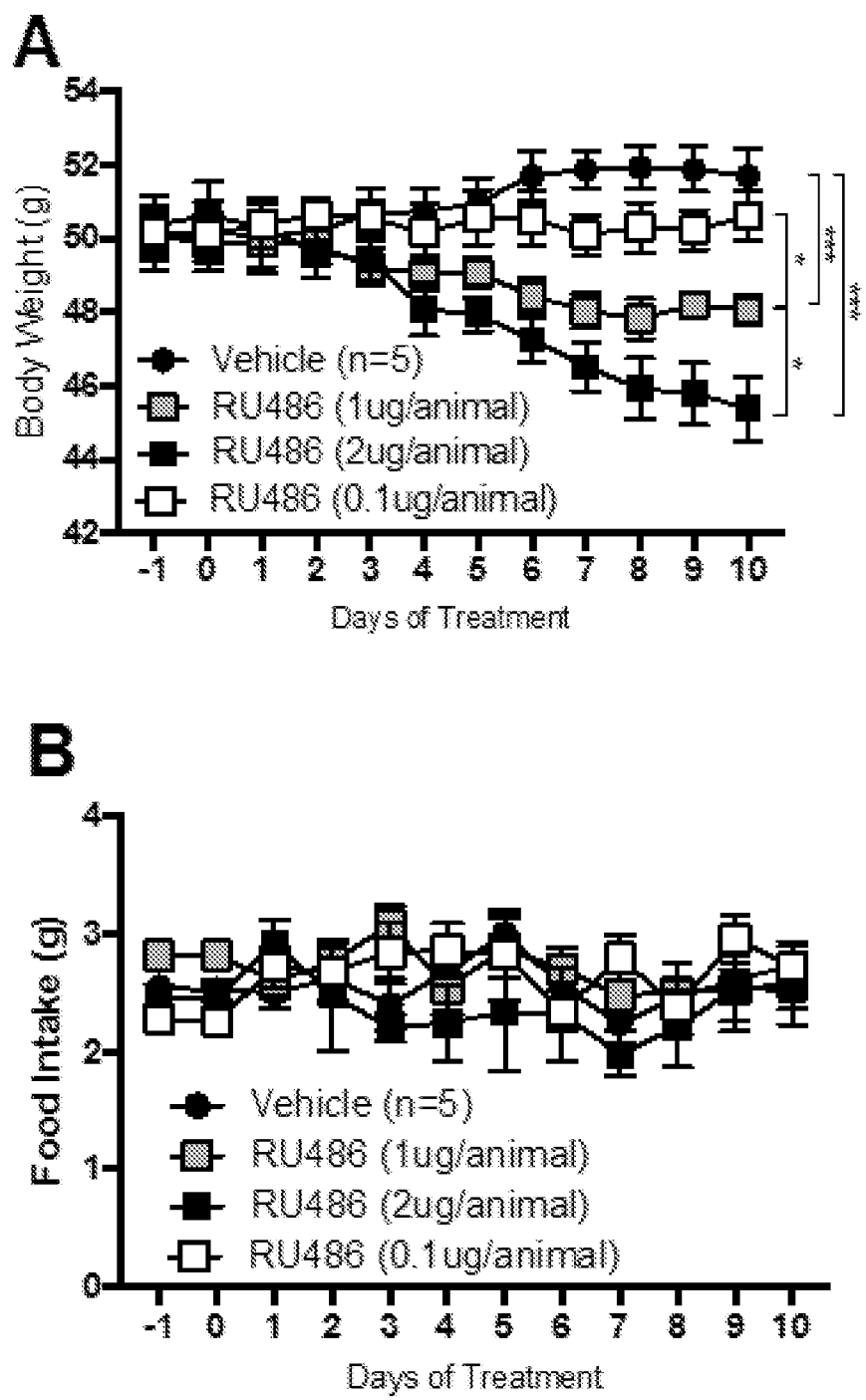
FIG. 22. CNS administration of glucocorticoid antagonist (RU486) dose dependently attenuates body weight, adiposity and energy expenditure but not food intake in diet-induced obese mice. 12-week high fat fed C57BL/6 male mice received glucocorticoid antagonist (RU486: 0.1, 1 and 2 μg/animal/day, ICV) for 10 consecutive days and a) body weights, b) food intake, c) adiposity (EchoMRI and fad pad weight), d) energy expenditure were determined.
Figure 22:
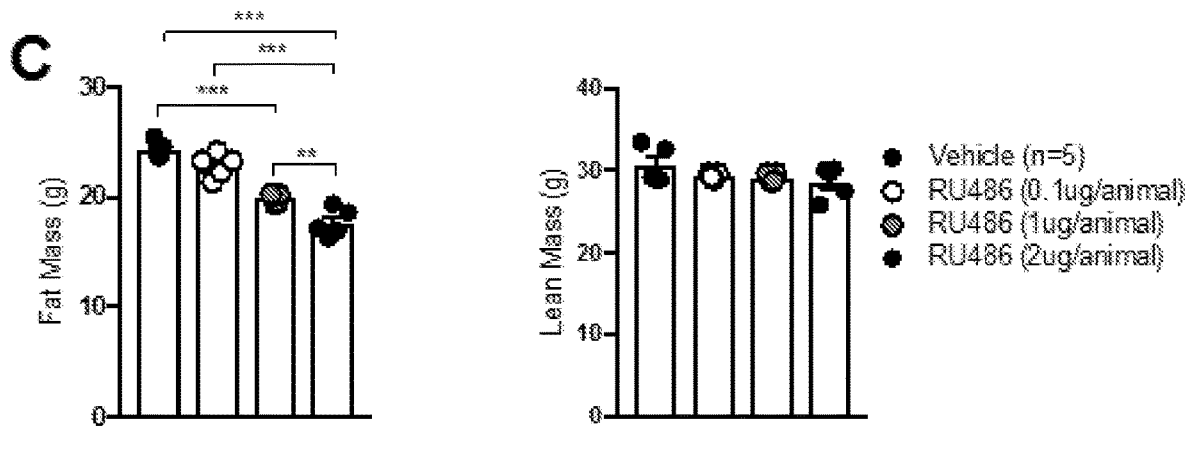
Figure 22:
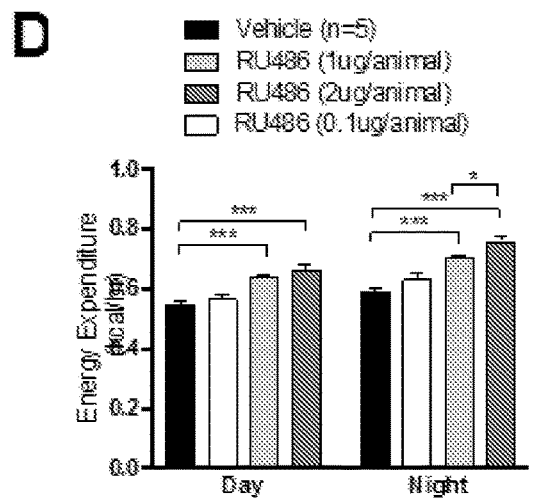
Figure 22:
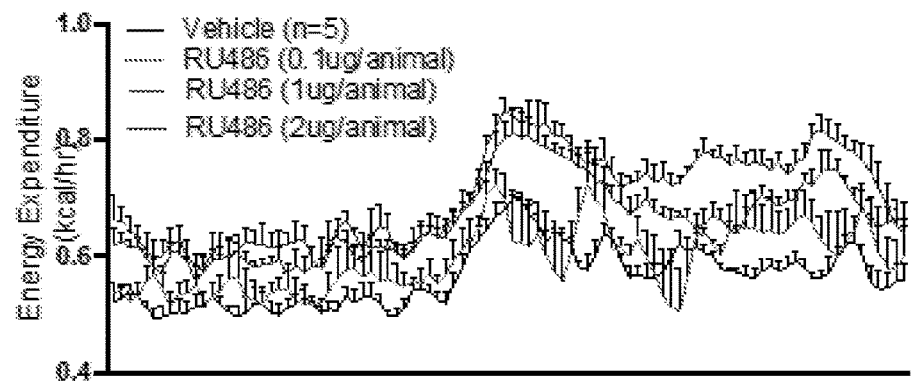

FIG. 22 shows 12-week high fat fed C57BL/6 male mice receiving RU486 (0.1, 1 and 2 µg/animal/day, ICV) for 10 consecutive days exhibit a dose dependent attenuation in body weight, adiposity and energy expenditure but not food intake.

CNS administration of PTP1B inhibitor (Claramine) dose dependently attenuates body weight, adiposity and food intake without regulating energy expenditure in diet-induced obese mice.

Figure 23:
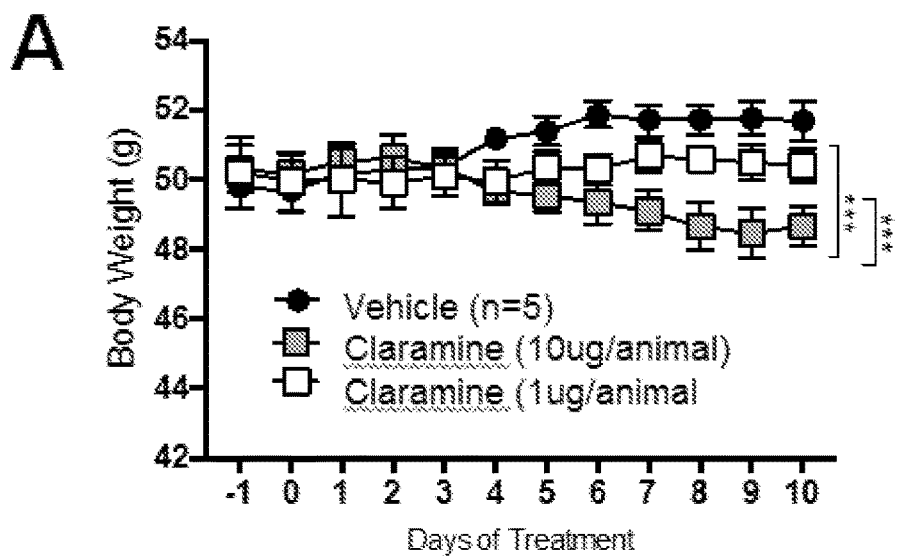
FIG. 23. CNS administration of PTP1B inhibitor (Claramine) dose dependently attenuates body weight, adiposity and food intake without regulating energy expenditure in diet-induced obese mice. 12-week high fat fed C57BL/6 male mice received PTP1B inhibitor administration (Claramine: 1 and 10 μg/animal/day, ICV) for 10 consecutive days and a) body weights, b) food intake, c) adiposity (EchoMRI and fad pad weight), d) energy expenditure were determined. e-f) Overnight fasted 12-week high fat fed C57BL/6 male mice were presented with food following ICV administration of either vehicle or PTP1B inhibitor (Claramine: 1 and 10 μg/animal). e) Stereotypical behaviors were then monitored every 30 s for 90 min and registered as feeding, drinking, active, grooming, inactive and resting. Data were collected into 5 min time bins and are presented as percentage of total behavior. Crossover graphs indicating the point of transition from eating to resting and the dashed line represents the time bin in which groups spent an equivalent amount of time eating and resting and is represented as f) time of cross over.
Figure 23:
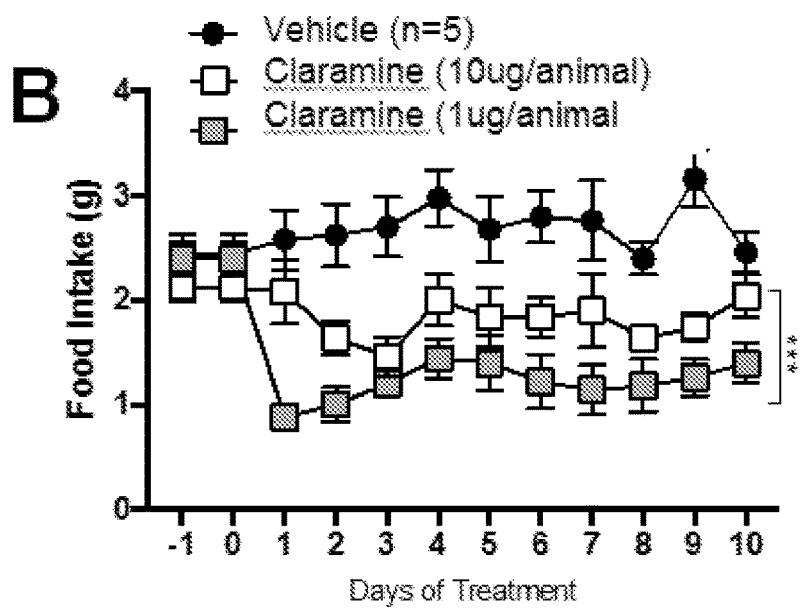
Figure 23:
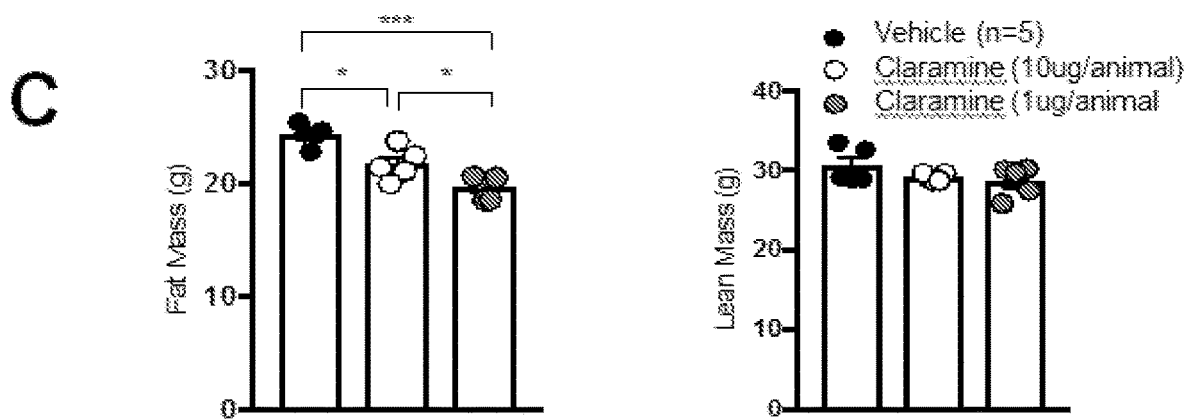
Figure 23:
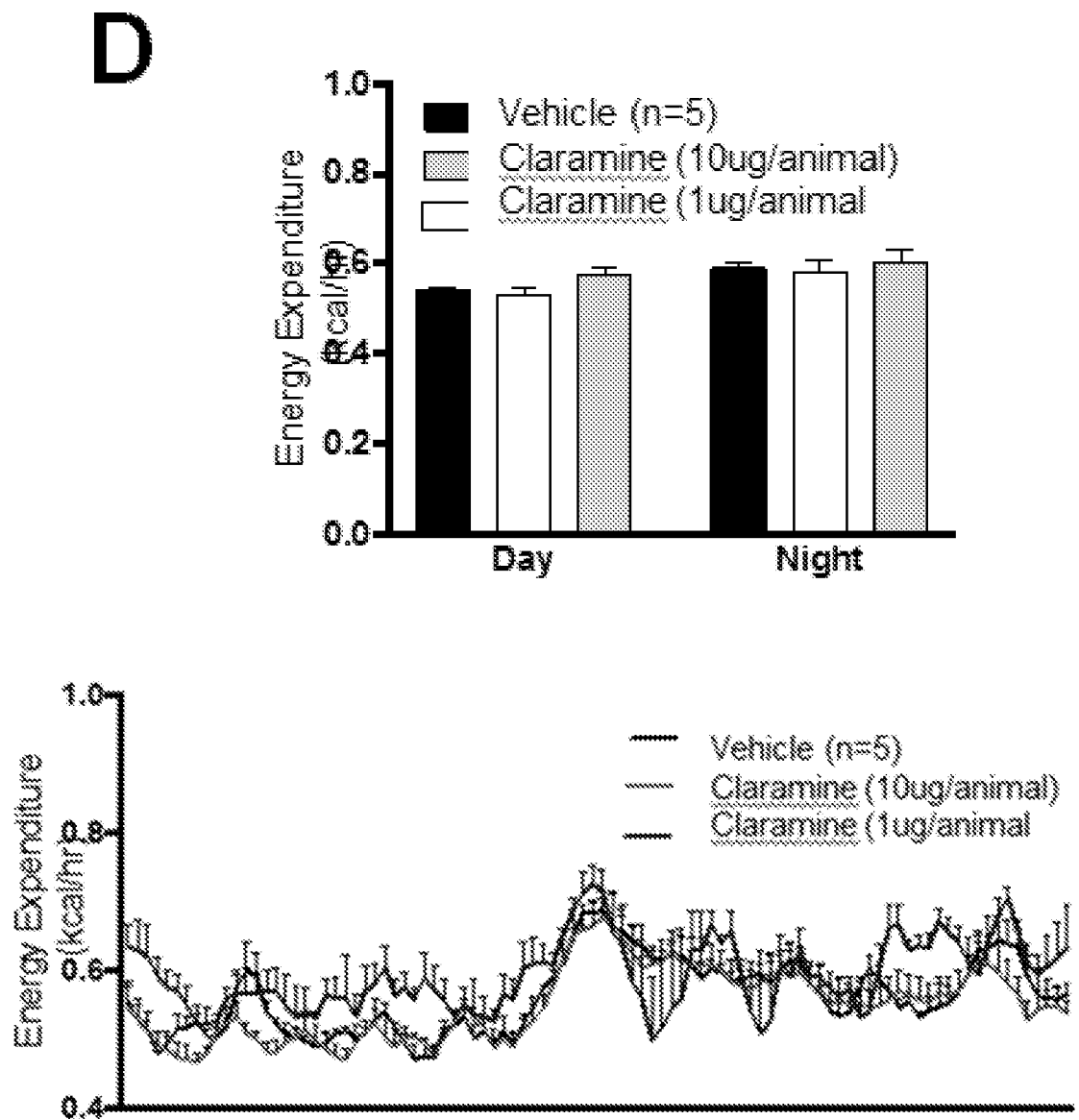
Figure 23:
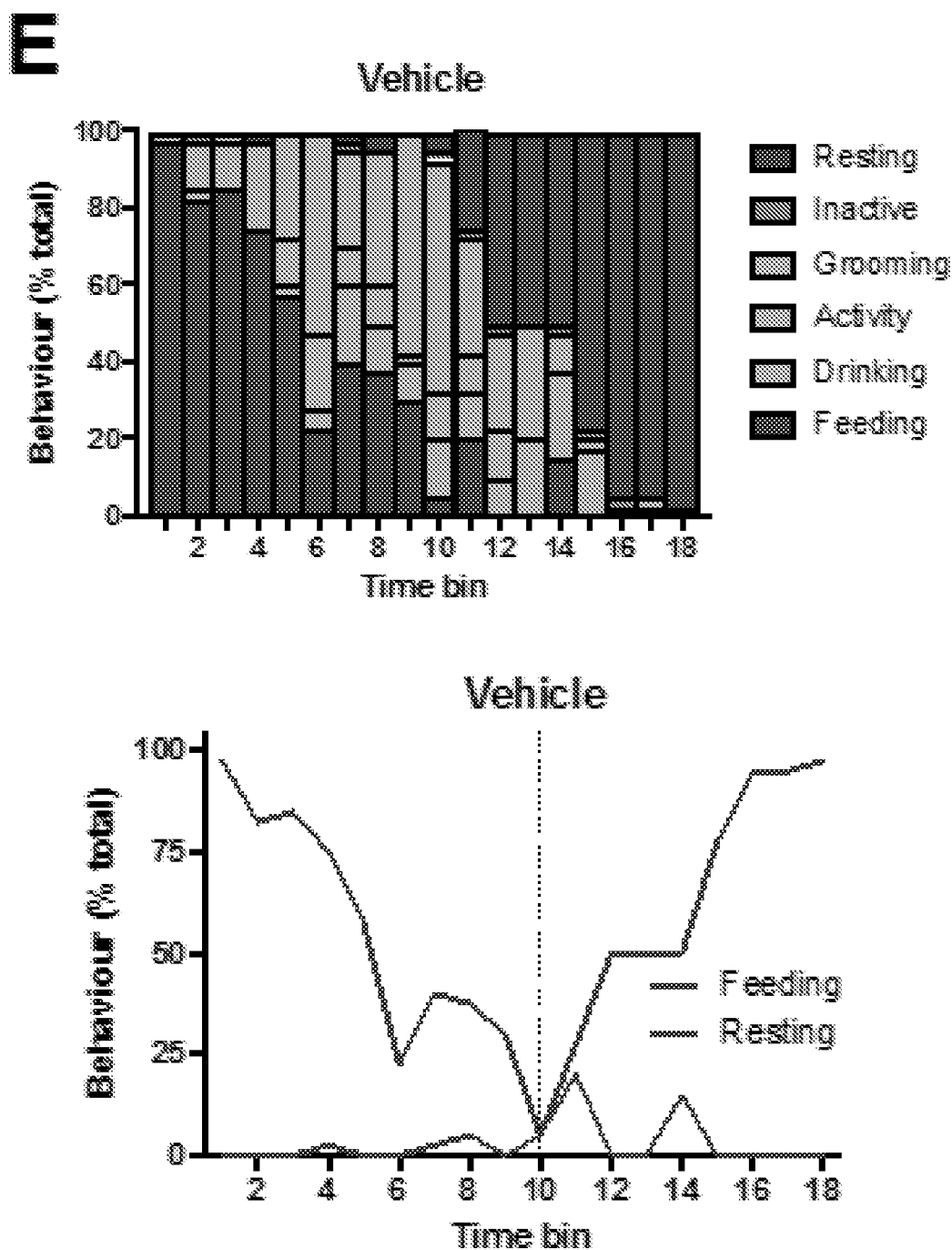
Figure 23:
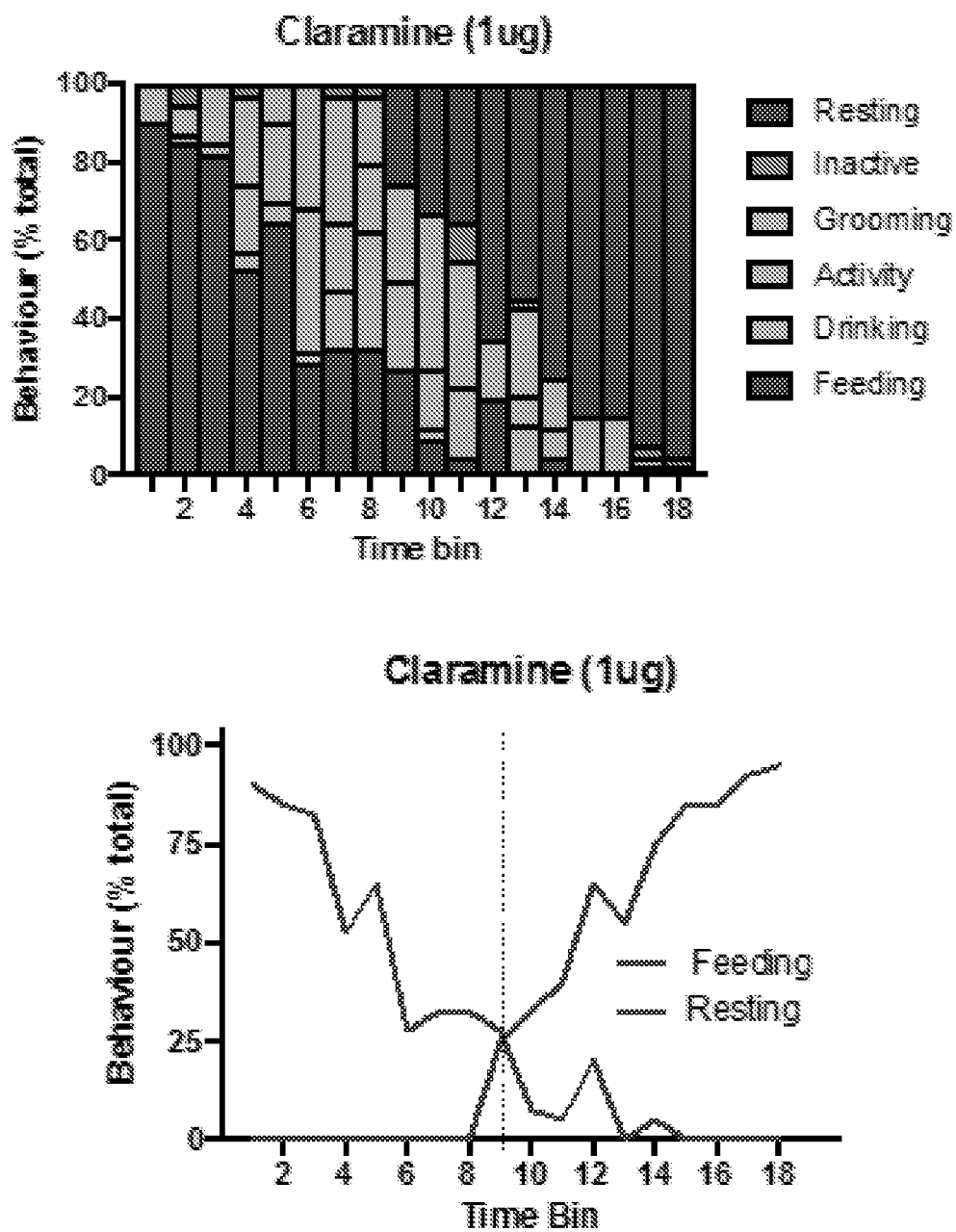
Figure 23:
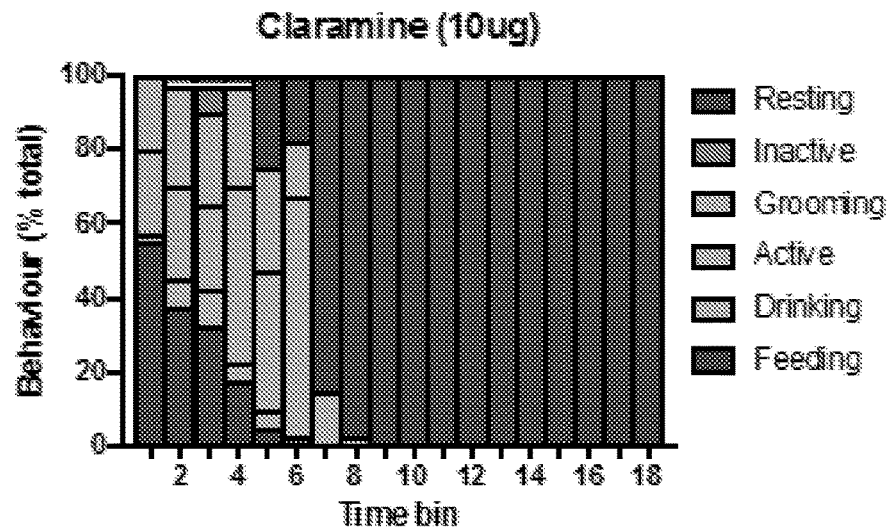
Figure 23:
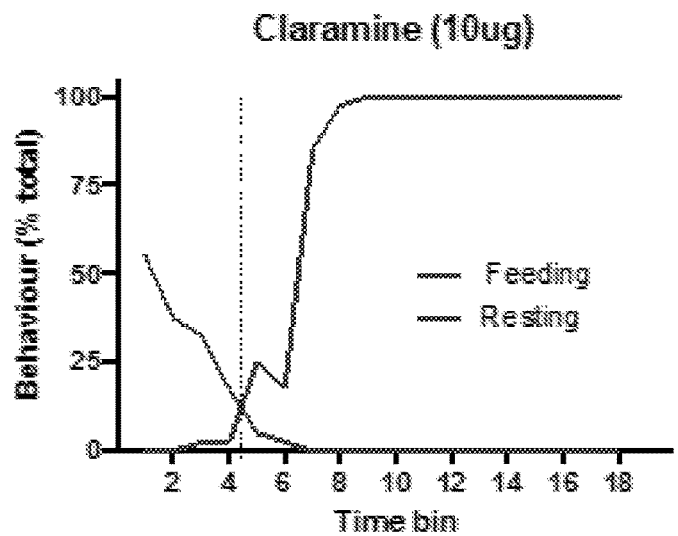
Figure 23:
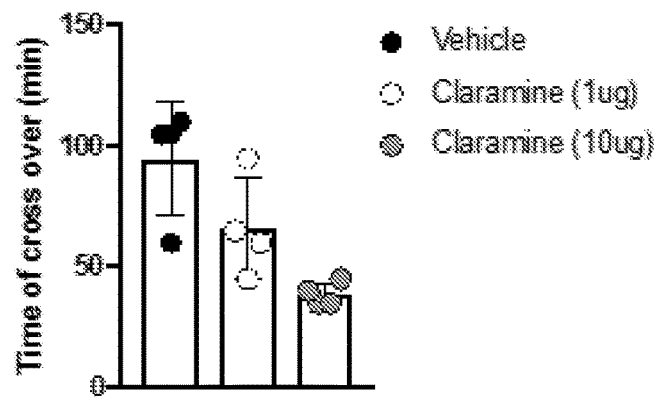

FIG. 23 shows 12-week high fat fed C57BL/6 male mice that received PTP1B inhibitor administration (Claramine: 1 and 10 µg/animal/day, ICV) for 10 consecutive days exhibit a dose dependent attenuation in body weights, food intake, adiposity (EchoMRI and fad pad weight) but not energy expenditure. Furthermore, 12-week high fat fed C57BL/6 male mice that were fasted overnight and presented with food following ICV administration of either vehicle or PTP1B inhibitor (Claramine: 1 and 10 µg/animal) showed a dose dependent shift in the behavioral satiety sequence indicating that PTP1B inhibitor (Claramine: 1 and 10 µg/animal) attenuate food intake in a feeding behavior specific manner and not by adverse side effects such as sedation or nausea.

Co-administration of PTP1B inhibitor (Claramine) and GR antagonist (RU486) synergistically attenuates body weight in diet-induced obese mice.

Figure 24:
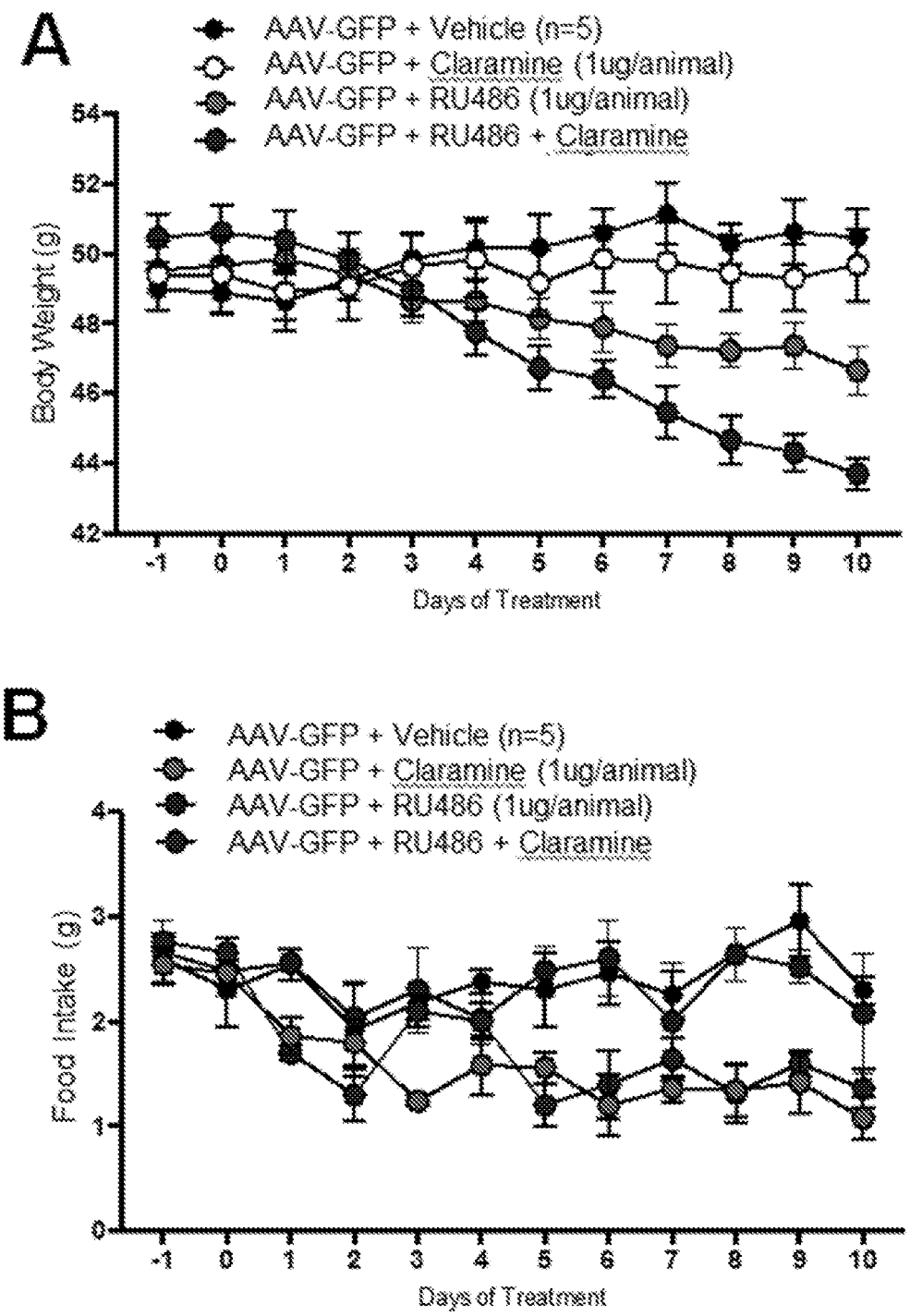
FIG. 24. CNS administration of PTP1B inhibitor (Claramine) and glucocorticoid antagonist (RU486) synergistically attenuates body weight in diet-induced obese mice. 12-week high fat fed C57BL/6 male mice received glucocorticoid antagonist (RU486: 1 μg/animal/day; ICV) and/or PTP1B inhibitor (Claramine: 1 and 10 μg/animal/day; ICV) for 10 consecutive days and effects on a) body weights, b) food intake, c) adiposity (EchoMRI and fad pad weight), d-e) energy expenditure, f) respiratory exchange ratio and g) ambulatory activity was determined.
Figure 24:
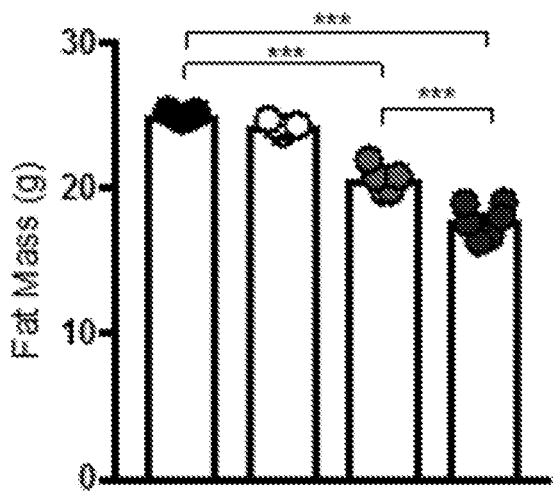
Figure 24:
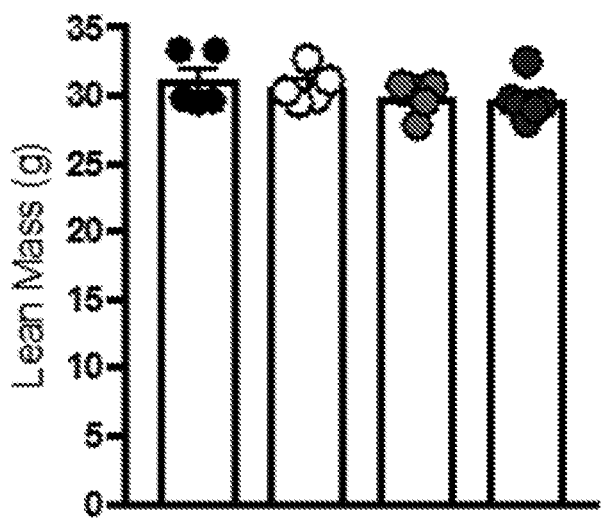
Figure 24:
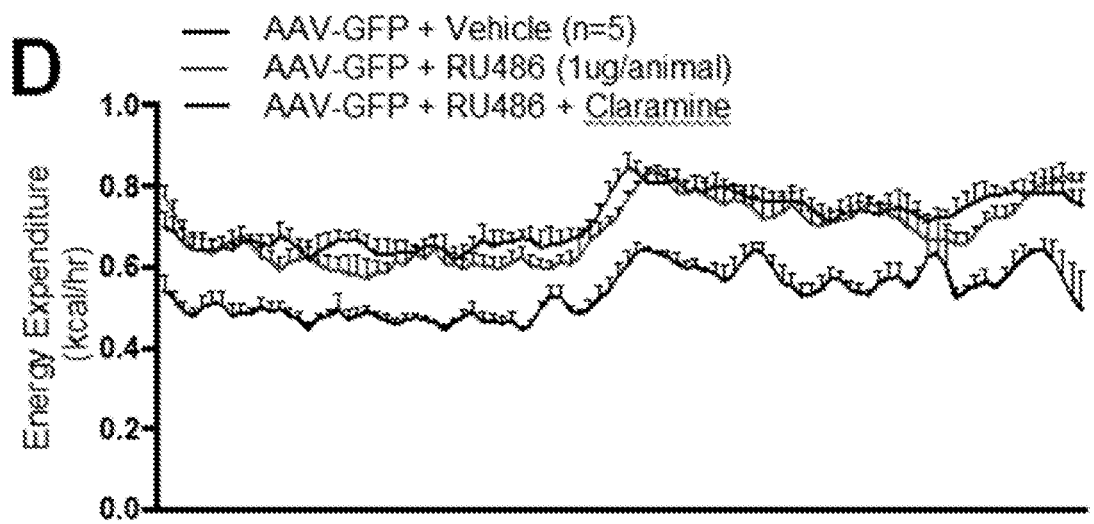
Figure 24:
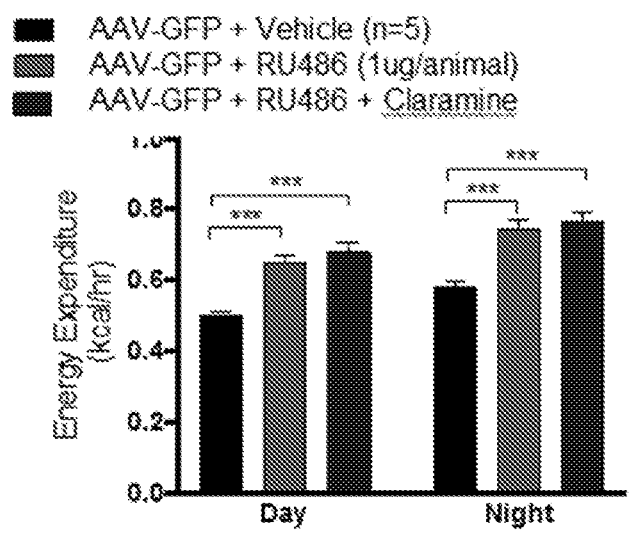
Figure 24:
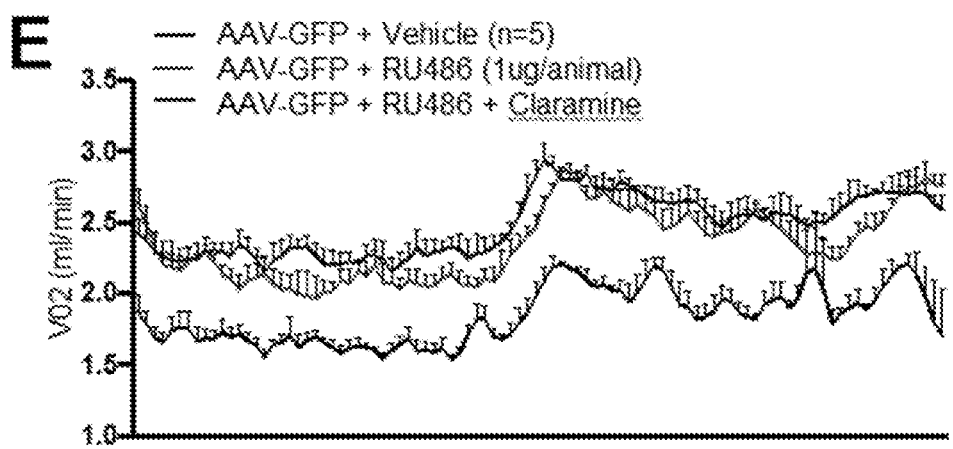
Figure 24:
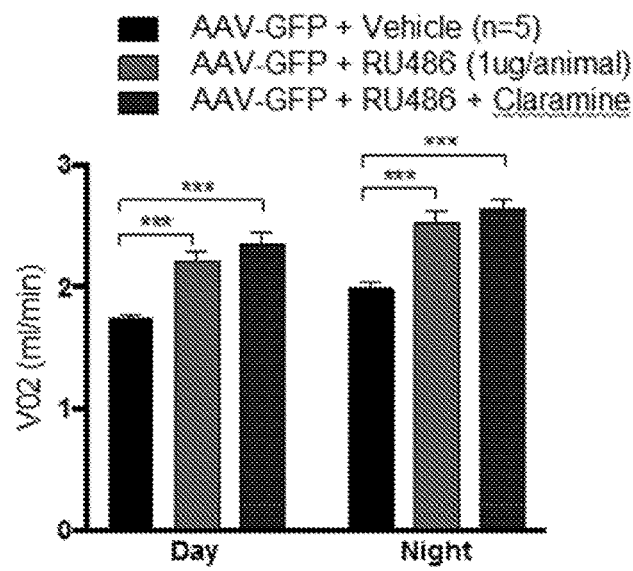
Figure 24:
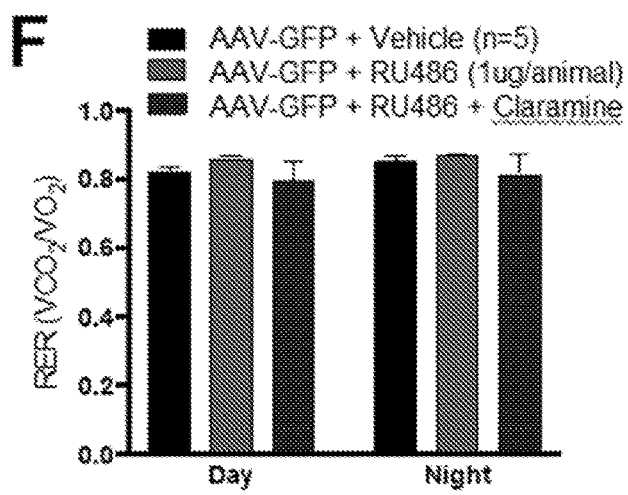
Figure 24:
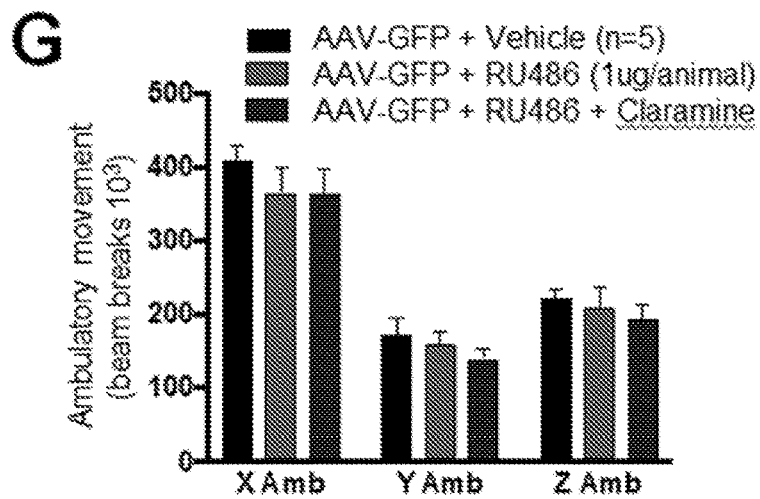

FIG. 24 shows that 12-week high fat fed C57BL/6 male mice were mice that received GR antagonist (RU486: 1 µg/animal/day; ICV) and/or PTP1B inhibitor (Claramine: 1 and 10 µg/animal/day; ICV) for 10 consecutive days showed a synergistic attenuation of body weights and adiposity mediated by effects on both food intake and energy expenditure.

The synergistic effects of PTP1B inhibitor (claramine) and GR antagonist (RU486) in diet-induced obese mice are meditated by TCPTP and PTP1B expression in the ARC.

Figure 25:
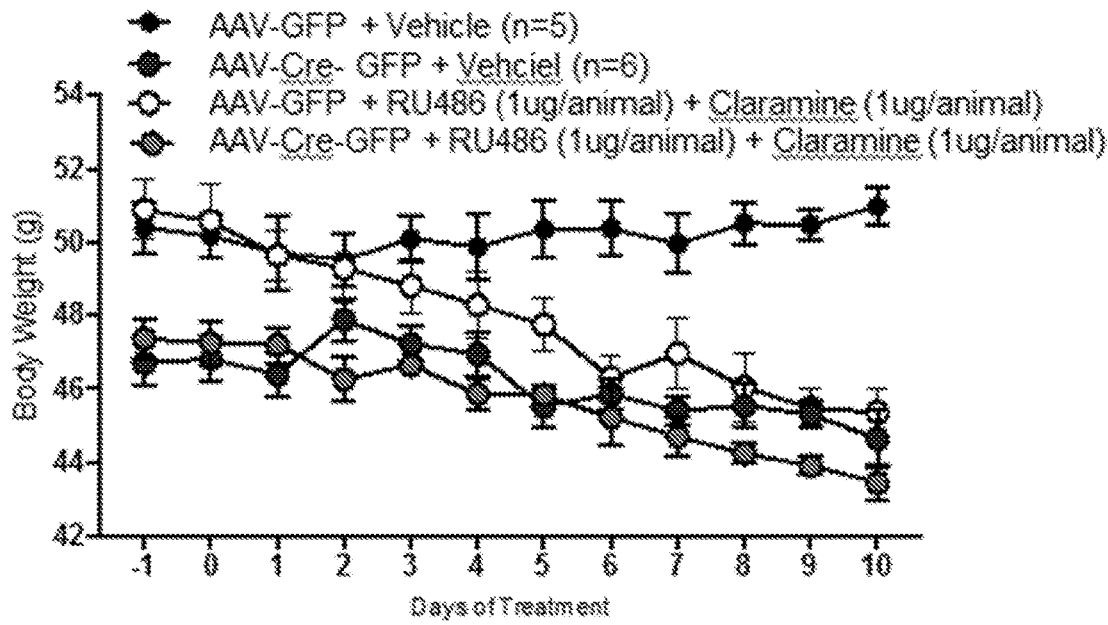
FIG. 25. The synergistic effects of PTP1B inhibitor (claramine) and glucocorticoid antagonist (RU486) in diet-induced obese mice are dependent on TCPTP and PTP1B in the ARC. 12-week high fat fed Ptpn1$^{fl/fl}$: Ptpn2$^{fl/fl}$ male mice were bilaterally injected with rAAV-eGFP or rAAV-Cre-eGFP into the arcuate nucleus of the hypothalamus (ARC). One-week post AAV administration mice received glucocorticoid antagonist (RU486: 1 μg/animal/day; ICV) and PTP1B inhibitor (Claramine: 1 and 10 μg/animal/day; ICV) for 10 consecutive days and effects on a) Body weights, b) food intake, c) adiposity (EchoMRI and fad pad weight), d-e) energy expenditure, f) respiratory exchange ratio and g) ambulatory activity was determined.
Figure 25:
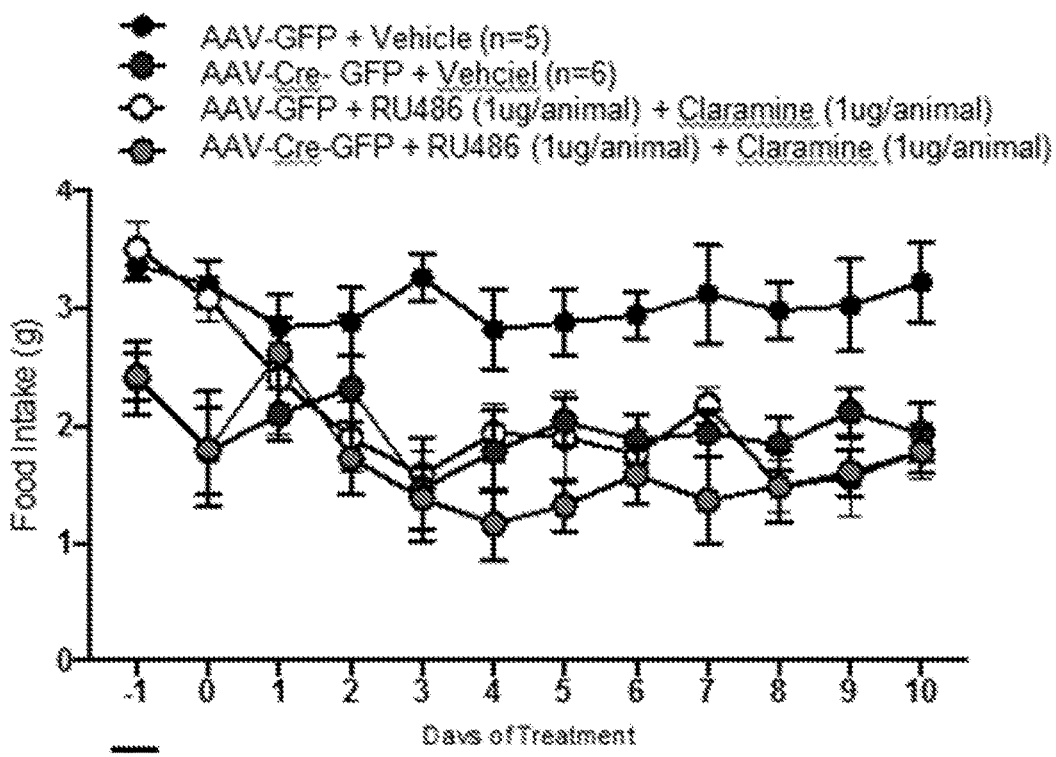
Figure 25:
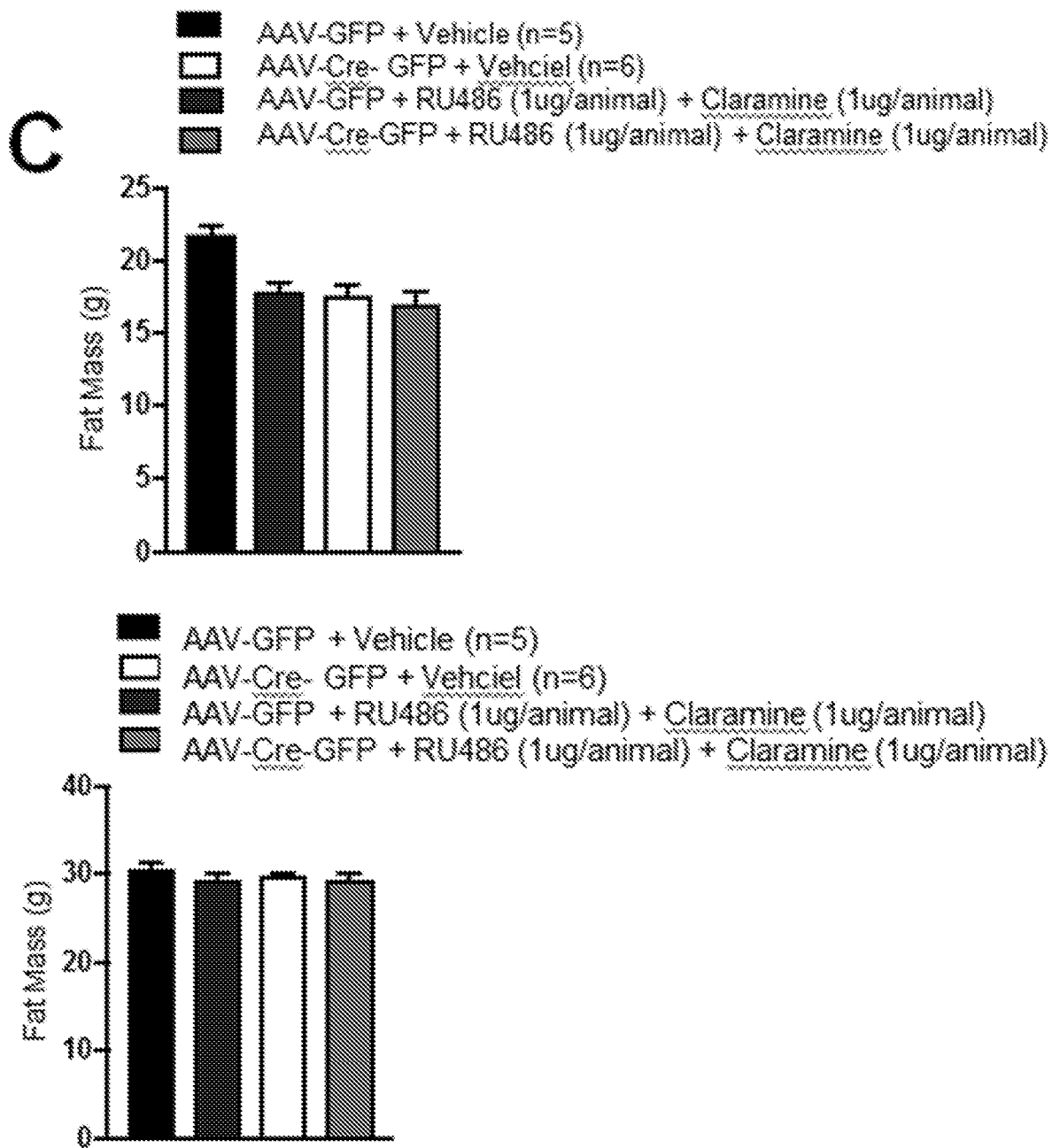
Figure 25:
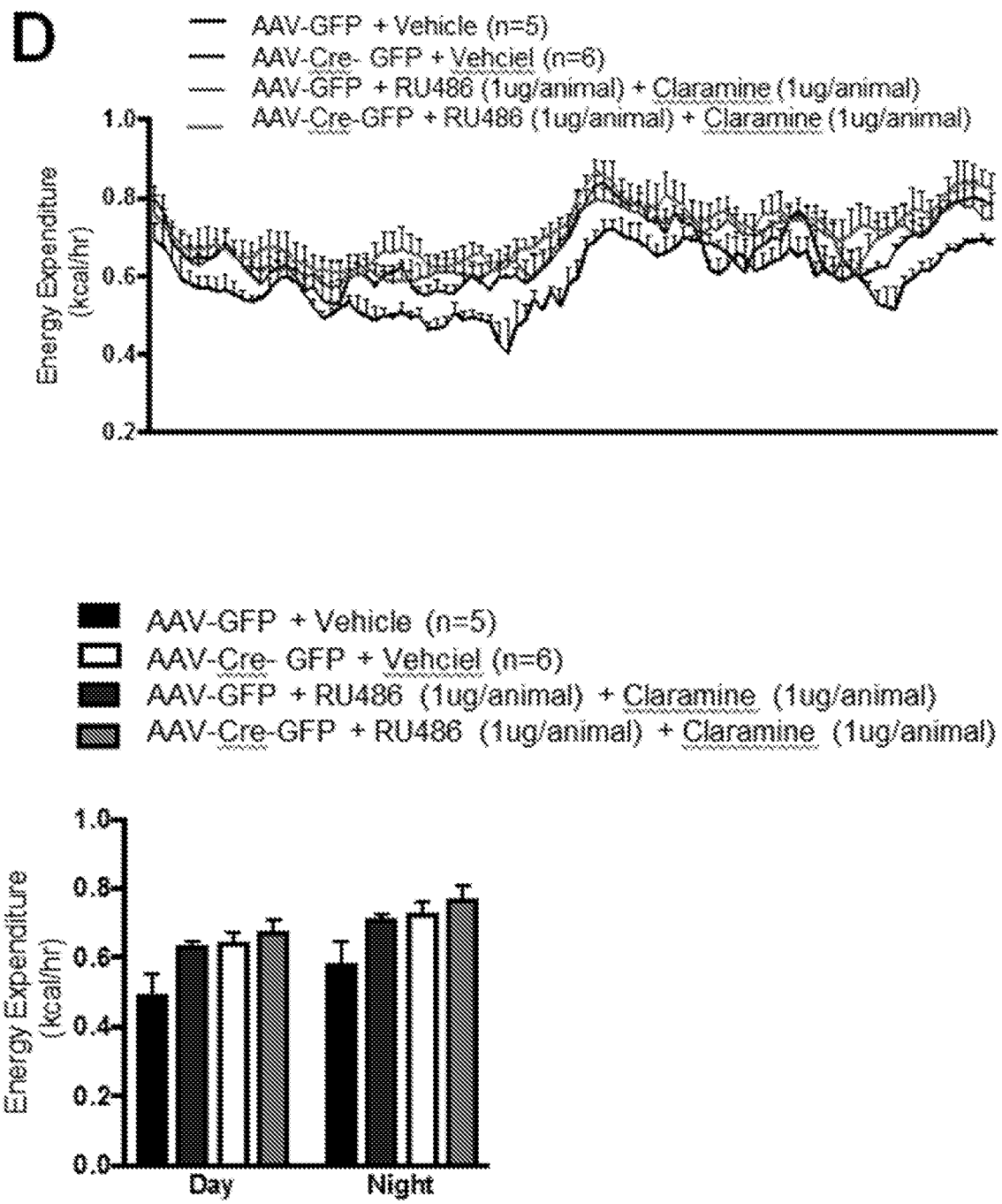
Figure 25:
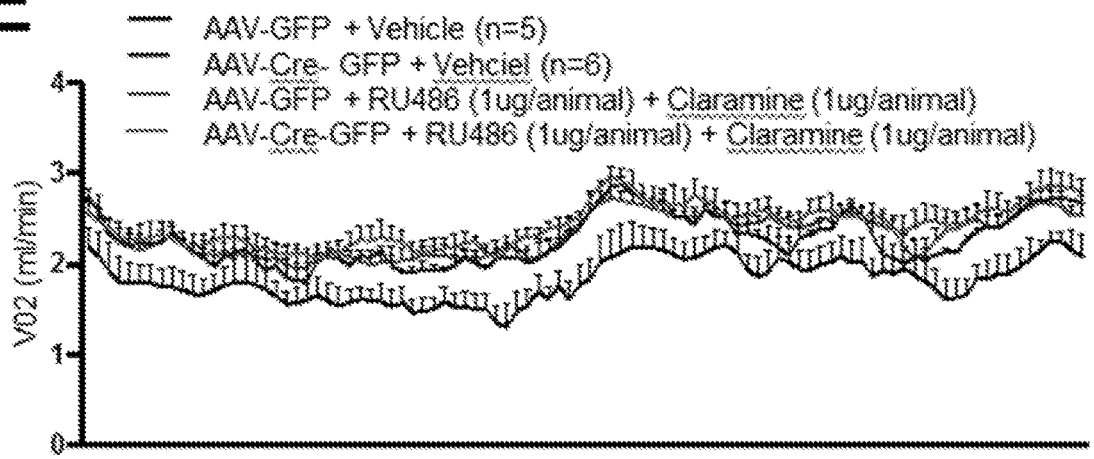
Figure 25:
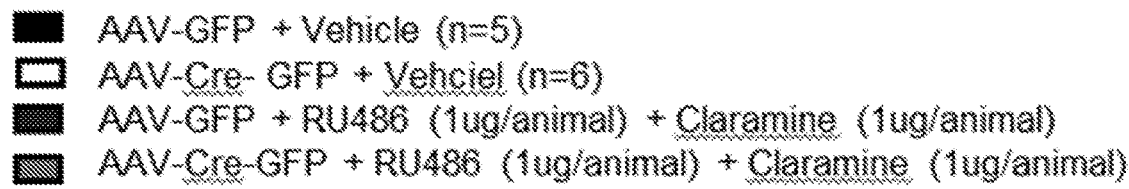
Figure 25:
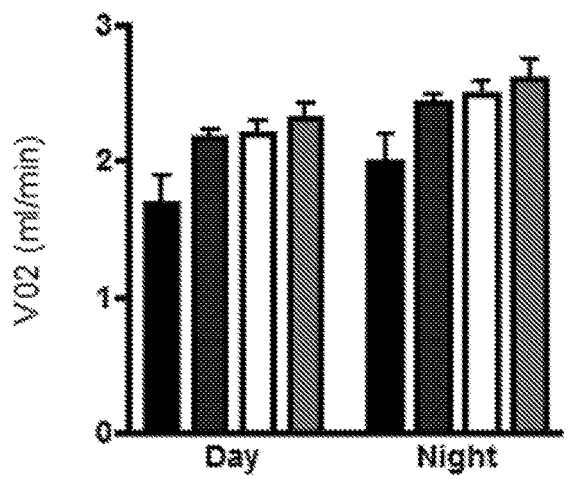
Figure 25:
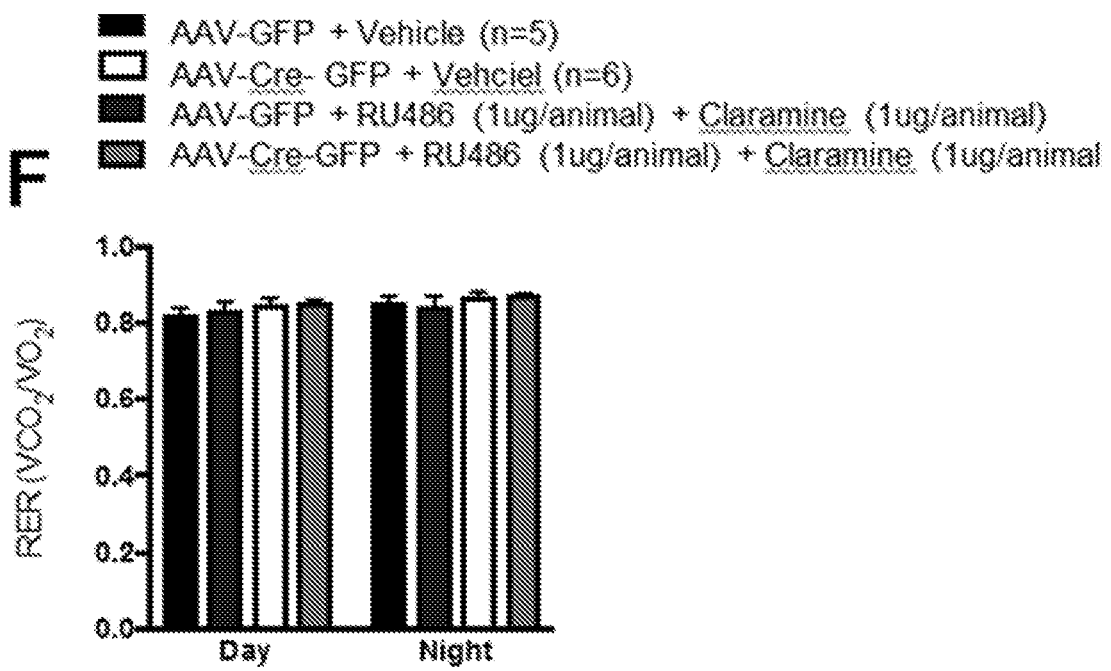
Figure 25:
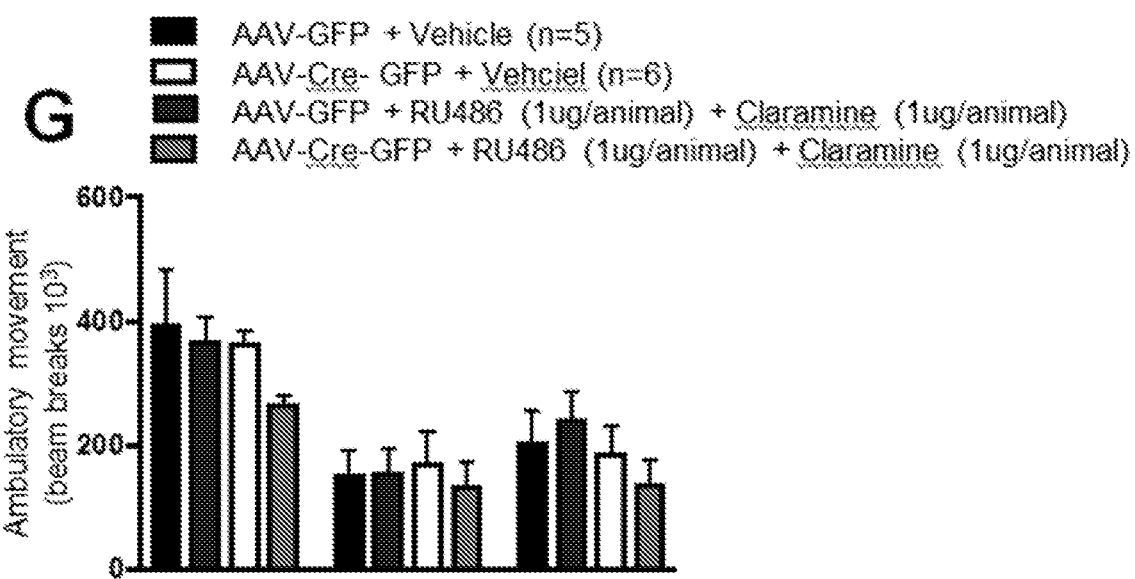

FIG. 25 shows that the synergistic effects of CNS GR antagonist (RU486: 1 µg/animal/day; ICV) and PTP1B inhibitor (Claramine: 1 and 10 µg/animal/day; ICV) administration on body weight, adiposity, energy expenditure and food intake is attenuated in 12-week high fat fed $Ptpn1^{fl/fl}$: $Ptpn2^{fl/fl}$ male mice bilaterally injected with rAAV-Cre-eGFP compared to rAAV-eGFP or into the arcuate nucleus of the hypothalamus (ARC).

Intranasal administration of PTP1B inhibitor (Claramine) or GR antagonist (RU486) dose dependently attenuates body weight, adiposity and food intake.

Figure 26:
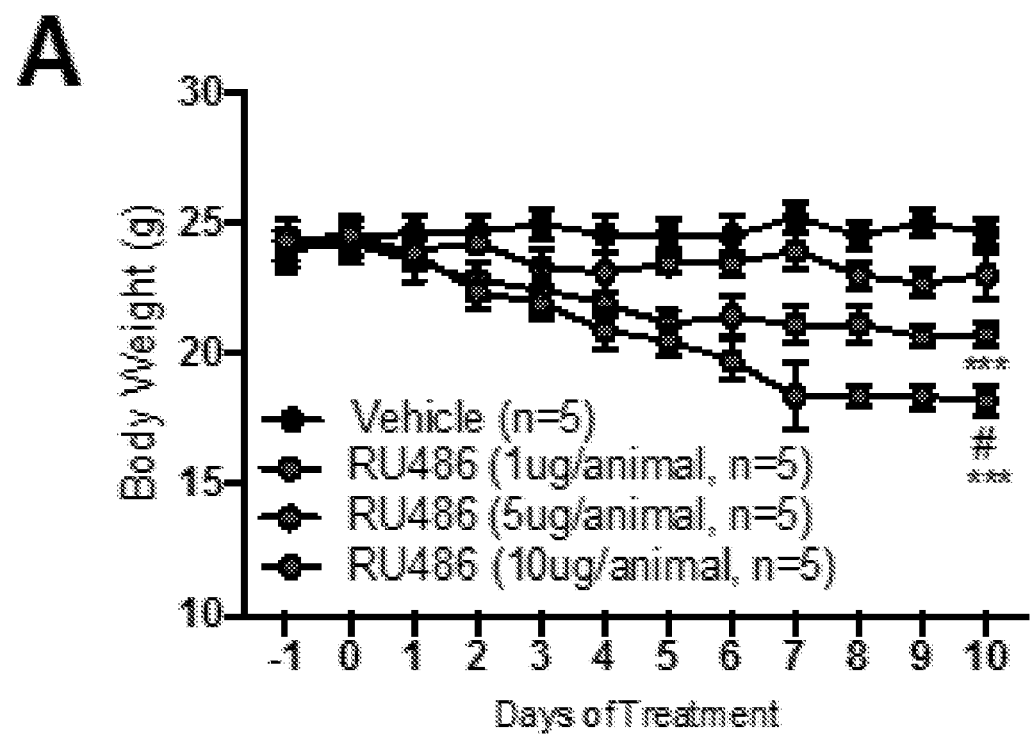
FIG. 26 Intranasal administration of PTP1B inhibitor (Claramine) or glucocorticoid antagonist (RU486) attenuates body weight, adiposity and food intake. 8-10-week C57BL/6 male mice were mice received glucocorticoid antagonist (RU486: 1, 5, 10 μg/animal/day; intranasal; 12 μl total volume) and/or PTP1B inhibitor (Claramine: 1, 10 and 20 μg/animal/day, intranasal; 12 μl total volume) for 10 consecutive days and effects on a, f) body weight, b, g) food intake, c, h) adiposity (EchoMRI and fad pad weight) was determined. At the end of the experiment d, i) brown adipose tissue and e, j) inguinal white adipose tissue was extracted for quantitative qPCR analysis.
Figure 26:
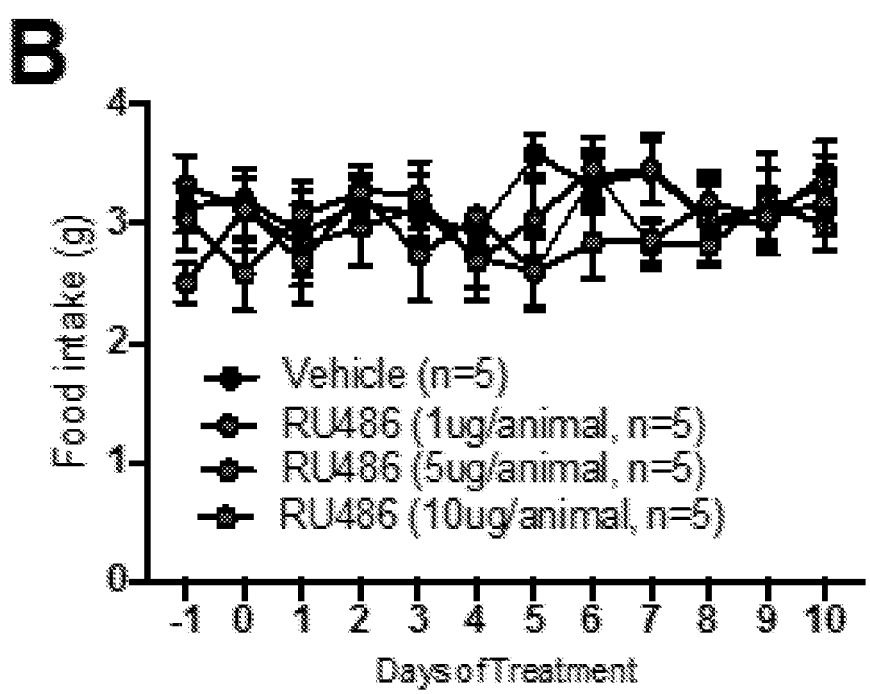
Figure 26:
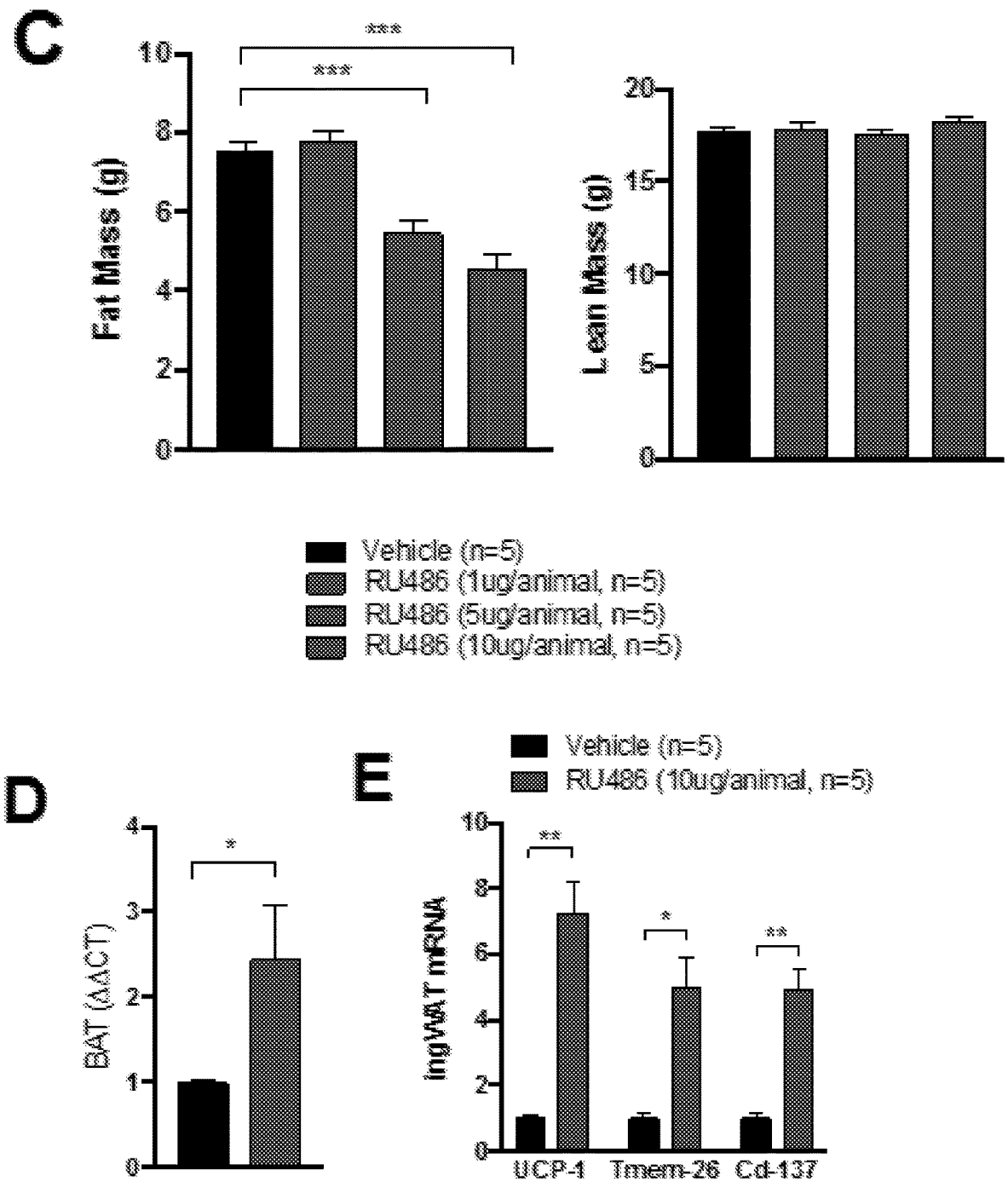
Figure 26:
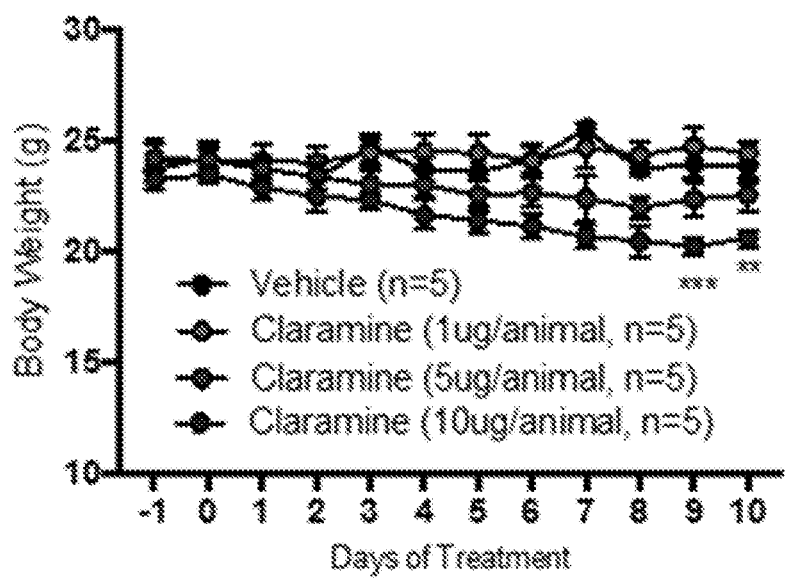
Figure 26:
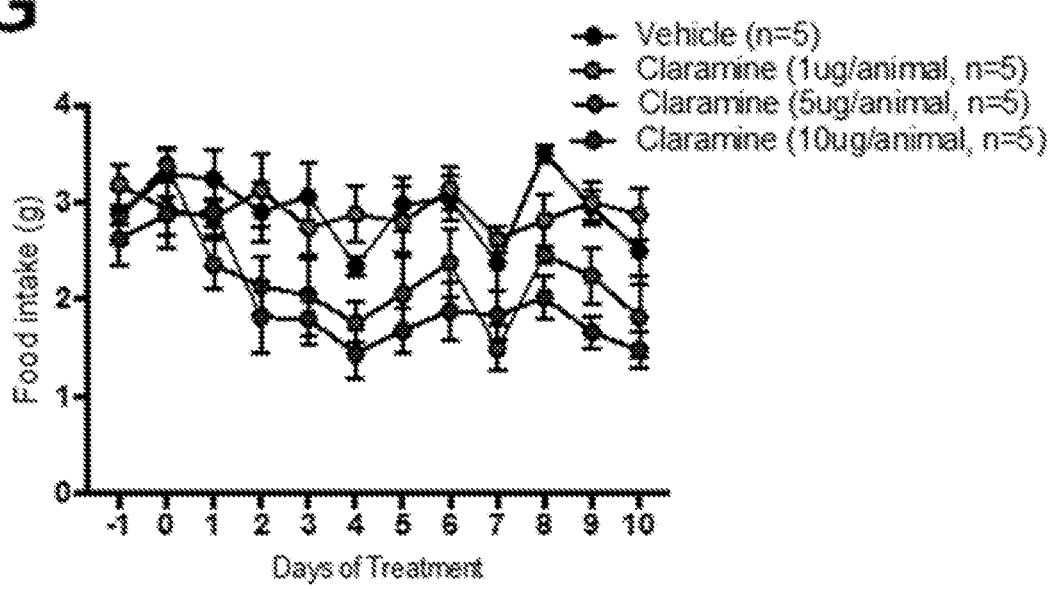
Figure 26:
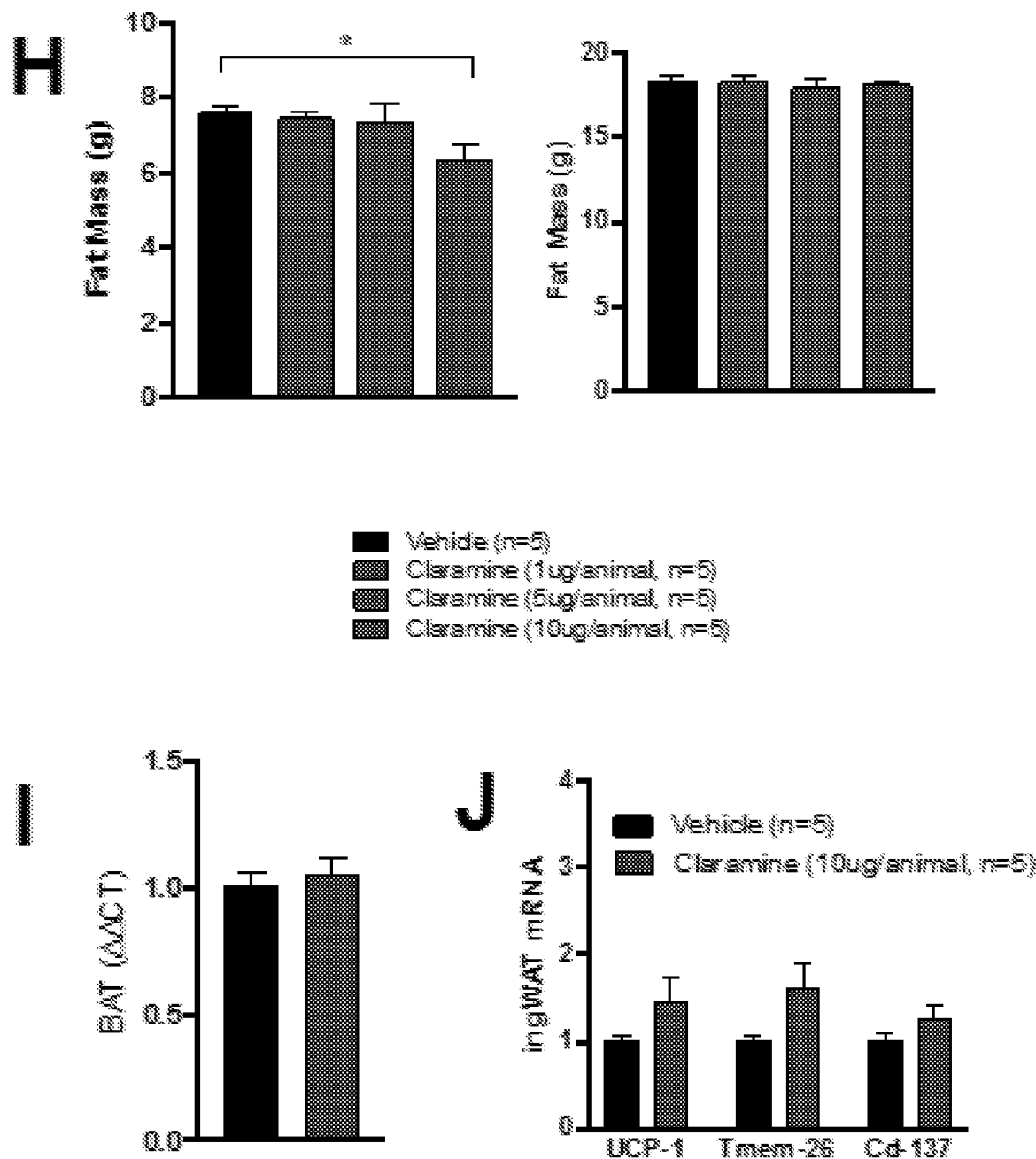
Figure 27:
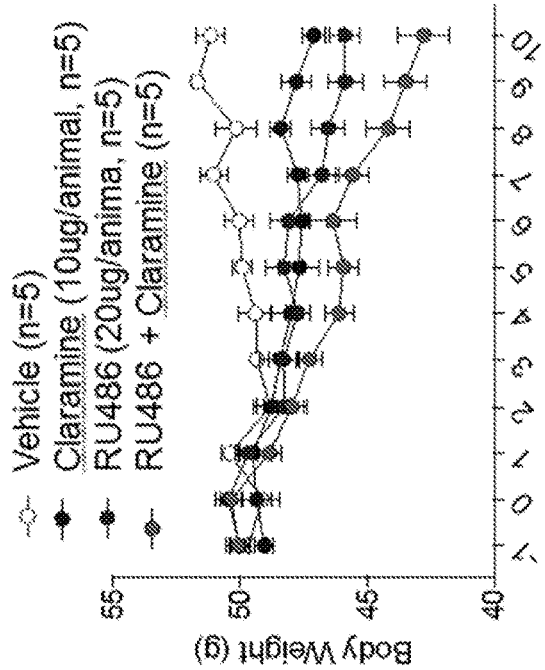
FIG. 27 Co-intranasal administration of PTP1B inhibitor (Claramine) and glucocorticoid antagonist (RU486) synergistically attenuates body weight in diet-induced obese mice. 12-week high fat fed C57BL/6 male mice received Intranasal administration of glucocorticoid antagonist (RU486, 10 μg/animal/day; intranasal; 12 μl total volume) and/or PTP1B inhibitor (Claramine: 20 μg/animal/day, intranasal; 12 μl total volume) for 10 consecutive days and effects on a) body weight, b) food intake, whole body c) oxygen consumption, d) energy expenditure and e) ambulatory activity was determined.
Figure 27:
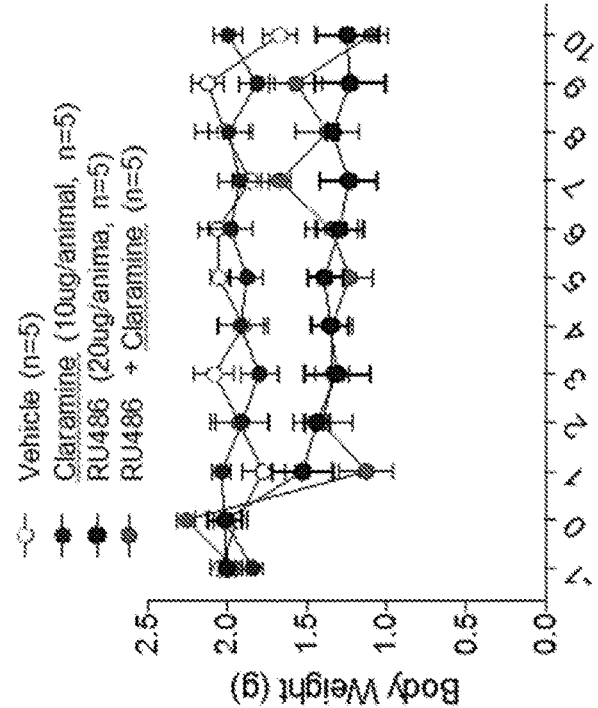
Figure 27:
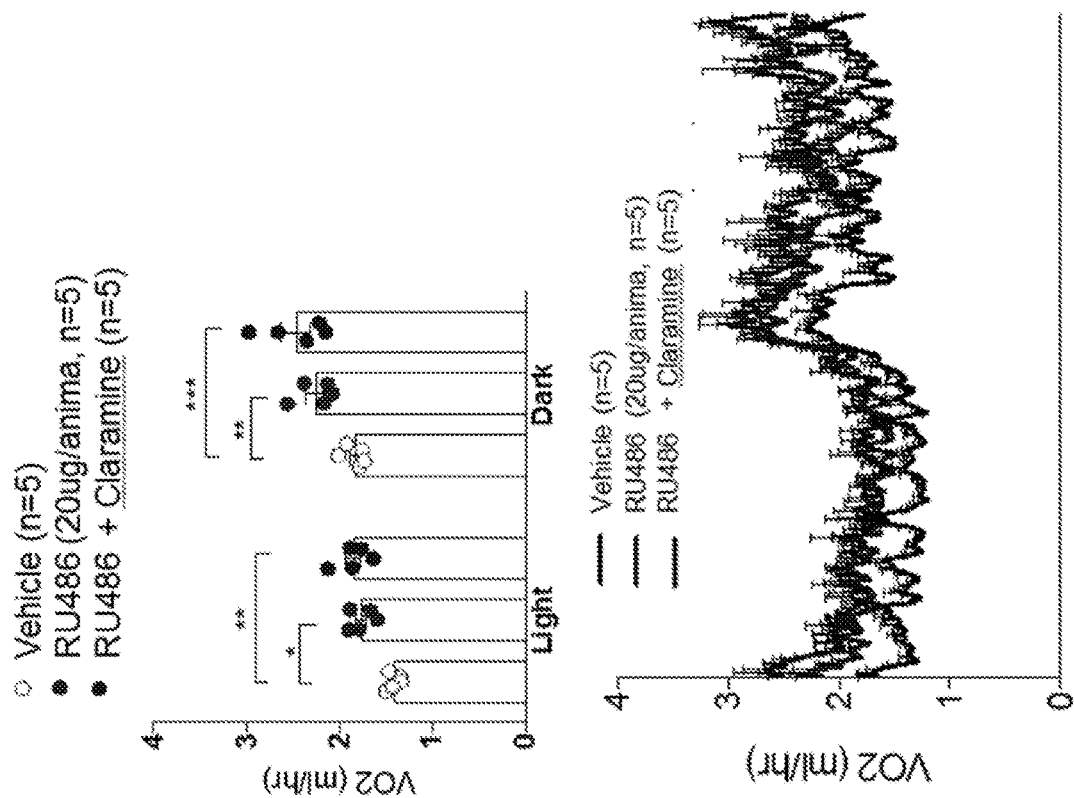
Figure 27:
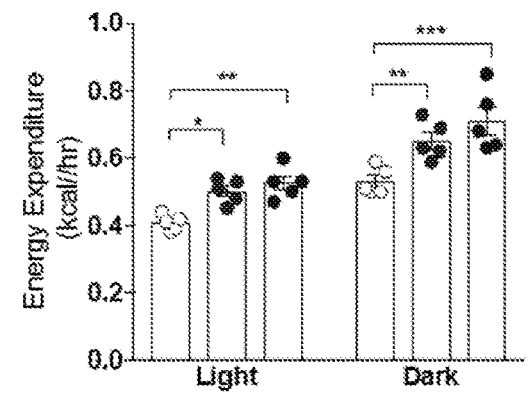
Figure 27:
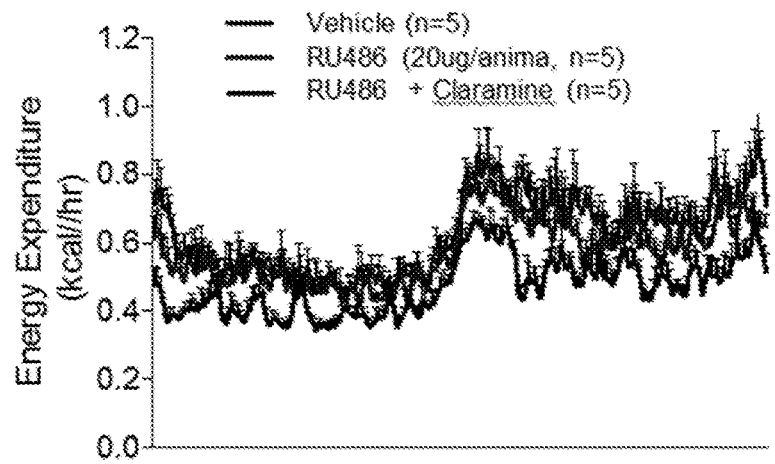
Figure 27:
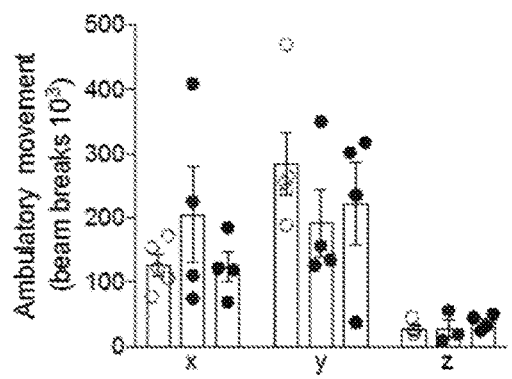
Figure 28:
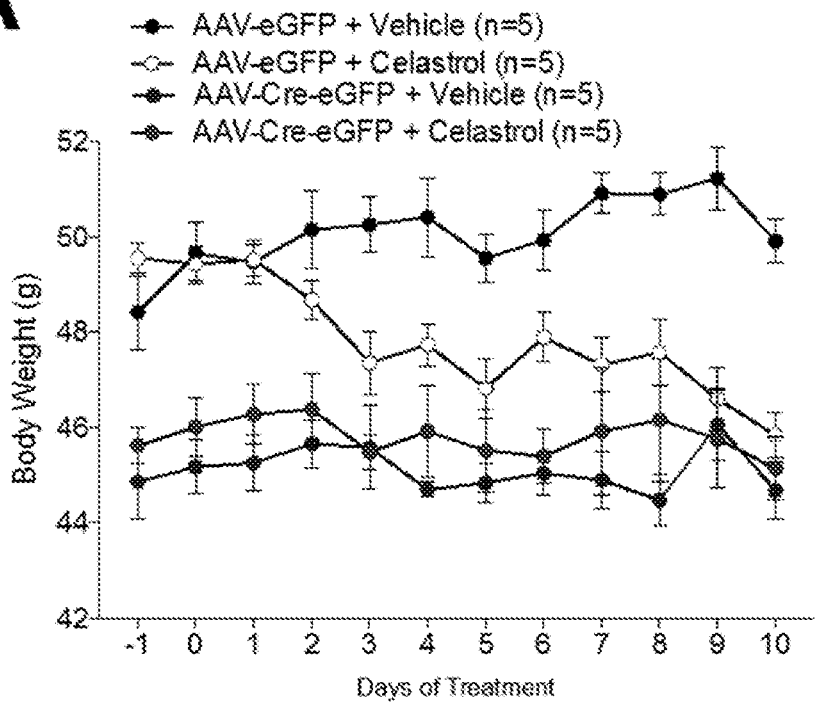
FIG. 28 The ability of celastrol to promote weight loss in obese mice is abrogated in mice lacking PTP1B and TCPTP in the arcuate nucleus of the hypothalamus. 12-week high fat fed Ptpn1$^{fl/fl}$: Ptpn2$^{fl/fl}$ male mice were bilateral injected with rAAV-eGFP or rAAV-Cre-eGFP into the arcuate nucleus of the hypothalamus (ARC). Two-week post AAV administration mice received Celastrol (20 μg/ml, i.p.) for 10 consecutive days and effects on a) Body weights, b) food intake, c-d) adiposity and lean mass (EchoMRI) was determined FIG. 29 The ability of celastrol to promote weight loss in obese mice is partially attenuated in mice lacking TCPTP in the arcuate nucleus of the hypothalamus. 12-week high fat fed Ptpn2$^{fl/fl}$ male mice were bilateral injected with rAAV-eGFP or rAAV-Cre-eGFP into the arcuate nucleus of the hypothalamus (ARC). Two-week post AAV administration mice received Celastrol (20 ug/ml, i.p.) for 10 consecutive days and effects on a-b) Body weights, b-c) food intake, e-f) adiposity and lean mass (EchoMRI) was determined.
Figure 28:
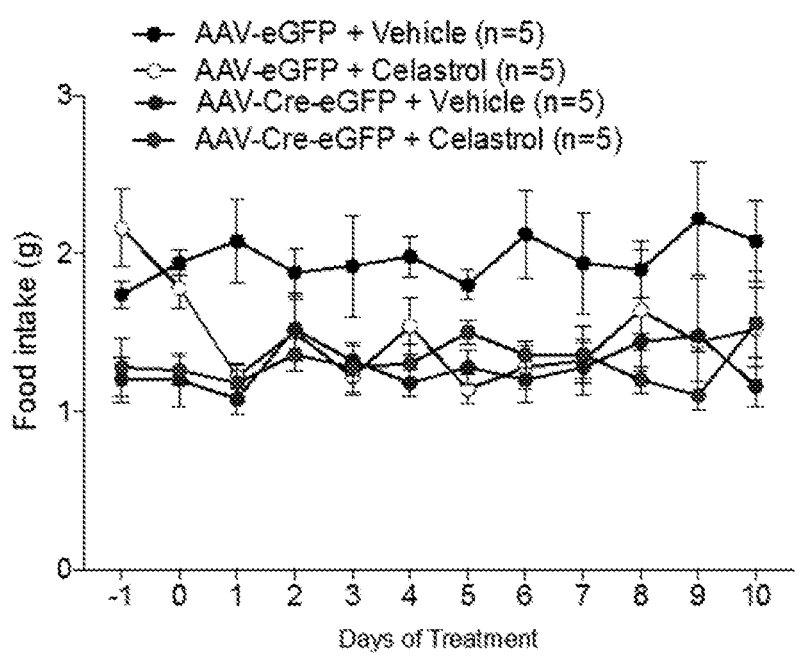
Figure 28:
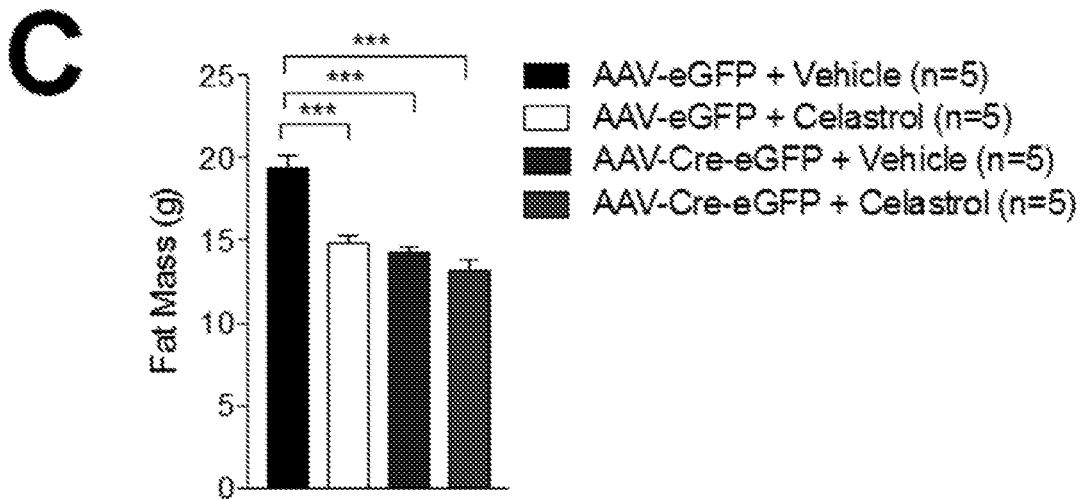
Figure 28:
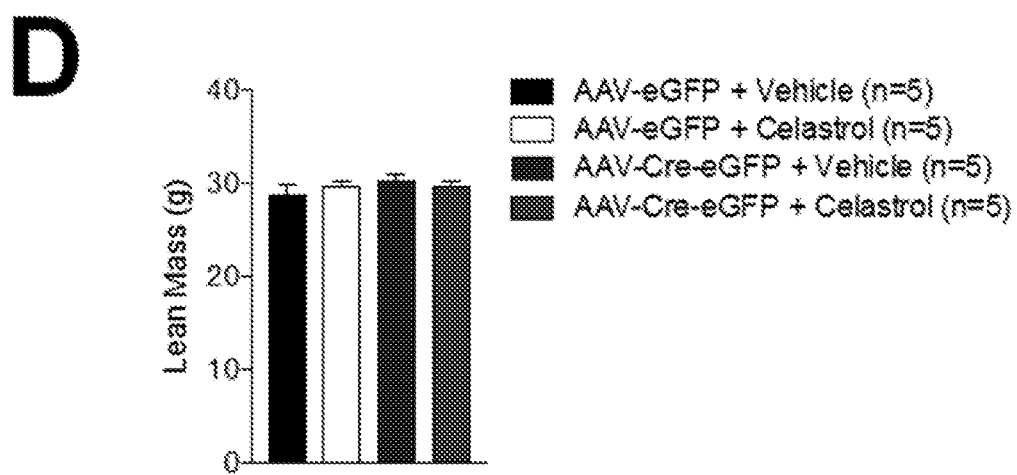
Figure 29:
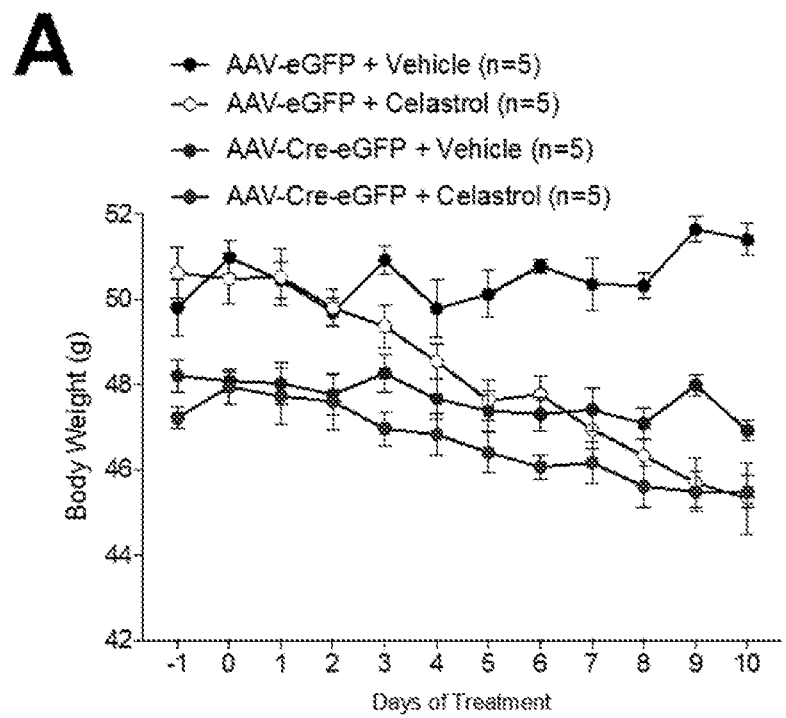
Figure 29:
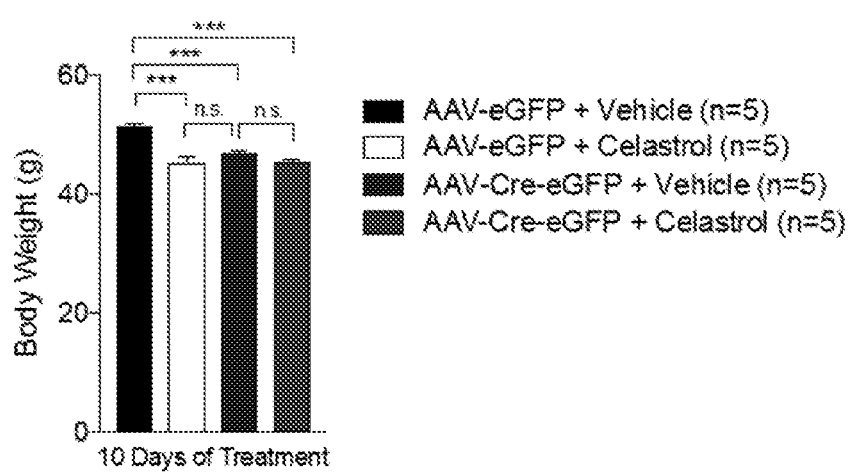
Figure 29:
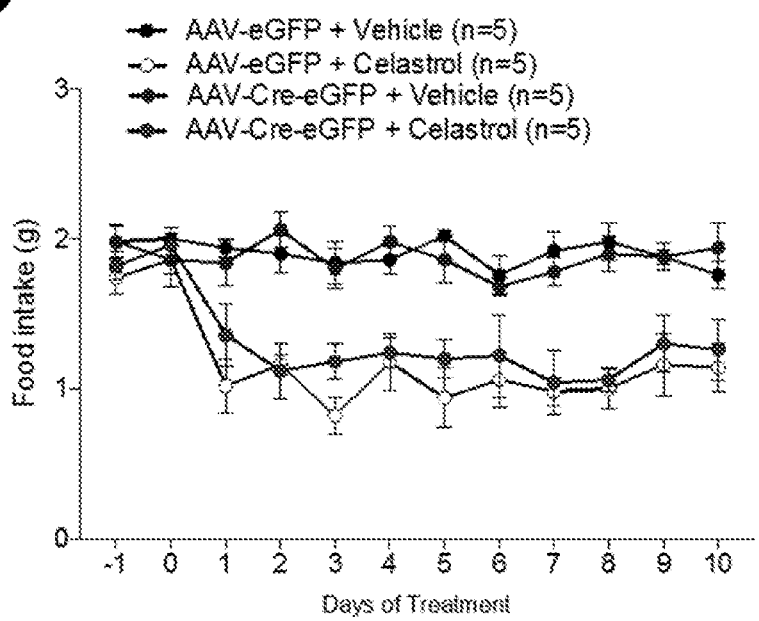
Figure 29:
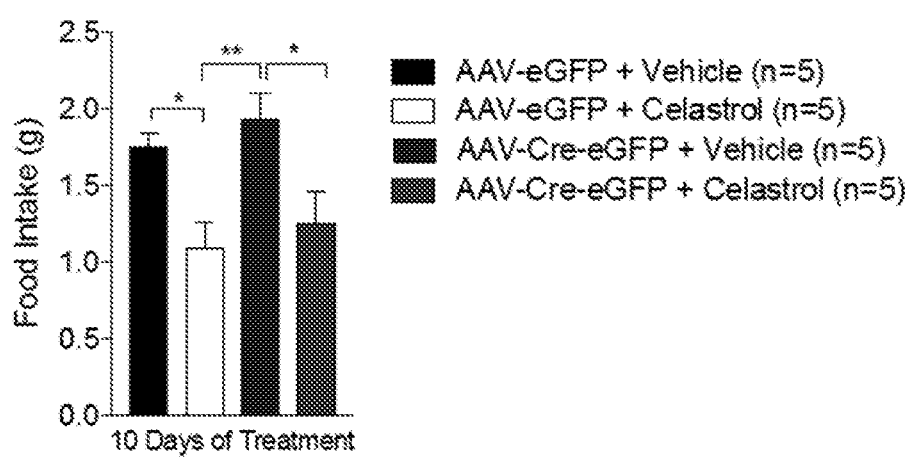
Figure 29:
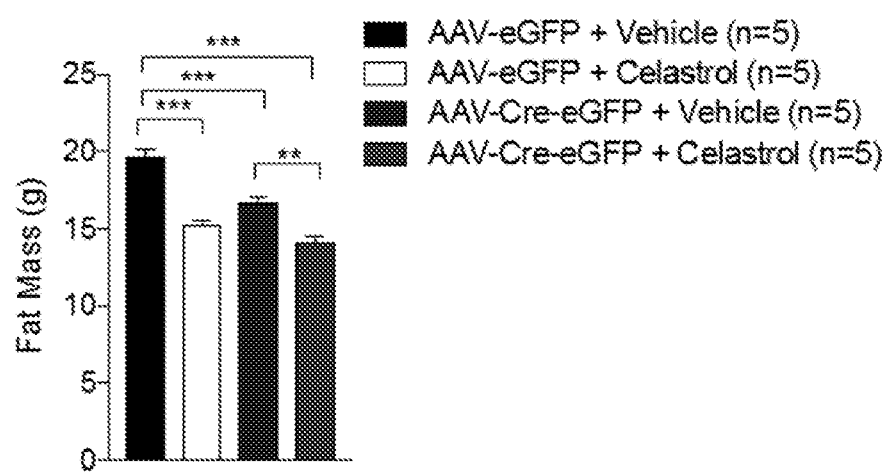
Figure 29:
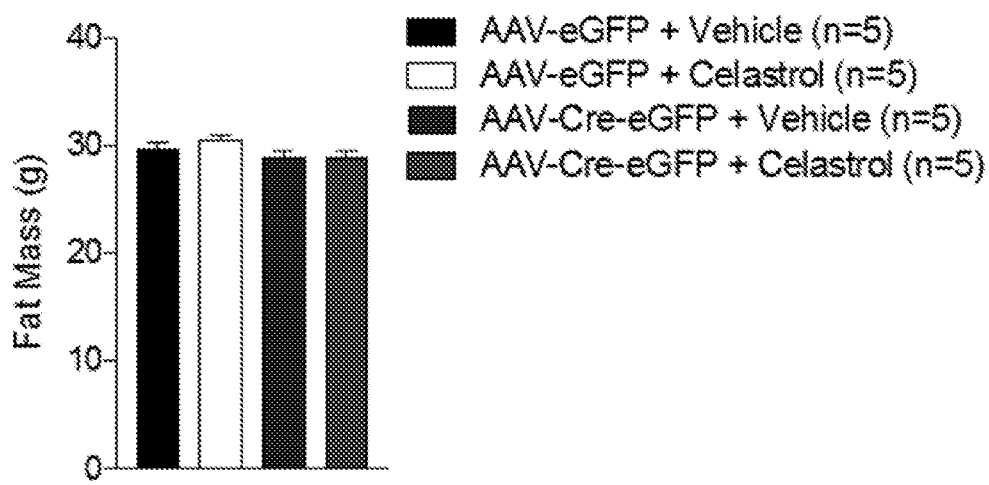
Figure 30:
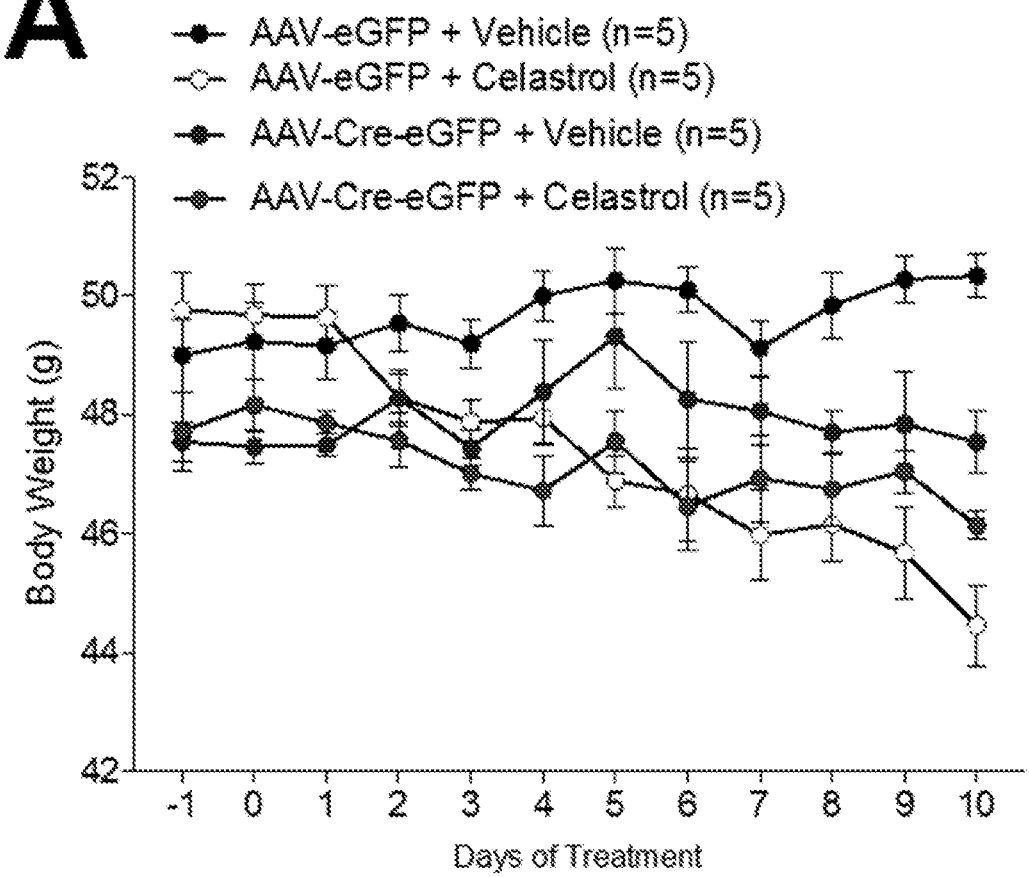
FIG. 30. The ability of celastrol is promote weight loss in obese mice is partially attenuated in mice lacking PTP1B in the arcuate nucleus of the hypothalamus. 12-week high fat fed Ptpn1$^{fl/fl}$ male mice were bilateral injected with rAAV-eGFP or rAAV-Cre-eGFP into the arcuate nucleus of the hypothalamus (ARC). Two-week post AAV administration mice received Celastrol (20 μg/ml, i.p.) for 10 consecutive days and effects on a-b) Body weights, c-d) food intake, e-f) adiposity and lean mass (EchoMRI) was determined.
Figure 30:
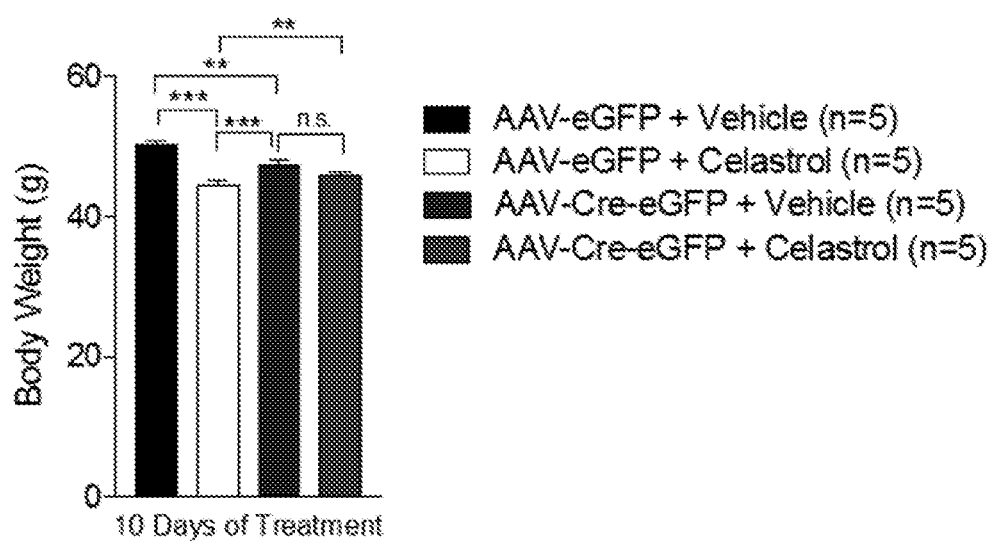
Figure 30:
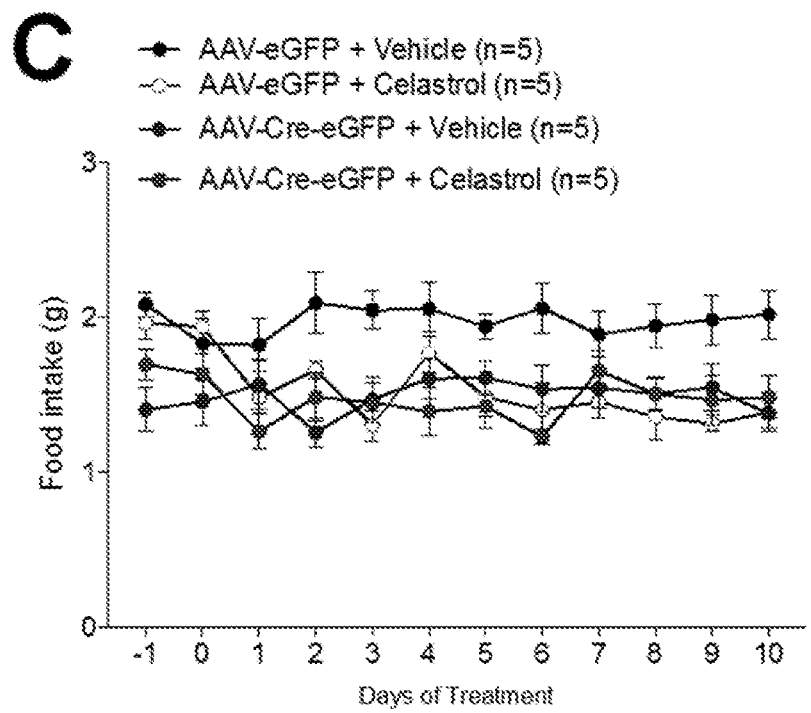
Figure 30:
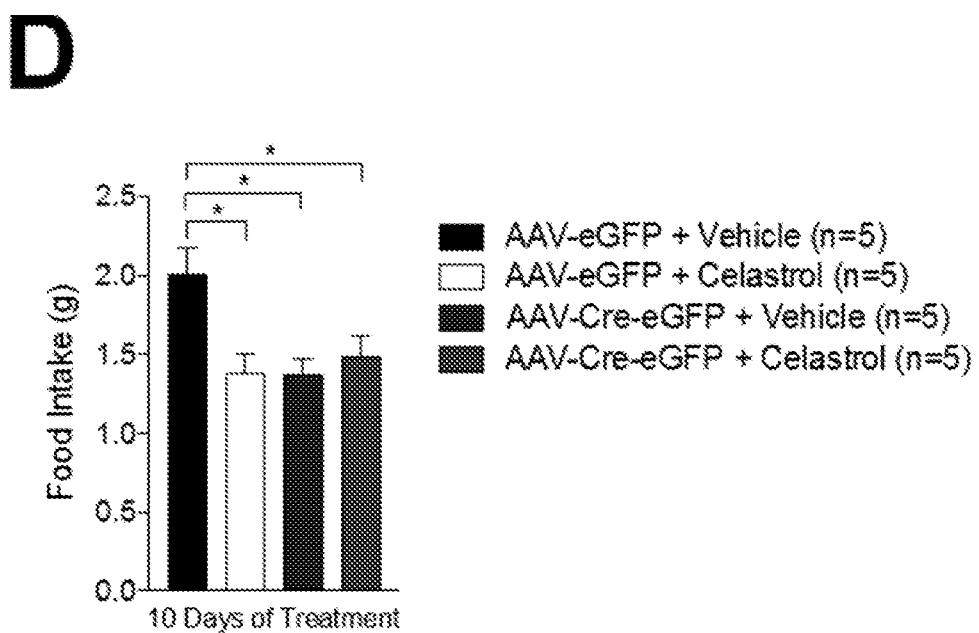
Figure 30:
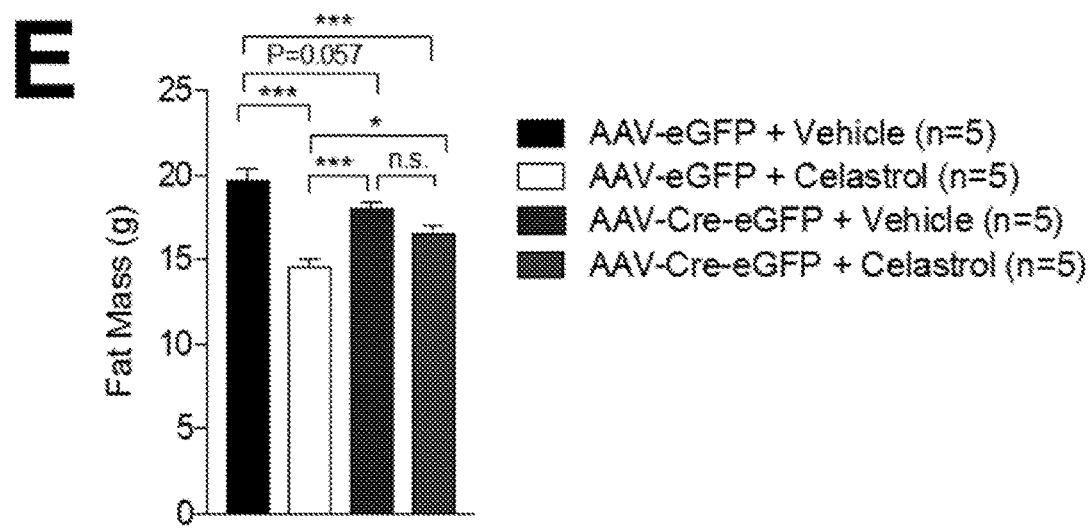
Figure 30:
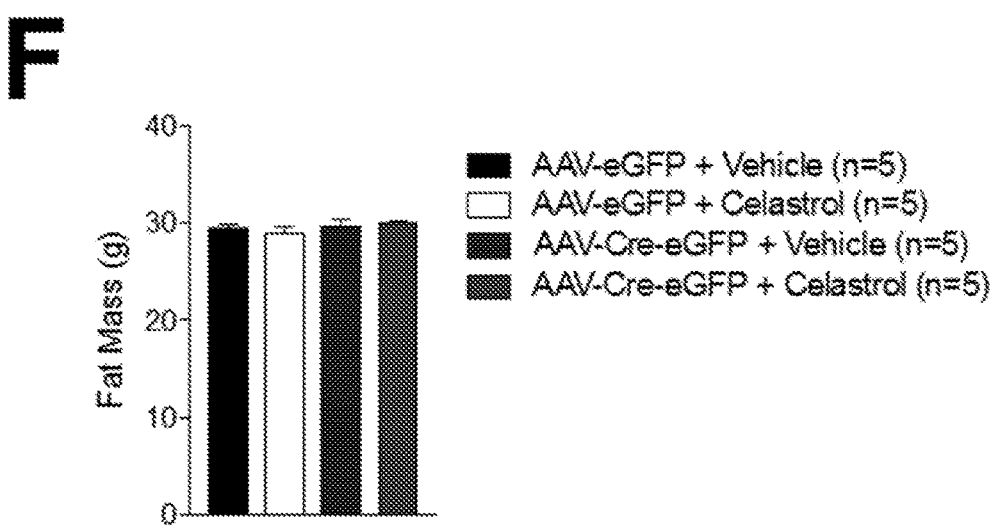

FIG. 26 shows that 8-10-week C57 male mice that were intranasally administered GR antagonist (RU486: 1, 5, 10 µg/animal/day; intranasal; 12 µl total volume) and/or PTP1B inhibitor (Claramine: 1, 10 and 20 µg/animal/day, intranasal; 12 µl total volume) for 10 consecutive days exhibited dose dependent effect on body weight, food intake, adiposity and adaptive thermogenesis.

Intranasal administration of PTP1B inhibitor (Claramine) or GR antagonist (RU486) synergistically attenuates body weight, adiposity and food intake in diet-induced obese mice.

FIG. 26 shows that 12-week high fat fed C57BL/6 male mice were mice that received intranasal GR antagonist (RU486: 1 µg/animal/day; ICV) and/or PTP1B inhibitor (Claramine: 1 and 10 µg/animal/day; ICV) administration for 10 consecutive days showed a synergistic attenuation of body weights an adiposity mediated by effects on both food intake and energy expenditure.

It will be understood that the invention disclosed and defined in this specification extends to all alternative combinations of two or more of the individual features mentioned or evident from the text or drawings. All of these different combinations constitute various alternative aspects of the invention.

The invention claimed is:

1. A method for reducing, or treating adiposity or obesity in an individual, or reducing body weight in an individual, the method comprises intranasally administering a glucocorticoid receptor (GR) antagonist and a protein tyrosine phosphatase 1B (PTP1B) inhibitor to the individual, wherein the GR antagonist reduces the expression of T-cell protein tyrosine phosphatase (TCPTP), thereby reducing or treating adiposity or obesity in the individual or reducing the body weight of the individual.

2. The method according to claim 1, wherein the body weight of the individual is reduced without any substantial change in lean muscle mass and/or bone density and is a result of a reduction in the total adipose weight of the individual.

3. The method according to claim 1, wherein a reduction in adiposity is a reduction in central obesity, peripheral obesity, and/or subcutaneous adiposity.

4. The method according to claim 1 wherein white adipose tissue browning in the individual is increased.

5. A method of minimising the weight gain of an individual consuming a high caloric diet compared to the weight gain that would occur without pharmacological intervention, the method comprises intranasally administering a GR antagonist and a PTP1B inhibitor to the individual, wherein the GR antagonist reduces the expression of TCPTP, thereby minimising the weight gain of the individual consuming a high caloric diet compared to the weight gain of the individual in the absence of a GR antagonist and PTP1B inhibition.

6. The method according to claim 1, wherein the individual has, or is, consuming a high caloric diet or wherein the obesity is diet induced.

7. The method according to claim 1, wherein the obesity is treated, adiposity is reduced, or weight gain is minimised without a change in diet or an increase in exercise.

8. The method according to claim 1, wherein the method further comprises the step of reducing the caloric intake in the individual and/or increasing the level of exercise undertaken by the individual.

9. The method according to claim 1, wherein the inhibitor of PTP1B directly inhibits the enzymatic activity of PTP1B.

10. The method according to claim 1, wherein the GR antagonist is RU486.

11. The method according to claim 1 wherein the PTP1B inhibitor is claramine or trodusquemine.

12. The method according to claim 1, wherein the GR antagonist is RU486 and the PTP1B inhibitor is claramine or trodusquemine.

13. The method according to claim 5, wherein the GR antagonist is RU486 and the PTP1B inhibitor is claramine or trodusquemine.

* * * * *